(12) United States Patent
Avery et al.

(10) Patent No.: US 9,808,003 B2
(45) Date of Patent: Nov. 7, 2017

(54) HERBICIDALLY ACTIVE 2-(SUBSTITUTED-PHENYL)-CYCLOPENTANE-1,3-DIONE COMPOUNDS AND DERIVATIVES THEREOF

(71) Applicant: Syngenta Limited, Guildford, Surrey (GB)

(72) Inventors: Alaric James Avery, Bracknell (GB); John Benjamin Taylor, Bracknell (GB); Russell Colin Viner, Bracknell (GB); Jeffery Steven Wailes, Bracknell (GB); Ian Stuart Cloudsdale, Chapel Hill, NC (US); John Kenneth Dickson, Jr., Chapel Hill, NC (US); Ian Henry Aspinall, Bracknell (GB); Janice Black, Bracknell (GB); Emma Briggs, Bracknell (GB); Shuji Hachisu, Bracknell (GB); Simon Hardy, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 36 days.

(21) Appl. No.: 14/785,470

(22) PCT Filed: Apr. 16, 2014

(86) PCT No.: PCT/EP2014/057835
§ 371 (c)(1),
(2) Date: Oct. 19, 2015

(87) PCT Pub. No.: WO2014/170413
PCT Pub. Date: Oct. 23, 2014

(65) Prior Publication Data
US 2016/0081334 A1    Mar. 24, 2016

(30) Foreign Application Priority Data

Apr. 19, 2013 (GB) .................................. 1307093.3
Jun. 6, 2013 (GB) .................................. 1310115.9

(51) Int. Cl.
*A01N 37/18* (2006.01)
*A01N 37/40* (2006.01)
(Continued)

(52) U.S. Cl.
CPC .............. *A01N 37/18* (2013.01); *A01N 25/32* (2013.01); *A01N 37/40* (2013.01); *A01N 43/08* (2013.01); *A01N 43/10* (2013.01); *A01N 43/16* (2013.01); *A01N 43/38* (2013.01); *A01N 43/40* (2013.01); *A01N 43/42* (2013.01); *A01N 43/52* (2013.01); *A01N 43/54* (2013.01); *A01N 43/56* (2013.01); *A01N 43/58* (2013.01); *A01N 43/60* (2013.01); *A01N 43/76* (2013.01); *A01N 43/78* (2013.01); *A01N 43/80* (2013.01); *A01N 43/82* (2013.01); *A01N 47/06* (2013.01); *C07C 233/31* (2013.01); *C07C 233/32* (2013.01); *C07C 233/61* (2013.01); *C07C 233/76* (2013.01); *C07C 235/46* (2013.01); *C07C 235/60* (2013.01); *C07D 207/46* (2013.01);
(Continued)

(58) Field of Classification Search
None
See application file for complete search history.

(56) References Cited

U.S. PATENT DOCUMENTS

| 4,338,122 A | 7/1982 | Wheeler |
| 5,808,135 A | 9/1998 | Fischer et al. |

FOREIGN PATENT DOCUMENTS

| WO | 96/03366 A1 | 2/1996 |
| WO | 01/17972 A2 | 3/2001 |

(Continued)

OTHER PUBLICATIONS

International Search Report of International Application PCT/EP2014/057835 dated Oct. 7, 2015.

*Primary Examiner* — Hasan Ahmed
*Assistant Examiner* — Frank Choi
(74) *Attorney, Agent, or Firm* — James Cueva

(57) ABSTRACT

The present invention relates to a compound of formula (I): wherein the substituents are as defined herein, and wherein the compound of formula (I) is optionally present as an agrochemically acceptable salt thereof. These compounds are thought to be suitable for use as herbicides. The invention therefore also relates to a method of controlling weeds, especially grassy monocotyledonous weeds, in crops of useful plants, comprising applying a compound of formula (I), or a herbicidal composition comprising such a compound, to the plants or to the locus thereof.

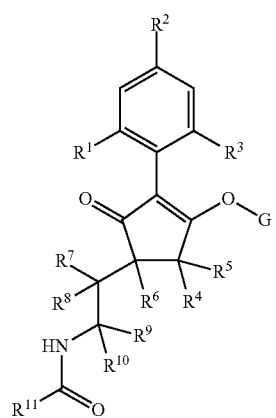

(I)

21 Claims, No Drawings

(51) Int. Cl.

| | | |
|---|---|---|
| A01N 43/00 | (2006.01) | |
| C07C 233/00 | (2006.01) | |
| C07C 235/46 | (2006.01) | |
| C07D 213/81 | (2006.01) | |
| C07D 213/82 | (2006.01) | |
| C07D 215/48 | (2006.01) | |
| C07D 237/24 | (2006.01) | |
| C07D 239/52 | (2006.01) | |
| C07D 241/24 | (2006.01) | |
| C07D 307/68 | (2006.01) | |
| C07D 333/38 | (2006.01) | |
| C07D 401/12 | (2006.01) | |
| C07D 401/14 | (2006.01) | |
| A01N 43/40 | (2006.01) | |
| C07D 231/14 | (2006.01) | |
| C07D 231/56 | (2006.01) | |
| C07D 233/90 | (2006.01) | |
| C07D 239/28 | (2006.01) | |
| C07D 471/04 | (2006.01) | |
| C07C 233/76 | (2006.01) | |
| C07D 207/46 | (2006.01) | |
| C07D 277/56 | (2006.01) | |
| A01N 25/32 | (2006.01) | |
| A01N 43/08 | (2006.01) | |
| A01N 43/10 | (2006.01) | |
| A01N 43/16 | (2006.01) | |
| A01N 43/38 | (2006.01) | |
| A01N 43/42 | (2006.01) | |
| A01N 43/52 | (2006.01) | |
| A01N 43/54 | (2006.01) | |
| A01N 43/56 | (2006.01) | |
| A01N 43/58 | (2006.01) | |
| A01N 43/60 | (2006.01) | |
| A01N 43/76 | (2006.01) | |
| A01N 43/78 | (2006.01) | |
| A01N 43/80 | (2006.01) | |
| A01N 43/82 | (2006.01) | |
| A01N 47/06 | (2006.01) | |
| C07C 233/31 | (2006.01) | |
| C07C 233/32 | (2006.01) | |
| C07C 235/60 | (2006.01) | |
| C07C 233/61 | (2006.01) | |

(52) U.S. Cl.
CPC ......... *C07D 213/81* (2013.01); *C07D 213/82* (2013.01); *C07D 215/48* (2013.01); *C07D 231/14* (2013.01); *C07D 231/56* (2013.01); *C07D 233/90* (2013.01); *C07D 237/24* (2013.01); *C07D 239/28* (2013.01); *C07D 239/52* (2013.01); *C07D 241/24* (2013.01); *C07D 277/56* (2013.01); *C07D 307/68* (2013.01); *C07D 333/38* (2013.01); *C07D 401/12* (2013.01); *C07D 401/14* (2013.01); *C07D 471/04* (2013.01); *C07C 2601/04* (2017.05); *C07C 2601/08* (2017.05); *C07C 2601/14* (2017.05)

(56) References Cited

FOREIGN PATENT DOCUMENTS

| | | |
|---|---|---|
| WO | 01/74770 A1 | 3/2001 |
| WO | 2009/019005 A2 | 2/2009 |
| WO | 2010/000773 A1 | 1/2010 |
| WO | 2010/069834 A1 | 6/2010 |
| WO | 2010069834 A1 | 6/2010 |
| WO | 2010/089210 A1 | 8/2010 |
| WO | 2010/102758 A2 | 9/2010 |
| WO | 2010/102848 A1 | 9/2010 |
| WO | 2011/007146 A1 | 1/2011 |
| WO | 2013/079708 A1 | 6/2013 |
| WO | 2013079708 A1 | 6/2013 |

HERBICIDALLY ACTIVE 2-(SUBSTITUTED-PHENYL)-CYCLOPENTANE-1,3-DIONE COMPOUNDS AND DERIVATIVES THEREOF

RELATED APPLICATION INFORMATION

This application is a 371 of International Application No. PCT/EP2014/057835, filed Apr. 16, 2014, which claims priority to GB1310115.9, filed Jun. 6, 2013 and GB1307093.3 filed Apr. 19, 2013 the contents of which are incorporated herein by reference herein.

The present invention relates to novel, herbicidally active cyclopentanedione compounds, specifically 2-(substituted-phenyl)-cyclopentane-1,3-dione compounds, and derivatives thereof (e.g. enol ketone tautomer derivatives thereof), to processes for their preparation, to herbicidal compositions comprising those compounds, and to their use in controlling weeds such as grassy monocotyledonous weeds, especially in crops of useful plants, or in inhibiting undesired plant growth.

U.S. Pat. No. 4,338,122 (assignee Union Carbide Corp.) discloses 2-aryl-1,3-cyclopentanedione compounds exhibiting acaricidal and herbicidal activity. WO 96/01798 (Bayer AG) and its derived patent U.S. Pat. No. 5,840,661 disclose 2-aryl-cyclopentane-1,3-dione derivatives and their use as pesticides and herbicides. WO 96/03366 (Bayer AG) and its derived patent U.S. Pat. No. 5,808,135 disclose fused 2-(2,4,6-trimethylphenyl)cyclopentane-1,3-dione derivatives and their use as pesticides and herbicides.

WO 99/43649 A1 (Bayer AG) discloses inter alia (4-aryl-phenyl)-substituted or (4-heteroaryl-phenyl)-substituted cyclic keto-enols, including several types of cyclic diones and derivatives thereof. WO 99/48869 A1 (Bayer AG) discloses inter alia (3-aryl-phenyl)-substituted or (3-eteroaryl-phenyl)-substituted cyclic keto-enols, including several types of cyclic diones and derivatives thereof.

WO 01/17972 A2 (Syngenta Participations AG) discloses phenyl-substituted (such as 4-methyl-2,6-diethyl-phenyl-substituted) heterocycles or cyclopentanedione derivatives, suitable for use as herbicides. WO 01/74770 (Bayer AG), and its equivalent US 2003/0216260 A1, disclose $C_2$-phenyl-substituted cyclic ketoenols and their use as pesticides and herbicides.

WO 2009/019005 A2 (Syngenta Limited) discloses fused bicyclic and oxygen-bridged cyclopentanedione derivatives, specifically 10-oxatricyclo-[5.2.1.0$^{2,6}$]decane-3,5-diones and derivatives, which are substituted by substituted-phenyl and which have herbicidal activity.

WO 2010/000773 A1 (Syngenta Limited) discloses 5-(heterocyclylalkyl)-3-hydroxy-2-phenyl-cyclopent-2-enones and certain derivatives thereof as herbicides.

WO 2010/069834 A1 (Syngenta Participations AG and Syngenta Limited) discloses cyclopentane-1,3-diones, having a heteroarylmethyl-substituent and a substituted phenyl substituent on the 4- and 2-positions of the cyclopentane ring respectively, and derivatives thereof containing latentiating groups; these compounds are disclosed as having herbicidal properties.

WO 2011/007146 A1 (Syngenta Limited) discloses certain 2-(substituted-phenyl)-cyclopentane-1,3-dione derivatives having herbicidal and/or plant-growth-inhibiting properties, in which at the 4-position of the cyclopentane-1,3-dione there is a substituent A-CHR$^4$— in which A is unsubstituted or substituted $C_3$-$C_7$cycloalkyl or A is optionally substituted phenyl.

Other cyclopentane-1,3-dione compounds substituted by substituted-phenyl and having herbicidal activity are described in WO 2010/089210 A1 and WO 2010/102848 A1 (both Syngenta Limited).

WO 2010/102758 A2 (Bayer CropScience AG) discloses (haloalkylmethoxy-)-phenyl-substituted cyclic keto-enols as pest control agents and/or as herbicides.

Copending PCT application PCT/EP2012/074172, filed on 30 Nov. 2012 and published on 6 Jun. 2013 as WO 2013/079708 A1 (Syngenta Limited and Syngenta Participations AG) discloses cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl, and derivatives of the enol ketone tautomer of such cyclopentanediones, which have herbicidal activity especially in the control of grassy monocotyledonous weeds and/or when used post-emergence.

2-(Substituted-phenyl)-cyclopentane-1,3-dione compounds, and derivatives of the enol ketone tautomer of such cyclopentane-1,3-diones, which have an amide-containing substituent (R$^{11}$—C(O)—NH—CR$^9$R$^{10}$—CR$^7$R$^8$—) at the 4- or 5-position of the cyclopentane-1,3-dione, and which have herbicidal activity and/or plant-growth-inhibiting properties, especially in the control of grassy monocotyledonous weeds and/or when used post-emergence, have now been found, which are encompassed by the present invention.

Therefore, in a first aspect of the present invention, there is provided a compound of formula (I):

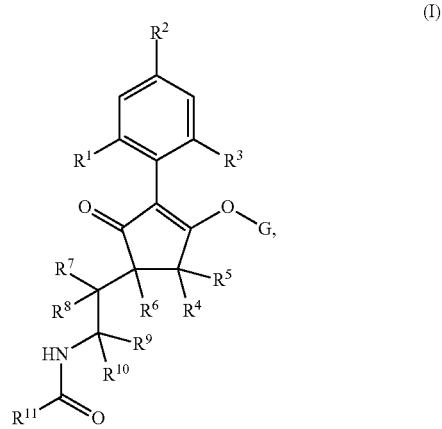

wherein:

R$^1$ is methyl, ethyl, n-propyl, cyclopropyl, trifluoromethyl, vinyl, ethynyl, fluorine, chlorine, bromine, methoxy, ethoxy or fluoromethoxy (i.e. $C_1$fluoroalkoxy);

R$^2$ is hydrogen, methyl, ethyl, n-propyl, isopropyl, cyclopropyl, fluoromethyl (i.e. $C_1$fluoroalkyl), fluoroethyl (i.e. $C_2$fluoroalkyl), vinyl, prop-1-enyl, ethynyl, prop-1-ynyl, 2-chloroethynyl, 2-fluoroethynyl, 2-(trifluoromethyl)ethynyl, but-1-ynyl, 2-(cyclopropyl)ethynyl, halogen (in particular chlorine or bromine), methoxy, prop-2-ynyloxy, or ($C_1$-$C_2$fluoroalkyl)-methoxy-;

or R$^2$ is phenyl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro;

or R$^2$ is monocyclic heteroaryl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro;

or $R^2$ is

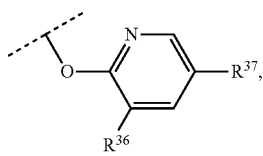

in which $R^{36}$ is fluorine or chlorine, and $R^{37}$ is fluorine, chlorine or $C_1$fluoroalkyl; and $R^3$ is hydrogen, methyl, ethyl, n-propyl, cyclopropyl, trifluoromethyl, vinyl, ethynyl, fluorine, chlorine, bromine, methoxy, ethoxy, n-propoxy, isopropoxy, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-;

$R^4$, $R^5$ and $R^6$, independently of each other, are hydrogen, $C_1$-$C_5$alkyl (in particular $C_1$-$C_4$alkyl, e.g. $C_1$-$C_2$alkyl), $C_2$-$C_3$ alkenyl (in particular ethenyl-$CH_2$—), $C_2$-$C_3$alkynyl (in particular ethynyl-$CH_2$—), $C_1$-$C_2$fluoroalkyl or $C_1$-$C_2$alkoxy$C_1$-$C_2$alkyl;

provided that: either (i) at least two of $R^4$, $R^5$ and $R^6$ are hydrogen, or (ii) two of $R^4$, $R^5$ and $R^6$ are methyl and the remaining one of $R^4$, $R^5$ and $R^6$ is hydrogen; and $R^7$ and $R^8$, independently of each other, are hydrogen, fluorine or $C_1$-$C_3$alkyl (preferably hydrogen or methyl); and $R^9$ and $R^{10}$, independently of each other, are hydrogen, fluorine or $C_1$-$C_3$alkyl (preferably hydrogen, methyl or ethyl);

provided that no more than two (preferably none) of $R^7$, $R^8$, $R^9$ and $R^{10}$ are fluorine;

and provided that at least two (preferably three or all) of $R^7$, $R^8$, $R^9$ and $R^{10}$ are hydrogen;

and wherein $R^{11}$ is $C_1$-$C_6$alkyl (in particular $C_3$-$C_5$alkyl such as tert-butyl), $C_3$-$C_7$cycloalkyl (in particular $C_4$-$C_6$cycloalkyl, more particularly cyclohexyl), tetrahydro-2H-pyranyl (such as tetrahydro-2H-pyran-4-yl, tetrahydro-2H-pyran-3-yl or tetrahydro-2H-pyran-2-yl), tetrahydrofuranyl (such as tetrahydrofuran-3-yl or tetrahydrofuran-2-yl), oxetanyl (such as oxetan-3-yl or oxetan-2-yl), tetrahydrothiophene-yl (such as tetrahydrothiophene-3-yl or tetrahydrothiophene-2-yl), or thietanyl (such as thietan-3-yl or thietan-2-yl);

or $R^{11}$ is a monocyclic 6-membered-ring heteroaryl, which is carbon-linked (i.e. linked by a ring carbon), and which is pyridinyl, pyrazinyl, pyrimidinyl, pyridazinyl, 1,3,5-triazinyl or 1,2,4-triazinyl, wherein the monocyclic 6-membered-ring heteroaryl is optionally substituted by 1, 2 or 3 substituents;

wherein the 1, 2 or 3 optional substituents on the monocyclic 6-membered-ring heteroaryl independently are fluorine, chlorine, bromine, iodine, $C_1$-$C_3$alkyl, $C_1$-$C_3$fluoroalkyl, $C_1$-$C_2$alkoxy, $C_1$-$C_2$fluoroalkoxy, cyclopropyl, $C_{n1}$alkoxy$C_{n2}$alkyl (wherein n1 is 1 or 2, n2 is 1 or 2, and n1+n2 is 2 or 3), vinyl, $C_2$fluoroalkenyl, $C_2$-$C_3$alkynyl, fluoroethynyl, cyano, amino, or phenyl in which the phenyl is optionally substituted at its meta and/or para position(s) by 1 or 2 fluorines; and wherein, when $R^{11}$ is pyrazinyl, pyrimidinyl, pyridazinyl, 1,3,5-triazinyl or 1,2,4-triazinyl, then each of these is optionally substituted by 1 or 2 of the substituents on the monocyclic 6-membered-ring heteroaryl, as defined herein;

wherein, when $R^{11}$ is pyridin-3-yl or pyridin-4-yl, then each of these is substituted by 1 or 2 of the substituents on the monocyclic 6-membered-ring heteroaryl, as defined herein, wherein, when $R^{11}$ is pyridin-2-yl substituted by 3 substituents, then one or more of the optional substituents on the pyridin-2-yl is or are fluorine;

wherein, when $R^{11}$ is monocyclic 6-membered-ring heteroaryl substituted by $C_2$alkyl, $C_2$fluoroalkyl, $C_2$alkoxy or $C_2$fluoroalkoxy, then: the monocyclic 6-membered-ring heteroaryl is substituted by 1 or 2 substituents independently being $C_2$alkyl, $C_2$fluoroalkyl, $C_2$alkoxy or $C_2$fluoroalkoxy, and the monocyclic 6-membered-ring heteroaryl is optionally further substituted by 1 or 2 substituents independently being fluorine, chlorine, bromine, $C_1$alkyl, $C_1$fluoroalkyl, $C_1$alkoxy, $C_1$fluoroalkoxy or cyano; provided that the monocyclic 6-membered-ring heteroaryl is substituted by no more than 2 substituents or in the case of a pyridin-2-yl is substituted by no more than 3 substituents;

wherein, when $R^{11}$ is monocyclic 6-membered-ring heteroaryl substituted by iodine, $C_3$alkyl, $C_3$fluoroalkyl, cyclopropyl, $C_{n1}$alkoxy$C_{n2}$alkyl, vinyl, $C_2$fluoroalkenyl, $C_2$-$C_3$alkynyl or fluoroethynyl, then: the monocyclic 6-membered-ring heteroaryl is pyridin-2-yl substituted by only one iodine, $C_3$alkyl, $C_3$fluoroalkyl, cyclopropyl, $C_{n1}$alkoxy$C_{n2}$alkyl, vinyl, $C_2$fluoroalkenyl, $C_2$-$C_3$alkynyl or fluoroethynyl, and in which the pyridin-2-yl ring is optionally further substituted by 1 or 2 fluorines;

wherein, when $R^{11}$ is monocyclic 6-membered-ring heteroaryl substituted by amino, then: either the monocyclic 6-membered-ring heteroaryl is 6-amino-pyridin-2-yl optionally further substituted by 1 or 2 fluorines; or the monocyclic 6-membered-ring heteroaryl is 3-amino-pyridin-2-yl or 3-amino-pyrazin-2-yl each of which is optionally further substituted at the 5-position of the pyridin-2-yl or pyrazin-2-yl ring by hydrogen, fluorine, methyl or $C_1$fluoroalkyl; and wherein, when $R^{11}$ is monocyclic 6-membered-ring heteroaryl substituted by optionally substituted phenyl, then the monocyclic 6-membered-ring heteroaryl is 6-phenyl-pyridin-2-yl in which the phenyl is optionally substituted at its meta and/or para position(s) by 1 or 2 fluorines, and in which the pyridin-2-yl ring is optionally further substituted by 1 or 2 fluorines;

or $R^{11}$ is a monocyclic 5-membered-ring heteroaryl, which is carbon-linked (i.e. linked by a ring carbon), and which is pyrrolyl, pyrazolyl, imidazol-2-yl, triazolyl (e.g. 1,2,3- or 1,2,4-triazolyl), tetrazolyl, furyl, thiophenyl, oxazolyl, isoxazolyl, thiazolyl, isothiazolyl, oxadiazolyl (e.g. 1,2,3-, 1,2,4-, 1,2,5- or 1,3,4-oxadiazolyl), or thiadiazolyl (e.g. 1,2,3-, 1,2,4-, 1,2,5- or 1,3,4-thiadiazolyl), wherein the monocyclic 5-membered-ring heteroaryl is optionally substituted by 1, 2 or 3 substituents;

wherein the 1, 2 or 3 optional substituents on the monocyclic 5-membered-ring heteroaryl are:

1, 2 or 3 optional ring-carbon substituents independently being fluorine, chlorine, bromine, $C_1$-$C_3$alkyl, $C_1$-$C_3$fluoroalkyl, $C_1$-$C_2$alkoxy, $C_1$-$C_2$fluoroalkoxy, cyclopropyl, $C_{n3}$alkoxy$C_{n4}$alkyl (wherein n3 is 1 or 2, n4 is 1 or 2, and n3+n4 is 2 or 3), vinyl, $C_2$fluoroalkenyl, $C_2$-$C_3$alkynyl, fluoroethynyl or cyano; and/or 1 substituent being $C_1$-$C_3$alkyl, $C_1$-$C_3$fluoroalkyl or cyclopropyl, substituted at a ring nitrogen not partaking in a double bond, when the monocyclic 5-memberedring heteroaryl has a ring nitrogen not partaking in a double bond (in particular pyrrolyl, pyrazolyl, imidazol-2-yl, triazolyl or tetrazolyl);

provided that the monocyclic 5-membered-ring heteroaryl has no more than 3 substituents, or has no more than the maximum number of substituents possible for the monocyclic 5-membered-ring heteroaryl in uncharged form if this maximum is less than 3 substituents; and wherein, when $R^{11}$ is a monocyclic 5-membered-ring heteroaryl having a ring nitrogen not partaking in a double bond (in particular pyrrolyl, pyrazolyl, imidazol-2-yl, triazolyl or tetrazolyl), then the ring nitrogen not partaking in a double bond is substituted by $C_1$-$C_3$alkyl, $C_1$-$C_3$fluoroalkyl or cyclopropyl; and wherein, when $R^{11}$ is a monocyclic 5-membered-ring heteroaryl, then: the monocyclic 5-membered-ring heteroaryl has no more than one $C_3$fluoroalkyl, vinyl, $C_2$fluoroalkenyl, $C_2$-$C_3$alkynyl or fluoroethynyl substituent; the monocyclic 5-membered-ring heteroaryl has no more than 2 substituents independently being bromine, $C_2$-$C_3$alkyl, $C_2$-$C_3$fluoroalkyl, $C_1$-$C_2$alkoxy, $C_1$-$C_2$fluoroalkoxy, cyclopropyl, $C_{n3}$alkoxy$C_{n4}$alkyl, vinyl, $C_2$fluoroalkenyl, $C_2$-$C_3$alkynyl, fluoroethynyl or cyano; and the monocyclic 5-membered-ring heteroaryl has no more than 2 substituents independently being chlorine or bromine;

or $R^{11}$ is one of the following sub-formulae B, E, F, GG, H, J, Q, R, S, T or U:

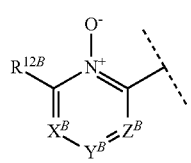
(B)

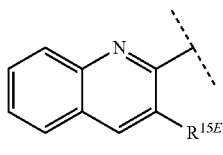
(E)

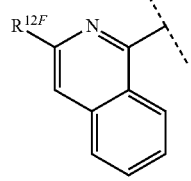
(F)

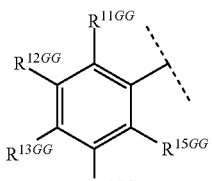
(GG)

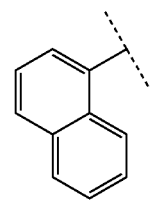
(H)

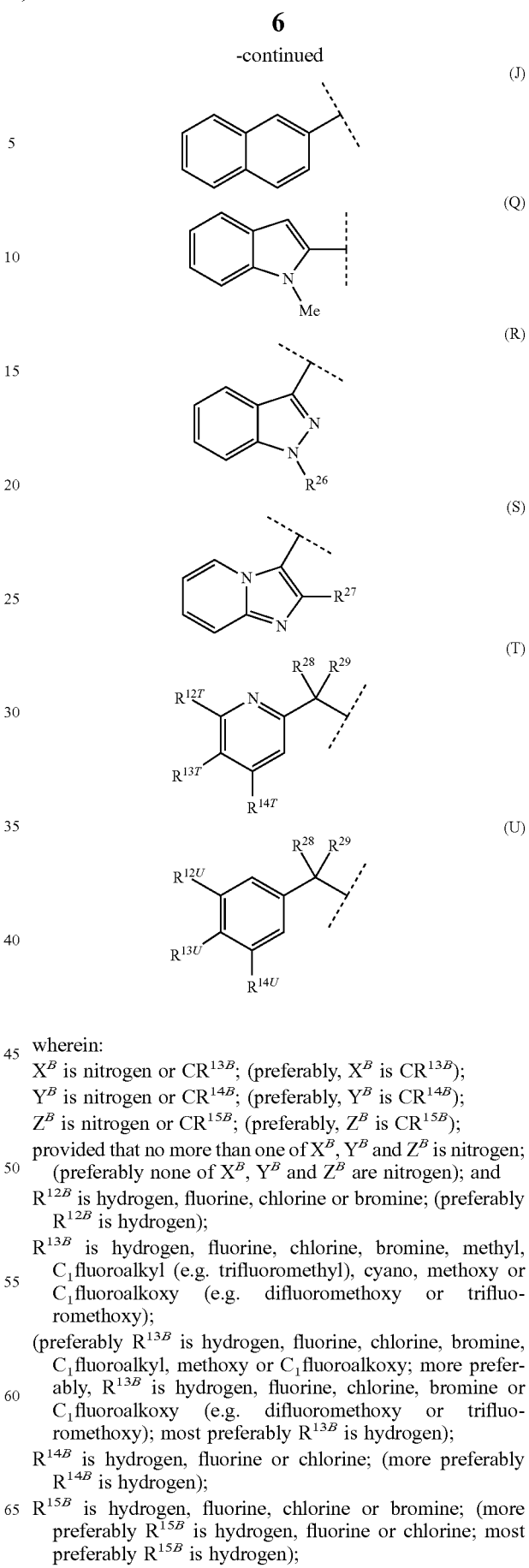

wherein:
$X^B$ is nitrogen or $CR^{13B}$; (preferably, $X^B$ is $CR^{13B}$);
$Y^B$ is nitrogen or $CR^{14B}$; (preferably, $Y^B$ is $CR^{14B}$);
$Z^B$ is nitrogen or $CR^{15B}$; (preferably, $Z^B$ is $CR^{15B}$);
provided that no more than one of $X^B$, $Y^B$ and $Z^B$ is nitrogen; (preferably none of $X^B$, $Y^B$ and $Z^B$ are nitrogen); and
$R^{12B}$ is hydrogen, fluorine, chlorine or bromine; (preferably $R^{12B}$ is hydrogen);
$R^{13B}$ is hydrogen, fluorine, chlorine, bromine, methyl, $C_1$fluoroalkyl (e.g. trifluoromethyl), cyano, methoxy or $C_1$fluoroalkoxy (e.g. difluoromethoxy or trifluoromethoxy);
(preferably $R^{13B}$ is hydrogen, fluorine, chlorine, bromine, $C_1$fluoroalkyl, methoxy or $C_1$fluoroalkoxy; more preferably, $R^{13B}$ is hydrogen, fluorine, chlorine, bromine or $C_1$fluoroalkoxy (e.g. difluoromethoxy or trifluoromethoxy); most preferably $R^{13B}$ is hydrogen);
$R^{14B}$ is hydrogen, fluorine or chlorine; (more preferably $R^{14B}$ is hydrogen);
$R^{15B}$ is hydrogen, fluorine, chlorine or bromine; (more preferably $R^{15B}$ is hydrogen, fluorine or chlorine; most preferably $R^{15B}$ is hydrogen);

provided that at least two (i.e. two, three or all; preferably three or all, most preferably all) of $R^{12B}$, $R^{13B}$, $R^{14B}$ and $R^{15B}$ are hydrogen;

and provided that, when $R^{13B}$ is bromine, then $X^A$ is $CR^{13B}$, and $R^{12B}$, $R^{14B}$ and $R^{15B}$ are independently hydrogen or fluorine, provided that at least two (i.e. two or three) of $R^{12B}$, $R^{14B}$ and $R^{15B}$ are hydrogen; (preferably, in this case, all of $R^{12B}$, $R^{14B}$ and $R^{15B}$ are hydrogen and/or $Y^B$ is $CR^{14B}$ and/or $Z^B$ is $CR^{15B}$); and $R^{15E}$ is hydrogen, fluorine or chlorine (preferably hydrogen);

$R^{12F}$ is hydrogen, fluorine or chlorine (preferably hydrogen);

$R^{11GG}$ is hydrogen, fluorine, methyl or $C_1$fluoroalkyl (e.g. trifluoromethyl);

(preferably $R^{11GG}$ is hydrogen or fluorine; most preferably $R^{11GG}$ is hydrogen);

$R^{12\ GG}$ hydrogen, fluorine or chlorine; (preferably $R^{12\ GG}$ is hydrogen);

$R^{13GG}$ is hydrogen, fluorine, chlorine, bromine, $C_1$fluoroalkyl (e.g. trifluoromethyl), methoxy or $C_1$fluoroalkoxy (e.g. trifluoromethoxy or difluoromethoxy);

(preferably $R^{13GG}$ is hydrogen, fluorine or $C_1$fluoroalkyl (e.g. trifluoromethyl); most preferably $R^{13GG}$ is hydrogen);

$R^{14GG}$ is hydrogen or fluorine; (preferably $R^{14GG}$ is hydrogen);

$R^{15GG}$ is hydrogen, fluorine, chlorine, methoxy or $C_1$fluoroalkoxy; (preferably $R^{15GG}$ is hydrogen or fluorine; more preferably $R^{15GG}$ is hydrogen);

provided that, when $R^{13GG}$ is bromine, then $R^{11GG}$, $R^{12GG}$, $R^{14GG}$ and $R^{15GG}$ are independently hydrogen or fluorine;

provided that, when $R^{11GG}$ methyl or $C_1$fluoroalkyl, then $R^{12GG}$, $R^{13GG}$, $R^{14GG}$ and $R^{15GG}$ are independently hydrogen or fluorine; and provided that at least two (i.e. two, three or all; preferably three or all, most preferably all) of $R^{12GG}$, $R^{13GG}$, $R^{14GG}$ and $R^{15GG}$ are hydrogen; and $R^{26}$ is hydrogen or methyl;

$R^{27}$ is hydrogen or methyl;

$R^{28}$ and $R^{29}$ independently are hydrogen or fluorine; (preferably, both are hydrogen);

$R^{12T}$, $R^{13T}$, $R^{14T}$ are independently hydrogen or fluorine, provided that at least two (i.e. two or, preferably, three) of $R^{12T}$, $R^{13T}$ and $R^{14T}$ are hydrogen; and $R^{12U}$, $R^{13U}$ and $R^{14U}$ are independently hydrogen or fluorine, provided that at least two (i.e. two or, preferably, three) of $R^{12U}$, $R^{13U}$ and $R^{14U}$ are hydrogen;

and wherein:

G is hydrogen; an agriculturally acceptable metal, or an agriculturally acceptable sulfonium or ammonium group; or G is $-C(X^a)-R^a$, $-C(X^b)-X^c-R^b$, $-C(X^d)-N(R^c)-R^d$, $-SO_2-R^e$, $-P(X^e)(R^f)-R^g$, $-CH_2-X^f-R^h$, or $-CH(Me)-X^f-R^h$; or phenyl-$CH_2-$ or phenyl-$CH(C_1-C_2alkyl)-$ (in each of which the phenyl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro), or heteroaryl-$CH_2-$ or heteroaryl-$CH(C_1-C_2alkyl)-$ (in each of which the heteroaryl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro), or phenyl-$C(O)-CH_2-$ (wherein the phenyl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro); or $C_1-C_6$alkoxy-$C(O)-CH_2-$, $C_1-C_6$alkyl-$C(O)-CH_2-$, $C_1-C_6$alkoxy-$C(O)-CH=CH-$, $C_2-C_7$alken-1-yl-$CH_2-$, $C_2-C_7$alken-1-yl-$CH(C_1-C_2alkyl)-$, $C_2-C_4$fluoroalken-1-yl-$CH_2-$, $C_2-C_7$alkyn-1-yl-$CH_2-$, or $C_2-C_7$alkyn-1-yl-$CH(C_1-C_2alkyl)-$;

wherein $X^a$, $X^b$, $X^c$, $X^d$, $X^e$ and $X^f$ are independently of each other oxygen or sulfur (preferably oxygen); and wherein $R^a$ is H, $C_1-C_{21}$alkyl, $C_2-C_{21}$alkenyl, $C_2-C_{18}$alkynyl, $C_1-C_{10}$fluoroalkyl, $C_1-C_{10}$cyanoalkyl, $C_1-C_{10}$nitroalkyl, $C_1-C_{10}$aminoalkyl, $C_1-C_5$alkylamino($C_1-C_5$)alkyl, $C_2-C_8$dialkylamino($C_1-C_5$)alkyl, $C_3-C_7$cycloalkyl($C_1-C_5$)alkyl, $C_1-C_5$alkoxy($C_1-C_5$)alkyl, $C_3-C_5$alkenyloxy($C_1-C_5$)alkyl, $C_3-C_5$alkynyloxy($C_1-C_5$)alkyl, $C_1-C_5$alkylthio($C_1-C_5$)alkyl, $C_1-C_5$alkylsulfinyl($C_1-C_5$)alkyl, $C_1-C_5$alkylsulfonyl($C_1-C_5$)alkyl, $C_2-C_8$alkylideneaminoxy($C_1-C_5$)alkyl, $C_1-C_5$alkylcarbonyl($C_1-C_5$)alkyl, $C_1-C_5$alkoxycarbonyl($C_1-C_5$)alkyl, aminocarbonyl($C_1-C_5$)alkyl, $C_1-C_5$alkylaminocarbonyl($C_1-C_5$)alkyl, $C_2-C_8$dialkylaminocarbonyl($C_1-C_5$)alkyl, $C_1-C_5$alkylcarbonylamino($C_1-C_5$)alkyl, N—($C_1-C_5$)alkylcarbonyl-N—($C_1-C_5$)alkylamino($C_1-C_5$)alkyl, $C_3-C_{68}$trialkylsilyl($C_1-C_5$)alkyl, phenyl($C_1-C_5$)alkyl (wherein the phenyl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), heteroaryl($C_1-C_5$)alkyl (wherein the heteroaryl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), $C_2-C_5$fluoroalkenyl, $C_3-C_{68}$cycloalkyl; phenyl or phenyl substituted by 1, 2 or 3 of, independently, $C_1-C_3$alkyl, $C_1-C_3$fluoroalkyl, $C_1-C_3$alkoxy, $C_1-C_3$fluoroalkoxy, halogen, cyano or nitro; or heteroaryl or heteroaryl substituted by 1, 2 or 3 of, independently, $C_1-C_3$alkyl, $C_1-C_3$fluoroalkyl, $C_1-C_3$alkoxy, $C_1-C_3$fluoroalkoxy, halogen, cyano or nitro;

$R^b$ is $C_1-C_{18}$alkyl, $C_3-C_{18}$alkenyl, $C_3-C_{18}$alkynyl, $C_2-C_{10}$fluoroalkyl, $C_1-C_{10}$cyanoalkyl, $C_1-C_{10}$nitroalkyl, $C_2-C_{10}$aminoalkyl, $C_1-C_5$alkylamino($C_1-C_5$)alkyl, $C_2-C_8$dialkylamino($C_1-C_5$)alkyl, $C_3-C_7$cycloalkyl($C_1-C_5$)alkyl, $C_1-C_5$alkoxy($C_1-C_5$)alkyl, $C_3-C_5$alkenyloxy($C_1-C_5$)alkyl, $C_3-C_5$alkynyloxy($C_1-C_5$)alkyl, $C_1-C_5$alkylthio($C_1-C_5$)alkyl, $C_1-C_5$alkylsulfinyl($C_1-C_5$)alkyl, $C_1-C_5$alkylsulfonyl($C_1-C_5$)alkyl, $C_2-C_8$alkylideneaminoxy($C_1-C_5$)alkyl, $C_1-C_5$alkylcarbonyl($C_1-C_5$)alkyl, $C_1-C_5$alkoxycarbonyl($C_1-C_5$)alkyl, aminocarbonyl($C_1-C_5$)alkyl, $C_1-C_5$alkylaminocarbonyl($C_1-C_5$)alkyl, $C_2-C_8$dialkylaminocarbonyl($C_1-C_5$)alkyl, $C_1-C_5$alkylcarbonylamino($C_1-C_5$)alkyl, N—($C_1-C_5$)alkylcarbonyl-N—($C_1-C_5$)alkylamino($C_1-C_5$)alkyl, $C_3-C_6$trialkylsilyl($C_1-C_5$)alkyl, phenyl($C_1-C_5$)alkyl (wherein the phenyl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), heteroaryl$C_1-C_5$alkyl (wherein the heteroaryl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkyl-thio, $C_1-C_3$alkylsulfinyl, $C_1-C_3$alkylsulfonyl, halogen, cyano, or nitro), $C_3-C_5$fluoroalkenyl, $C_3-C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{18}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxyl($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxyl($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{18}$fluoroalkoxy, $C_1$-$C_5$alkylamino or di($C_1$-$C_4$alkyl)amino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; $C_1$-$C_6$alkoxy-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present (e.g. where chemically possible) as an agrochemically acceptable salt thereof.

Preferably, e.g. in all aspects and/or embodiments of the invention, in the compound of formula (I), $R^{11}$ is as defined below:

$R^{11}$ is $C_1$-$C_6$alkyl (in particular $C_3$-$C_5$alkyl such as tert-butyl), $C_3$-$C_7$cycloalkyl (in particular $C_4$-$C_6$cycloalkyl, more particularly cyclohexyl), tetrahydro-2H-pyranyl (such as tetrahydro-2H-pyran-4-yl, tetrahydro-2H-pyran-3-yl or tetrahydro-2H-pyran-2-yl), tetrahydrofuranyl (such as tetrahydrofuran-3-yl or tetrahydrofuran-2-yl), oxetanyl (such as oxetan-3-yl or oxetan-2-yl), tetrahydrothiophene-yl (such as tetrahydrothiophene-3-yl or tetrahydrothiophene-2-yl), or thietanyl (such as thietan-3-yl or thietan-2-yl);

or $R^{11}$ is one of the following sub-formulae A, B, C, D, E, F, GG, H, J, K, L, M, N, O, P, Q, R, S, T, U, V, W, X, Y or Z:

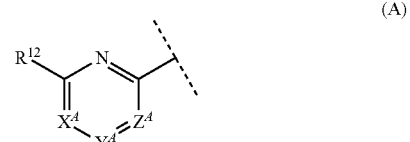
(A)

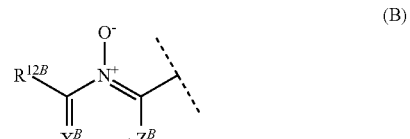
(B)

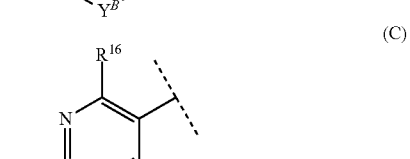
(C)

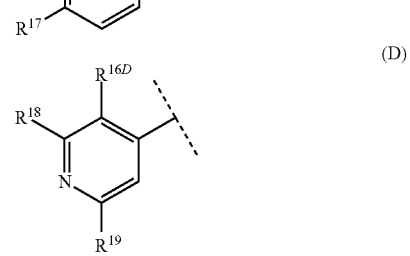
(D)

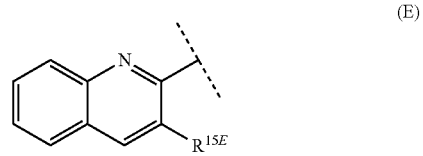
(E)

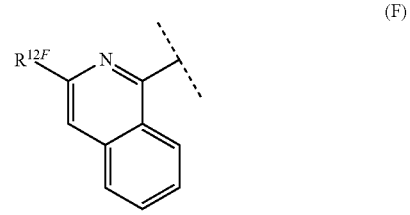
(F)

-continued
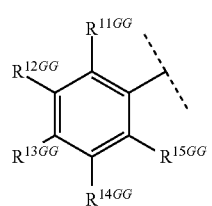 (G)
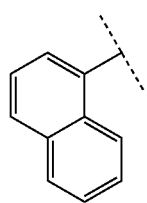 (H)
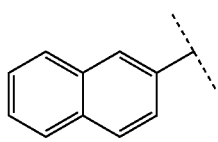 (J)
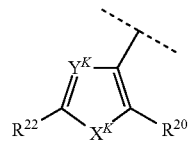 (K)
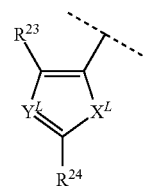 (L)
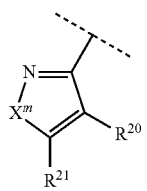 (M)
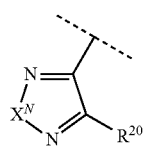 (N)
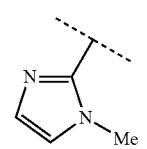 (O)
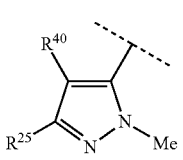 (P)
-continued
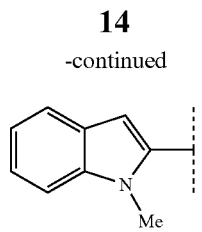 (Q)
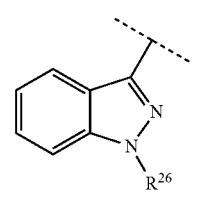 (R)
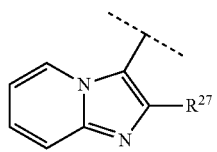 (S)
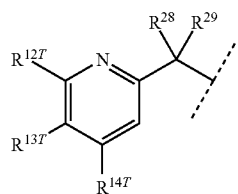 (T)
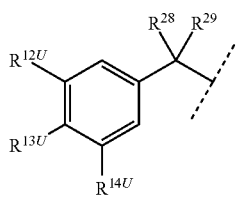 (U)
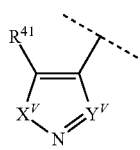 (V)
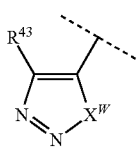 (W)
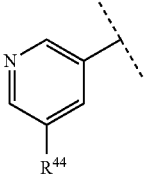 (X)
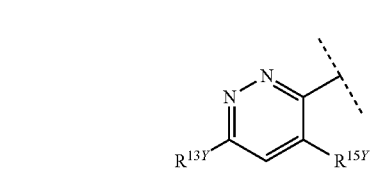 (Y)

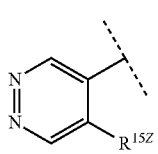
(Z)

wherein:
$X^A$ is nitrogen or $CR^{13}$;
$Y^A$ is nitrogen or $CR^{14}$;
$Z^A$ is nitrogen or $CR^{15}$;
provided that no more than one of $X^A$, $Y^A$ and $Z^A$ is nitrogen; (preferably none of $X^A$, $Y^A$ and $Z^A$ are nitrogen); and
$R^{12}$ is hydrogen, fluorine, chlorine, bromine, iodine, $C_1$-$C_2$alkyl (e.g. methyl), $C_1$-$C_2$fluoroalkyl (e.g. $C_1$fluoroalkyl such as trifluoromethyl), $C_1$-$C_2$alkoxy (e.g. methoxy), $C_1$-$C_2$fluoroalkoxy (e.g. $C_1$fluoroalkoxy such as trifluoromethoxy or difluoromethoxy), cyano, amino, or phenyl optionally substituted at meta and/or para position(s) by 1 or 2 fluorine substituents; (preferably $R^{12}$ is hydrogen, fluorine, chlorine or bromine; most preferably $R^{12}$ is hydrogen); $R^{13}$ is hydrogen, fluorine, chlorine, bromine, methyl, ethyl, $C_1$fluoroalkyl (e.g. trifluoromethyl), $C_2$fluoroalkyl, vinyl, $C_2$fluoroalkenyl, $C_2$-$C_3$alkynyl, fluoroethynyl, cyano, methoxy, ethoxy, $C_1$fluoroalkoxy, or $C_2$fluoroalkoxy;
(preferably $R^{13}$ is hydrogen, fluorine, chlorine, bromine, methyl, $C_1$fluoroalkyl (e.g. trifluoromethyl), cyano, methoxy or $C_1$fluoroalkoxy (e.g. difluoromethoxy or trifluoromethoxy); more preferably $R^{13}$ is hydrogen, fluorine, chlorine, bromine, $C_1$fluoroalkyl, methoxy or $C_1$fluoroalkoxy; even more preferably, $R^{13}$ is hydrogen, fluorine, chlorine, bromine or $C_1$fluoroalkoxy (e.g. difluoromethoxy or trifluoromethoxy); most preferably $R^{13}$ is hydrogen);
$R^{14}$ is hydrogen, fluorine, chlorine, bromine, methoxy, $C_1$fluoroalkoxy, methyl, $C_1$fluoroalkyl or cyano;
(preferably $R^{14}$ is hydrogen, fluorine or chlorine; most preferably $R^{14}$ is hydrogen);
$R^{15}$ is hydrogen, fluorine, chlorine, bromine, $C_1$-$C_2$alkyl (e.g. methyl), $C_1$fluoroalkyl, methoxy, $C_1$fluoroalkoxy (e.g. trifluoromethoxy or difluoromethoxy), cyano or amino;
(preferably $R^{15}$ is hydrogen, fluorine, chlorine or bromine; more preferably $R^{15}$ is hydrogen, fluorine or chlorine; most preferably $R^{15}$ is hydrogen);
provided that at least two (i.e. two, three or all; preferably three or all, most preferably all) of $R^{12}$, $R^{13}$, $R^{14}$ and $R^{15}$ are hydrogen;
and provided that, when $R^{12}$ is iodine, amino, or optionally substituted phenyl, then $X^A$ is $CR^{13}$, $Y^A$ is $CR^{14}$, $Z^A$ is $CR^{15}$, and $R^{13}$, $R^{14}$ and $R^{15}$ are independently hydrogen or fluorine, provided that at least two (i.e. two or three) of $R^{13}$, $R^{14}$ and $R^{15}$ are hydrogen; (preferably, in this case, all of $R^{13}$, $R^{14}$ and $R^{15}$ are hydrogen);
and provided that, when $R^{13}$ is bromine, then $X^A$ is $CR^{13}$, and $R^{12}$, $R^{14}$ and $R^{15}$ are independently hydrogen or fluorine, provided that at least two (i.e. two or three) of $R^{12}$, $R^{14}$ and $R^{15}$ are hydrogen; (preferably, in this case, all of $R^{12}$, $R^{14}$ and $R^{15}$ are hydrogen and/or $Y^A$ is $CR^{14}$ and/or $Z^A$ is $CR^{15}$);
and provided that, when $R^{13}$ is ethyl, $C_2$fluoroalkyl, vinyl, $C_2$fluoroalkenyl, $C_2$-$C_3$alkynyl, fluoroethynyl, ethoxy or $C_2$fluoroalkoxy, then $X^A$ is $CR^{13}$, $Y^A$ is $CR^{14}$, $Z^A$ is $CR^{15}$, and $R^{12}$, $R^{14}$ and $R^{15}$ are independently hydrogen or fluorine, provided that at least two (i.e. two or three) of $R^{12}$, $R^{14}$ and $R^{15}$ are hydrogen; (preferably, in this case, all of $R^{12}$, $R^{14}$ and $R^{15}$ are hydrogen);
and provided that, when $R^{14}$ is bromine or cyano, then $X^A$ is $CR^{13}$, $Y^A$ is $CR^{14}$, $Z^A$ is $CR^{15}$, and $R^{12}$, $R^{13}$ and $R^{15}$ are independently hydrogen or fluorine, provided that at least two (i.e. two or three) of $R^{12}$, $R^{13}$ and $R^{15}$ are hydrogen; (preferably, in this case, all of $R^{12}$, $R^{13}$ and $R^{15}$ are hydrogen);
and provided that, when $R^{15}$ is amino, then $X^A$ is $CR^{13}$, $Y^A$ is nitrogen or $CR^{14}$, $Z^A$ is $CR^{15}$, and $R^{13}$ is hydrogen, methyl or $C_1$fluoroalkyl (e.g. H, Me or trifluoromethyl), and $R^{12}$ and $R^{14}$ are hydrogen;
and wherein:
$X^B$ is nitrogen or $CR^{13B}$; (preferably, $X^B$ is $CR^{13B}$);
$Y^B$ is nitrogen or $CR^{14B}$; (preferably, $Y^B$ is $CR^{14B}$);
$Z^B$ is nitrogen or $CR^{15B}$; (preferably, $Z^B$ is $CR^{15B}$);
provided that no more than one of $X^B$, $Y^B$ and $Z^B$ is nitrogen; (preferably none of $X^B$, $Y^B$ and $Z^B$ are nitrogen); and
$R^{12B}$ is hydrogen, fluorine, chlorine or bromine; (preferably $R^{12B}$ is hydrogen);
$R^{13B}$ is hydrogen, fluorine, chlorine, bromine, methyl, $C_1$fluoroalkyl (e.g. trifluoromethyl), cyano, methoxy or $C_1$fluoroalkoxy (e.g. difluoromethoxy or trifluoromethoxy);
(preferably $R^{13B}$ is hydrogen, fluorine, chlorine, bromine, $C_1$fluoroalkyl, methoxy or $C_1$fluoroalkoxy; more preferably, $R^{13B}$ is hydrogen, fluorine, chlorine, bromine or $C_1$fluoroalkoxy (e.g. difluoromethoxy or trifluoromethoxy); most preferably $R^{13B}$ is hydrogen);
$R^{14B}$ is hydrogen, fluorine or chlorine; (more preferably $R^{14B}$ is hydrogen);
$R^{15B}$ is hydrogen, fluorine, chlorine or bromine; (more preferably $R^{15B}$ is hydrogen, fluorine or chlorine; most preferably $R^{15B}$ is hydrogen);
provided that at least two (i.e. two, three or all; preferably three or all, most preferably all) of $R^{12B}$, $R^{13B}$, $R^{14B}$ and $R^{15B}$ are hydrogen;
and provided that, when $R^{13B}$ is bromine, then $X^A$ is $CR^{13B}$, and $R^{12B}$, $R^{14B}$ and $R^{15B}$ are independently hydrogen or fluorine, provided that at least two (i.e. two or three) of $R^{12B}$, $R^{14B}$ and $R^{15B}$ are hydrogen; (preferably, in this case, all of $R^{12B}$, $R^{14B}$ and $R^{15B}$ are hydrogen and/or $Y^B$ is $CR^{14B}$ and/or $Z^B$ is $CR^{15B}$); and
$R^{16}$ is hydrogen, fluorine, chlorine, bromine, methyl or $C_1$fluoroalkyl (preferably hydrogen, chlorine, methyl or $C_1$fluoroalkyl);
$R^{17}$ is hydrogen, fluorine, chlorine, methyl or $C_1$fluoroalkyl (preferably hydrogen, chlorine or $C_1$fluoroalkyl);
provided that no more than one of $R^{16}$ and $R^{17}$ is hydrogen;
and provided that when $R^{16}$ is bromine then $R^{17}$ is hydrogen or fluorine;
$R^{16D}$ is hydrogen or fluorine (preferably hydrogen);
$R^{18}$ is hydrogen, fluorine or chlorine (preferably chlorine);
$R^{19}$ is hydrogen, fluorine, chlorine, methoxy, $C_1$fluoroalkoxy, methyl or $C_1$fluoroalkyl (preferably chlorine, methoxy or $C_1$fluoroalkoxy);
provided that no more than one (preferably none) of $R^{18}$ and $R^{19}$ is hydrogen;
$R^{15E}$ is hydrogen, fluorine or chlorine (preferably hydrogen);
$R^{12F}$ is hydrogen, fluorine or chlorine (preferably hydrogen);
$R^{11GG}$ is hydrogen, fluorine, methyl or $C_1$fluoroalkyl (e.g. trifluoromethyl);

(preferably $R^{11GG}$ is hydrogen or fluorine; most preferably $R^{12GG}$ is hydrogen);

$R^{12GG}$ is hydrogen, fluorine or chlorine; (preferably $R^{12GG}$ is hydrogen);

$R^{13GG}$ is hydrogen, fluorine, chlorine, bromine, $C_1$fluoroalkyl (e.g. trifluoromethyl), methoxy or $C_1$fluoroalkoxy (e.g. trifluoromethoxy or difluoromethoxy);

(preferably $R^{13GG}$ is hydrogen, fluorine or $C_1$fluoroalkyl (e.g. trifluoromethyl); most preferably $R^{13GG}$ is hydrogen);

$R^{14GG}$ is hydrogen or fluorine; (preferably $R^{14GG}$ is hydrogen);

$R^{15GG}$ is hydrogen, fluorine, chlorine, methoxy or $C_1$fluoroalkoxy; (preferably $R^{15GG}$ is hydrogen or fluorine; more preferably $R^{15GG}$ is hydrogen);

provided that, when $R^{13GG}$ is bromine, then $R^{11GG}$, $R^{12GG}$, $R^{14GG}$ and $R^{15GG}$ are independently hydrogen or fluorine;

provided that, when $R^{11GG}$ is methyl or $C_1$fluoroalkyl, then $R^{12GG}$, $R^{13GG}$, $R^{14GG}$ and $R^{15GG}$ are independently hydrogen or fluorine; and provided that at least two (i.e. two, three or all; preferably three or all, most preferably all) of $R^{12GG}$, $R^{13GG}$, $R^{14GG}$ and $R^{15GG}$ are hydrogen;

$X^K$ is O or S; and $Y^K$ is C—H or N (preferably, $Y^K$ is N);

$X^L$ is O, S or N-Me; and $Y^L$ is C—H or N; provided that when $X^L$ is N-Me then $Y^L$ is not N (preferably, when $X^L$ is O or S, then $Y^L$ is N; more preferably, $X^L$ is S; most preferably, $X^L$ is S and $Y^L$ is N);

$X^m$ is O, S or N-Me (preferably, $X^m$ is N-Me);

$X^N$ is O, S or N-Me;

$X^V$ is O, S or N-Me (preferably, $X^V$ is S or N-Me); and $Y^V$ is N or $CR^{42}$; and $X^W$ is O, S or N-Me (in particular, $X^W$ can be O or S);

$R^{20}$ is hydrogen, methyl, $C_1$fluoroalkyl, fluorine or chlorine (in particular H, Me, difluoromethyl, trifluoromethyl, fluorine or chlorine);

$R^{21}$ is hydrogen, methyl, $C_1$fluoroalkyl, ethyl, cyclopropyl, fluorine or chlorine (preferably hydrogen, methyl, difluoromethyl, trifluoromethyl, fluorine or chlorine);

$R^{22}$ is hydrogen, methyl, $C_1$fluoroalkyl, fluorine or chlorine (in particular H, Me, difluoromethyl, trifluoromethyl, fluorine or chlorine);

$R^{23}$ is hydrogen, methyl, $C_1$fluoroalkyl, ethyl or cyclopropyl (in particular H, Me, difluoromethyl, trifluoromethyl, ethyl or cyclopropyl; preferably difluoromethyl, trifluoromethyl or cyclopropyl);

$R^{24}$ is hydrogen, methyl, $C_1$fluoroalkyl, ethyl or methoxymethyl (in particular H, Me, difluoromethyl, trifluoromethyl, ethyl or methoxymethyl; preferably difluoromethyl, trifluoromethyl or methoxymethyl);

$R^{25}$ is hydrogen, methyl, $C_1$fluoroalkyl, fluorine or chlorine (in particular H, Me, difluoromethyl, trifluoromethyl, preferably methyl, difluoromethyl or trifluoromethyl, most preferably trifluoromethyl);

$R^{26}$ is hydrogen or methyl; and $R^{27}$ is hydrogen or methyl; and $R^{28}$ and $R^{29}$ independently are hydrogen or fluorine; (preferably, both are hydrogen);

$R^{40}$ is hydrogen, methyl, $C_1$fluoroalkyl, fluorine or chlorine (in particular hydrogen, methyl, difluoromethyl, trifluoromethyl, fluorine or chlorine, preferably hydrogen, fluorine or chlorine);

$R^{41}$ is hydrogen, methyl, $C_1$fluoroalkyl, fluorine or chlorine (in particular hydrogen, methyl, difluoromethyl, trifluoromethyl, fluorine or chlorine, preferably methyl, trifluoromethyl or chlorine);

$R^{42}$ is hydrogen, methyl, $C_1$fluoroalkyl, fluorine or chlorine (in particular hydrogen, methyl, difluoromethyl, trifluoromethyl, fluorine or chlorine, preferably methyl, trifluoromethyl or chlorine);

$R^{43}$ is hydrogen, methyl or $C_1$fluoroalkyl (in particular hydrogen, methyl, difluoromethyl or trifluoromethyl, preferably methyl or trifluoromethyl);

$R^{44}$ is fluorine, chlorine or bromine (preferably chlorine);

$R^{12T}$, $R^{13T}$ and $R^{14T}$ are independently hydrogen or fluorine, provided that at least two (i.e. two or, preferably, three) of $R^{12T}$, $R^{13T}$ and $R^{14T}$ are hydrogen; and $R^{12U}$, $R^{13U}$ and $R^{14U}$ are independently hydrogen or fluorine, provided that at least two (i.e. two or, preferably, three) of $R^{12U}$, $R^{13U}$ and $R^{14U}$ are hydrogen; and $R^{13Y}$ is hydrogen, fluorine, chlorine, bromine, $C_1$fluoroalkyl (e.g. trifluoromethyl), methoxy or $C_1$fluoroalkoxy (e.g. trifluoromethoxy or difluoromethoxy);

(preferably $R^{13Y}$ is hydrogen, fluorine, chlorine, bromine or $C_1$fluoroalkoxy (e.g. trifluoromethoxy or difluoromethoxy); more preferably $R^{13Y}$ is hydrogen, chlorine or bromine);

$R^{15Y}$ is hydrogen, fluorine, chlorine, bromine, methoxy or $C_1$fluoroalkoxy; (preferably $R^{15Y}$ is hydrogen or fluorine; more preferably $R^{15Y}$ is hydrogen);

provided that one or both of $R^{13Y}$ and $R^{15Y}$ are independently hydrogen or fluorine; and $R^{15Z}$ is hydrogen, fluorine or chlorine (preferably, $R^{15Z}$ is hydrogen or fluorine);

and wherein the compound of formula (I) is optionally present (e.g. where chemically possible) as an agrochemically acceptable salt thereof.

Preferably, e.g. in all aspects and/or embodiments of the invention, in the compound of formula (I), $R^2$ and/or $R^{11}$ and/or G and/or $R^h$ (even more preferably $R^2$ and $R^{11}$ and G and $R^h$) are as defined below:

$R^2$ is hydrogen, methyl, ethyl, n-propyl, isopropyl, cyclopropyl, fluoromethyl (i.e. $C_1$fluoroalkyl), fluoroethyl (i.e. $C_2$fluoroalkyl), vinyl, prop-1-enyl, ethynyl, prop-1-ynyl, 2-chloroethynyl, 2-fluoroethynyl, 2-(trifluoromethyl)ethynyl, but-1-ynyl, 2-(cyclopropyl)ethynyl, halogen (in particular chlorine or bromine), or $(C_1\text{-}C_2\text{fluoroalkyl})$-methoxy-;

or $R^2$ is phenyl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro;

or $R^2$ is monocyclic heteroaryl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro;

and/or $R^{11}$ is $C_1$-$C_6$alkyl (in particular $C_3$-$C_5$alkyl such as tert-butyl), $C_3$-$C_7$cycloalkyl (in particular $C_4$-$C_6$cycloalkyl, more particularly cyclohexyl), tetrahydro-2H-pyranyl (such as tetrahydro-2H-pyran-4-yl, tetrahydro-2H-pyran-3-yl or tetrahydro-2H-pyran-2-yl), or tetrahydrofuranyl (such as tetrahydrofuran-3-yl or tetrahydrofuran-2-yl);

or $R^{11}$ is one of the following sub-formulae A, B1, C, D1, E, F, G1, H, J, K, L, M, N, O, P1, Q, R, S, T or U:

-continued
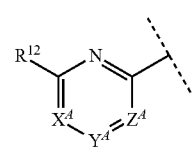
(A)
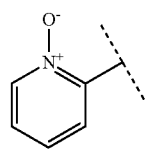
(B1)
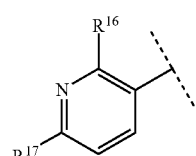
(C)
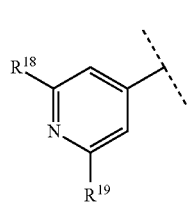
(D1)
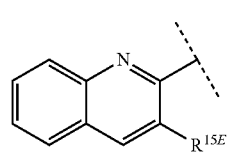
(E)
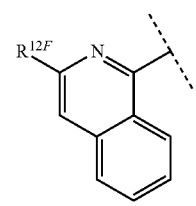
(F)
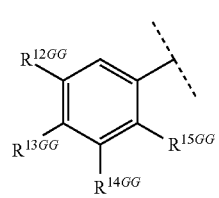
(G1)
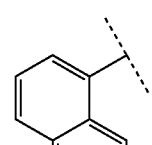
(H)
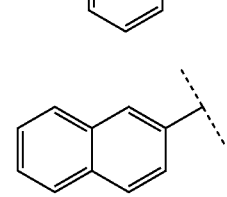
(J)
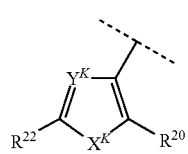
(K)
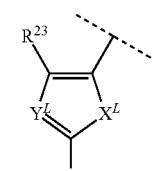
(L)
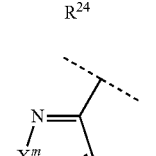
(M)
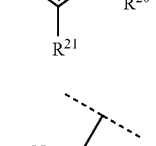
(N)
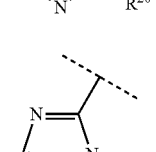
(O)
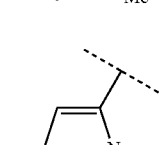
(P1)
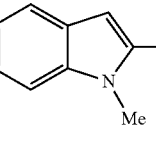
(Q)
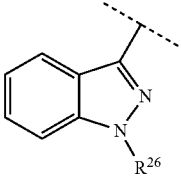
(R)
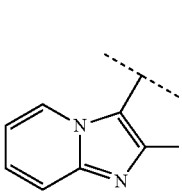
(S)

-continued

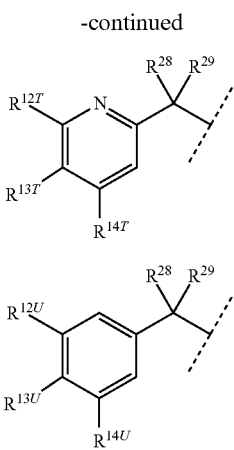
(T)

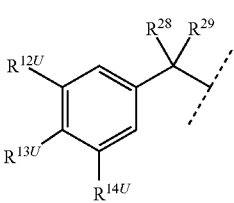
(U)

wherein:
$X^A$ is nitrogen or $CR^{13}$;
$Y^A$ is nitrogen or $CR^{14}$;
$Z^A$ is nitrogen or $CR^{15}$;
provided that no more than one of $X^A$, $Y^A$ and $Z^A$ is nitrogen; (preferably none of $X^A$, $Y^A$ and $Z^A$ is nitrogen); and
$R^{12}$ is hydrogen, fluorine, chlorine, bromine, iodine, $C_1$-$C_2$alkyl (e.g. methyl), $C_1$-$C_2$fluoroalkyl (e.g. $C_1$fluoroalkyl such as trifluoromethyl), $C_1$-$C_2$alkoxy (e.g. methoxy), $C_1$-$C_2$fluoroalkoxy (e.g. $C_1$fluoroalkoxy such as trifluoromethoxy or difluoromethoxy), cyano, amino, or phenyl optionally substituted at meta and/or para position(s) by 1 or 2 fluorine substituents;
(preferably $R^{12}$ is hydrogen, fluorine, chlorine or bromine; more preferably $R^{12}$ is hydrogen);
$R^{13}$ is hydrogen, fluorine, chlorine, methyl, $C_1$fluoroalkyl (e.g. trifluoromethyl), or cyano;
(preferably $R^{13}$ is hydrogen, fluorine, methyl, $C_1$fluoroalkyl (e.g. trifluoromethyl), or cyano;
more preferably $R^{13}$ is hydrogen, fluorine, $C_1$fluoroalkyl or cyano; most preferably $R^{13}$ is hydrogen);
$R^{14}$ is hydrogen, fluorine, chlorine, methoxy, $C_1$fluoroalkoxy, methyl or $C_1$fluoroalkyl;
(preferably $R^{14}$ is hydrogen, fluorine or chlorine; more preferably $R^{14}$ is hydrogen);
$R^{15}$ is hydrogen, fluorine, chlorine, bromine, $C_1$-$C_2$alkyl (e.g. methyl), $C_1$fluoroalkyl, methoxy, $C_1$fluoroalkoxy (e.g. trifluoromethoxy or difluoromethoxy), cyano or amino;
(preferably $R^{15}$ is hydrogen, fluorine or chlorine; more preferably $R^{15}$ is hydrogen);
provided that at least two (i.e. two, three or all; preferably three or all, most preferably all) of $R^{12}$, $R^{13}$, $R^{14}$ and $R^{15}$ are hydrogen;
and provided that, when $R^{12}$ is iodine, amino, or optionally substituted phenyl, then $X^A$ is $CR^{13}$, $Y^A$ is $CR^{14}$, $Z^A$ is $CR^{15}$, and $R^{13}$, $R^{14}$ and $R^{15}$ are independently hydrogen or fluorine, provided that at least two (i.e. two or three) of $R^{13}$, $R^{14}$ and $R^{15}$ are hydrogen; (preferably, in this case, all of $R^{13}$, $R^{14}$ and $R^{15}$ are hydrogen);
and provided that, when $R^{15}$ is amino, then $X^A$ is $CR^{13}$, $Y^A$ is nitrogen or $CR^{14}$, $Z^A$ is $CR^{15}$, and $R^{13}$ is hydrogen, methyl or $C_1$fluoroalkyl (e.g. H, Me or trifluoromethyl), and $R^{12}$ and $R^{14}$ are hydrogen; and
$R^{16}$ is hydrogen, fluorine or chlorine (preferably hydrogen or chlorine);

$R^{17}$ is hydrogen, fluorine, chlorine, methyl or $C_1$fluoroalkyl (preferably hydrogen, chlorine or $C_1$fluoroalkyl);
provided that no more than one of $R^{16}$ and $R^{17}$ is hydrogen;
$R^{18}$ is chlorine;
$R^{19}$ is fluorine, chlorine, methoxy, $C_1$fluoroalkoxy, methyl or $C_1$fluoroalkyl (preferably chlorine, methoxy or $C_1$fluoroalkoxy);
$R^{15E}$ is hydrogen, fluorine or chlorine (preferably hydrogen);
$R^{12F}$ is hydrogen, fluorine or chlorine (preferably hydrogen);
$R^{12GG}$ is hydrogen, fluorine, or chlorine; (preferably $R^{12GG}$ is hydrogen);
$R^{13GG}$ is hydrogen, fluorine, chlorine, $C_1$fluoroalkyl (e.g. trifluoromethyl), methoxy or $C_1$fluoroalkoxy (e.g. trifluoromethoxy or difluoromethoxy);
(preferably $R^{13GG}$ is hydrogen, fluorine or $C_1$fluoroalkyl (e.g. trifluoromethly); most preferably $R^{13GG}$ is hydrogen);
$R^{14GG}$ is hydrogen or fluorine; (preferably $^{14GG}$ is hydrogen);
$R^{15GG}$ is hydrogen, fluorine, chlorine, methoxy or $C_1$fluoroalkoxy; (preferably $R^{15GG}$ is hydrogen or fluorine; more preferably $R^{15GG}$ is hydrogen);
provided that at least two (i.e. two, three, or all; preferably three or all, most preferably all) of $R^{12GG}$, $R^{13GG}$, $R^{14GG}$ and $R^{15GG}$ are hydrogen;
$X^K$ is O or S; and $Y^K$ is C—H or N (preferably $Y^K$ is N);
$X^L$ is O, S or N-Me; and $Y^L$ is C—H or N; provided that when $X^L$ is N-Me then $Y^L$ is not N (preferably, when $X^L$ is not N-Me, then $Y^L$ is N);
$X^m$ is O, S or N-Me;
$X^N$ is O, S or N-Me;
$R^{20}$ is hydrogen, methyl or $C_1$fluoroalkyl (in particular H, Me or trifluoromethyl);
$R^{21}$ is hydrogen, methyl or $C_1$fluoroalkyl (in particular H, Me or trifluoromethyl);
$R^{22}$ is hydrogen, methyl or $C_1$fluoroalkyl (in particular H, Me or trifluoromethyl);
$R^{23}$ is hydrogen, methyl or $C_1$fluoroalkyl (in particular H, Me or trifluoromethyl);
$R^{24}$ is hydrogen, methyl or $C_1$fluoroalkyl (in particular H, Me or trifluoromethyl);
$R^{25}$ is hydrogen, methyl or $C_1$fluoroalkyl (in particular H, Me or trifluoromethyl);
$R^{26}$ is hydrogen or methyl; and
$R^{27}$ is hydrogen or methyl; and
$R^{28}$ and $R^{29}$ independently are hydrogen or fluorine; (preferably, both are hydrogen);
$R^{12T}$, $R^{13T}$ and $R^{14T}$ are independently hydrogen or fluorine, provided that at least two (i.e. two or, preferably, three) of $R^{12T}$, $R^{13T}$ and $R^{14T}$ are hydrogen; and
$R^{12U}$, $R^{13U}$ and $R^{14U}$ are independently hydrogen or fluorine, provided that at least two (i.e. two or, preferably, three) of $R^{12U}$, $R^{13U}$ and $R^{14U}$ are hydrogen;
and/or
G is hydrogen; an agriculturally acceptable metal, or an agriculturally acceptable sulfonium or ammonium group; or
G is —C($X^a$)—$R^a$, —C($X^b$)—$X^c$—$R^b$, —C($X^d$)—N($R^c$)—$R^d$, —$SO_2$—$R^e$, —P($X^e$)($R^f$)—$R^g$, or —$CH_2$—$X^f$—$R^h$; or phenyl-$CH_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—

CH$_2$— (wherein the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro); or C$_1$-C$_6$alkoxy-C(O)—CH$_2$—, C$_1$-C$_6$alkyl-C(O)—CH$_2$—, C$_1$-C$_6$alkoxy-C(O)—CH=CH—, C$_2$-C$_7$alken-1-yl-CH$_2$—, C$_2$-C$_7$alken-1-yl-CH(C$_1$-C$_2$alkyl)-, C$_2$-C$_4$fluoroalken-1-yl-CH$_2$—, C$_2$-C$_7$alkyn-1-yl-CH$_2$—, or C$_2$-C$_7$alkyn-1-yl-CH(C$_1$-C$_2$alkyl)-;

and/or

R$^h$ is C$_1$-C$_{10}$alkyl, C$_3$-C$_{10}$alkenyl, C$_3$-C$_{10}$alkynyl, C$_1$-C$_{10}$fluoroalkyl, C$_1$-C$_{10}$cyanoalkyl, C$_1$-C$_{10}$nitroalkyl, C$_2$-C$_{10}$aminoalkyl, C$_1$-C$_5$alkylamino(C$_1$-C$_5$)alkyl, C$_2$-C$_8$dialkylamino(C$_1$-C$_5$)alkyl, C$_3$-C$_7$cycloalkyl(C$_1$-C$_5$)alkyl, C$_1$-C$_5$alkoxy(C$_1$-C$_5$)alkyl, C$_3$-C$_5$alkenyloxy(C$_1$-C$_5$)alkyl, C$_3$-C$_5$alkynyloxy(C$_1$-C$_5$)alkyl, C$_1$-C$_5$alkylthio(C$_1$-C$_5$)alkyl, C$_1$-C$_5$alkylsulfinyl(C$_1$-C$_5$)alkyl, C$_1$-C$_5$alkylsulfonyl(C$_1$-C$_5$)alkyl, C$_2$-C$_8$alkylideneaminoxy(C$_1$-C$_5$)alkyl, C$_1$-C$_5$alkylcarbonyl(C$_1$-C$_5$)alkyl, C$_1$-C$_5$alkoxycarbonyl(C$_1$-C$_5$)alkyl, aminocarbonyl(C$_1$-C$_5$)alkyl, C$_1$-C$_5$alkylaminocarbonyl(C$_1$-C$_5$)alkyl, C$_2$-C$_8$dialkylaminocarbonyl(C$_1$-C$_5$)alkyl, C$_1$-C$_5$alkylcarbonylamino(C$_1$-C$_5$)alkyl, N—(C$_1$-C$_5$)alkylcarbonyl-N—(C$_1$-C$_5$)alkylamino(C$_1$-C$_5$)alkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$ alkylsulfonyl, halogen, cyano or nitro), heteroaryl(C$_1$-C$_5$)alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$ alkylsulfonyl, halogen, cyano or nitro), phenoxy (C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$ alkylsulfonyl, halogen, cyano or nitro), heteroaryloxy(C$_1$-C$_5$)alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$ alkylsulfonyl, halogen, cyano or nitro), C$_3$-C$_5$fluoroalkenyl, C$_3$-C$_8$cycloalkyl; phenyl or phenyl substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; heteroaryl or heteroaryl substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, halogen, cyano or nitro; C$_1$-C$_6$alkyl-C(O)—; or phenyl-C(O)— wherein the phenyl is optionally substituted by 1 or 2 of, independently, C$_1$-C$_2$alkyl, C$_1$fluoroalkyl, C$_1$-C$_2$alkoxy, C$_1$fluoroalkoxy, fluorine, chlorine, bromine, cyano or nitro;

and wherein, independently for each of the above preferred embodiments of R$^2$ and/or R$^{11}$ and/or G and/or R$^h$:

"heteroaryl" means an aromatic ring system containing at least one ring heteroatom and consisting either of a single ring or of two fused rings;

and the compound of formula (I) is optionally present (e.g. where chemically possible) as an agrochemically acceptable salt thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be C$_1$-C$_6$alkyl groups (except where already defined more narrowly), but are preferably C$_1$-C$_4$alkyl or C$_1$-C$_3$alkyl groups (except where already defined more narrowly), and, more preferably, are C$_1$-C$_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically C$_2$-C$_3$alkenyl or C$_2$-C$_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine. More preferably, in various aspects and/or embodiments of the invention, halogen is fluorine or chlorine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically C$_1$-C$_3$fluoroalkyl or C$_1$-C$_2$fluoroalkyl (preferably C$_1$fluoroalkyl), such as CF$_3$, CHF$_2$, CH$_2$F, CH$_3$CHF—, CF$_3$CH$_2$—, CHF$_2$CH$_2$—, CH$_2$FCH$_2$—, CHF$_2$CF$_2$— or (CH$_3$)$_2$CF—. Fluoroalkoxy is typically C$_1$-C$_3$fluoroalkoxy or C$_1$-C$_2$fluoroalkoxy (preferably C$_1$fluoroalkoxy), such as CF$_3$O, CHF$_2$O, CH$_2$FO, CH$_3$CHFO—, CF$_3$CH$_2$O—, CHF$_2$CH$_2$O— or CH$_2$FCH$_2$O—.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single rings will contain 1, 2 or 3 ring heteroatoms and bicyclic systems 1, 2, 3 or 4 ring heteroatoms which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula [N($R_a$ $R_b$ $R_c$ $R_d$)]OH, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e$$R_f$$R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups (i.e. leaving or removeable groups) within G (for example, without limitation, the latentiating groups where G is —C($X^a$)—$R^a$ or —C($X^b$)—$X^c$—$R^b$, et al.) are generally selected to allow their removal, typically by one or a combination of biochemical, chemical or physical processes, to afford the corresponding compound of formula (I) where G is H, before, during or following (preferably during or following) application of the compound of formula (I) to the treated area (e.g. field) or to plants. Examples of these processes include enzymatic cleavage or other in/on-plant cleavage (e.g. cleavage of ester and/or carbonate moieties), chemical hydrolysis, and/or photolysis. Some compounds bearing such groups G occasionally offer certain advantages or different technical properties, such as improved and/or more consistent and/or different penetration of the cuticula of the plants treated, increased and/or different tolerance of certain crops, improved and/or different compatibility or stability in formulated mixtures containing other herbicides, herbicide safeners, plant growth regulators, fungicides or insecticides, or reduced and/or different leaching properties in soils.

The preferred, suitable and/or particular values of the substituents in, or other features of, the compound of formula (I), in particular G, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{31C}$, $R^{31B}$, $R^{31C}$, $R^{32}$, $R^{33}$, $R^{34}$, $R^{35}$, $R^{36}$, $R^{37}$, $R^{40}$, $R^{41}$, $R^{42}$, $R^{43}$, $R^{44}$, $R^{12B}$, $R^{13B}$, $R^{14B}$, $R^{15B}$, $R^{16D}$, $R^{12E}$, $R^{15F}$, $R^{11GG}$, $R^{12GG}$, $R^{13GG}$, $R^{14GG}$, $R^{15GG}$, $R^{12Y}$, $R^{13T}$, $R^{14T}$, $R^{12U}$, $R^{13U}$, $R^{14U}$, $R^{13Y}$, $R^{15Y}$, $R^{15Z}$, $X^A$, $Y^A$, $Z^A$, $X^B$, $Y^B$, $Z^B$, $X^K$, $Y^K$, $X^L$, $Y^L$, $X^m$, $X^N$, $X^V$, $Y^W$, n1, n2, n3, n4, $R^a$, $R^b$, $R^c$, $R^d$, $R^e$, $R^f$, $R^g$, $R^h$, $X^a$, $X^b$, $X^c$, $X^d$, $X^e$, and/or $X^f$, are set out below (and/or generally herein), and can be either taken alone or taken together with one or more of any other preferred, suitable and/or particular values of the substituents in, or other features of, the compound of formula (I), in any and all possible combination(s) thereof.

Preferably, e.g. in all aspects and/or embodiments of the invention, G is not $C_1$-$C_6$alkyl-C(O)—$CH_2$—.

Preferably, e.g. in all aspects and/or embodiments of the invention, G is hydrogen; an agriculturally acceptable metal (e.g. an agriculturally acceptable alkali metal or alkaline earth metal), or an agriculturally acceptable sulfonium or ammonium group;
or G is —C($X^a$)—$R^a$, C($X^b$)—$X^c$$R^b$, —$SO_2$—$R^e$, —$CH_2$—$X^f$—$R^h$, or —CH(Me)-$X^f$—$R^h$; wherein $X^a$, $X^b$, $X^c$, $X^f$, $R^a$, $R^b$, $R^e$ and $R^h$ are as defined herein.

More preferably, e.g. in all aspects and/or embodiments of the invention, G is hydrogen; an agriculturally acceptable metal (e.g. an agriculturally acceptable alkali metal or alkaline earth metal), or an agriculturally acceptable sulfonium or ammonium group; or G is —C($X^a$)—$R^a$ or —C($X^b$)—$X^c R^b$, wherein $X^a$, $R^a$, $X^b$, $X^c$ and $R^b$ are as defined herein.

In a particular embodiment, G is a group —C($X^a$)—$R^a$ or —C($X^b$)—$X^c$—$R^b$, wherein $X^a$, $R^a$, $X^b$, $X^c$ and $R^b$ are as defined herein.

Preferably, e.g. in all aspects and/or embodiments of the invention, $X^a$, $X^b$, $X^c$, $X^d$, $X^e$ and/or $X^f$ are oxygen; and/or $X^c$ is sulfur. More preferably, $X^a$, $X^b$, $X^d$, $X^e$ and $X^f$ are oxygen; and $X^c$ is oxygen or sulfur. Even more preferably, $X^a$, $X^b$, $X^c$, $X^d$, $X^e$ and $X^f$ are oxygen.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl. Alternatively, preferably, $R^a$ is $C_3$-$C_6$cycloalkyl($C_1$-$C_2$)alkyl (in particular $C_3$-$C_6$cycloalkyl-methyl-), or phenyl or phenyl substituted by 1, 2 or 3 (e.g. 1 or 2) of, independently, $C_1$-$C_3$alkyl (e.g. $C_1$-$C_2$alkyl), $C_1$-$C_2$fluoroalkyl, $C_1$-$C_3$alkoxy (e.g. $C_1$-$C_2$alkoxy), $C_1$-$C_2$fluoroalkoxy, fluorine, chlorine, bromine, cyano or nitro, or a monocyclic 5- or 6-membered heteroaryl or a monocyclic 5- or 6-membered heteroaryl substituted by 1, 2 or 3 (e.g. 1 or 2) of, independently, $C_1$-$C_3$alkyl (e.g. $C_1$-$C_2$alkyl), $C_1$-$C_2$fluoroalkyl, $C_1$-$C_3$alkoxy (e.g. $C_1$-$C_2$alkoxy), $C_1$-$C_2$fluoroalkoxy, fluorine, chlorine, bromine or cyano. More preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, $C_1$-$C_4$alkoxy$C_1$-$C_4$alkyl, $C_3$-$C_6$cycloalkyl-methyl-, or phenyl or phenyl substituted by 1, 2 or 3 (e.g. 1 or 2) of, independently, $C_1$-$C_3$alkyl (e.g. $C_1$-$C_2$alkyl), $C_1$-$C_2$fluoroalkyl, $C_1$-$C_3$alkoxy (e.g. $C_1$-$C_2$alkoxy), $C_1$-$C_2$fluoroalkoxy, fluorine, chlorine, bromine, cyano or nitro.

Preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl. Alternatively, preferably, $R^b$ is $C_3$-$C_6$cycloalkyl($C_1$-$C_2$)alkyl (in particular $C_3$-$C_6$cycloalkyl-methyl-), or phenyl or phenyl substituted by 1, 2 or 3 (e.g. 1 or 2) of, independently, $C_1$-$C_3$alkyl (e.g. $C_1$-$C_2$alkyl), $C_1$-$C_2$fluoroalkyl, $C_1$-$C_3$alkoxy (e.g. $C_1$-$C_2$alkoxy), $C_1$-$C_2$fluoroalkoxy, fluorine, chlorine, bromine, cyano or nitro, or a monocyclic 5- or 6-membered heteroaryl or a monocyclic 5- or 6-membered heteroaryl substituted by 1, 2 or 3 (e.g. 1 or 2) of, independently, $C_1$-$C_3$alkyl (e.g. $C_1$-$C_2$alkyl), $C_1$-$C_2$fluoroalkyl, $C_1$-$C_3$alkoxy (e.g. $C_1$-$C_2$alkoxy), $C_1$-$C_2$fluoroalkoxy, fluorine, chlorine, bromine or cyano. More preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, $C_1$-$C_2$alkoxy$C_1$-$C_4$alkyl, $C_3$-$C_6$cycloalkyl-methyl-, or phenyl or phenyl substituted by 1, 2 or 3 (e.g. 1 or 2) of, independently, $C_1$-$C_3$alkyl (e.g. $C_1$-$C_2$alkyl), $C_1$-$C_2$fluoroalkyl, $C_1$-$C_3$alkoxy (e.g. $C_1$-$C_2$alkoxy), $C_1$-$C_2$fluoroalkoxy, fluorine, chlorine, bromine, cyano or nitro.

Preferably, $R^e$ is $C_1$-$C_{10}$alkyl (e.g. $C_1$-$C_6$alkyl or $C_1$-$C_4$alkyl), $C_1$-$C_{10}$fluoroalkyl (e.g. $C_1$-$C_3$fluoroalkyl), or phenyl or phenyl substituted by 1, 2 or 3 (e.g. 1 or 2) of, independently, $C_1$-$C_3$alkyl (e.g. $C_1$-$C_2$alkyl), $C_1$-$C_2$fluoroalkyl, $C_1$-$C_3$alkoxy (e.g. $C_1$-$C_2$alkoxy), $C_1$-$C_2$fluoroalkoxy, fluorine, chlorine, bromine, cyano or nitro. More preferably, $R^e$ is $C_1$-$C_{10}$alkyl (in particular $C_1$-$C_6$alkyl or $C_1$-$C_4$alkyl).

Preferably, $R^h$ is $C_1$-$C_{10}$alkyl (e.g. $C_1$-$C_6$alkyl or $C_1$-$C_4$alkyl), $C_1$-$C_{10}$fluoroalkyl (e.g. $C_1$-$C_3$fluoroalkyl), $C_1$-$C_6$alkyl-C(O)— (e.g. $C_1$-$C_4$alkyl-C(O)—), or $C_1$-$C_6$alkoxy-C(O)— (e.g. $C_1$-$C_4$alkoxy-C(O)—). More preferably, $R^h$ is $C_1$-$C_4$alkyl or $C_1$-$C_4$alkoxy-C(O)—.

Preferably, when G is —C($X^a$)—$R^a$ or —C($X^b$)—$X^c$—$R^b$, then
$X^a$ and $X^b$ are oxygen,
$X^c$ is oxygen or sulfur,
$R^a$ is $C_1$-$C_{10}$alkyl, $C_2$-$C_6$alkenyl, $C_2$-$C_6$alkynyl, $C_3$-$C_6$cycloalkyl, $C_1$-$C_4$alkoxy$C_1$-$C_4$alkyl, $C_3$-$C_6$cycloalkyl($C_1$-$C_2$)alkyl, or phenyl or phenyl substituted by 1, 2 or 3 of, independently, $C_1$-$C_3$alkyl, $C_1$-$C_2$fluoroalkyl, $C_1$-$C_3$alkoxy, $C_1$-$C_2$fluoroalkoxy, fluorine, chlorine, bromine, cyano or nitro, or a monocyclic 5- or 6-membered heteroaryl or a monocyclic 5- or 6-membered heteroaryl substituted by 1, 2 or 3 of, independently, $C_1$-$C_3$alkyl, $C_1$-$C_2$fluoroalkyl, $C_1$-$C_3$alkoxy, $C_1$-$C_2$fluoroalkoxy, fluorine, chlorine, bromine or cyano; and
$R^b$ is $C_1$-$C_{10}$alkyl, $C_2$-$C_5$alkenyl-$CH_2$—, $C_2$-$C_4$alkenyl-CH(Me)-, $C_2$-$C_5$alkynyl-$CH_2$—, $C_2$-$C_4$alkynyl-CH(Me)-, $C_3$-$C_6$cycloalkyl, $C_1$-$C_4$alkoxy$C_1$-$C_4$alkyl, $C_3$-$C_6$cycloalkyl($C_1$-$C_2$)alkyl, or phenyl or phenyl substituted by 1, 2 or 3 of, independently, $C_1$-$C_3$alkyl, $C_1$-$C_2$fluoroalkyl, $C_1$-$C_3$alkoxy, $C_1$-$C_2$fluoroalkoxy, fluorine, chlorine, bromine, cyano or nitro, or a monocyclic 5- or 6-membered heteroaryl or a monocyclic 5- or 6-membered heteroaryl substituted by 1, 2 or 3 of, independently, $C_1$-$C_3$alkyl, $C_1$-$C_2$fluoroalkyl, $C_1$-$C_3$alkoxy, $C_1$-$C_2$fluoroalkoxy, fluorine, chlorine, bromine or cyano.

More preferably, when G is —C($X^a$)—$R^a$ or —C($X^b$)—$X^c$—$R^b$, then $X^a$, $X^b$ and $X^c$ are oxygen, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-alkynyl), $C_3$-$C_6$cycloalkyl or $C_1$-$C_4$alkoxy$C_1$-$C_4$alkyl; and $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl.

In a preferable embodiment, G is hydrogen, or an agriculturally acceptable alkali metal or alkaline earth metal, or an agriculturally acceptable sulfonium or ammonium group. More preferably, G is hydrogen, or an agriculturally acceptable alkali metal or alkaline earth metal.

In a preferable embodiment, G is hydrogen, —C($X^a$)—$R^a$ or —C($X^b$)—$X^c$—$R^b$.

Most preferably G is hydrogen.

Preferably, e.g. in all aspects and/or embodiments of the invention:

$R^1$ is methyl, ethyl, n-propyl, cyclopropyl, vinyl, ethynyl, fluorine, chlorine, bromine, methoxy, ethoxy or fluoromethoxy (i.e. $C_1$fluoroalkoxy); and $R^2$ is hydrogen, methyl, ethyl, n-propyl, isopropyl, cyclopropyl, fluoromethyl, fluoroethyl, vinyl, prop-1-enyl, ethynyl, prop-1-ynyl, 2-chloroethynyl, 2-fluoroethynyl, 2-(trifluoromethyl)ethynyl, but-1-ynyl, or halogen (in particular chlorine or bromine);

or $R^2$ is phenyl optionally substituted by 1, 2 or 3 of, independently, halogen, $C_1$-$C_2$alkyl, $C_1$-$C_2$fluoroalkyl, cyano or nitro;

or $R^2$ is monocyclic heteroaryl optionally substituted by 1, 2 or 3 of, independently, halogen, $C_1$-$C_2$alkyl, $C_1$-$C_2$fluoroalkyl, cyano or nitro; and $R^3$ is hydrogen, methyl, ethyl, n-propyl, cyclopropyl, vinyl, ethynyl, fluorine, chlorine, bromine, methoxy, ethoxy or fluoromethoxy (i.e. $C_1$fluoroalkoxy).

Preferably, e.g. in all aspects and/or embodiments of the invention, $R^1$ is methyl, ethyl, n-propyl, cyclopropyl, vinyl, ethynyl, fluorine, chlorine, bromine, methoxy, ethoxy or fluoromethoxy (i.e. $C_1$fluoroalkoxy).

More preferably, e.g. in all aspects and/or embodiments of the invention, $R^1$ is methyl, ethyl, ethynyl, chlorine, bromine or methoxy.

More preferably, $R^1$ is methyl, ethyl, chlorine or bromine.

Even more preferably, $R^1$ is methyl or chlorine.

Most preferably, e.g. in all aspects and/or embodiments of the invention, $R^1$ is methyl.

Preferably, when $R^3$ is $C_1$-$C_2$alkoxy-$C_1$-$C_3$alkoxy- or $C_1$fluoroalkoxy-$C_1$-$C_3$alkoxy-, then $R^3$ is $R^{3A}$O—CH($R^{3B}$)—CH($R^{3C}$)—O—;

wherein $R^{3A}$ is $C_1$-$C_2$alkyl (in particular methyl) or $C_1$fluoroalkyl (such as trifluoromethyl);

and $R^{3B}$ and $R^{3C}$ are independently hydrogen or methyl, provided that one or both of $R^{3B}$ and $R^{3C}$ are hydrogen.

Preferably, $R^{3A}$ is methyl or $C_1$fluoroalkyl, more preferably methyl.

Preferably, both of $R^{3B}$ and $R^{3C}$ are hydrogen.

More preferably, when $R^3$ is $C_1$-$C_2$alkoxy-$C_1$-$C_3$alkoxy- or $C_1$fluoroalkoxy-$C_1$-$C_3$alkoxy- (in particular when $R^3$ is $R^{3A}$O—CH($R^{3B}$)—CH($R^{3C}$)—O—), then $R^3$ is MeO—CH$_2$—CH$_2$—O—.

Preferably, when $R^3$ is $C_1$-$C_2$fluoroalkoxy, then $R^3$ is $C_1$fluoroalkyl-methoxy- such as trifluoromethyl-methoxy- or difluoromethyl-methoxy-.

Preferably, e.g. in all aspects and/or embodiments of the invention, $R^3$ is hydrogen, methyl, ethyl, n-propyl, cyclopropyl, vinyl, ethynyl, fluorine, chlorine, bromine, methoxy, ethoxy or fluoromethoxy (i.e. $C_1$fluoroalkoxy, e.g. monofluoromethoxy, difluoromethoxy or trifluoromethoxy).

Preferably, e.g. in all aspects and/or embodiments of the invention, $R^3$ is methyl, ethyl, n-propyl, cyclopropyl, vinyl, ethynyl, fluorine, chlorine, bromine, methoxy, ethoxy or fluoromethoxy (i.e. $C_1$fluoroalkoxy, e.g. monofluoromethoxy, difluoromethoxy or trifluoromethoxy).

Alternatively or additionally, preferably, e.g. in all aspects and/or embodiments of the invention, $R^3$ is hydrogen, methyl, ethyl, ethynyl, chlorine, bromine, methoxy or fluoromethoxy (i.e. $C_1$fluoroalkoxy, e.g. monofluoromethoxy, difluoromethoxy or trifluoromethoxy); or $R^3$ is fluorine.

More preferably, e.g. in all aspects and/or embodiments of the invention, $R^3$ is methyl, ethyl, ethynyl, chlorine, bromine, methoxy or fluoromethoxy (i.e. $C_1$fluoroalkoxy, e.g. monofluoromethoxy, difluoromethoxy or trifluoromethoxy); in particular $R^3$ is methyl, ethyl, ethynyl, chlorine or bromine.

Even more preferably, e.g. in all aspects and/or embodiments of the invention, $R^3$ is methyl, ethyl, ethynyl or chlorine; in particular $R^3$ is methyl, ethyl or chlorine.

Still more preferably, e.g. in all aspects and/or embodiments of the invention, $R^3$ is methyl or chlorine.

Most preferably, e.g. in all aspects and/or embodiments of the invention, $R^3$ is methyl.

Therefore, more preferably, e.g. in all aspects and/or embodiments of the invention:

$R^1$ is methyl, ethyl, ethynyl, chlorine, bromine or methoxy; or even more preferably methyl or chlorine; or most preferably methyl; and $R^3$ is methyl, ethyl, ethynyl, chlorine, bromine, methoxy or fluoromethoxy (i.e. $C_1$fluoroalkoxy); or even more preferably methyl, ethyl, ethynyl or chlorine; or still more preferably methyl or chlorine; or most preferably methyl.

Preferably, e.g. in all aspects and/or embodiments of the invention:

$R^2$ is hydrogen, methyl, ethyl, n-propyl, isopropyl, cyclopropyl, fluoromethyl (i.e. $C_1$fluoroalkyl), fluoroethyl (i.e. $C_2$fluoroalkyl), vinyl, prop-1-enyl, ethynyl, prop-1-ynyl, 2-chloroethynyl, 2-fluoroethynyl, 2-(trifluoromethyl)ethynyl, but-1-ynyl, 2-(cyclopropyl)ethynyl, halogen (in particular chlorine or bromine), or ($C_1$-$C_2$fluoroalkyl)-methoxy-;

or $R^2$ is phenyl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro;

or $R^2$ is monocyclic heteroaryl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro.

Preferably, e.g. in all aspects and/or embodiments of the invention, $R^2$ is hydrogen, methyl, ethyl, n-propyl, isopropyl, cyclopropyl, fluoromethyl, fluoroethyl, vinyl, prop-1-enyl, ethynyl, prop-1-ynyl, 2-chloroethynyl, 2-fluoroethynyl, 2-(trifluoromethyl)ethynyl, but-1-ynyl, or halogen (in particular chlorine or bromine);

or $R^2$ is phenyl optionally substituted by 1, 2 or 3 of, independently, halogen, $C_1$-$C_2$alkyl, $C_1$-$C_2$fluoroalkyl, cyano or nitro;

or $R^2$ is monocyclic heteroaryl optionally substituted by 1, 2 or 3 of, independently, halogen, $C_1$-$C_2$alkyl, $C_1$-$C_2$fluoroalkyl, cyano or nitro.

Alternatively or additionally, preferably, e.g. in all aspects and/or embodiments of the invention, $R^2$ is methyl, ethynyl, prop-1-ynyl, 2-chloroethynyl, 2-fluoroethynyl, 2-(trifluoromethyl)ethynyl, but-1-ynyl, or halogen (in particular chlorine or bromine);

or $R^2$ is phenyl optionally substituted by 1, 2 or 3 (in particular 1 or 2) of, independently, halogen, $C_1$-$C_2$alkyl, $C_1$-$C_2$fluoroalkyl, $C_1$-$C_2$alkoxy, $C_1$-$C_2$fluoroalkoxy, or cyano;

or $R^2$ is monocyclic heteroaryl (in particular pyridin-2-yl, pyrimidin-2-yl, pyrimidin-5-yl, pyrazol-1-yl or 1,2,3-triazol-1-yl) optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro. Alternatively, preferably, $R^2$ is ($C_1$fluoroalkyl)-methoxy-, in particular trifluoromethyl-methoxy-.

More preferably, e.g. in all aspects and/or embodiments of the invention, $R^2$ is methyl, ethynyl, prop-1-ynyl, 2-chloroethynyl, 2-fluoroethynyl, 2-(trifluoromethyl)ethynyl, but-1-ynyl, or halogen (in particular chlorine or bromine);

or $R^2$ is phenyl optionally substituted by 1, 2 or 3 (in particular 1 or 2) of, independently, halogen, $C_1$-$C_2$alkyl, $C_1$-$C_2$fluoroalkyl or cyano;

or $R^2$ is monocyclic heteroaryl (in particular pyridin-2-yl, pyrimidin-2-yl, pyrimidin-5-yl, pyrazol-1-yl or 1,2,3-triazol-1-yl) optionally substituted by 1, 2 or 3 of, independently, halogen, $C_1$-$C_2$alkyl, $C_1$-$C_2$fluoroalkyl, cyano or nitro.

Alternatively, also more preferably, $R^2$ is ($C_1$fluoroalkyl)-methoxy-, in particular trifluoromethyl-methoxy-.

Even more preferably, e.g. in all aspects and/or embodiments of the invention, $R^2$ is methyl, ethynyl, prop-1-ynyl, 2-chloroethynyl, chlorine or bromine;

or R² is phenyl optionally substituted by 1 or 2 of, independently, halogen, $C_1$-$C_2$alkyl, $C_1$-$C_2$fluoroalkyl or cyano (more preferably phenyl optionally substituted by 1 or 2 of, independently, halogen or $C_1$fluoroalkyl; even more preferably phenyl optionally substituted by 1 or 2 of, independently, fluorine or chlorine);

or R² is monocyclic heteroaryl (in particular pyridin-2-yl, pyrimidin-2-yl, pyrimidin-5-yl, pyrazol-1-yl or 1,2,3-triazol-1-yl) optionally substituted by 1 or 2 of, independently, halogen, $C_1$-$C_2$alkyl, $C_1$-$C_2$fluoroalkyl, cyano or nitro (more preferably monocyclic heteroaryl (in particular pyridin-2-yl, pyrimidin-2-yl, pyrimidin-5-yl, pyrazol-1-yl or 1,2,3-triazol-1-yl) optionally substituted by 1 or 2 of, independently, halogen, methyl or $C_1$fluoroalkyl; even more preferably monocyclic heteroaryl (in particular pyridin-2-yl, pyrimidin-2-yl, pyrimidin-5-yl, pyrazol-1-yl or 1,2,3-triazol-1-yl) optionally substituted by 1 or 2 of, independently, fluorine, chlorine, methyl or $C_1$fluoroalkyl).

Alternatively, also even more preferably, R² is ($C_1$fluoroalkyl)-methoxy-, in particular trifluoromethyl-methoxy-.

When R² is optionally substituted phenyl, then preferably the phenyl is substituted.

When R² is optionally substituted monocyclic heteroaryl (in particular pyridin-2-yl, pyrimidin-2-yl, pyrimidin-5-yl, pyrazol-1-yl or 1,2,3-triazol-1-yl, each optionally substituted), then preferably the monocyclic heteroaryl is substituted.

Preferably, when R² is optionally substituted phenyl, then R² is

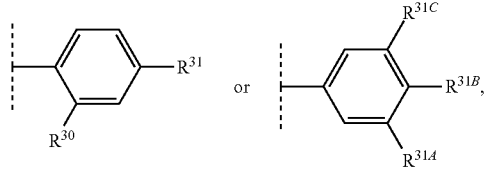

in which $R^{30}$ is hydrogen, fluorine, chlorine, bromine, $C_1$fluoroalkyl (e.g. trifluoromethyl), $C_1$fluoroalkoxy (e.g. difluoromethoxy or trifluoromethoxy), or cyano; and
either $R^{31}$ is hydrogen, fluorine, chlorine, bromine, $C_1$fluoroalkyl (e.g. trifluoromethyl), $C_1$fluoroalkoxy (e.g. difluoromethoxy or trifluoromethoxy), or cyano; or $R^{31}$ is methyl; and
$R^{31A}$ is fluorine or chlorine;
$R^{31B}$ is hydrogen, fluorine or chlorine; and
$R^{31C}$ is hydrogen, fluorine or chlorine;
wherein one or both of $R^{31B}$ and $R^{31C}$ is or are hydrogen.

Preferably, when R² is optionally substituted phenyl, then R² is

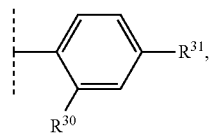

in which $R^{30}$ is hydrogen, fluorine, chlorine, bromine, $C_1$fluoroalkyl (e.g. trifluoromethyl), $C_1$fluoroalkoxy (e.g. difluoromethoxy or trifluoromethoxy), or cyano; and
either $R^{31}$ is hydrogen, fluorine, chlorine, bromine, $C_1$fluoroalkyl (e.g. trifluoromethyl), $C_1$fluoroalkoxy (e.g. difluoromethoxy or trifluoromethoxy), or cyano; or $R^{31}$ is methyl.

Preferably, one or both of $R^{30}$ and $R^{31}$ is or are not hydrogen. More preferably, $R^{31}$ is not hydrogen.

More preferably, $R^{30}$ is hydrogen, fluorine, chlorine or $C_1$fluoroalkyl (e.g. trifluoromethyl).

Even more preferably, $R^{30}$ is hydrogen, fluorine or chlorine.

Most preferably, $R^{30}$ is hydrogen or fluorine, in particular hydrogen.

More preferably, $R^{31}$ is hydrogen, fluorine, chlorine or $C_1$fluoroalkyl (e.g. trifluoromethyl); or, also more preferably, $R^{31}$ is methyl.

Even more preferably, $R^{31}$ is fluorine, chlorine, $C_1$fluoroalkyl (e.g. trifluoromethyl), or methyl.

Most preferably, $R^{31}$ is fluorine or chlorine.

Preferably, $R^{31A}$ is fluorine; and/or $R^{31B}$ is hydrogen or fluorine; and/or $R^{31C}$ is hydrogen or fluorine; wherein one or both of $R^{31B}$ and $R^{31C}$ is or are hydrogen.

Particularly preferably, when R² is optionally substituted phenyl, then
R² is

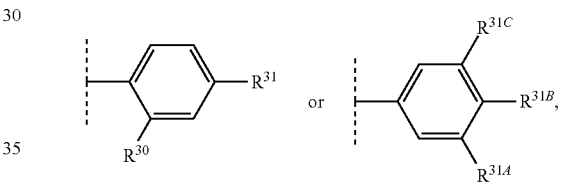

in which:
$R^{30}$ is hydrogen, fluorine, chlorine or $C_1$fluoroalkyl;
$R^{31}$ is fluorine, chlorine, $C_1$fluoroalkyl or methyl;
$R^{31A}$ is fluorine or chlorine;
$R^{31B}$ is hydrogen, fluorine or chlorine; and
$R^{31C}$ is hydrogen, fluorine or chlorine;
wherein one or both of $R^{31B}$ and $R^{31C}$ is or are hydrogen.

Preferably, when R² is optionally substituted monocyclic heteroaryl, then R² is

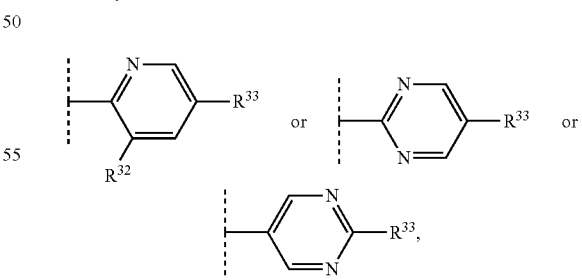

in which $R^{32}$ is hydrogen, fluorine, chlorine, bromine, $C_1$fluoroalkyl (e.g. trifluoromethyl), $C_1$fluoroalkoxy (e.g. difluoromethoxy or trifluoromethoxy), or cyano, and $R^{33}$ is hydrogen, fluorine, chlorine, bromine, $C_1$fluoroalkyl (e.g. trifluoromethyl), $C_1$fluoroalkoxy (e.g. difluoromethoxy or trifluoromethoxy), or cyano;

or, more preferably, $R^2$ is

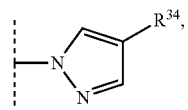

in which $R^{34}$ is hydrogen, fluorine, chlorine, bromine, methyl, $C_1$fluoroalkyl (e.g. trifluoromethyl), $C_1$fluoroalkoxy (e.g. difluoromethoxy or trifluoromethoxy), or cyano.
or $R^2$ is

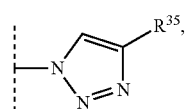

in which $R^{35}$ is fluorine, chlorine, bromine, methyl, $C_1$fluoroalkyl (e.g. trifluoromethyl), $C_1$fluoroalkoxy (e.g. difluoromethoxy or trifluoromethoxy), or cyano.

Preferably, when $R^2$ is optionally substituted monocyclic heteroaryl, then $R^2$ is

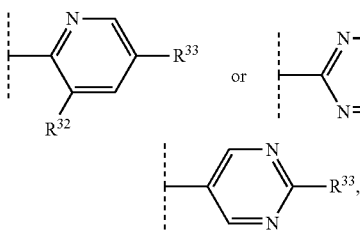

or, more preferably, $R^2$ is

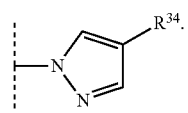

More preferably, in all embodiments of the invention, $R^{32}$ is hydrogen, fluorine, chlorine or $C_1$fluoroalkyl (e.g. trifluoromethyl). Even more preferably, $R^{32}$ is hydrogen, fluorine or chlorine.

Most preferably, $R^{32}$ is hydrogen or fluorine.

More preferably, in all embodiments of the invention, $R^{33}$ is hydrogen, fluorine, chlorine or $C_1$fluoroalkyl (e.g. trifluoromethyl); even more preferably fluorine, chlorine or $C_1$fluoroalkyl (e.g. trifluoromethyl). Preferably, $R^{33}$ is not hydrogen.

Most preferably, $R^{33}$ is fluorine or chlorine.

Preferably, in all embodiments of the invention, $R^{34}$ is hydrogen, fluorine, chlorine, methyl, $C_1$fluoroalkyl (e.g. trifluoromethyl), or $C_1$fluoroalkoxy (e.g. difluoromethoxy or trifluoromethoxy); alternatively, also preferably, $R^{34}$ is cyano. Preferably, $R^{34}$ is not hydrogen.

Alternatively, preferably, in all embodiments of the invention, $R^{34}$ is hydrogen, fluorine, chlorine, bromine, methyl or $C_1$fluoroalkyl (e.g. trifluoromethyl); alternatively, also preferably, $R^{34}$ is cyano. Preferably, $R^{34}$ is not hydrogen.

More preferably, $R^{34}$ is hydrogen, fluorine, chlorine, methyl or $C_1$fluoroalkyl (e.g. trifluoromethyl); alternatively, also more preferably, $R^{34}$ is cyano. Preferably, $R^{34}$ is not hydrogen.

Even more preferably, $R^{34}$ is fluorine, chlorine, methyl, $C_1$fluoroalkyl (e.g. trifluoromethyl), or cyano. Still more preferably, $R^{34}$ is fluorine, chlorine or cyano.

Most preferably $R^{34}$ is chlorine. Alternatively, it is particularly preferred that $R^{34}$ is cyano.

Preferably, in all embodiments of the invention, $R^{35}$ is fluorine, chlorine, bromine, methyl, $C_1$fluoroalkyl (e.g. trifluoromethyl) or cyano; and more particularly $R^{35}$ is fluorine, chlorine, methyl, $C_1$fluoroalkyl (e.g. trifluoromethyl) or cyano.

More preferably, $R^{35}$ is chlorine or cyano. Most preferably, $R^{35}$ is chlorine.

Particularly preferably, when $R^2$ is optionally substituted monocyclic heteroaryl, then $R^2$ is

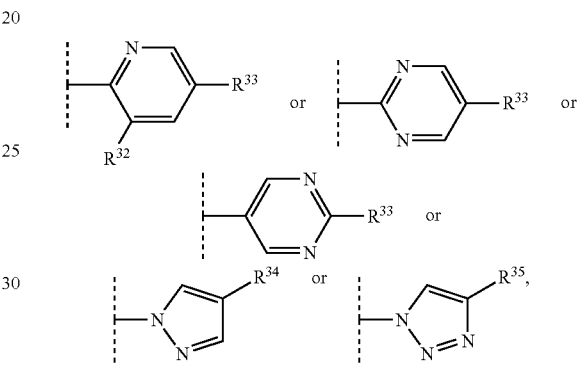

in which:
$R^{32}$ is hydrogen, fluorine, chlorine or $C_1$fluoroalkyl; and
$R^{33}$ is fluorine, chlorine or $C_1$fluoroalkyl;
$R^{34}$ is fluorine, chlorine, bromine, methyl, $C_1$fluoroalkyl or cyano; and
$R^{35}$ is fluorine, chlorine, bromine, methyl, $C_1$fluoroalkyl or cyano.

When $R^2$ is

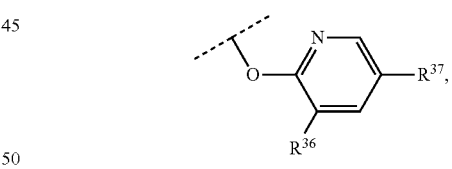

then preferably $R^{37}$ is chlorine or $C_1$fluoroalkyl, more preferably $C_1$fluoroalkyl (in particular trifluoromethyl); and/or preferably $R^{36}$ is chlorine.

In the invention, $R^4$, $R^5$ and $R^6$, independently of each other, are hydrogen, $C_1$-$C_5$alkyl (in particular $C_1$-$C_4$alkyl, e.g. $C_1$-$C_2$alkyl), $C_2$-$C_3$ alkenyl (in particular ethenyl-$CH_2$—), $C_2$-$C_3$alkynyl (in particular ethynyl-$CH_2$—), $C_1$-$C_2$fluoroalkyl or $C_1$-$C_2$alkoxy$C_1$-$C_2$alkyl (in particular methoxymethyl);
provided that: either (i) at least two of $R^4$, $R^5$ and $R^6$ are hydrogen, or (ii) two of $R^4$, $R^5$ and $R^6$ are methyl and the remaining one of $R^4$, $R^5$ and $R^6$ is hydrogen.

Preferably, e.g. in all aspects and/or embodiments of the invention, $R^4$, $R^5$ and $R^6$, independently of each other, are hydrogen, $C_1$-$C_2$alkyl, ethynyl-$CH_2$—, $C_1$fluoroalkyl or methoxymethyl;

provided that: either (i) at least two of $R^4$, $R^5$ and $R^6$ are hydrogen, or (ii) two of $R^4$, $R^5$ and $R^6$ are methyl and the remaining one of $R^4$, $R^5$ and $R^6$ is hydrogen.

More preferably, e.g. in all aspects and/or embodiments of the invention, $R^4$, $R^5$ and $R^6$, independently of each other, are hydrogen or methyl;

provided that: either (i) at least two of $R^4$, $R^5$ and $R^6$ are hydrogen, or (ii) two of $R^4$, $R^5$ and $R^6$ are methyl and the remaining one of $R^4$, $R^5$ and $R^6$ is hydrogen.

Most preferably, e.g. in all aspects and/or embodiments of the invention, all of $R^4$, $R^5$ and $R^6$ are hydrogen.

Most preferably, e.g. in all aspects and/or embodiments of the invention, all of $R^7$, $R^8$, $R^9$ and $R^{10}$ are hydrogen.

Most preferably, e.g. in all aspects and/or embodiments of the invention, all of $R^4$, $R^5$, $R^6$, $R^7$, $R^8$, $R^9$ and $R^{10}$ are hydrogen.

Preferred and/or particular features of $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{40}$, $R^{41}$, $R^{42}$, $R^{43}$, $R^{44}$, $R^{12B}$, $R^{13B}$, $R^{14B}$, $R^{15B}$, $R^{16D}$, $R^{12E}$, $R^{15F}$, $R^{11GG}$, $R^{12GG}$, $R^{13GG}$, $R^{14GG}$, $R^{15GG}$, $R^{12Y}$, $R^{13T}$, $R^{14T}$, $R^{12U}$, $R^{13U}$, $R^{14U}$, $R^{13Y}$, $R^{15Y}$, $R^{15Z}$, $X^A$, $Y^A$, $Z^A$, $X^B$, $Y^B$, $Z^B$, $X^K$, $Y^K$, $X^L$, $Y^L$, $X^m$, $X^N$, $X^V$, $Y^V$, $X^W$, n1, n2, n3 and/or n4 are disclosed herein, e.g. in particular hereinabove. Some particular preferences for some of these variables follow.

Preferably, e.g. in all aspects and/or embodiments of the invention, $R^{11}$ is $C_3$-$C_5$alkyl (in particular tert-butyl), $C_4$-$C_6$cycloalkyl (in particular cyclohexyl), or tetrahydrofuranyl (such as tetrahydrofuran-3-yl or tetrahydrofuran-2-yl), or is one of sub-formulae A, B, C, D, E, F, G, H, J, K, L, M, N, O, P, Q, R, S, T or U, as defined herein. Alternatively, preferably, $R^{11}$ is one of sub-formulae V, W X, Y or Z as defined herein.

More preferably, e.g. in all aspects and/or embodiments of the invention, $R^{11}$ is $C_3$-$C_5$alkyl (in particular tert-butyl), or is one of sub-formulae A, E, F, G, K, L, M, N, P or Q, as defined herein. Alternatively, also more preferably, $R^{11}$ is sub-formula V or Y as defined herein.

Even more preferably, e.g. in all aspects and/or embodiments of the invention, $R^{11}$ is one of sub-formulae A, E, F, G, K, M or N, as defined herein. Alternatively, also even more preferably, $R^{11}$ is sub-formula P or Y as defined herein.

Still more preferably, e.g. in all aspects and/or embodiments of the invention, $R^{11}$ is one of sub-formulae A, E, F or G, as defined herein. Alternatively, also still more preferably, $R^{11}$ is one of sub-formulae M, P or Y as defined herein.

Most preferably, e.g. in all aspects and/or embodiments of the invention, $R^{11}$ is sub-formula A, as defined herein.

Preferably, e.g. in all aspects and/or embodiments of the invention, $X^A$ is $CR^{13}$, and/or $Y^A$ is $CR^{14}$, and/or $Z^A$ is $CR^{15}$. Particularly preferably, in the most preferred embodiment of $R^{11}$ being sub-formula A), $X^A$ is $CR^{13}$, $Y^A$ is $CR^{14}$, and $Z^A$ is $CR^{15}$.

Preferably, e.g. in all aspects and/or embodiments of the invention:
when $R^{11}$ is sub-formula B, then it is sub-formula B1 as defined herein; and/or
when $R^{11}$ is sub-formula D, then it is sub-formula D1 as defined herein; and/or
when $R^{11}$ is sub-formula G, then it is sub-formula G1 as defined herein; and/or
when $R^{11}$ is sub-formula P, then it is sub-formula P1 as defined herein.

Preferably, e.g. in all aspects and/or embodiments of the invention, when $R^{13}$ is bromine, then $X^A$ is $CR^{13}$, $Y^A$ is $CR^{14}$, $Z^A$ is $CR^{15}$, and $R^{12}$, $R^{14}$ and $R^{15}$ are independently hydrogen or fluorine, provided that at least two (i.e. two or three) of $R^{12}$, $R^{14}$ and $R^{15}$ are hydrogen. More preferably, in this case, all of $R^{12}$, $R^{14}$ and $R^{15}$ are hydrogen.

Particularly preferably, e.g. in all aspects and/or embodiments of the invention,
$R^{12}$ is hydrogen, fluorine, chlorine or bromine;
$R^{13}$ is hydrogen, fluorine, chlorine, bromine, $C_1$fluoroalkyl, methoxy or $C_1$fluoroalkoxy; (even more preferably, $R^{13}$ is hydrogen, fluorine, chlorine, bromine or $C_1$fluoroalkoxy (e.g. difluoromethoxy or trifluoromethoxy));
$R^{14}$ is hydrogen, fluorine or chlorine; and
$R^{15}$ is hydrogen, fluorine, chlorine or bromine; (even more preferably $R^{15}$ is hydrogen, fluorine or chlorine);
provided that at least two (i.e. two, three or all, preferably three or all) of $R^{12}$, $R^{13}$, $R^{14}$ and $R^{15}$ are hydrogen;
and provided that, when $R^{13}$ is bromine, then $R^{12}$, $R^{14}$ and $R^{15}$ are independently hydrogen or fluorine, provided that at least two (i.e. two or three) of $R^{12}$, $R^{14}$ and $R^{15}$ are hydrogen.

In this particularly preferred embodiment, preferably:
$R^{11}$ is sub-formula A; and/or
$X^A$ is $CR^{13}$, $Y^A$ is $CR^{14}$, and $Z^A$ is $CR^{15}$.

Even more particularly preferably, e.g. in all aspects and/or embodiments of the invention,
$R^{12}$, $R^{14}$ and $R^{15}$ are all hydrogen, and
$R^{13}$ is hydrogen, fluorine, chlorine, bromine or $C_1$fluoroalkoxy (e.g. difluoromethoxy or trifluoromethoxy).

In this even more particularly preferred embodiment, preferably:
$R^{11}$ is sub-formula A; and/or
$X^A$ is $CR^{13}$, $Y^A$ is $CR^{14}$, and $Z^A$ is $CR^{15}$.

Still more particularly preferably, e.g. in all aspects and/or embodiments of the invention,
$R^{12}$, $R^{14}$ and $R^{15}$ are all hydrogen, and
$R^{13}$ is hydrogen, bromine or $C_1$fluoroalkoxy (in particular hydrogen, bromine, difluoromethoxy or trifluoromethoxy).

In this still more particularly preferred embodiment, preferably:
$R^{11}$ is sub-formula A; and/or
$X^A$ is $CR^{13}$, $Y^A$ is $CR^{14}$, and $Z^A$ is $CR^{15}$.

Most preferably, e.g. in all aspects and/or embodiments of the invention, $R^{12}$ is hydrogen, and/or $R^{13}$ is hydrogen, and/or $R^{14}$ is hydrogen, and/or $R^{15}$ is hydrogen. Most preferably, $R^{12}$, $R^{13}$, $R^{14}$ and $R^{15}$ are all hydrogen.

In these most preferred embodiments, preferably:
$R^{11}$ is sub-formula A; and/or
$X^A$ is $CR^{13}$, $Y^A$ is $CR^{14}$, and $Z^A$ is $CR^{15}$.

In a more particularly preferable embodiment of the invention (which e.g. can apply to all aspects and/or embodiments of the invention), the compound of formula (I) is any of (e.g. any one of) compounds A1 to A99, or compound A100 or A101, or any of (e.g. any one of) compounds A102 to A108, as described and/or illustrated herein, present either as a free compound (i.e. a compound not substantially in the form of a salt) and/or (e.g. where chemically possible) present as an agrochemically acceptable salt thereof.

In another preferable embodiment of the invention (which e.g. can apply to all aspects and/or embodiments of the invention), the compound of formula (I) is any of (e.g. any one of) compounds A109 to A211 or any of (e.g. any one of)

compounds P1 to P30, as described and/or illustrated herein, present either as a free compound (i.e. a compound not substantially in the form of a salt) and/or (e.g. where chemically possible) present as an agrochemically acceptable salt thereof.

In all embodiments or aspects of the invention, it is strongly preferred that the compound of formula (I) is a compound of formula (IC):

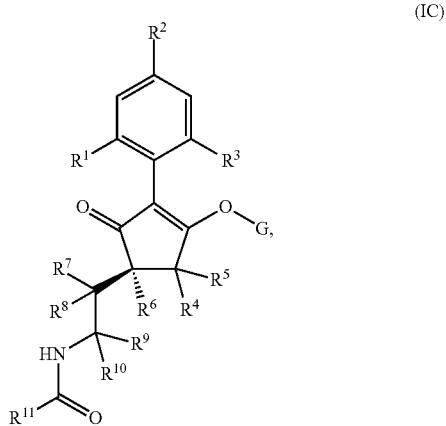

(IC)

wherein $R^1$, $R^2$, $R^3$, $R^4$, $R^5$, $R^6$, $R^7$, $R^8$, $R^9$, $R^{10}$, $R^{11}$, and G are as defined herein, and wherein 40% or more (in particular 45% or more) by molarity of the compound of formula (IC) has the indicated stereochemistry at the ring-carbon atom bonded to $R^6$ and —$CR^7R^8$—$CR^9R^{10}$—NHC(O)—$R^{11}$. For example, this broadest definition of formula (IC) includes compounds which are substantially racemic at the ring-carbon atom bonded to $R^6$ and —$CR^7R^8$—$CR^9R^{10}$—NHC(O)—$R^{11}$, and also includes compounds enriched with isomer(s) having the stereochemistry indicated at the ring-carbon atom bonded to $R^6$ and —$CR^7R^8$—$CR^9R^{10}$—NHC(O)—$R^{11}$.

More preferably, more than 50% (still more preferably more than 70% or more than 80%, most preferably more than 90% or more than 95%) by molarity of the compound of formula (IC) has the indicated stereochemistry at the ring-carbon atom bonded to $R^6$ and —$CR^7R^8$—$CR^9R^{10}$—NHC(O)—$R^{11}$. This more preferred definition of formula (IC) includes compounds enriched with isomer(s) having the stereochemistry indicated at the ring-carbon atom bonded to $R^6$ and —$CR^7R^8$—$CR^9R^{10}$—NHC(O)—$R^{11}$.

Based on the biological results shown herein (see Biological Example 1B herein, comparing the results for the chiral-column-separated enantiomers Compounds A98 and A99, and Compounds A100 and A101), it is believed that the compounds with the stereochemistry indicated in formula (IC) (such as for example Compound A98 or A100) typically have more potent herbicidal activity against grassy monocotyledonous weeds (e.g. when applied post-emergence to the weeds) than the compounds with the opposite stereochemistry (such as for example Compound A99 or A101).

Depending on the nature of the substituents G, $R^1$, $R^2$, $R^3$, $R^4$, $R^5$, $R^6$, $R^7$, $R^8$, $R^9$, $R^{10}$ and $R^{11}$, compounds of formula (I) may exist in different isomeric or tautomeric forms.

For example, when G is hydrogen, compounds of formula (I) may exist in different tautomeric forms, as shown below:

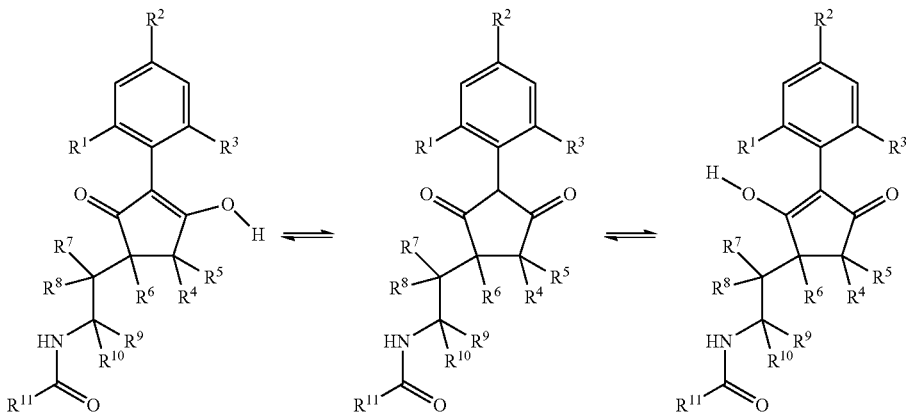

Also, when substituents contain double bonds, cis- and trans-isomers can exist.

This invention covers all such isomers and/or tautomers and/or mixtures thereof in all proportions. These isomers and/or tautomers are within the scope of the claimed compounds of formula (I).

Processes for Preparation of Compounds, e.g. Compounds of Formula (I)

Processes for preparation of compounds, e.g. a compound of formula (I) (which optionally can be an agrochemically acceptable salt thereof), are now described, and form further aspects of the present invention.

A compound of formula I, wherein G is:
—C($X^a$)—$R^a$, —C($X^b$)—$X^c$—$R^b$, —C($X^d$)—N($R^c$)—$R^d$, —SO$_2$—$R^e$, —P($X^e$)($R^f$)—$R^g$, —CH$_2$—$X^f$—$R^h$, —CH(Me)-$X^f$-$R^h$; or phenyl-CH$_2$— or phenyl-CH(C$_1$-C$_2$alkyl)- (in each of which the phenyl is optionally substituted by 1, 2 or 3 of, independently, C$_1$-C$_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-$CH(C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—$CH_2$—, $C_1$-$C_6$alkyl-C(O)—$CH_2$—, $C_1$-$C_6$alkoxy-C(O)—CH=CH—, $C_2$-$C_7$alken-1-yl-$CH_2$—, $C_2$-$C_7$alken-1-yl-$CH(C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-$CH(C_1$-$C_2$alkyl)-;

may be prepared by treating a compound of formula (A), which is a compound of formula I wherein G is H, (a) with a reagent G1-Z, wherein G1-Z is an alkylating agent (wherein G1 is an organic group according to G within the compound of formula (I) and which is linked by a non-carbonyl, non-thiocarbonyl carbon atom) such as an organic halide (in which Z=halogen such as chlorine, bromine or iodine); wherein the organic halide (e.g. chloride) can typically be a substituted alkyl halide (e.g. chloride) such as a chloromethyl alkyl ether Cl—$CH_2$—$X^f$—$R^h$ wherein $X^f$ is oxygen, a chloromethyl alkyl sulfide Cl—$CH_2$—$X^f$—$R^h$ wherein $X^f$ is sulphur, a suitable optionally substituted benzyl halide (e.g. chloride) such as Cl—$CH_2$-[optionally substituted phenyl], [optionally substituted phenyl]-C(O)—$CH_2$-[halogen e.g. Cl], $C_1$-$C_6$alkoxy-C(O)—$CH_2$-[halogen e.g. Cl], $C_1$-$C_6$alkyl-C(O)—$CH_2$-[halogen e.g. Cl], $C_1$-$C_6$alkoxy-C(O)—CH=CH-[halogen e.g. Cl], a suitable alkenyl or alkynyl halide (e.g. chloride) such as $C_2$-$C_7$alken-1-yl-$CH_2$-[halogen e.g. Cl] or $C_2$-$C_7$alkyn-1-yl-$CH_2$-[halogen e.g. Cl], or another organic halide suitable for preparing a (non-carbonyl, non-thiocarbonyl carbon)-linked G (or G1) group; or (b) [e.g. to prepare carbonyl-carbon-linked or thiocarbonyl-carbon-linked G groups] with an acylating agent such as a carboxylic acid, HO—$C(X^a)R^a$, wherein $X^a$ is oxygen, an acid chloride, Cl—$C(X^a)R^a$, wherein $X^a$ is oxygen, or an acid anhydride, $[R^aC(X^a)]_2O$, wherein $X^a$ is oxygen, or an isocyanate, $R^cN$=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$(X^d)$—$N(R^c)$—$R^d$ (wherein $X^d$ is sulfur and with the proviso that neither $R^c$ or $R^d$ is hydrogen), or a chloroformate, Cl—$C(X^b)$—$X^c$—$R^b$ (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$ (wherein $X^b$ and $X^c$ are sulfur), or an isothiocyanate, $R^cN$=C=S; or (c) by sequential treatment with carbon disulfide and an alkylating agent; or (d) with a phosphorylating agent such as a phosphoryl chloride, Cl—$P(X^e)(R^f)$—$R^g$; or (e) with a sulfonylating agent such as a sulfonyl chloride Cl—$SO_2$—$R^e$, preferably in the presence of at least one equivalent of base.

Where substituents $R^4$ and $R^5$ are not equal to substituents $R^6$ and —$CR^7R^8$—$CR^9R^{10}$—NHC(O)—$R^{11}$, the above-described reactions may produce, in addition to a compound of formula (I), a second compound of formula (IA) (see below).

The present invention covers both a compound of formula (I) and a compound of formula (IA), either (I) alone or (IA) alone or as a mixture of compounds (I) and (IA) in any ratio.

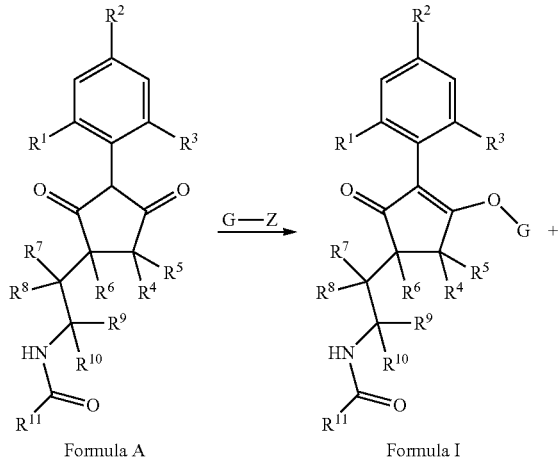

Formula A      Formula I

Formula IA

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected e.g. by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, or sodium hydride, and suitable organic bases include trialkylamines, such as trimethylamine or triethylamine, pyridines or other amine bases such as 1,4-diazobicyclo[2.2.2]-octane or 1,8-diazabicyclo[5.4.0]

undec-7-ene. Preferred bases include triethylamine and pyridine. Suitable solvents for this reaction are selected to be compatible with the reagents and include ethers such as tetrahydrofuran or 1,2-dimethoxyethane or halogenated solvents such as dichloromethane or chloroform. Certain bases, such as pyridine or triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide or N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected e.g. using a phosphoryl halide or thiophosphoryl halide and a base e.g. by procedures analogous to those described by L. Hodakowski, U.S. Pat. No. 4,409,153.

Sulfonylation of a compound of formula (A) may be achieved e.g. using an alkyl or aryl sulfonyl halide, preferably in the presence of at least one equivalent of base, for example by the procedure of C. Kowalski and K. Fields, J. Org. Chem., (1981), 46, 197-201.

A compound of Formula A may be prepared by the deprotection of a compound of Formula IB or IB1 (which is sometimes also a compound of Formula (I) or (IA) respectively), wherein $G^2$ is typically $C_1$-$C_6$alkyl, —C(O)OC$_1$-$C_6$alkyl, —C(O)NH—C$_1$-C$_6$alkyl or —C(O)N(C$_1$-C$_6$alkyl)$_2$, e.g. as shown above. The deprotection is typically carried out in the presence of a suitable solvent (e.g. an aqueous solvent, or an organic solvent e.g. non-aqueous organic solvent, and/or a mixture of aqueous and/or organic solvents), in the presence of a suitable base and/or suitable acid. The deprotection is typically carried out either at ambient (room) temperature, or is heated thermally or under microwave irradiation. Suitable solvents include N,N-dimethylformamide, acetone, tetrahydrofuran, water or dichloromethane or mixtures thereof. Suitable bases include inorganic or organic bases such as metal hydroxide or tertiary amines such as morpholine. Suitable acids include aqueous or organic acids such as trifluoroacetic acid, 4-methylbenzenesulfonic acid (p-TSA, para-toluenesulfonic acid), triflic acid (trifluoromethanesulfonic acid), or hydrochloric acid.

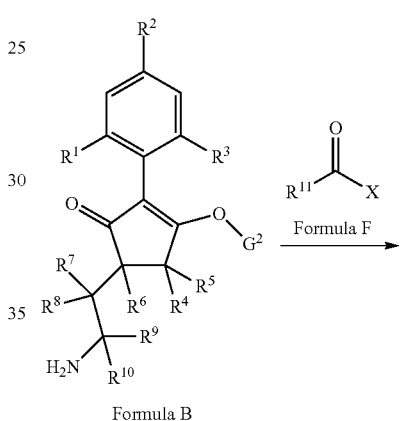

Formula B

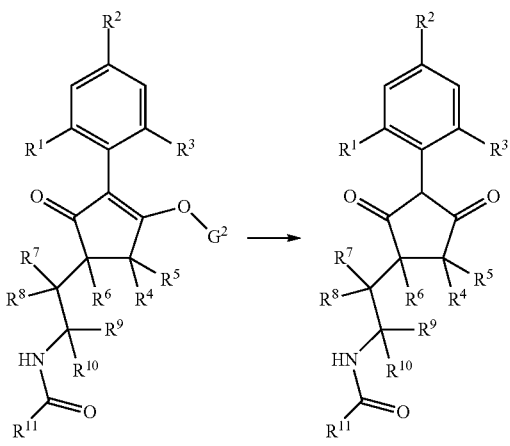

Formula IB → Formula A

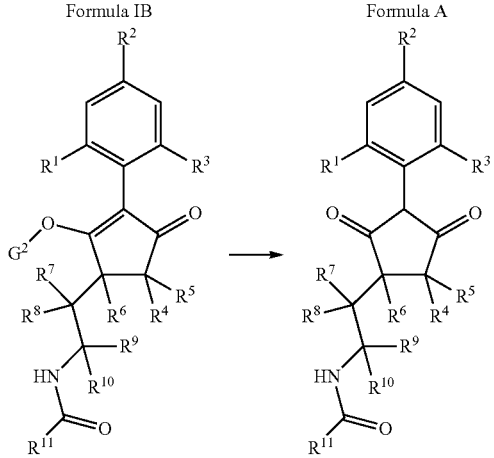

Formula IB1 → Formula A

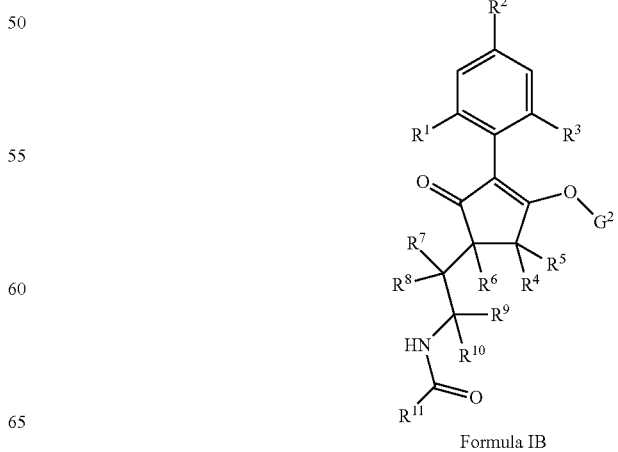

Formula IB

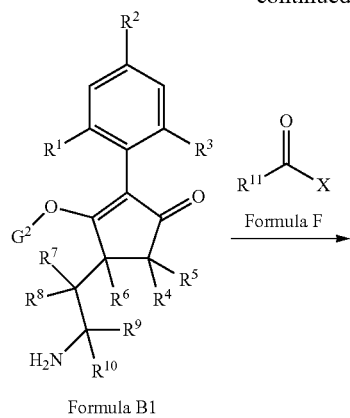

Formula B1

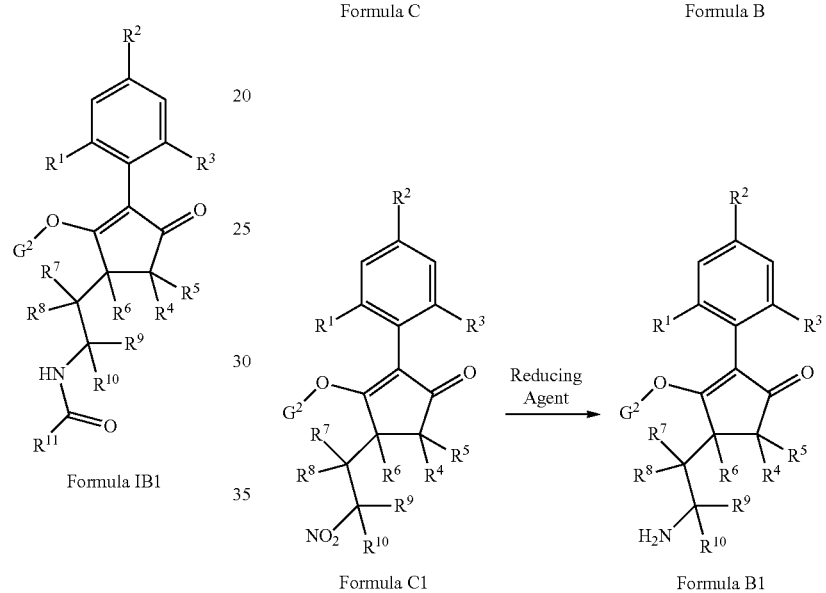

Formula C → Formula B

Formula C1 → Formula B1

A compound of Formula IB or IB1 (which is sometimes also a compound of Formula (I) or (IA) respectively), wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by an amide bond forming reaction between a compound of Formula B or B1 respectively and a compound of Formula F, wherein X=halogen, OH or OR (OR being a leaving group attached by oxygen, e.g. pentafluorophenoxy, or e.g. an alkyl, fluoroalkyl or aryl sulfonate such as methanesulfonate, trifluoromethanesulfonate or para-toluenesulfonate), e.g. as shown above. The amide bond forming reaction is typically carried out in the presence of a suitable solvent (e.g. an organic and/or non-aqueous solvent), and/or in the presence of a suitable coupling reagent, and/or in the presence of a suitable base. Suitable solvents include N,N-dimethylformamide or dichloromethane. Suitable coupling reagents include a carbodiimide (e.g. dicyclohexylcarbodiimide, "DCC") or a phosphonic anhydride (e.g. 2,4,6-tripropyl-1,3,5,2,4,6-trioxatriphosphorinane-2,4,6-trioxide) or a (benzotriazol-1-yloxy)trialkylaminophosphonium salt (e.g. benzotriazol-1-yloxy(tripyrrolidin-1-yl)phosphonium hexafluorophosphate). Suitable bases include organic non-aqueous bases such as tertiary amines such as N,N-diisopropylethylamine or triethylamine.

Compounds of Formula F can be prepared by known methods.

Compounds of Formula B or B1 may be prepared by the reduction of compounds of Formula C or C1 respectively in the presence of a suitable reducing agent, optionally in a suitable (e.g. organic) solvent, and/or in the presence of a suitable catalyst, e.g. as shown above. Suitable reducing agents include ammonium formate (see for example R. Ballini, F. Papa, C. Abate, *European Journal of Organic Chemistry*, 1, 87-90, 1999) or zinc dust. Suitable solvents include methanol or acetic acid. Suitable catalysts include palladium on carbon.

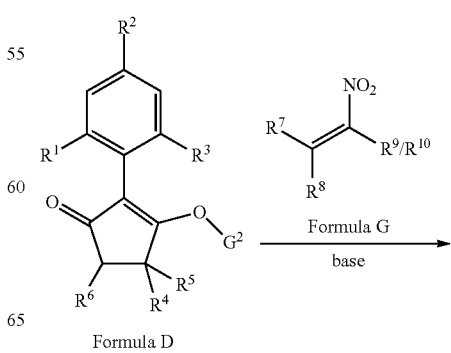

Formula D + Formula G —base→

-continued

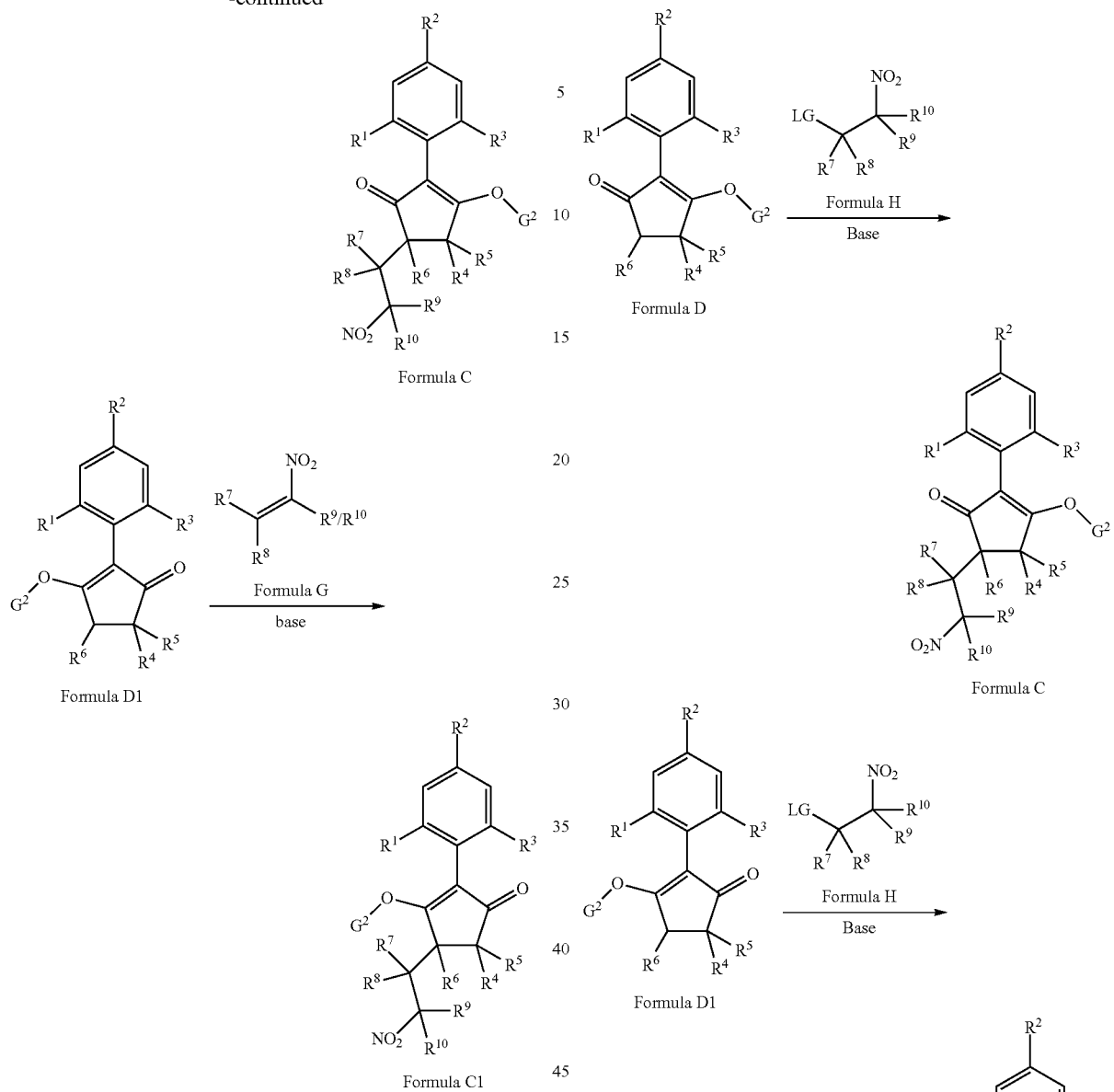

Formula C

Formula D

Formula D1

Formula C

Formula C1

Formula D1

Formula C1

Compounds of Formula C or C1 (in which typically at least one of $R^9$ and $R^{10}$ is hydrogen) may be prepared by reaction of a compound of Formula D or D1 respectively with a compound of Formula G, which has the structure or formula $(R^7)(R^8)C=C(NO_2)(R^9$ or $R^{10})$, in the presence of a suitable base, typically at a suitable temperature, optionally in the presence of a suitable (e.g. organic) solvent, e.g. as shown above. Suitable bases include organic and/or non-aqueous bases, particularly strong organic and/or non-aqueous bases, such as lithium diisopropylamide (see for example T. J. Dickerson, T. Lovell, M. M. Meijler, L. Noodleman, K. D. Janda, *Journal of Organic Chemistry*, (2004) 69(20), 6603-6609) or potassium bis(trimethylsilyl) amide. Suitable temperatures range from −100° C. to 0° C. Suitable solvents include tetrahydrofuran.

Compounds of Formula G can be prepared by known methods.

In an alternative approach, compounds of Formula C or C1 may be prepared by alkylation of a compound of Formula D or D1 respectively with a compound of Formula H, where LG is a suitable leaving group (such as a halogen e.g. Cl or Br, or trifluoromethanesulfonate or acetate) in the presence of a suitable base at a suitable temperature, optionally in the presence of a suitable solvent, e.g. as shown above. Suitable bases include lithium diisopropylamide.

Suitable solvents include tetrahydrofuran. Suitable temperatures range from −100° C. to 0° C.

Compounds of Formula H can be prepared by known methods.

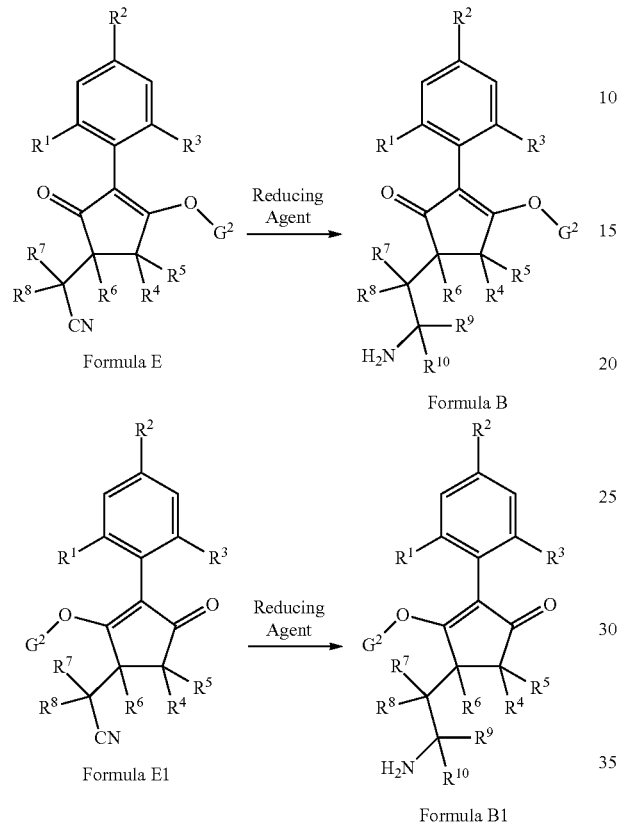

In another alternative approach, compounds of Formula B or B1 may be prepared by reduction of compounds of Formula E or E1 respectively in the presence of a suitable reducing agent, optionally in the presence of a suitable (e.g. organic) solvent and/or in the presence of a suitable catalyst, e.g. as shown above. Suitable reducing agents include hydrogen gas, suitable solvents include methanol, tetrahydrofuran or 1,4-dioxane. Suitable catalysts include Raney®-Nickel (see for example C. Jellimann, M. Mathe-Allainmat, J. Andrieux, S. Kloubert, J. A. Boutin, J-P. Nicolas, C. Bennejean, P. Delagrange, M. Langlois, *Journal of Medicinal Chemistry*, (2000), 43(22), 4051-4062).

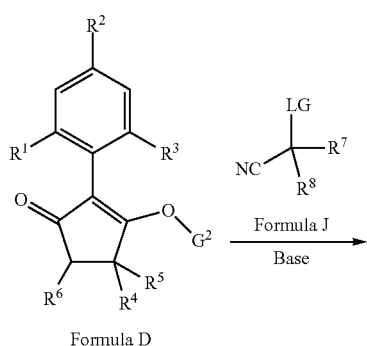

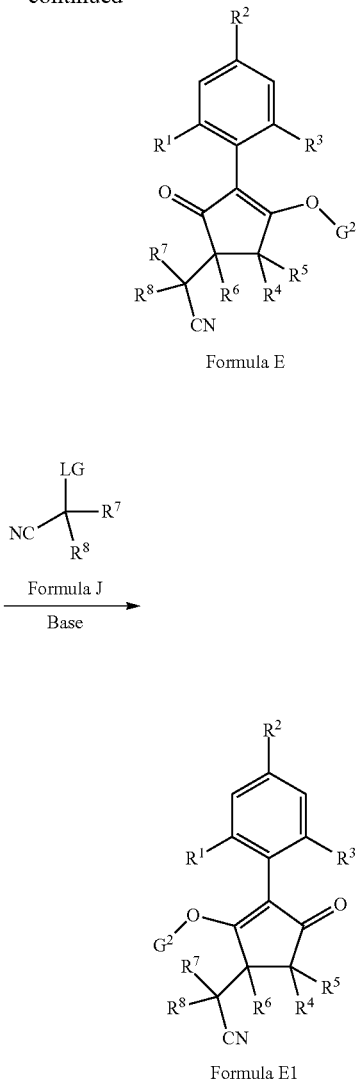

Compounds of formula E or E1 may be prepared by alkylation of a compound of Formula D or D1 respectively with a compound of Formula J (wherein LG is a suitable leaving group, such as halogen e.g. Cl or Br, or such as an alkyl, fluoroalkyl or aryl sulfonate e.g. methanesulfonate, trifluoromethanesulfonate or para-toluenesulfonate) in the presence of a suitable base, typically at a suitable temperature, optionally in the presence of a suitable (e.g. organic and/or non-aqueous) solvent, e.g. as shown above. Suitable bases include lithium diisopropylamide (LDA) (see for example R. Goswami, M. G. Moloney, *Chemical Communications*, (1999) 23, 2333-2334). Suitable solvents include tetrahydrofuran. Suitable temperatures range from −100° C. to 0° C.

Compounds of Formula J can be prepared by known methods.

In one embodiment, compounds within Formula D or D1 are made using the processes described in detail in Intermediate 2 hereinafter (these are compounds in which $R^2$ is Br, $R^1$ and $R^3$ are Me; $R^4$, $R^5$, and $R^6$ are H; and $G^2$ is Me). The reaction scheme for these Intermediate 2 processes is shown below (and is illustrated for compounds of Formula D or D1 in which $R^2$ is Br, $R^1$ and $R^3$ are Me; $R^4$, $R^5$, and $R^6$ are H; and $G^2$ is Me):

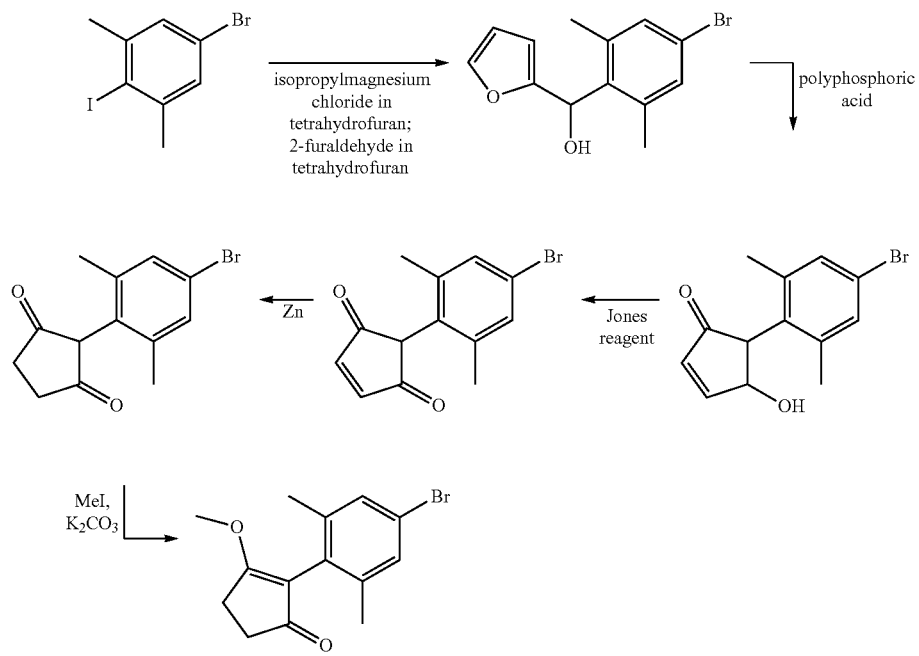

In an alternative embodiment, compounds within Formula D or D1 are made via the following coupling process scheme, as disclosed in Example 1 step 1 on pages 54-55 of WO 2010/000773 A1 (Syngenta Limited) (presented again as Intermediate 1 herein), and/or as disclosed in WO 2010/069834 A1 and/or WO 2011/073060 A2 (both Syngenta Limited and Syngenta Participations AG). The coupling process scheme below is illustrated for compounds of Formula D or D1 in which $R^1$, $R^2$ and $R^3$ are Me; $R^4$, $R^5$, and $R^6$ are H; and $G^2$ is Me:

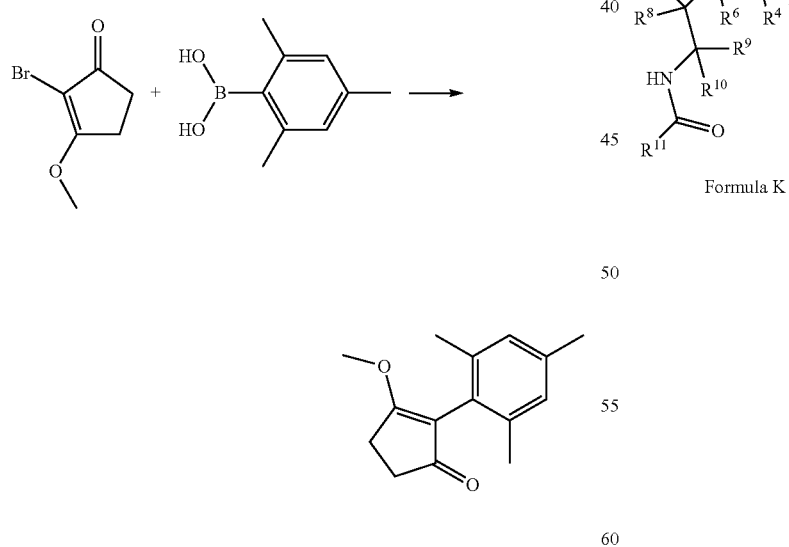

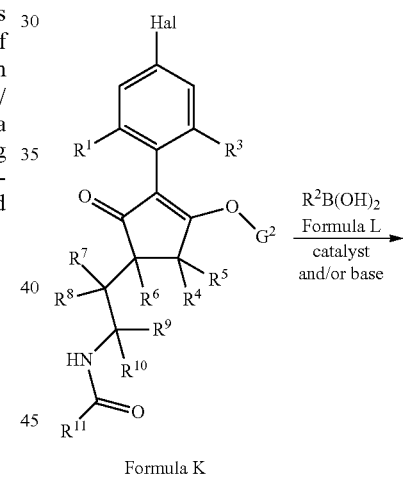

Formula K

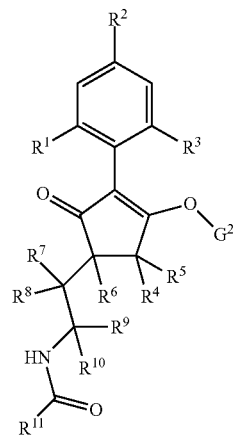

Formula IB

Typical reagents for the above-shown coupling process (the reagents used in Intermediate 1 herein, and in WO 2010/000773 A1) are potassium phosphate, Pd(OAc)$_2$, and S-Phos (which is 2-(dicyclohexylpho'ph'no)-2',6'-dimethoxybiphenyl). The 2,4,6-trimethyl-phenyl boronic acid shown above is commercially available.

-continued

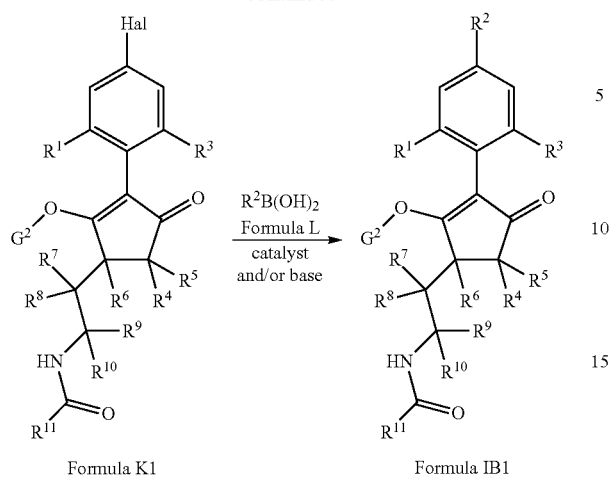

Formula K1 → Formula IB1

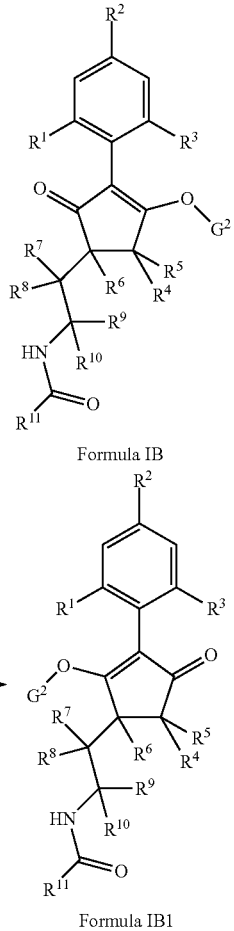

Formula IB

In another approach, a compound of Formula IB or IB1 (which is sometimes also a compound of Formula (I) or (IA) respectively), wherein R²=optionally substituted phenyl, $C_1$-$C_3$alkyl or cyclopropyl, and wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reaction of compounds of Formula K or K1 respectively (where Hal=Cl, Br or I or a suitable "pseudohalogen" such as trifluoromethanesulfonate) with compound of Formula L in the presence of a suitable catalyst, and/or in the presence of a suitable base, typically at a suitable temperature, optionally in the presence of a suitable (e.g. organic and/or non-aqueous) solvent, e.g. as shown above. Suitable catalysts include bis(diphenylphosphino)ferrocene-dichloropalladium(II) (see for example A. M Thompson, H. S. Sutherland, B. D. Palmer, I. Kmentova, A. Blaser, W. A. Denny, S. G. Franzblau, B. Wan, Y. Wang, Z. Ma, *Journal of Medicinal Chemistry*, (2011), 54(19), 6563-6585). Suitable bases include cesium fluoride. Suitable solvents include 1,4-dioxane. Suitable temperatures range from room temperature (e.g. 15-30° C.) to 140° C.

Compounds of Formula L may be prepared by known methods.

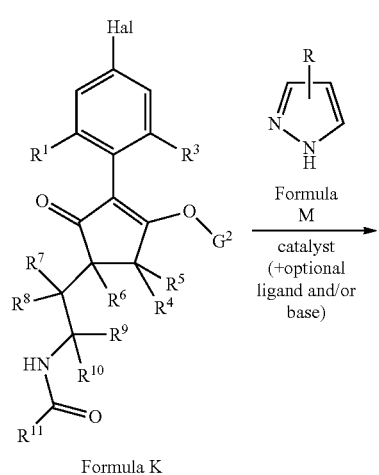

Formula K

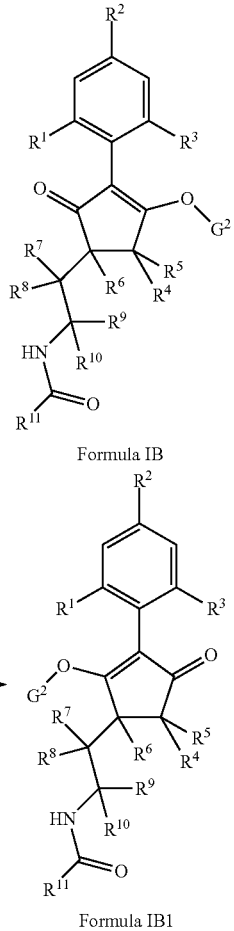

Formula K1 → Formula IB1

In a further approach, a compound of Formula IB or IB1 (which is sometimes also a compound of Formula (I) or (IA) respectively), wherein R²=optionally substituted pyrazol-1-yl, and wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reaction of compounds of Formula K or K1 respectively (where Hal=Cl, Br or I or a suitable "pseudohalogen" such as trifluoromethanesulfonate) with compounds of Formula M in the presence of a suitable catalyst, optionally in the presence of a suitable ligand, optionally in the presence of a suitable base, typically at a suitable temperature, optionally in the presence of a suitable (e.g. organic) solvent, e.g. as shown above. Suitable catalysts include copper (I) iodide (see for example H. Zhang, Q. Cai, D. Ma, *Journal of Organic Chemistry*, (2005), 70(13), 5164-5173) or tris(dibenzylideneacetone)dipalladium(0) (see for example S. Tasler, J. Mies, M. Lang, *Advanced Synthesis and Catalysis*, (2007), 349(14-15), 2286-2300). Suitable ligands include dimethyl glycine or 2-di-tert-butylphosphino-2',4',6'-triisopropylbiphenyl. Suitable temperatures range from room temperature to 180° C. Suitable bases include potassium carbonate or sodium hydride. Suitable solvents include dimethyl sulfoxide, toulene or diethylene glycol dimethyl ether.

Compounds of Formula M are available or may be prepared by known methods.

For a method of preparing compounds of formula (I) in which R² is optionally substituted 1,2,3-triazol-1-yl, see Example 11 (synthesis of compound A170) hereinafter.

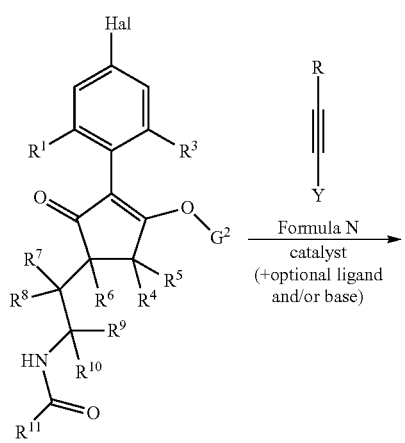

Formula K

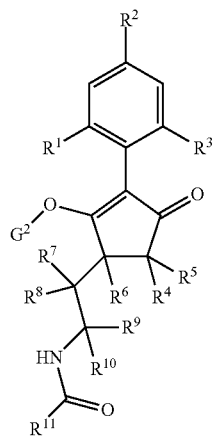

Formula IB1

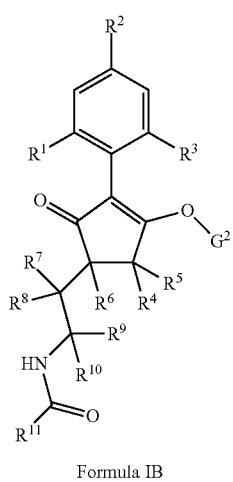

Formula IB

In another approach, a compound of Formula IB or IB1 (which is sometimes also a compound of Formula (I) or (IA) respectively), wherein $R^2$=optionally substituted alkyn-1-yl (as defined herein), and wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reaction of compounds of Formula K or K1 respectively (wherein R is suitable to form in formula I an $R^2$=optionally substituted alkyn-1-yl as defined herein) with compounds of Formula N (wherein Y is a suitable cross-coupling group such as H, $CO_2$H, $Bu_3$Sn) in the presence of a suitable catalyst, typically at a suitable temperature, optionally in the presence of a suitable (e.g. organic) solvent, optionally in the presence of a suitable ligand and/or a suitable base, e.g. as shown above. Suitable catalysts include [1,1'-Bis(diphenylphosphino)ferrocene]-dichloropalladium(II), copper (I) iodide or bis(triphenyl-phosphine)palladium(II) dichloride (see for example Y. Okuno, M. Yamashita, K. Nozaki, *European Journal of Organic Chemistry*, (2011), 20-21, 3951-3958). Suitable ligands include 1,4-bis(diphenylphosphino)butane. Suitable bases include cesium fluoride or 1,8-diazabicyclo[5.4.0]undec-7-ene. Suitable temperatures range from room temperature (e.g. 15-30° C.) to 140° C. Suitable solvents include N,N-dimethylformamide or dimethylsulfoxide.

Compounds of Formula N may be prepared by known methods.

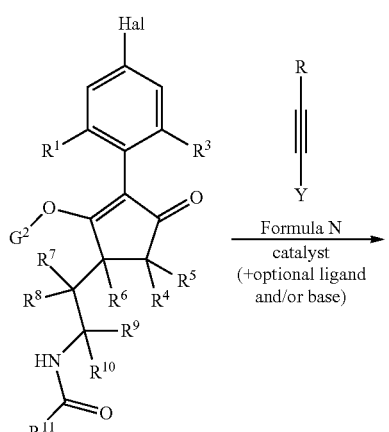

Formula K1

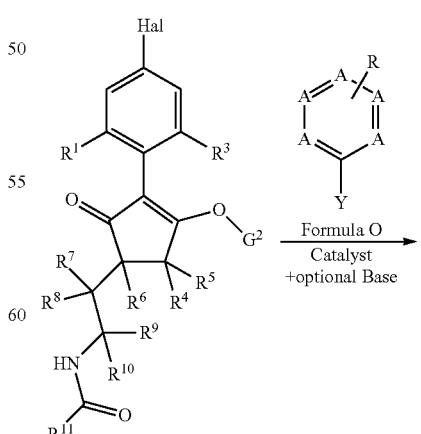

Formula K

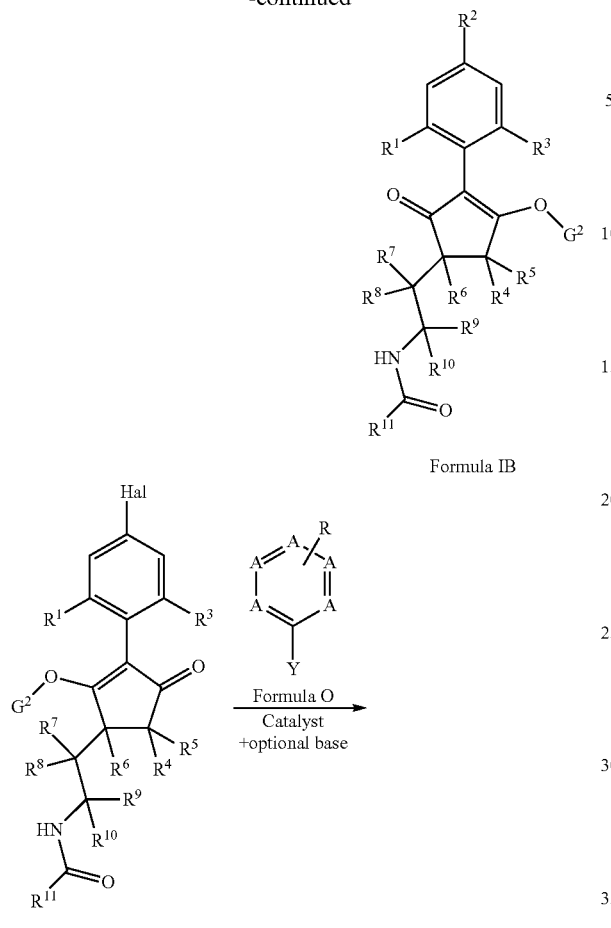

Formula IB

Formula K1

Formula IB1

In a further approach, a compound of Formula IB or IB1 (which is sometimes also a compound of Formula (I) or (IA) respectively), wherein R²=optionally substituted heteroaryl (e.g. optionally substituted 6-membered heteroaryl), and wherein G² is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, may be prepared by reactions of compounds of Formula K or K1 respectively with compounds of Formula O (wherein Y is a suitable cross-coupling partner group e.g. B(OH)$_2$ or Bu$_3$Sn, and each A is independently C—R or N) in the presence of a suitable catalyst, typically at a suitable temperature, optionally in the presence of a suitable (e.g. organic) solvent, optionally in the presence of a suitable ligand and/or a suitable base, e.g. as shown above. Suitable catalysts include [1,1'-Bis(diphenylphosphino)ferrocene]dichloropalladium (II) (see for example N. Joubert, M. Urban, R. Pohl, M. Hocek, *Synthesis*, (2008), 12, 1918-1932) and copper (I) iodide. Suitable bases include cesium fluoride. Suitable solvents include N,N-dimethylformamide. Suitable temperatures range from room temperature (e.g. 15-30° C.) to 140° C.

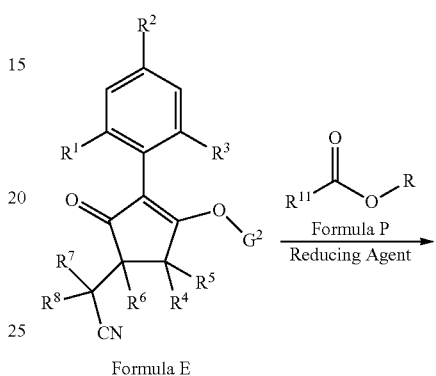

Formula E

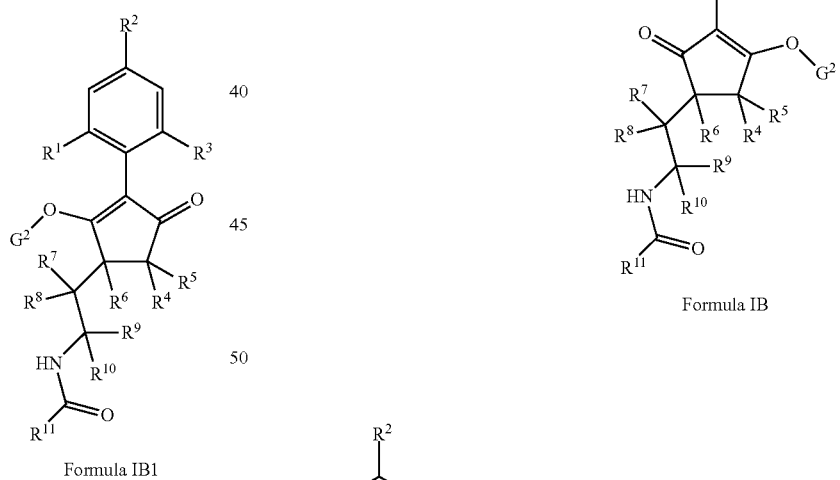

Formula IB

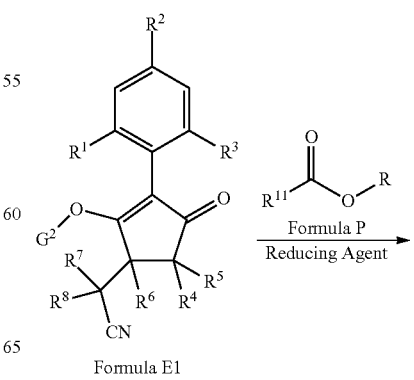

Formula E1

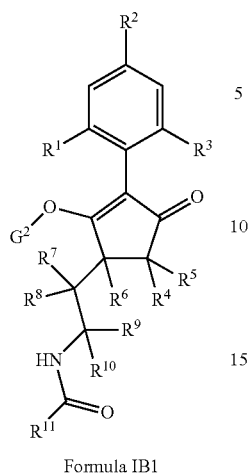

Formula IB1

In yet another approach, a compound of Formula IB or IB1 (which is sometimes also a compound of Formula (I) or (IA) respectively), wherein $G^2$ is typically $C_1$-$C_6$alkyl, —C(O)O$C_1$-$C_6$alkyl, —C(O)NH—$C_1$-$C_6$alkyl or —C(O)N($C_1$-$C_6$alkyl)$_2$, can be prepared by reduction of compounds of Formula E or E1 in the presence of compounds of Formula P (in which O—R is a suitable leaving group, for example pentafluorophenoxy) in the presence of a suitable reducing agent, optionally in the presence of a suitable (e.g. organic) solvent and/or in the presence of a suitable catalyst, e.g. as shown above. Suitable reducing agents include sodium borohydride and hydrogen gas. Suitable solvents include methanol, tetrahydrofuran or 1,4-dioxane. Suitable catalysts include NiCl$_2$ or Raney®-Nickel (see for example D. E. Gonzalez-Juarez, J. B. Garcia-Vazquez, V. Zuniga-Garcia, J. J. Trujillo-Serrato, P. Joseph-Nathan, M. S. Morales-Rios, O. R. Suarez-Castillo, *Tetrahedron*, (2012), 68 (35), 7187-7195).

Compounds of Formula P can be prepared by known methods.

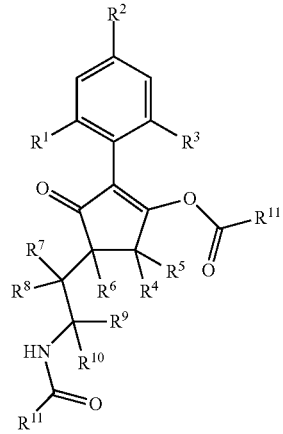

Formula IC

A compound of formula (I) which is a compound of Formula A or of Formula IC, may be prepared by an amide and/or ester bond forming reaction between a compound of Formula Q, or a salt thereof in particular an acid addition salt (e.g. HCl salt) thereof, and a compound of Formula F, wherein X=halogen, OH or OR (OR being a leaving group attached by oxygen, e.g. pentafluorophenoxy, or e.g. an alkyl, fluoroalkyl or aryl sulfonate such as methanesulfonate, trifluoromethanesulfonate or para-toluenesulfonate), e.g. as shown above. The amide bond forming reaction is typically carried out in the presence of a suitable solvent (e.g. an organic and/or non-aqueous solvent), and/or in the presence of a suitable coupling reagent, and/or in the presence of a suitable base. Suitable solvents include N,N-dimethylformamide or dichloromethane. Suitable coupling reagents include a carbodiimide (e.g. dicyclohexylcarbodiimide, "DCC") or a phosphonic anhydride (e.g. 2,4,6-tripropyl-1,3,5,2,4,6-trioxatriphosphorinane-2,4,6-trioxide) or a (benzotriazol-1-yloxy)trialkylaminophosphonium salt (e.g. benzotriazol-1-yloxy(tripyrrolidin-1-yl)phosphonium hexafluorophosphate). Suitable bases include organic non-aqueous bases such as tertiary amines such as N,N-diisopropylethylamine or triethylamine.

Example 16B hereinafter is one example of a compound of Formula Q (as an HCl salt) being converted to a compound of Formula IC.

Compounds of Formula F can be prepared by known methods.

The present invention also provides a compound of formula (Q):

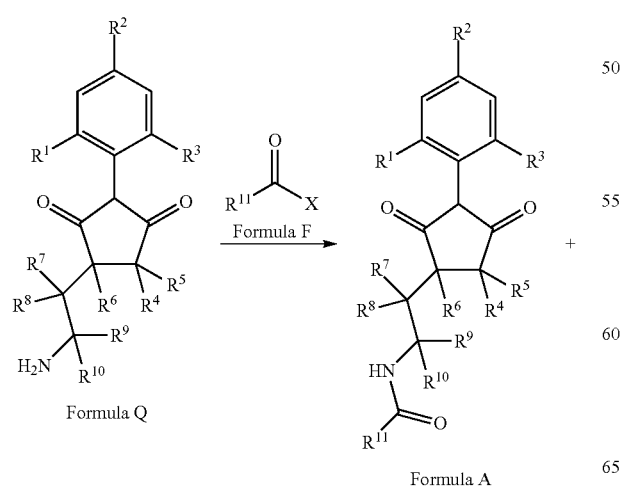

Formula Q → Formula A

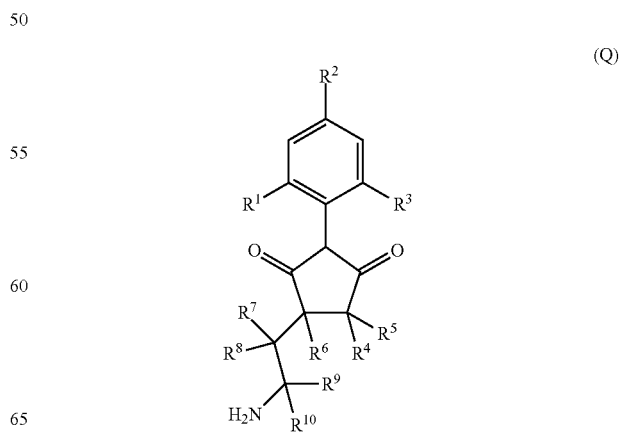

(Q)

or a salt thereof (in particular an acid addition salt e.g. HCl salt thereof, and/or in particular an agrochemically acceptable salt thereof),
wherein $R^1$, $R^2$, $R^3$, $R^4$, $R^5$, $R^6$, $R^7$, $R^8$, $R^9$ and $R^{10}$ are as defined herein.

Example 16B hereinafter includes one example of an HCl salt of a compound of Formula Q being prepared from a compound of Formula R1 in which PG is tert-butyloxycarbonyl (t-Boc) and $G^2$ is methyl.

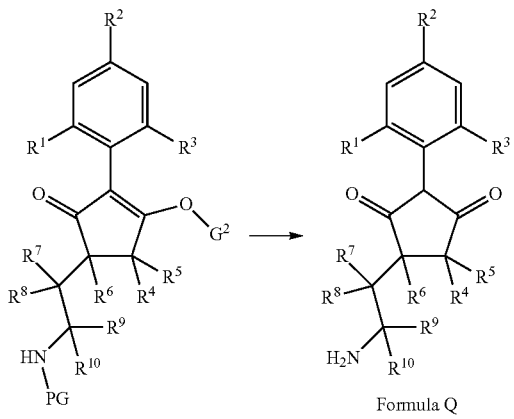

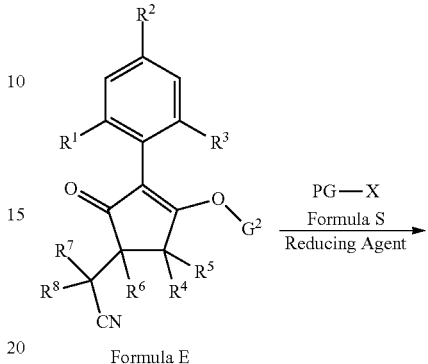

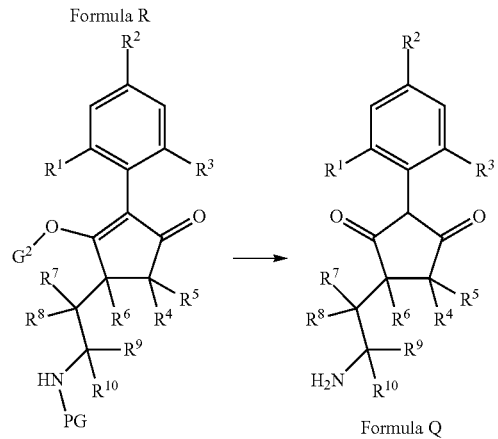

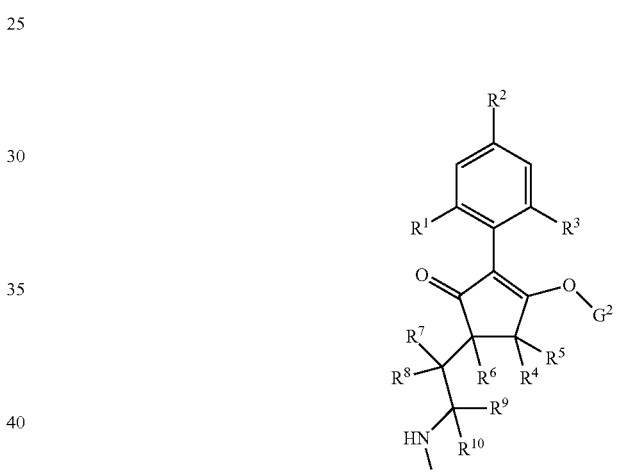

A compound of Formula Q or a salt (e.g. acid addition salt, e.g. HCl salt) thereof may be prepared from a compound of Formula R or R1, e.g. as shown above, by removing the protecting group PG attached to compound of Formula R or R1, wherein PG is a suitable protecting group, preferably tert-butyloxycarbonyl (t-Boc), carboxybenzyl (CBz), para-toluenesulfonyl (tosyl, Ts), para-bromobenzenesulfonyl, 2- or 4-nitrobenzenesulfonyl (nosyl, Nos), 2,2,2-trichloroethoxycarbonyl (Troc), benzyl (Bn), p-methoxybenzyl (PMB), fluorenylmethyloxycarbonyl (Fmoc) or any other suitable protecting group. The removal of the protecting group PG is typically carried out in the presence of a suitable solvent (e.g. an organic and/or aqueous solvent), in the presence of a suitable acid, base, reducing agent and/or oxidizing agent. Suitable solvents include N,N-dimethylformamide, dichloromethane, tetrahydrofuran, diethylether, water, ethyl acetate or acetone or mixtures thereof. Suitable acids include trifluoroacetic acid, hydrochloric acid or triflic acid (trifluoromethanesulfonic acid). Suitable bases include tertiary amines such as N,N-diisopropylethylamine or triethylamine, or a metal alkoxide, or a metal hydroxide or morpholine. Suitable reducing agents include zinc, hydrogen gas in the presence of suitable metal catalysts, alkali metals dissolved in ammonia, or a sodium amalgam. Suitable oxidizing agent include ceric ammonium nitrate (CAN).

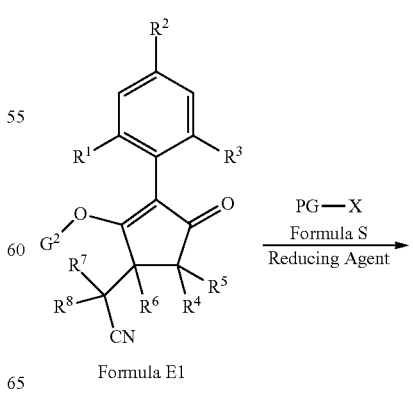

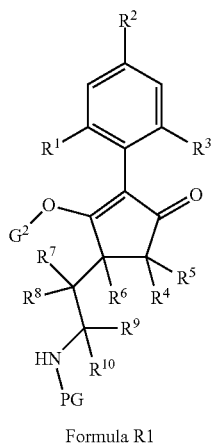

Formula R1

Compounds of Formula R or R1 can be prepared by reduction of compounds of Formula E or E1 respectively in the presence of compounds of Formula S (in which X is a suitable leaving group, for example halogen or anhydride where X=O—PG) in the presence of a suitable reducing agent, optionally in the presence of a suitable (e.g. organic) solvent and/or in the presence of a suitable catalyst. Suitable reducing agents include hydrogen gas or sodium borohydride. Suitable solvents include methanol, tetrahydrofuran or 1,4-dioxane. Suitable catalysts include $NiCl_2$ or Raney®-Nickel (see for example D. E. Gonzalez-Juarez, J. B. Garcia-Vazquez, V. Zuniga-Garcia, J. J. Trujillo-Serrato, P. Joseph-Nathan, M. S. Morales-Rios, O. R. Suarez-Castillo, *Tetrahedron*, (2012), 68 (35), 7187-7195).

Compounds of Formula S can be prepared by known methods.

Herbicidal Compositions

In another aspect, the present invention provides a herbicidal composition, e.g. for use in a method of controlling weeds (e.g. monocotyledonous such as grassy weeds) in crops of useful plants, which composition comprises a compound of formula (I) as defined herein (e.g. a herbicidally effective amount thereof), and a substantially-inert agrochemically acceptable substance (e.g. an agrochemically acceptable carrier, diluent and/or solvent, an agrochemically acceptable adjuvant, an an agrochemically acceptable emulsifier/surfactant/surface-active substance, and/or another agrochemically acceptable additive).

In a further aspect, the present invention provides a herbicidal composition, e.g. for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt thereof.

The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agrochemically acceptable substances (e.g. an agrochemically acceptable carrier, diluent and/or solvent, an agrochemically acceptable adjuvant, an an agrochemically acceptable emulsifier/surfactant/surface-active substance, and/or another agrochemically acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc. Other suitable matrix materials for slow release formulations are starch, stearin, lignin.

The formulation ingredients (e.g. inert ingredients) suitable for the preparation of the compositions according to the invention are generally known per se.

As a liquid carrier and/or solvent (e.g. organic solvent), e.g. for use in the herbicidal composition(s) according to the invention, there may be used: water, an aromatic solvent such as toluene, m-xylene, o-xylene, p-xylene or a mixture thereof, cumene, an aromatic hydrocarbon blend with a boiling range between 140 and 320° C. (e.g. known under various trademarks such as Solvesso®, Shellsol A®, Caromax®, Hydrosol®), a paraffinic or isoparaffinic carrier such as paraffin oil, mineral oil, a de-aromatized hydrocarbon solvent with a boiling range between 50 and 320° C. (e.g. known for instance under the trademark Exxsol®), a non-dearomatized hydrocarbon solvent with a boiling range between 100 and 320° C. (e.g. known under the tradename Varsol®), an isoparaffinic solvent with a boiling range between 100 and 320° C. (e.g. known under tradenames like Isopar® or Shellsol T®), a hydrocarbon such as cyclohexane, tetrahydronaphthalene (tetralin), decahydronaphthalene, alpha-pinene, d-limonene, hexadecane, isooctane; an ester solvent such as ethyl acetate, n- or iso-butyl acetate, amyl acetate, i-bornyl acetate, 2-ethylhexyl acetate, a $C_6$-$C_{18}$ alkyl ester of acetic acid (e.g. known under the tradename Exxate®), lactic acid ethylester, lactic acid propylester, lactic acid butylester, benzyl benzoate, benzyl lactate, dipropyleneglycol dibenzoate, or a dialkyl ester of succinic, maleic or fumaric acid; a polar solvent such as N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, a $C_4$-$C_{18}$ fatty acid dimethylamide, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, or butylene carbonate; an alcoholic solvent or diluent such as methanol, ethanol, propanol, n- or iso-butanol, n- or iso-pentanol, 2-ethyl hexanol, n-octanol, tetrahydrofurfuryl alcohol, 2-methyl-2,4-pentanediol, 4-hydroxy-4-methyl-2-pentanone, cyclohexanol, benzyl alcohol, ethylene glycol, ethylene glycol butyl ether, ethylene glycol methyl ether, diethylene glycol, diethylene glycol butyl ether, diethylene glycol monoethyl ether, diethylene glycol monomethyl ether, propylene glycol, dipropylene glycol, dipropylene glycol monomethyl ether, or another similar glycol monoether solvent based on a ethylene glycol, propylene glycol or butylene glycol feedstock, triethylene glycol, polyethylene glycol (e.g. PEG 400), a polypropylenglycol with a molecular mass of 400-4000, or glycerol;

glycerol acetate, glycerol diacetate, glycerol triacetate, 1,4-dioxane, diethylene glycol abietate, chlorobenzene, chlorotoluene; a fatty acid ester such as methyl octanoate, isopropyl myristate, methyl laurate, methyl oleate, a mixture of $C_8$-$C_{10}$ fatty acid methyl esters, rapeseed oil methyl ester, rapeseed oil ethyl ester, soybean oil methyl ester, soybean oil ethyl ester; a vegetable oil (e.g. rapeseed oil or soybean oil); a fatty acid such as oleic acid, linoleic acid, or linolenic acid; or an ester of phosphoric or phosphonic acid such as triethyl phosphate, a $C_3$-$C_{18}$-trisalkyl phosphate, an alkylaryl phosphate, or bis-octyl-octyl phosphonate.

Water is generally the liquid carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifiying, wetting, dispersing or suspending agents or for other purposes. Typical surface-active substances include, for example, salts of alkyl sulfates, such as diethanolammonium lauryl sulfate; sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), $C_1$-$C_6$alkyl esters of oils of vegetable origin, for example the methyl esters, or an oil of animal origin, such as fish oil or beef tallow. A preferred oil additive contains methylated rapeseed oil. Another preferred oil additive contains, for example, as active components essentially 80% by weight alkyl esters of fish oils and 15% by weight methylated rapeseed oil, and also 5% by weight of customary emulsifiers and pH modifiers. Especially preferred oil additives comprise $C_1$-$C_6$alkyl ester(s) of $C_8$-$C_{22}$ fatty acid(s), especially the methyl ester(s) of $C_8$-$C_{22}$ (especially $C_{12}$-$C_{18}$) fatty acid(s); preferably the methyl ester of lauric acid, of palmitic acid, or of oleic acid. Those esters are known as methyl laurate (CAS-111-82-0), methyl palmitate (CAS-112-39-0) and methyl oleate (CAS-112-62-9) respectively. A preferred fatty acid methyl ester derivative is AGNIQUE ME 18 RD-F® (e.g. available from Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols preferably having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The above-mentioned surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations/compositions have especially the following representative compositions:
(%=percent by weight of the composition):
Emulsifiable Concentrates:
active ingredient: 0.3 to 95%, preferably 0.5 to 60% such as 1 to 40%
surface-active agents: 1 to 30%, preferably 3 to 20% such as 5 to 15%
solvents as liquid carrier: 1 to 80%, preferably 1 to 60% such as 1 to 40%
Dusts:
active ingredient: 0.1 to 10%, preferably 0.1 to 5%
solid carriers: 99.9 to 90%, preferably 99.9 to 99%
Suspension Concentrates:
active ingredient: 1 to 75%, preferably 3 to 50% or 10 to 50%
water: 98 to 24%, preferably 95 to 30% or 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | | | | |
|---|---|---|---|---|
| | a) | b) | c) | d) |
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture $C_9$-$C_{12}$ | 85% | 68% | 65% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP (N-methyl-2-pyrrolidone) | — | — | 50% | 10% |
| aromatic hydrocarbon mixture $C_9$-$C_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

| F8. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F9. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 88% | 80% | 60% | 38% |

The finely ground active ingredient is intimately mixed with the adjuvants, yielding a suspension concentrate from which suspensions of any desired concentration can be prepared by dilution with water.

Herbicidal Uses—Crops of Useful Plants, Weeds, Application Rates, et al.

In a further aspect, the present invention provides a method of controlling weeds (e.g. monocotyledonous weeds such as grassy monocotyledonous weeds) in crops of useful plants, which comprises applying a compound of the formula (I), or a herbicidal composition comprising such a compound, to the weeds and/or to the plants and/or to the locus thereof.

In a further aspect, the present invention provides a herbicidal composition, in particular for use in a method of controlling weeds (e.g. monocotyledonous weeds such as grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt thereof.

In one embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. on or in which or at the locus of which the compounds or compositions according to the invention can be used, comprise (e.g. are), in particular, cereals (preferably non-oat cereals, in particular wheat, barley, rye and/or triticale), rice, corn (maize), sugarcane, leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, linseed, sugarbeet, fodder beet, potato, vegetables (preferably dicotyledonous vegetables), flax, tobacco, plantation crops (such as conifer trees, olives and/or olive trees, oil palms, coffee, or vines), and/or fruit crops (in particular dicotyledonous and/or broadleaved fruit, and/or in particular pome fruit, stone fruit, bush fruit, citrus fruit, pineapple, banana, and/or strawberry).

Preferably, in all aspects of the invention, the crops of useful plants, e.g. on or in which or at the locus of which the compounds or compositions according to the invention can be used, comprise (e.g. are) cereals (preferably non-oat cereals, more particularly wheat, barley, rye and/or triticale), rice, corn (maize), sugarcane, leguminous crops (preferably soybean, peanut, and/or pulse crops, more preferably soybean), cotton, rape (in particular oilseed rape or canola), sunflower, linseed, sugarbeet, fodder beet, potato, and/or vegetables (preferably dicotyledonous vegetables).

Most preferably, in all aspects of the invention, the crops of useful plants, e.g. on or in which or at the locus of which the compounds or compositions according to the invention can be used, comprise (e.g. are) non-oat cereals, more particularly wheat, barley, rye and/or triticale.

The term "crops" is to be understood as also including crops that have been rendered tolerant to herbicides or classes of herbicides (for example ALS, GS, EPSPS, PPO and/or HPPD inhibitors, and/or 2,4-D or dicamba) as a result of conventional methods of breeding or genetic engineering. Examples of crops that have been rendered tolerant e.g. to imid-azolinones (which are ALS inhibitors), such as imazamox, by conventional methods of breeding include Clearfield® summer rape (canola) and/or Clearfield® wheat and/or Clearfield® rice (all from BASF). Examples of crops that have been rendered tolerant to herbicides by genetic engineering methods include e.g. glyphosate- or glufosinate-resistant/tolerant maize or soybean varieties, in particular those commercially available under the trade names RoundupReady® or RoundupReady® 2 (both from Monsanto, both glyphosate-resistant) and LibertyLink® (from Bayer, glufosinate-resistant). Glufosinate-resistant rice (LibertyLink®) also has been published.

Other crops of useful plants include 2,4-D-tolerant soybean, e.g. soybean genetically-modified to be tolerant to the herbicide 2,4-D, or dicamba-tolerant soybean, e.g. soybean genetically-modified to be tolerant to the herbicide dicamba. Such 2,4-D-tolerant or dicamba-tolerant soybean crops can also, in particular, be tolerant to glyphosate or glufosinate. For example, crops of useful plants include soybeans containing a dicamba-tolerance trait combined (stacked) with a glyphosate-tolerance trait, such that these soybeans have tolerance to the herbicides glyphosate and dicamba (for example Genuity® Roundup Ready® 2 Xtend soybeans, currently under development by Monsanto).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds. Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy monocotyledonous) weeds, e.g. to be controlled and/or growth-inhibited, comprise (e.g. are) weeds from the genus *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), Juncus (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass").

In one preferred embodiment of all aspects of the invention, the monocotyledonous weeds, e.g. to be controlled and/or growth-inhibited, are grassy monocotyledonous weeds; in which case they typically comprise (e.g. are) weeds from the genus *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*.

In one particular embodiment of all aspects of the invention, the grassy monocotyledonous weeds, e.g. to be controlled and/or growth-inhibited, are "warm-season" grassy weeds; in which case they typically comprise (e.g. are) weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*.

In another particular embodiment of all aspects of the invention, the grassy monocotyledonous weeds, e.g. to be controlled and/or growth-inhibited, are "cool-season" grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens, Setaria faberi* and/or *Setaria glauca*).

In all aspects of the invention, in a particular embodiment, the weeds, e.g. to be controlled and/or growth-inhibited e.g. by applying a compound of formula (I), may be grassy monocotyledonous weeds (e.g. *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, flazasulfuron, iofensulfuron, metsulfuron-methyl, or any other sulfonyl urea herbicide disclosed in The Pesticide Manual, 15th edition, 2009, ed. C. D. S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylamino-carbonyl-triazolinone herbicides (e.g. thiencarbazone-methyl, propoxycarbazone-sodium or flucarbazone-sodium) and/or one or more imidazolinone herbicides (e.g. imazamox).

Such resistant (in particular ACCase-inhibitor-resistant, glyphosate-resistant, and/or ALS-inhibitor-resistant) grassy weeds can more particularly comprise *Alopecurus myosuroides, Apera spica-venti, Avena fatua, Avena sterilis, Brachiaria decumbens, Brachiaria plantaginea, Digitaria horizontalis, Digitaria insularis, Digitaria sanguinalis, Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi, Setaria glauca*, and/or *Sorghum halepense*.

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 322-324 therein in particular Table 2, incorporated herein by reference, for examples of such resistant weeds and/or amino acid substitutions); and/or (b) which are resistant to: one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.*, 2010, 61, pp. 317-347, e.g. see Table 4 on page 328 therein, incorporated herein by reference, for examples of such resistant weeds).

Typically, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria, Viola, Veronica* and/or *Xanthium*.

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application (typically to the weeds and/or to the crops of useful plants and/or to the locus thereof) of the compound of formula (I) (which optionally may be an agrochemically acceptable salt thereof) is generally from 1 to 2000 g of the compound of formula (I) per hectare (ha) (measured as the free compound, i.e. excluding the weight of any associated salt counterion(s)), in particular from 5 to 500 g/ha, preferably from 10 to 400 g/ha, of the compound of formula (I) (measured as the salt-free compound, i.e. excluding the weight of any associated salt counterion(s)).

In all aspects of the invention, the compound of formula (I) can be applied (typically to the weeds and/or to the crops of useful plants and/or to the locus thereof) pre- and/or post-emergence, but preferably is applied post-emergence.

Combinations and Mixtures

In a further aspect, the present invention provides a herbicidal composition, e.g. for use in a method of controlling weeds (e.g. monocotyledonous such as grassy weeds) in crops of useful plants, comprising a compound of formula (I) as defined herein (e.g. a herbicidally effective amount thereof), and an agrochemically acceptable carrier, diluent and/or solvent, and also comprising one or more further herbicides, and/or a safener.

In all aspects of the invention, the compound of the formula (I) is optionally present (e.g. where chemically possible) as an agrochemically acceptable salt thereof.

Examples of these mixtures/compositions, comprising one or more further herbicides and/or a safener, follow.

The compounds of formula (I) according to the invention can be used in combination with one or more further herbicides, e.g. as mixture partner(s) for the compound of formula (I). Preferably, in these mixtures (in particular in the specific mixtures disclosed hereinbelow), the compound of the formula (I) is one of the specific compounds disclosed herein e.g. hereinbelow (in particular, any of compounds A1 to A99, or compound A100 or A101, or any of compounds A102 to A108, or any of compounds A109 to A211, or any of compounds P1 to P30), present either as a free compound and/or as an agrochemically acceptable salt thereof.

In particular, the following mixtures of the compound of formula (I) with one or more further herbicides are particularly disclosed:
compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloransulam, compound of formula I+chloransulam-methyl, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+2,4-D+glyphosate, compound of formula I+2,4-D-dimethylammonium+glyphosate, compound of formula I+2,4-D-2-ethylhexyl+glyphosate, compound of formula I+a choline salt of 2,4-D+glyphosate (see e.g. Examples 2 and 3 of WO2010/123871A1), compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dicamba+glyphosate, compound of formula I+dicamba-dimethylammonium+glyphosate, compound of formula I+dicamba-potassium+glyphosate, compound of formula I+dicamba-sodium+glyphosate, compound of formula I+dicamba-diglycolamine+glyphosate, compound of formula I+a N,N-bis-[aminopropyl]methylamine salt of dicamba+glyphosate, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metil-sulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula (I)+fenoxaprop, compound of formula (I)+fenoxaprop-ethyl, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+glyphosate-diammonium, compound of formula I+glyphosate-isopropylammonium, compound of formula I+glyphosate-potassium, compound of formula I+halosulfuron, compound of formula I+halosulfuron-methyl, compound of formula I+haloxyfop, compound of formula I+haloxyfop-P, compound of formula (I)+haloxyfop-methyl, compound of formula (I)+haloxyfop-P-methyl, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl]-bicyclo[3.2.1]oct-3-en-2-one, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2- cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N'-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), compound of formula I+clacyfos (which is dimethyl[(1RS)-1-(2,4-dichlorophenoxyacetoxy)ethyl]phosphonate, also named Ivxiancaolin or Iüxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6).

The mixture partners for the compound of formula (I) are optionally in the form of an ester (in particular an agrochemically acceptable ester) or a salt (in particular an agrochemically acceptable salt) thereof (e.g. where chemically possible). The above-mentioned mixture partners for the compound of formula (I), are generally mentioned e.g. in The Pesticide Manual, 15th Edition, 2009, ed. C. D. S. Tomlin, British Crop Production Council.

In the present patent specification, "CAS Reg. No." or "CAS RN" means the Chemical Abstracts Service Registry Number of the stated compound.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl] methylamine salt of dicamba (see e.g. US2012/0184434A1), compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula (I)+fenoxaprop, compound of formula (I)+fenoxaprop-ethyl, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+triallate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in cereals, more preferred is a mixture comprising: a compound of formula (I)+amidosulfuron, compound of formula (I)+aminopyralid, compound of formula (I)+beflubutamid, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluroxypyr, compound of formula I+fluroxypyr-meptyl, compound of formula I+fluroxypyr-butometyl, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+diquat, compound of formula (I)+diquat dibromide, compound of formula (I)+esprocarb, compound of formula (I)+ethoxysulfuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula (I)+metamifop, compound of formula I+metazosulfuron (NC-620, CAS Reg. No. 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H, 6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2', 4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl) pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl) pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3, 5-triazin-2-yl)carbonyl]-6-fluorophenyl]-N-methyl-1,1-difluoromethanesulfonamide, CAS Reg. No. 874195-61-6); wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, more preferred is a mixture comprising: a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+2,4-D-dimethylammonium, compound of formula (I)+ 2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+ esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+halosulfuron, compound of formula (I)+halosulfuron-methyl, compound of formula (I)+ imazosulfuron, compound of formula I+ipfencarbazone (CAS Reg. No. 212201-70-2), compound of formula (I)+ MCPA, compound of formula (I)+mefenacet, compound of formula (I)+mesotrione, compound of formula I+metazosulfuron (NC-620, CAS Reg. No. 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+ pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5 (4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);
wherein the mixture partners for the compound of formula (I) may optionally be in the form of an ester (in particular an agrochemically acceptable ester) or a salt (in particular an agrochemically acceptable salt) thereof (e.g. where chemically possible).

For applications in soybean, the following mixtures are preferred:
compound of formula (I)+acifluorfen, compound of formula (I)+acifluorfen-sodium, compound of formula (I)+ametryn, compound of formula (I)+atrazine, compound of formula (I)+bentazone, compound of formula (I)+bicyclopyrone, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chloransulam, compound of formula (I)+chloransulam-methyl, compound of formula (I)+chlorimuron, compound of formula (I)+chlorimuron-ethyl, compound of formula (I)+clethodim, compound of formula (I)+clomazone, compound of formula (I)+cyanazine, compound of formula (I)+2,4-D (especially for applications to 2,4-D-tolerant soybean, e.g. genetically-modified), compound of formula (I)+2,4-D-dimethylammonium (especially for applications to 2,4-D-tolerant soybean, e.g. genetically-modified), compound of formula (I)+2,4-D-2-ethylhexyl (especially for applications to 2,4-D-tolerant soybean, e.g. genetically-modified), compound of formula (I)+a choline salt of 2,4-D (see e.g. Examples 2 and 3 of WO2010/123871 A1) (especially for applications to 2,4-D-tolerant soybean, e.g. genetically-modified), compound of formula (I)+2,4-D+glyphosate (especially for applications to 2,4-D-tolerant and/or glyphosate-tolerant soybean, e.g. genetically-modified), compound of formula (I)+2,4-D-dimethylammonium+glyphosate (especially for applications to 2,4-D-tolerant and/or glyphosate-tolerant soybean, e.g. genetically-modified), compound of formula (I)+2,4-D-2-ethylhexyl+glyphosate (especially for applications to 2,4-D-tolerant and/or glyphosate-tolerant soybean, e.g. genetically-modified), compound of formula (I)+a choline salt of 2,4-D+glyphosate (see e.g. Examples 2 and 3 of WO2010/123871A1) (especially for applications to 2,4-D-tolerant and/or glyphosate-tolerant soybean, e.g. genetically-modified), compound of formula (I)+dicamba (especially for applications to dicamba-tolerant soybean, e.g. genetically-modified), compound of formula (I)+dicamba-dimethylammonium (especially for applications to dicamba-tolerant soybean, e.g. genetically-modified), compound of formula (I)+dicamba-potassium (especially for applications to dicamba-tolerant soybean, e.g. genetically-modified), compound of formula (I)+dicamba-sodium (especially for applications to dicamba-tolerant soybean, e.g. genetically-modified), compound of formula (I)+dicamba-diglycolamine (especially for applications to dicamba-tolerant soybean, e.g. genetically-modified), compound of formula (I)+a N,N-bis-[aminopropyl]methylamine salt of dicamba (see e.g. US2012/0184434A1) (especially for applications to dicamba-tolerant soybean, e.g. genetically-modified), compound of formula (I)+dicamba+glyphosate (especially for applications to dicamba-tolerant and/or glyphosate-tolerant soybean, e.g. genetically-modified), compound of formula (I)+dicamba-dimethylammonium+glyphosate (especially for applications to dicamba-tolerant and/or glyphosate-tolerant soybean, e.g. genetically-modified), compound of formula (I)+dicamba-potassium+glyphosate (especially for applications to dicamba-tolerant and/or glyphosate-tolerant soybean, e.g. genetically-modified), compound of formula (I)+dicamba-sodium+glyphosate (especially for applications to dicamba-tolerant and/or glyphosate-tolerant soybean, e.g. genetically-modified), compound of formula (I)+dicamba-diglycolamine+glyphosate (especially for applications to dicamba-tolerant and/or glyphosate-tolerant soybean, e.g. genetically-modified), compound of formula (I)+a N,N-bis-[aminopropyl]methylamine salt of dicamba+glyphosate (see e.g. US2012/0184434A1) (especially for applications to dicamba-tolerant and/or glyphosate-tolerant soybean, e.g. genetically-modified), compound of formula (I)+diclosulam, compound of formula (I)+dimethenamid, compound of formula (I)+dimethenamid-P, compound of formula (I)+diquat, compound of formula (I)+diquat dibromide, compound of formula (I)+diuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula (I)+ fluazifop, compound of formula (I)+fluazifop-butyl, compound of formula (I)+fluazifop-P, compound of formula (I)+fluazifop-P-butyl, compound of formula (I)+flufenacet, compound of formula (I)+flumetsulam, compound of formula (I)+flumioxazin, compound of formula (I)+fluthiacet, compound of formula (I)+fluthiacet-methyl, compound of formula (I)+fomesafen, compound of formula (I)+glufosinate (especially for applications to glufosinate-tolerant soybean, e.g. genetically-modified), compound of formula (I)+glufosinate-ammonium (especially for applications to glufosinate-tolerant soybean, e.g. genetically-modified), compound of formula (I)+glyphosate (especially for applications to glyphosate-tolerant soybean, e.g. genetically-modified), compound of formula (I)+glyphosate-diammonium (especially for applications to glyphosate-tolerant soybean, e.g. genetically-modified), compound of formula (I)+glyphosate-isopropylammonium (especially for applications to glyphosate-tolerant soybean, e.g. genetically-modified), compound of formula (I)+glyphosate-potassium (especially for applications to glyphosate-tolerant soybean, e.g. genetically-modified), compound of formula (I)+imazethapyr, compound of formula (I)+lactofen, compound of formula (I)+mesotrione, compound of formula (I)+metolachlor, compound of formula (I)+S-metolachlor, compound of formula (I)+metribuzin, compound of formula (I)+oxyfluorfen, compound of formula (I)+paraquat, compound of formula (I)+paraquat dichloride, compound of formula (I)+pendimethalin, compound of formula (I)+pyroxasulfone, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula (I)+saflufenacil, compound of formula (I)+sethoxydim, compound of formula (I)+sulfentrazone, compound of formula (I)+thifensulfuron, compound of formula (I)+thifensulfuron-methyl, compound of formula (I)+tribenuron, compound of formula (I)+tribenuron-methyl, compound of formula (I)+trifluralin, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H, 6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), or compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference); wherein the mixture partners for the compound of formula (I) may optionally be in the form of an ester (in particular an agrochemically acceptable ester) or a salt (in particular an agrochemically acceptable salt) thereof (e.g. where chemically possible).

In the above-mentioned compositions or mixtures comprising a compound of formula (I) (in particular, one of the specific compounds disclosed herein, e.g. any of compounds A1 to A99, or compound A100 or A101, or any of compounds A102 to A108, or any of compounds A109 to A211, or any of compounds P1 to P30, present either as a free compound and/or as an agrochemically acceptable salt thereof) and one or more further herbicides, the weight ratio of the compound of formula (I) to each further herbicide can vary over a large range and is, typically, from 300:1 to 1:500, especially from 150:1 to 1:200, more especially from 100:1 to 1:100, even more especially from 30:1 to 1:30. Typically, these weight ratios are measured as the free compound(s), i.e. excluding the weight of any associated salt counterion(s).

Alternatively or additionally, in herbicidal compositions, the compounds of formula I according to the invention can also be used in combination with a safener. Preferably, in these mixtures, the compound of the formula I is one of the specific compounds disclosed herein e.g. hereinbelow (in particular, any of compounds A1 to A99, or compound A100 or A101, or any of compounds A102 to A108, or any of compounds A109 to A211, or any of compounds P1 to P30), present either as a free compound and/or as an agrochemically acceptable salt thereof. The following mixtures with safeners, especially, come into consideration:

compound of formula I+cloquintocet-mexyl, compound of formula I+cloquintocet acid or an agrochemically acceptable salt thereof, compound of formula I+fenchlorazole-ethyl, compound of formula I+fenchlorazole acid or an agrochemically acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292.

The above-mentioned safeners and herbicides are described, for example, in the Pesticide Manual, 14th Edition, British Crop Production Council, 2006; or The Pesticide Manual, 15$^{th}$ edition, 2009, ed. C. D. S. Tomlin, British Crop Production Council. R-29148 is described, for example by P. B. Goldsbrough et al., *Plant Physiology*, (2002), Vol. 130 pp. 1497-1505 and references therein. PPG-1292 is known from WO 2009/211761 and N-(2-methoxybenzoyl)-4-[(methylaminocarbonyl)amino]benzenesulfonamide is known from EP365484.

Especially preferably, in a composition or mixture comprising a compound of formula (I) (in particular, one of the specific compounds disclosed herein, e.g. any of compounds A1 to A99, or compound A100 or A101, or any of compounds A102 to A108, or any of compounds A109 to A211, or any of compounds P1 to P30, present either as a free compound and/or as an agrochemically acceptable salt thereof) and a safener, the safener comprises (e.g. is) benoxacor, cloquintocet-mexyl, cloquintocet acid or an agrochemically acceptable salt thereof, cyprosulfamide, mefenpyr-diethyl, isoxadifen-ethyl and/or N-(2-methoxybenzoyl)-4-[(methylaminocarbonyl)amino]-benzenesulfonamide. Even more preferably, the safener comprises (e.g. is) cloquintocet-mexyl, cloquintocet acid or an agrochemically acceptable salt thereof, mefenpyr-diethyl and/or isoxadifen-ethyl; in particular for use on non-oat cereals such as wheat, barley, rye and/or triticale. Cloquintocet-mexyl is particularly valuable and is the most preferred safener, especially for use on non-oat cereals such as wheat, barley, rye and/or triticale.

In the above-mentioned compositions or mixtures comprising a compound of formula (I) (in particular, one of the specific compounds disclosed herein, e.g. any of compounds A1 to A99, or compound A100 or A101, or any of compounds A102 to A108, or any of compounds A109 to A211, or any of compounds P1 to P30, present either as a free compound and/or as an agrochemically acceptable salt thereof) with a safener, the weight ratio of the compound of formula (I) to the safener can vary over a large range and is, typically, from 200:1 to 1:200, especially from 50:1 to 1:50 or from 50:1 to 1:20, more especially from 20:1 to 1:20, even more especially from 20:1 to 1:10. Preferably, the safener comprises (e.g. is) cloquintocet-mexyl, cloquintocet acid or an agrochemically acceptable salt thereof, mefenpyr-diethyl and/or isoxadifen-ethyl, and the weight ratio of the compound of formula (I) to the safener is from 50:1 to 1:20, more preferably from 20:1 to 1:10, even more preferably from 15:1 to 1:2 (this can be, for example, for use on non-oat cereals). Typically, these weight ratios are measured as the free compound(s), i.e. excluding the weight of any associated salt counterion(s).

Application rates of herbicide (e.g. compound of formula (I)) and/or safener: The rate of application of safener relative to the compound of formula (I) is largely dependent upon the mode of application. In the case of field and/or soil and/or plant treatment (e.g. in a field or glasshouse): for example from 0.5 to 1000 g of safener per ha, or preferably from 1 to 250 g or from 2 to 200 g of safener per ha, are applied; and/or generally from 1 to 2000 g of compound of formula (I) per ha, or preferably from 5 to 500 g or from 10 to 400 g of compound of formula (I) per ha, are applied. ha=hectare. Typically, these application rates are measured as the free compound, i.e. excluding the weight of any associated salt counterion(s). In field treatment, the application of the compound of formula (I) is preferably post-emergence.

The compounds and/or herbicidal compositions according to the invention are suitable for all methods of application customary in agriculture, such as, for example, pre-emergence application, post-emergence application and seed dressing. Post-emergence application is preferred. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field and/or soil and/or plant treatment (e.g. in a field or glasshouse), generally from 0.001 to 5.0 kg of safener/ha, preferably from 0.001 to 0.5 kg of safener/ha, are applied. Ha=hectare. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

In the invention, in the case of field and/or soil and/or plant treatment (e.g. post-emergence application), generally from 1 to 2000 g of herbicide (in particular compound of formula (I))/ha, but preferably from 5 to 1000 g of herbicide (in particular compound of formula (I))/ha, more preferably from 10 to 400 g of herbicide (in particular compound of formula (I))/ha, is applied. If a safener is used, in the case of field and/or soil and/or plant treatment (e.g. post-emergence application), generally from 0.5 to 1000 g of safener/ha, preferably from 2 to 500 g of safener/ha, more preferably from 5 to 200 g of safener/ha, is applied.

In one particular embodiment, the composition or mixture comprising the compound of formula (I) and one or more further herbicides (e.g. as mentioned hereinabove) can be applied together with one of the safeners mentioned herein, e.g. hereinabove.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Tables A1, A2, A3 or P1 below, are usually drawn as an arbitrary single enol tautomer, but it should be inferred that this description covers both the diketone form and any possible enols which could arise through tautomerism. Where more than one tautomer is observed in proton NMR ($^1$H NMR), the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

Abbreviations Used Herein:

DCM—dichloromethane
DMF—N,N-dimethylformamide
DMSO—dimethyl sulfoxide
EDTA—ethylenediaminetetraacetic acid
Hunig's base—N,N-diisopropylethylamine
LDA—lithium diisopropylamide
LiHMDS—lithium hexamethyldisilazide, also called lithium 1,1,1,3,3,3-hexamethyldisilazan-2-ide, or lithium bis(trimethylsilyl)amide
P2tBu—1-tert-butyl-2,2,4,4,4-pentakis(dimethylamino)-2$\lambda^5$,4$\lambda^5$-catenadi(phosphazene)
PTFE—polytetrafluoroethylene
SPhos (S-Phos)—2-(dicyclohexylphosphino)-2',6'-dimethoxybiphenyl
TFA—trifluoroacetic acid
THF—tetrahydrofuran
RT—room temperature (typically ca. 15-30° C. such as ca. 18-25° C.)
HPLC—high performance (or high pressure) liquid chromatography
MS—mass spectrometry
NMR—nuclear magnetic resonance
within $^1$H NMR spectral data given herein: s=singlet, d=doublet, t=triplet, q=quartet, dd=doublet of doublets, m=multiplet, br.=broad
SFC—supercritical fluid chromatography Intermediate 1

Preparation of 3-methoxy-2-(2,4,6-trimethylphenyl)-cyclopent-2-en-1-one (previously described as Example 1 step 1 on pages 54-55 of WO 2010/000773 A1)

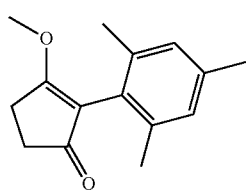

To a suspension of 2-bromo-3-methoxy-cyclopent-2-en-1-one (6.75 g, 35.3 mmol), 2,4,6-trimethylphenyl boronic acid (6.99 g, 42.6 mmol) and freshly ground potassium phosphate (15 g, 70.6 mmol) in degassed toluene (180 ml) under nitrogen are added Pd(OAc)$_2$ (159 mg, 0.71 mmol) and S-Phos (2-(dicyclohexylphosphino)-2',6'-dimethoxybiphenyl) (579 mg, 1.41 mmol), and the reaction heated to 90° C. with stirring under nitrogen for 4 hours. The reaction mixture is partitioned between ethyl acetate (150 ml) and water (150 ml), and the organic layer is removed, silica gel is added to the organic layer, the solvent is evaporated under reduced pressure and the residue is purified by flash chromatography on silica gel to give 3-methoxy-2-(2,4,6-trimethylphenyl)-cyclopent-2-en-1-one (6.2 g).

Example 1

Synthesis of Compound A1

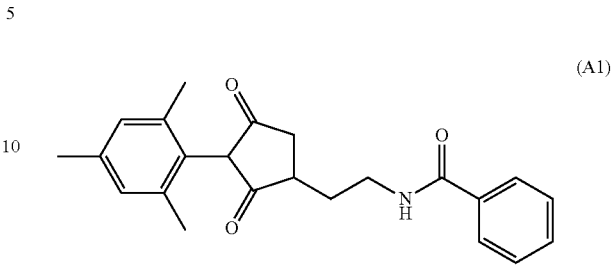

Step One: Synthesis of 2-nitroethyl trifluoromethanesulfonate

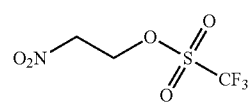 [SMILES: O=[N+]([O-])CCOS(=O)(=O)C(F)(F)F]

To a stirred solution of 2-nitroethanol (4.88 ml, 68 mmol) in dichloromethane (200 ml) at 0° C. was added pyridine (11 ml, 136 mmol) followed by dropwise addition of trifluoromethanesulfonic anhydride. The colour of the reaction transitioned from pale pink through dark red to yellow during the addition of the anhydride. The reaction was allowed to warm to room temperature over three hours and then quenched by cautious addition of H$_2$O (200 ml). The phases were separated and the aqueous phase was extracted with further dichloromethane (2×100 ml). The combined organics were washed with saturated aqueous NH$_4$Cl solution (100 ml) and H$_2$O (100 ml), dried over MgSO$_4$, filtered and evaporated to dryness under reduced pressure to give the desired product (4.2 g, 28%) as a yellow/brown oil with was used in subsequent steps without additional purification. $^1$H NMR (400 MHz, CDCl$_3$) $\delta_H$ 5.00 (t, 2H), 4.75 (t, 2H). $^{19}$F NMR (375 MHz, CDCl$_3$)$\delta_F$-74.1

Step Two: Synthesis of 3-methoxy-5-(2-nitroethyl)-2-(2,4,6-trimethylphenyl)cyclopent-2-en-1-one

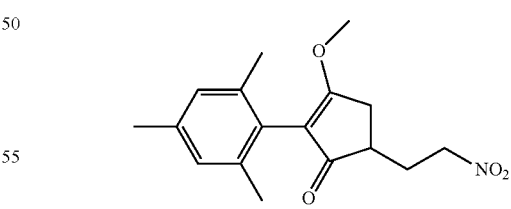

To a stirred solution of 3-methoxy-2-(2,4,6-trimethylphenyl)cyclopent-2-en-1-one (2.30 g, 10.0 mmol) (e.g. preparable by the method shown in Intermediate 1 herein, or preparable by method(s) disclosed in WO 2010/069834 A1 and/or WO 2011/073060 A2) in tetrahydrofuran (100 ml) at −78° C. under an atmosphere of N$_2$ was added dropwise lithium diisopropylamide (6.11 ml of a 1.8M solution in tetrahydrofuran/ethylbenzene/heptane, 11.0 mmol). The reaction was stirred at −78° C. for 105 minutes and then a solution of 2-nitroethyl trifluoromethanesulfonate (2.68 g, 12.0 mmol) in tetrahydrofuran (10 ml) was added dropwise. The reaction was stirred at −78° C. for 30 minutes and then allowed to warm to room temperature. The reaction was quenched cautiously with H$_2$O (200 ml) and extracted with EtOAc (3×100 ml). The combined organic extracts were washed with brine (50 ml), dried over MgSO$_4$, filtered and evaporated to dryness under reduced pressure to give a brown oil. The crude product was purified by flash chromatography over silica using a 100% hexane to 100% EtOAc gradient to give the desired compound (780 mg, 26%) as a colourless oil. $^1$H NMR (400 MHz, CDCl$_3$) δ 6.85 (s, 2H), 4.65 (t, 2H), 3.70 (s, 3H), 3.05 (dd, 1H), 2.75-2.65 (m, 1H) 2.55-2.40 (m, 2H), 2.30 (s, 3H), 2.30 (m, 1H), 2.05 (s, 6H).

Step Three: Synthesis of 5-(2-aminoethyl)-3-methoxy-2-(2,4,6-trimethylphenyl)cyclopent-2-en-1-one

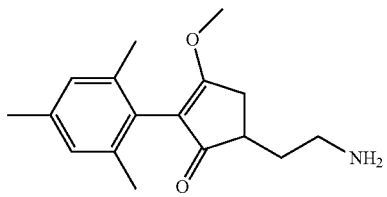 [SMILES: COC1=C(c2c(C)cc(C)cc2C)C(=O)C(CCN)C1]

To a stirred solution of 3-methoxy-5-(2-nitroethyl)-2-(2,4,6-trimethylphenyl)cyclopent-2-en-1-one (108 mg, 0.356 mmol) in MeOH (10 ml) under an N$_2$ atmosphere was added ammonium formate (67 mg, 1.07 mmol) followed by 10% Pd/C (5 mg, catalytic). The reaction was heated at reflux for 1 hour, allowed to cool to room temperature and then filtered through a pad of celite, washing through with further MeOH (10 ml). The solvent was removed under reduced pressure to give the crude product (64 mg) which was used without further purification. $^1$H NMR (400 MHz, CDCl$_3$) δ 6.85 (s, 2H), 3.70 (s, 3H), 2.95 (dd, 1H), 2.90-2.75 (m, 2H), 2.75-2.65 (m, 1H), 2.50 (d, 1H), 2.25 (s, 3H), 2.10-2.05 (m, 1H), 2.05 (2×s, 2×3H), 1.65-1.55 (m, 1H).

Step Four: Synthesis of N-[2-[4-methoxy-2-oxo-3-(2,4,6-trimethylphenyl)cyclopent-3-en-1-yl]ethyl]benzamide

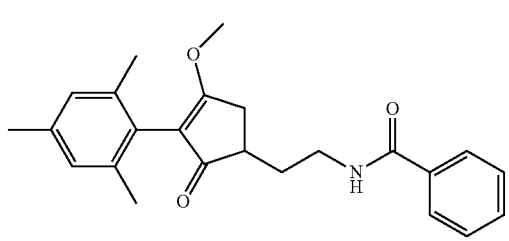 [SMILES: COC1=C(c2c(C)cc(C)cc2C)C(=O)C(CCNC(=O)c2ccccc2)C1]

To a stirred solution of the crude 5-(2-aminoethyl)-3-methoxy-2-(2,4,6-trimethylphenyl)cyclopent-2-en-1-one (64 mg, 0.234 mmol) in dichloromethane (5 ml), was added Et$_3$N (65 ul, 0.468 mmol) followed by benzoyl chloride (29 ul, 0.25 mmol). The reaction was stirred at room temperature for 72 hours and then quenched with H$_2$O (15 ml) and extracted with EtOAc (3×10 ml). The combined organic extracts were washed with brine (10 ml), dried over MgSO$_4$, filtered and evaporated to dryness under reduced pressure to give a brown oil. The crude product was purified by flash chromatography over silica using a 100% hexane to 100% EtOAc gradient to give the desired product (61 mg, 69%) as a colourless oil. $^1$H NMR (400 MHz, CDCl$_3$) δ 7.80 (d, 2H), 7.50-7.35 (m, 4H), 6.85 (2×s, 2H), 3.80 (s, 3H), 3.70-3.60 (m, 2H), 3.10 (dd, 1H), 2.80-2.75 (m, 1H), 2.55 (d, 1H), 2.25 (s, 3H), 2.05 (2×s, 6H), 2.05-1.90 (2H, m).

Step Five: Synthesis of N-[2-[2,4-dioxo-3-(2,4,6-trimethylphenyl)cyclopentyl]ethyl]-benzamide

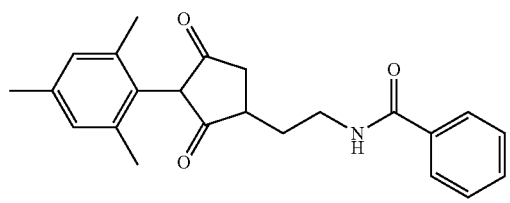 [SMILES: Cc1cc(C)c(C2C(=O)CC(CCNC(=O)c3ccccc3)C2=O)c(C)c1]

A solution of N-[2-[4-methoxy-2-oxo-3-(2,4,6-trimethylphenyl)cyclopent-3-en-1-yl]ethyl]benzamide (48 mg, 0.127 mmol) in acetone (1 ml) and 2M HCl (1 ml) was heated at 80° for 50 minutes under microwave irradiation. The reaction was cooled to room temperature, diluted with H$_2$O and extracted with EtOAc (3×10 ml). The combined organic extracts were washed with brine (10 ml), dried over MgSO$_4$, filtered and evaporated to dryness under reduced pressure to give a pale brown oil. The crude product was purified by flash chromatography over silica using a 100% hexane to 100% EtOAc gradient to give the desired product (25 mg, 54%) as a colourless oil. $^1$H NMR (400 MHz, d6-acetone) δ 8.30 (br, 1H), 7.97-7.93 (m, 2H), 7.60-7.55 (m, 1H), 7.50-7.45 (m, 2H), 6.85 (s, 2H), 3.80-3.70 (br, 1H), 3.60-3.50 (m, 1H), 3.00-2.70 (m, 2H), 2.25 (s, 3H), 2.15-2.05 (m, 1H), 2.05 (2×s, 2×3H), 1.95-1.90 (m, 1H)

Example 2

Synthesis of Compound A44

(A44)

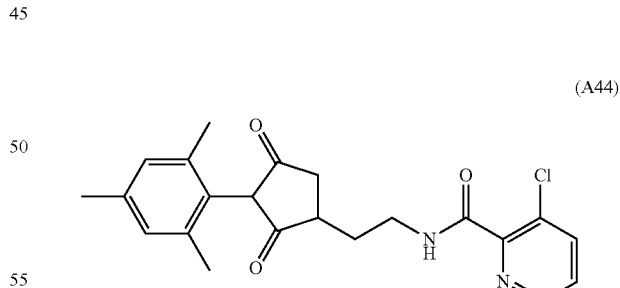

Step One: Synthesis of 1-nitroethylene

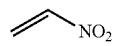

To a flask equipped with distillation apparatus was added nitroethanol (60.0 g, 0.44 mol) and phthalic anhydride (146.38 g, 0.66 mol). The flask was evacuated to 110 mmbar and the receiver flask cooled with dry ice and acetone. The mixture was then heated to 130° C. After 1 hr at 130° C. the temperature was slowly increased to 180° C. over 2 hrs. Once the distillation was complete the heating was removed and the distillate dissolved in 100 mL of anhydrous tetrahydrofuran, dried over anhydrous CaCl$_2$ and stored as a solution in tetrahydrofuran (33.34 g, 69%). $^1$H NMR (400 MHz, CDCl$_3$) δ 6.85-6.95(br, 1H), 6.25-6.35(br, 1H), 5.60-5.70(br s, 1H).

Step two: Synthesis of 3-methoxy-5-(2-nitroethyl)-2-(2,4,6-trimethylphenyl)cyclopent-2-en-1-one

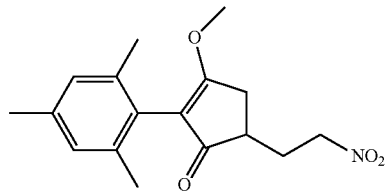 [SMILES: COC1=C(c2c(C)cc(C)cc2C)C(=O)C(CC[N+](=O)[O-])C1]

To a solution of 3-methoxy-2-(2,4,6-trimethylphenyl)cyclopent-2-en-1-one (2.50 g, 10.86 mmol) in anhydrous tetrahydrofuran (25 mL) at −78° C. under an argon atmosphere was added dropwise lithium diisopropylamide (1.8M in tetrahydrofuran, 6.03 mL, 10.86 mmol) keeping the temperature below −50° C. Once the addition was complete the mixture was allowed to stir for 30 mins. A solution of the nitroethylene (2.38 mL, 10.86 mmol) was then added dropwise over 1 hr using a dropping funnel. Once the addition was complete the mixture was stirred 30 mins before being allowed to warm to room temperature. After stirring 1 hr the reaction was quenched by the addition of water (50 mL) followed by saturated ammonium chloride solution (50 mL). The mixture was then extracted with ethyl acetate (3×20 mL). The combined organic extracts were dried, filtered and evaporated to dryness. The crude product was purified by flash chromatography over silica using a hexane/ethyl acetate gradient to give the desired product (2.00 g, 60%) as a colourless oil. $^1$H NMR (400 MHz, CDCl$_3$) δ 6.85 (s, 2H), 4.65 (t, 2H), 3.70 (s, 3H), 3.05 (dd, 1H), 2.75-2.65 (m, 1H) 2.55-2.40 (m, 2H), 2.30 (s, 3H), 2.30 (m, 1H), 2.05 (s, 6H).

Step Three: Synthesis of 5-(2-aminoethyl)-3-methoxy-2-(2,4,6-trimethylphenyl)cyclopent-2-en-1-one

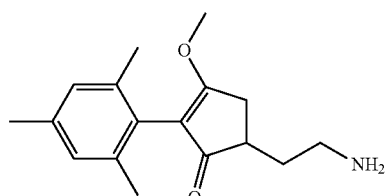

To a solution of 3-methoxy-5-(2-nitroethyl)-2-(2,4,6-trimethylphenyl)cyclopent-2-en-1-one (2.00 g, 6.59 mmol) in MeOH (40.0 mL) was added ammonium formate (2.08 g, 32.96 mmol) followed by palladium on carbon (10%, 0.50 g). The mixture was then stirred two hours at room temperature and then filtered through a pad of celite and the filtrate evaporated to dryness under reduced pressure. The residue was then dissolved in dichloromethane (20 mL) and washed with saturated sodium bicarbonate solution (2×10 mL). The organic phase was dried over magnesium sulphate, filtered and evaporated to dryness under reduced pressure to give the crude product (0.35 g, 19%) as a brown oil which was used without further purification. $^1$H NMR (400 MHz, d4-methanol) 6.86-6.89 (s, 2H), 4.64-4.70 (t, 2H), 3.71-3.73 (s, 3H), 3.00-3.08 (m, 1H), 2.66-2.75 (m, 1H), 2.39-2.52 (m, 2H), 2.24-2.32 (m, 4H), 2.06-2.09 (d, 6H).

Step Four: Synthesis of 3-chloro-N-[2-[2,4-dioxo-3-(2,4,6-trimethylphenyl)cyclopentyl]ethyl]pyridine-2-carboxamide

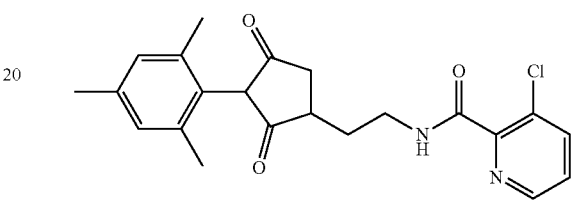

To a stirred solution of the 5-(2-aminoethyl)-3-methoxy-2-(2,4,6-trimethylphenyl)cyclopent-2-en-1-one (0.250 g, 0.91 mmol) in N,N-dimethylformamide (9 mL) was added Hunig's base (N,N-diisopropylethylamine) (0.40 mL, 2.29 mmol) and 3-chloropicolinic acid (0.16 g, 1.01 mmol). The reaction was then cooled to 0° C. and benzotriazol-1-yloxy (tripyrrolidin-1-yl)phosphonium hexafluorophosphate (0.97 g, 1.83 mmol) was added. Once the addition was complete the reaction was allowed to warm to room temperature and stirred two hours. The reaction was then evaporated to dryness under reduced pressure and the crude product carried forward to the next step without further purification.

To a solution of the crude enol ether in EtOH (4 mL) was added 2M hydrochloric acid (4 mL) and the mixture was then heated to 60° C. for 4 hours. The reaction was then allowed to cool to room temperature and then evaporated to dryness under reduced pressure. The crude product was then purified on a FractionLynx mass-directed purification system to give the desired product (0.072 g, 18%) as an off-white solid. $^1$H NMR (400 MHz, d4-methanol) δ, 8.50-8.54 (m, 1H), 7.94-7.98 (m, 1H), 7.47-7.52 (m, 1H), 6.84-6.88 (s, 2H) 3.49-3.64 (m, 2H), 2.91-2.99 (m, 1H), 2.81-2.90 (m, 1H), 2.47-2.55 (m, 1H), 2.16-2.27 (m, 4H), 2.03-2.07 (s, 6H), 1.67-1.78 (1H, m).

Example 3

Synthesis of Compound A84

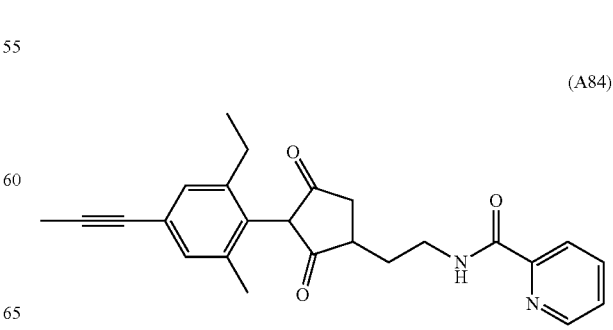

(A84)

Step One: Synthesis of 2-(4-bromo-2-ethyl-6-methyl-phenyl)-3-methoxy-5-(2-nitroethyl)cyclopent-2-en-1-one

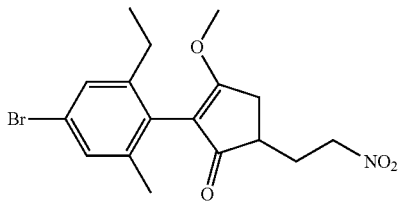 [SMILES: CCc1cc(Br)cc(C)c1C1=C(OC)CC(CC[N+](=O)[O-])C1=O]

To a solution of 2-(4-bromo-2-ethyl-6-methyl-phenyl)-3-methoxy-cyclopent-2-en-1-one (8.0 g, 25.87 mmol) in tetrahydrofuran (130 mL), under a nitrogen atmosphere at −50° C. to −60° C. was added dropwise lithium diisopropylamide solution (1.8M in tetrahydrofuran/ether/benzene) (25.87 mmol, 14.4 mL) keeping the temperature constant. The mixture was then stirred for 30 mins at −50° C. to −60° C. A solution of 1-nitroethylene (0.98 equiv., 25.36 mmol, 14.94 mL, 1.852 g) in tetrahydrofuran was then added very slowly, once again keeping the temperature constant. The reaction mixture was stirred for 30 mins before being allowed to warm to room temperature. The mixture was stirred at room temperature for 1 hr before being quenched by the addition of saturated ammonium chloride (100 ml). The mixture was then extracted with dichloromethane (3×100 ml). The combined organic extracts were dried over MgSO$_4$, filtered and evaporated to dryness under reduced pressure. The crude product was purified by flash chromatography over silica using an EtOAc/hexane gradient to give the desired product (5.64 g, 57%) as a brown oil. $^1$H NMR (400 MHz, CDCl$_3$) δ 7.22 (s, 2H), 4.67 (t, 2H), 3.75 (s, 3H), 3.10-3.03 (m, 1H), 2.75-2.65 (m, 1H), 2.50-2.15 (m, 5H), 2.09 (s, 3H), 1.15-1.08 (m, 3H).

Step Two: Synthesis of N-[2-[3-(4-bromo-2-ethyl-6-methyl-phenyl)-4-methoxy-2-oxo-cyclopent-3-en-1-yl]ethyl]pyridine-2-carboxamide

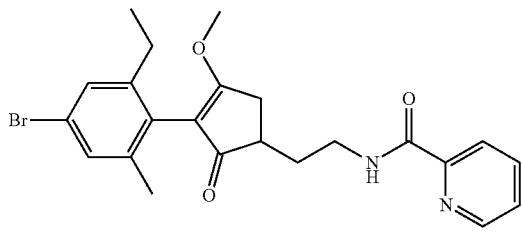 [SMILES: CCc1cc(Br)cc(C)c1C1=C(OC)CC(CCNC(=O)c2ccccn2)C1=O]

To a suspension of 2-(4-bromo-2-ethyl-6-methyl-phenyl)-3-methoxy-5-(2-nitroethyl)cyclopent-2-en-1-one (5.269 g, 13.79 mmol) in EtOH (70 mL) under a nitrogen atmosphere was added conc. HBr (10.54 mL, 194 mmol). Zn dust (1.80 g, 27.57 mmol) was added and the substrate immediately went into solution and an exotherm was observed. The reaction was brought back to room temperature using ice bath cooling and stirred at room temperature for 4 hrs. The reaction was then cooled to 0° C., and a further portion of Zn dust (1.80 g, 27.57 mmol) was added portion wise. The reaction was allowed to warm to room temperature, and stirred for a further 2 hours. The reaction was poured onto water (100 ml) and the pH was carefully adjusted to ~7 by the addition of saturated aqueous sodium hydrogen carbonate solution. The resulting white powder was filtered off, washed with saturated aqueous sodium hydrogen carbonate, hexane and a little ether and dried under reduced pressure to give the crude amine as a white solid (9.8 g).

To the crude amine (8.84 g) in dichloromethane (90 ml) at 10° C. was added Hunig's base (5.14 ml, 30.1 mmol) followed by portion wise addition of pyridine-2-carbonyl chloride hydrochloride (5.36 g, 30.1 mmol), keeping the temperature under 10° C. The reaction was then allowed to warm to room temperature and stirred for a further 3 hours. The reaction was quenched by the addition of saturated aqueous ammonium chloride (200 ml) and extracted with dichloromethane (2×200 ml). The combined organics were passed through a PTFE frit and purified by flash chromatography over silica to give the desired compound (1.27 g, 11%) as a sticky, off-white solid. $^1$H NMR (400 MHz, CDCl$_3$) δ (delta) 1.08 (td, 3H), 1.73-1.84 (m, 1H), 2.06 (s, 1.5H), 2.08 (s, 1.5H), 2.19-2.31 (m, 1H), 2.32-2.47 (m, 2H), 2.63 (dd, 1H), 2.70-2.79 (m, 1H), 3.10 (ddd, 1H), 3.55-3.66 (m, 1H), 3.69-3.76 (m, 1H), 3.78 (s, 3H), 7.18-7.25 (m, 2H), 7.44 (ddd, 1H), 7.86 (td, 1H), 8.19 (d, 1H), 8.27 (br. s., 1H), 8.56 (d, 1H).

Step Three: Synthesis of N-[2-[3-(2-ethyl-6-methyl-4-prop-1-ynyl-phenyl)-4-methoxy-2-oxo-cyclopent-3-en-1-yl]ethyl]pyridine-2-carboxamide

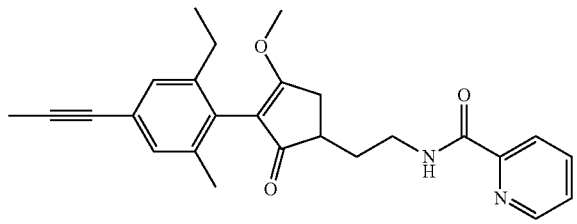 [SMILES: CC#Cc1cc(C)c(C2=C(OC)CC(CCNC(=O)c3ccccn3)C2=O)c(CC)c1]

To a flask charged with N-[2-[3-(4-bromo-2-ethyl-6-methyl-phenyl)-4-methoxy-2-oxo-cyclopent-3-en-1-yl] ethyl]pyridine-2-carboxamide (320 mg, 0.6996 mmol), Dichloro[1,1-bis(diphenylphosphino)ferrocene]palladium (II) dichloromethane adduct (78.4 mg, 0.105 mmol), Copper (I) iodide (27 mg, 0.14 mmol) and caesium fluoride (0.2147 g, 1.4 mmol) under a nitrogen atmosphere is added dry, degassed N,N-dimethylformamide (3.2 mL), followed by tributyl(1-propynyl)tin (0.2666 g, 0.77 mmol) and the reaction heated to 100° C. for 3 hours. The reaction was allowed to cool to room temperature and diluted with EtOAc (50 ml) and washed with saturated aqueous ammonium chloride (50 ml). The organic layer was separated, washed with saturated brine (2×50 ml), and the organic layer passed through a PTFE frit, dry loaded onto silica and purified by flash chromatography over silica using an EtOAc/hexane gradient to give the desired compound (0.184 g, 63%) as a mixture of atropisomers. $^1$H NMR (400 MHz, CDCl$_3$) δ (delta) 8.56 (d, 1H), 8.27 (br, 1H), 8.19 (d, 1H), 7.90-7.80 (m, 1H), 7.47-7.40 (m, 1H), 7.15-7.07 (m, 2H), 3.78-3.69 (m, 4H) 3.10-3.06 (m, 1H), 3.66-3.55 (m, 1H), 2.77-2.69 (m, 1H), 2.61 (dd, 1H) 2.4-2.32 (m, 2H), 2.31-2.21 (m, 1H), 2.07 (s, 1.5H), 2.05 (s, 1.5H), 2.03 (s, 3H), 1.85-1.73 (m, 1H), 1.10-1.06 (m, 3H).

Step Four: Synthesis of N-[2-[3-(2-ethyl-6-methyl-4-prop-1-ynyl-phenyl)-2,4-dioxo-cyclopentyl]ethyl]pyridine-2-carboxamide

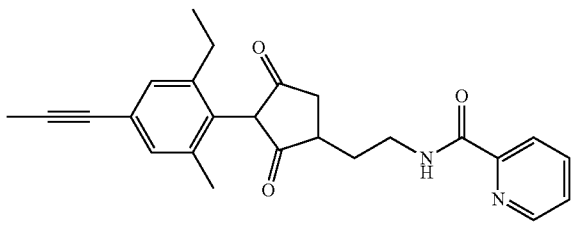 [SMILES: CC#Cc1cc(C)c(C2C(=O)CC(CCNC(=O)c3ccccn3)C2=O)c(CC)c1]

To a stirred solution of N-[2-[3-(2-ethyl-6-methyl-4-prop-1-ynyl-phenyl)-4-methoxy-2-oxo-cyclopent-3-en-1-yl]ethyl]pyridine-2-carboxamide (184 mg, 0.4418 mmol) in acetone (1 mL) was added 2M HCl (1 ml) and the reaction was heated to 50° C. for 5 hours. The reaction was concentrated under reduced pressure to remove excess acetone, diluted with EtOAc (25 ml) and extracted with 1M $K_2OC_3$ solution (25 ml). The organic layer was set aside and the aqueous layer was then acidified to pH6 with concentrated HCl (a precipitate was observed) and extracted with EtOAc (25 ml). This organic layer gave a poor recovery, so the initial EtOAc layer was washed with saturated aqueous ammonium chloride (25 ml), and combined with the other organic washing. This was then dry loaded onto silica and purified by flash chromatography over silica using a 2-10% MeOH in dichloromethane gradient to give the desired compound (105 mg, 59%) as a brown gum as a mixture of atropisomers. $^1$H NMR (400 MHz, CDCl$_3$) δ (delta) 1.12 (dt, 3H), 1.78-1.94 (m, 2H), 2.04 (s, 3H), 2.11 (s, 1.5H), 2.15 (s, 1.5H), 2.18 (d, 1H), 2.44 (dt, 2H), 2.81-3.04 (m, 2H), 3.35-3.53 (m, 1H), 4.04-4.25 (m, 1H), 7.05-7.19 (m, 2H), 7.46-7.60 (m, 1H), 7.91 (t, 1H), 8.22 (d, 1H), 8.61 (d, 1H), 8.69 (br. s., 1H), 12.25 (br. s., 1H).

Example 4

Synthesis of Compound A85

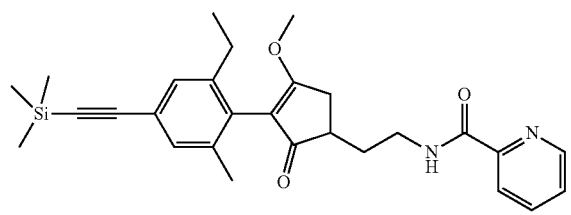 [SMILES: CCc1cc(C#C[Si](C)(C)C)cc(C)c1C1=C(OC)CC(CCNC(=O)c2ccccn2)C1=O]

(A85)

Step One: Synthesis of N-[2-[3-[2-ethyl-6-methyl-4-(2-trimethylsilylethynyl)phenyl]-4-methoxy-2-oxo-cyclopent-3-en-1-yl]ethyl]pyridine-2-carboxamide

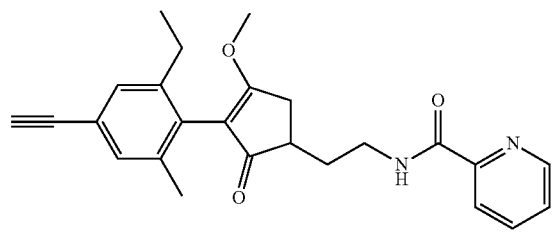 [SMILES: C#Cc1cc(C)c(C2=C(OC)CC(CCNC(=O)c3ccccn3)C2=O)c(CC)c1]

To a flask charged with N-[2-[3-(4-bromo-2-ethyl-6-methyl-phenyl)-4-methoxy-2-oxo-cyclopent-3-en-1-yl]ethyl]pyridine-2-carboxamide (314 mg, 0.69 mmol) and palladium-tetrakis(triphenylphosphine) (0.034 mmol, 0.04 g) under nitrogen was added degassed, dry toluene (10 ml), followed by trimethyl(2-tributylstannylethynyl)silane (0.83 mmol, 0.32 g), and the reaction heated to 100° C. for 17 hours. Reaction was filtered through a frit, dry loaded onto silica and purified by flash chromatography over silica using a 30-100% EtOAc in hexane gradient to give the desired compound (283 mg, 97%) as a pale yellow gum as a mixture of atropisomers. $^1$H NMR (400 MHz, CDCl$_3$) δ 8.56 (d, 1H), 8.27 (br s, 1H), 8.19 (d, 1H), 7.86 (td, 1H), 7.41-7.46 (m, 1H), 7.15-7.22 (m, 2H), 3.73-3.80 (m, 1H), 3.72 (s, 3H), 3.56-3.65 (m, 1H), 3.07 (ddd,1H), 2.69-2.78 (m, 1H), 2.61 (dd, 1H), 2.33-2.45 (m, 2H), 2.25 (dd, 1H), 2.07 (s, 1.5H), 2.05 (s, 1.5H), 1.75-1.84 (m, 1H), 1.08 (td, 3H), 0.21-0.26 (m, 9H).

Step Two: Synthesis of N-[2-[3-(2-ethyl-4-ethynyl-6-methyl-phenyl)-4-methoxy-2-oxo-cyclopent-3-en-1-yl]ethyl]pyridine-2-carboxamide To a solution of N-[2-[3-[2-ethyl-6-methyl-4-(2-trimethylsilylethynyl)phenyl]-4-methoxy-2-oxo-cyclopent-3-en-1-yl]ethyl]pyridine-2-carboxamide (283 mg, 0.5962 mmol) in tetrahydrofuran (10 mL) at 0° C. was added dropwise, tetrabutyl ammonium fluoride (1.0 mol/L) in tetrahydrofuran (3 equiv., 1.8 mL, 1.789 mmol, 1.0 mol/L) over a period of 2 minutes. The reaction was then allowed to warm to ambient and stirred for a further 90 minutes. The reaction was quenched by the addition saturated aqueous ammonium chloride (25 ml), and extracted with ethyl acetate (25 ml), the organic layer is then filtered through a PTFE frit, dry loaded onto silica and purified by flash chromatography over silica using a 50-100% EtOAc in hexane gradient to give the desired product as a mixture of atropisomers (207 mg, 86%) as a gum without need for further purification. $^1$H NMR (400 MHz, CDCl$_3$) δ 8.56 (d, 1H), 8.27 (br, 1H), 8.19 (d, 1H) 7.86 (td, 1H) 7.17-7.25 (m, 2H), 7.41-7.47 (m, 1H), 3.76 (s, 3H) 3.69-3.74 (m, 1H), 3.55-3.65 (m, 1H), 3.10 (ddd, 1H), 3.02 (s, 1H), 2.74 (ddd, 1H), 2.63 (dd, 1H), 2.34-2.45 (m, 2H), 2.20-2.32 (m, 1H) 2.09 (s, 1.5H), 2.07 (s, 1.5H), 1.73-1.85, (m, 1H) 1.09 (td, 3H).

Step Three: Synthesis of N-[2-[3-(2-ethyl-4-ethynyl-6-methyl-phenyl)-2,4-dioxo-cyclopentyl]ethyl]pyridine-2-carboxamide

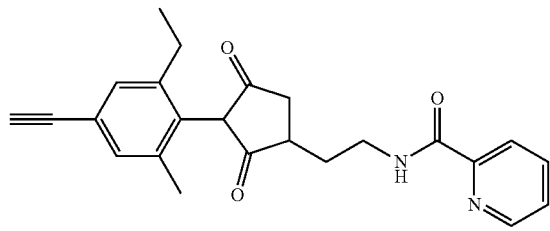 [SMILES: C#Cc1cc(C)c(C2C(=O)CC(CCNC(=O)c3ccccn3)C2=O)c(CC)c1]

To a solution of N-[2-[3-(2-ethyl-4-ethynyl-6-methyl-phenyl)-4-methoxy-2-oxo-cyclopent-3-en-1-yl]ethyl]pyridine-2-carboxamide (207 mg, 0.5143 mmol) in acetone (1 mL) was added 2 N HCl (1 mL) and the reaction heated to 50° C. for 5 hours. The reaction was concentrated in vacuo to remove excess acetone, diluted with 2 N HCl (25 ml), and extracted with EtOAc (25 ml) (the organic layer was reserved). The aqueous layer was then adjusted to pH6 with 2N $K_2CO_3$ and extracted with EtOAc (25 ml). The initial EtOAc layer was washed with saturated aqueous ammonium chloride (25 ml), and combined with the other organic washing. This was then dry loaded onto silica and purified by flash chromatography over silica using a 2-10% MeOH in dichloromethane gradient to give the desired product (167 mg, 84%) as a sticky solid. $^1$H NMR (400 MHz, $CDCl_3$) δ (delta) 1.05-1.18 (m, 3H), 1.87 (t, 1H), 2.10-2.23 (m, 4H), 2.40-2.56 (m, 2H), 2.83-3.00 (m, 2H), 3.01 (s, 1H), 3.43 (d, 1H), 4.08-4.21 (m, 1H), 7.20-7.26 (m, 2H), 7.42-7.50 (m, 1H), 7.92 (t, 1H), 8.22 (d, 1H), 8.61 (d, 1H), 8.71 (br. s., 1H).

Example 5

Synthesis of Compound A86

(A86)

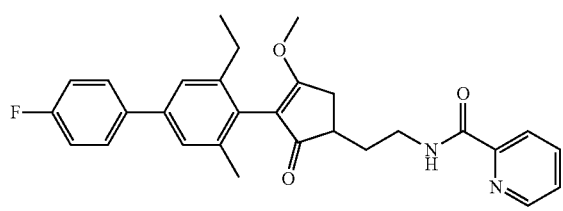 [SMILES: CCc1cc(-c2ccc(F)cc2)cc(C)c1C1=C(OC)CC(CCNC(=O)c2ccccn2)C1=O]

Step One: Synthesis of N-[2-[3-[2-ethyl-4-(4-fluorophenyl)-6-methyl-phenyl]-4-methoxy-2-oxo-cyclopent-3-en-1-yl]ethyl]pyridine-2-carboxamide

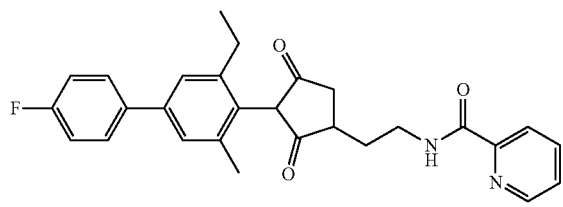

To a solution of N-[2-[3-(4-bromo-2-ethyl-6-methyl-phenyl)-4-methoxy-2-oxo-cyclopent-3-en-1-yl]ethyl]pyridine-2-carboxamide (200 mg, 0.4373 mmol) in 1,4-dioxane (2 mL) was added cesium fluoride (3 equiv., 1.312 mmol, 0.1993 g), (4-fluorophenyl)boronic acid (1.5 equiv., 0.6559 mmol, 0.09177 g) and bis(diphenylphosphino)ferrocenedichloropalladium (II) (0.2 equiv., 0.08745 mmol, 0.06399 g). The reaction was then heated under microwave irradiation at 120° C. for 45 mins. The reaction was diluted with ethyl acetate (20 ml) and filtered through celite. The organic filtrate was then reduced in vacuo before purification by flash chromatography over silica using an EtOAc/hexane gradient to give the desired product (183 mg, 89%) as a brown gum.

Step Two: Synthesis of N-[2-[3-[2-ethyl-4-(4-fluorophenyl)-6-methyl-phenyl]-2,4-dioxo-cyclopentyl]ethyl]pyridine-2-carboxamide

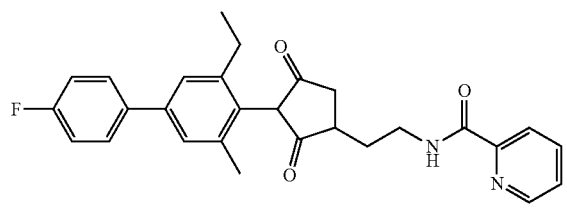 [SMILES: CCc1cc(-c2ccc(F)cc2)cc(C)c1C1C(=O)CC(CCNC(=O)c2ccccn2)C1=O]

To a solution of N-[2-[3-[2-ethyl-4-(4-fluorophenyl)-6-methyl-phenyl]-4-methoxy-2-oxo-cyclopent-3-en-1-yl]ethyl]pyridine-2-carboxamide (187 mg, 0.3957 mmol) in acetone (1 mL) was added 2 N HCl (1 mL) and the reaction heated to 50° C. for 5 hours. The reaction was concentrated in vacuo to remove excess acetone, the aqueous layer adjusted to a pH of about 7 with 2N $K_2CO_3$ followed by saturated aqueous ammonium chloride (25 ml) and extracted with EtOAc (25 ml). The organic layer is dry loaded onto silica and purified by flash chromatography over silica using a 50-100% EtOAc in hexane gradient to give the desired product (169 mg, 93% yield) as a mixture of atropisomers. $^1$H NMR (400 MHz, $CDCl_3$) δ 12.35 (br, 1H), 8.71 (br, 1H), 8.62 (d, 1H), 8.23 (d, 1H), 7.96-7.88 (m, 1H), 7.57-7.49 (m, 3H), 7.26 (s, 2H), 7.10 (t, 2H), 4.18 (d, 1H), 3.44 (d, 1H), 3.04-2.96 (m, 1H), 2.96-2.88 (m, 1H), 2.58-2.54 (m, 2H), 2.26 (s, 1.5H), 2.22 (s, 1.5H), 2.26-2.17 (m, 2H), 1.89 (t, 1H), 1.20-1.16 (m, 3H).

Example 6

Synthesis of Compound A87

(A87)

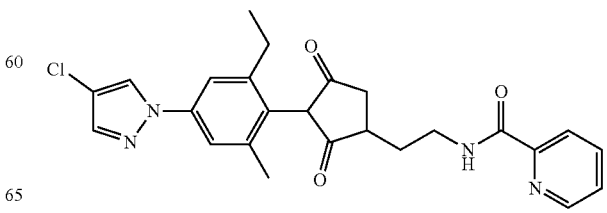

Step One: Synthesis of N-[2-[3-[4-(4-chloropyrazol-1-yl)-2-ethyl-6-methyl-phenyl]-2,4-dioxo-cyclopentyl]ethyl]pyridine-2-carboxamide

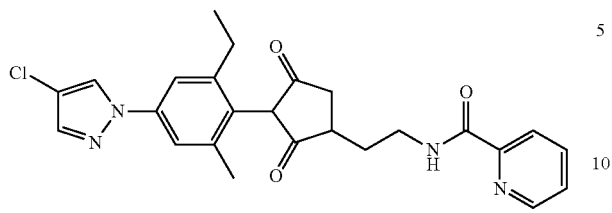

To a 3-neck flask charged with N-[2-[3-(4-bromo-2-ethyl-6-methyl-phenyl)-4-methoxy-2-oxo-cyclopent-3-en-1-yl]ethyl]pyridine-2-carboxamide (340 mg, 0.7433 mmol) was added 4-chloropyrazole (2 equiv., 1.487 mmol, 0.1524 g), copper iodide (2 equiv., 1.487 mmol, 0.2831 g), dimethyl glycine (4 equiv., 2.973 mmol, 0.3066 g) and potassium carbonate (4 equiv., 2.973 mmol, 0.4151 g) and the vessel was purged with nitrogen. Dimethyl sulfoxide (anhydrous) (6.8 mL) was then added, and the reaction heated to 140° C. for 90 mins. The reaction was filtered through a PTFE frit, diluted with EtOAc (50 ml) and extracted with 2N $K_2CO_3$ (25 ml). The organic layer was neutralised with saturated aqueous ammonium chloride (50 ml) and extracted with EtOAc (50 ml) and washed with brine (3×50 ml). The organic layer was then filtered through a PTFE frit, dry loaded onto silica and purified by flash chromatography over silica using an EtOAc/hexane gradient to give the desired product (63 mg, 18%) as a brown gum. $^1$H NMR (400 MHz, $CDCl_3$) δ 8.71 (br s, 1H), 8.61 (d, 1H), 8.22 (d, 1H), 7.84-8.01, (m, 2H), 7.62 (s, 1H), 7.49-7.57 (m, 1H), 7.32-7.40 (m, 2H), 4.11-4.25 (m, 1H), 3.46 (br s, 1H), 2.83-3.05 (m, 2H), 2.54 (dt, 2H), 2.23 (d, 5H), 1.88 (br s, 1H), 1.11-1.23 (m, 3H).

Example 7

Chiral HPLC separation of enantiomers of compound A34 (to compounds A98 and A99)

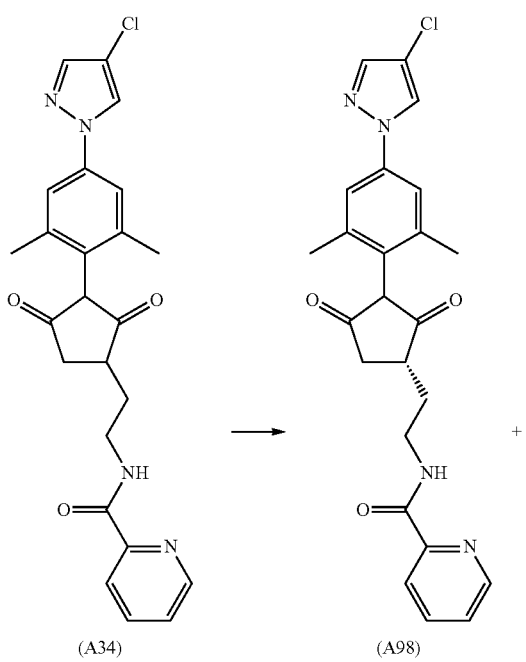

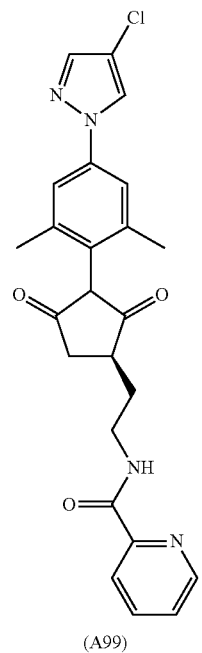

(A99)

Compound A34 (racemic), was separated into the enantiomer compounds A98 and A99 using a chiral HPLC column, by the following method and under the following conditions.

The chiral HPLC column used was a (s,s) WhelkO1—5 micron—21 mm×250 mm HPLC column, manufactured by Regis Technologies, Inc. In this column, the chiral stationary phase is (S,S) 1-(3-5-dinitrobenzamido)-1,2,3,4-tetrahydrophenanthrene.

The solvent system used as an eluent for the column was a 30:70 (by volume) mixture of Solvent A and Solvent B, in which:

Solvent A is isohexane containing 0.1% v/v of trifluoroacetic acid (TFA), and Solvent B is ethanol.

Other conditions were as follows:

Flow rate through column: 21 ml/minute. Run time: 20 minutes.

Loading (compound loaded onto column): 50 mg/ml of compound in ethanol.

Volume of sample (compound) injected per run=1800 microliters.

Number of injections of compound=5.

Amount of racemic compound A34 used: 350 mg

Chiral HPLC on a total of 350 mg of compound A34 under the above conditions gave 131 mg of compound A98 (100% enantiomeric excess (e.e.), retention time 12.04 minutes under the above conditions) and 135 mg of compound A99 (99.1% enantiomeric excess (e.e.), retention time 14.26 minutes under the above conditions).

Abbreviation: HPLC=high performance (or high pressure) liquid chromatography.

Alternative Embodiment: Chiral HPLC Separation of Compound A87 into Enantiomer Compounds A100 and A101

Using generally similar conditions (e.g. see above, and see below), compound A87 was separated into enantiomer compounds A100 and A101.

General Note on Chiral HPLC Separation of Enantiomers:

The above procedure using chiral HPLC can be used to separate the enantiomers of other compounds of formula (I)

of the present the invention. Chiral columns which might be useful to achieve this are as follows:

(s,s) WhelkO1—5 micron—21 mm×250 mm HPLC column, manufactured by Regis Technologies, Inc [in this column, the chiral stationary phase is (S,S) 1-(3-5-dinitrobenzamido)-1,2,3,4-tetrahydrophenanthren];

Kromasil® AmyCoat™ [whose chiral stationary phase is tris-(3,5-dimethylphenyl)carbamoyl amylose];

Kromasil® CelluCoat™ [whose chiral stationary phase is tris-(3,5-dimethylphenyl)carbamoyl cellulose];

Chiralpak® IA [whose chiral stationary phase is a (3,5-dimethylphenyl)carbamate derivative of amylose];

Chiralpak® IB [whose chiral stationary phase is tris-(3,5-dimethylphenyl)carbamate derivative of cellulose];

Chiralpak® IC [whose chiral stationary phase is cellulose tris(3,5-dichlorophenyl)carbamate];

Lux® Amylose-2 [whose chiral stationary phase is amylose tris(5-chloro-2-methylphenylcarbamate)]; or Lux® Cellulose-2 [whose chiral stationary phase is Cellulose tris(3-chloro-4-methylphenylcarbamate)].

Intermediate 2

Preparation of 2-(4-bromo-2,6-dimethyl-phenyl)-3-methoxy-cyclopent-2-en-1-one

Step 1: Preparation of ([4-bromo-2,6-dimethylphenyl]furan-2-yl)methanol (previously described in Example 1 step 1 on pages 51-52 of WO 2010/089210 A1)

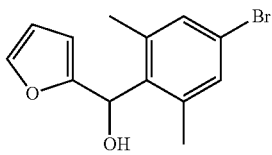 [SMILES: Cc1cc(Br)cc(C)c1C(O)c1ccco1]

4-bromo-2,6-dimethyl-1-iodobenzene (5 g, 16 mmol) is dissolved in dry tetrahydrofuran (20 ml) and cooled to −78° C. under an atmosphere of dry nitrogen. Isopropylmagnesium chloride (2M solution in tetrahydrofuran, 10 ml, 20 mmol) is added dropwise with vigorous stirring over 30 minutes. When the addition is complete, the reaction is allowed to warm to room temperature and is stirred for 30 minutes at room temperature. The reaction mixture is cooled to −78° C. and a solution of 2-furaldehyde (2.4 g, 25 mmol) in dry tetrahydrofuran (10 ml) is added dropwise over 30 minutes. Once the addition is complete, the mixture is allowed to warm to room temperature and stirring continued for 2 hours. A solution of saturated aqueous ammonium chloride (30 ml) is added, and the mixture is extracted with dichloromethane (3×25 ml). The organic extracts are combined, washed with brine, dried over anhydrous magnesium sulfate, filtered and the filtrate is evaporated under reduced pressure. The residue is purified by column chromatography on silica gel to give ([4-bromo-2,6-dimethylphenyl]furan-2-yl)methanol (3.71 g).

Step 2: Preparation of 5-(4-bromo-2,6-dimethylphenyl)-4-hydroxycyclopent-2-enone (previously described in Example 1 step 2 on page 52 of WO 2010/089210 A1)

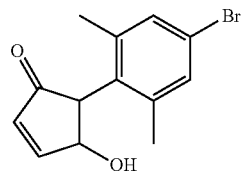 [SMILES: Cc1cc(Br)cc(C)c1C1C(=O)C=CC1O]

Polyphosphoric acid (500 mg) is added to a warm (55° C.) solution of ([4-bromo-2,6-dimethylphenyl]furan-2-yl) methanol (843 mg, 3 mmol) in acetone (8 ml) and water (2 ml) and the mixture is heated at 55° C. for 24 hours. The mixture is cooled to room temperature and the acetone is removed under reduced pressure. The remaining mixture is partitioned between diethyl ether (20 ml) and water (20 ml). The aqueous phase is extracted with ether (2×50 ml), and then the organic phases are combined, washed with saturated aqueous sodium bicarbonate solution (20 ml), and brine (20 ml), dried over anhydrous magnesium sulfate, filtered and the filtrate is evaporated under reduced pressure. The residue is purified by column chromatography on silica gel to give 5-(4-bromo-2,6-dimethylphenyl)-4-hydroxycyclopent-2-enone (596 mg).

Step 3: Preparation of 2-(4-bromo-2,6-dimethylphenyl)cyclopent-4-ene-1,3-dione (previously described in Example 1 step 3 on page 52 of WO 2010/089210 A1)

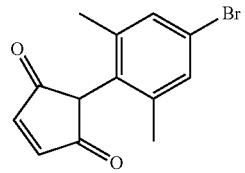 [SMILES: Cc1cc(Br)cc(C)c1C1C(=O)C=CC1=O]

To a solution of 5-(4-bromo-2,6-dimethylphenyl)-4-hydroxycyclopent-2-enone (18.33 g. 65 mmol) in acetone (200 ml) at 0° C. is added, dropwise, a solution of Jones reagent (1.67 M, 39 ml, 65 mmol) and the resulting yellow solution is stirred at 0° C. for 90 minutes. The reaction is quenched by the addition of propan-2-ol (1 ml) and stirred for a further 2 hours. Brine (300 ml) is added and the reaction is extracted with ethyl acetate (3×250 ml). The organic extracts are combined, washed with brine, dried over anhydrous magnesium sulfate, filtered and the filtrate is concentrated under reduced pressure. The residue is purified by column chromatography on silica gel to give 2-(4-bromo-2,6-dimethylphenyl)cyclopent-4-ene-1,3-dione (17.2 g).

Step 4: Preparation of 2-(4-Bromo-2,6-dimethyl-phenyl)cyclopentane-1,3-dione

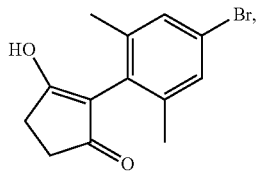

also present as

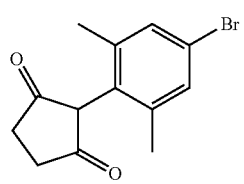 [SMILES: Cc1cc(Br)cc(C)c1C1C(=O)CCC1=O]

To a solution of 2-(4-bromo-2,6-dimethylphenyl)cyclo-pent-4-ene-1,3-dione (50 g, 0.18 mol) in acetic acid (2000 ml) at 25-30° C. is added zinc powder (82.3 g, 1.26 mol). The resulting suspension is heated to 90° C. for 2 hours, followed by cooling to room temperature then filtration through a bed of diatomaceous earth. The residue is washed with methanol (100 ml×2) and the solution is concentrated in vacuo. Distilled water is added and the crude product is extracted with ethyl acetate (500 ml×3). Organic fractions are combined then washed with distilled water, brine, then dried over sodium sulfate, filtered and the filtrate is concentrated in vacuo to afford 2-(4-bromo-2,6-dimethylphenyl)cyclopentane-1,3-dione. This material is used directly in the next step without further purification.

Step 5: Preparation of 2-(4-bromo-2,6-dimethyl-phenyl)-3-methoxy-cyclopent-2-en-1-one

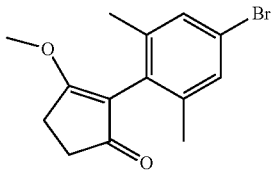 [SMILES: COC1=C(c2c(C)cc(Br)cc2C)C(=O)CC1]

To a solution of 2-(4-bromo-2,6-dimethylphenyl)cyclo-pentane-1,3-dione (40 g, 0.143 mol) in acetone (2000 ml) is added anhydrous potassium carbonate (98.5 g, 0.714 mol) and iodomethane (45 ml, 0.72 mol). The resulting mixture is stirred at 25-30° C. for 16 hours, then volatile solvents are removed in vacuo, and the residue is diluted with distilled water (200 ml) and extracted with ethyl acetate (3×500 ml). Organic fractions are combined, washed with distilled water, brine, then dried over sodium sulphate, filtered and the filtrate concentrated in vacuo. The crude product is purified by flash column chromatography to afford 2-(4-bromo-2,6-dimethyl-phenyl)-3-methoxy-cyclopent-2-en-1-one.

Example 8

Synthesis of Compound A126

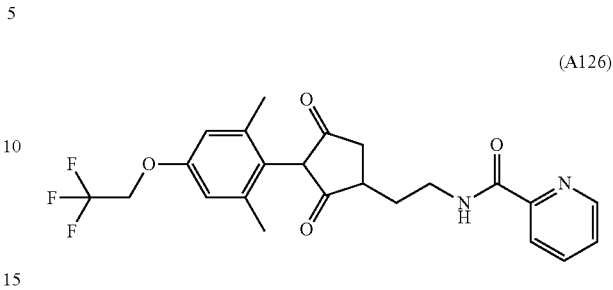

(A126)

Step One: Synthesis of 2-[3-(4-bromo-2,6-dimethyl-phenyl)-2-methoxy-4-oxo-cyclopent-2-en-1-yl]acetonitrile

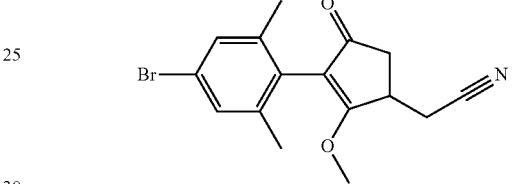

To a solution of 2-(4-bromo-2,6-dimethyl-phenyl)-3-methoxy-cyclopent-2-en-1-one (11.0 g, 37.3 mmol) (which can e.g. be prepared by the method described in Intermediate 2 herein) in dry THF (90 mL) at −78° C. was added potassium hexamethyldisilazide (45 mL, 41 mmol, 0.91 mol/L in THF) over 2 min. The mixture was warmed to 0° C. and stirred for 30 min, then cooled to −78° C. 2-Bromo-acetonitrile (2.90 mL, 41.6 mmol) was added dropwise and the mixture was then warmed to 0° C. and stirred for 1 h. 0.5M saturated aqueous NH$_4$Cl (200 mL) was added and the THF was removed under reduced pressure. The residue was extracted with ethyl acetate (2×100 mL) and the combined organic layers were washed with brine (50 mL), then dried over MgSO$_4$ and concentrated under reduced pressure. The residue was purified by flash chromatography over silica using an EtOAc/hexane gradient to give the desired product (6.42 g, 52%) as a pale brown solid. $^1$H NMR (400 MHz, CDCl$_3$) δ 7.24 (s, 1H), 7.23 (s, 1H), 3.57 (s, 3H), 3.20-3.30 (m, 1H), 2.73-2.93 (m, 3H), 2.50 (dd, 1H), 2.21 (s, 3H), 2.12 (s, 3H).

Step Two: Synthesis of 2-[3-[2,6-dimethyl-4-(4,4,5,5-tetramethyl-1,3,2-dioxaborolan-2-yl)phenyl]-2-methoxy-4-oxo-cyclopent-2-en-1-yl]acetonitrile

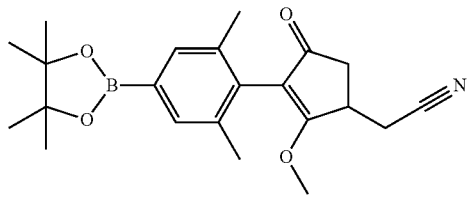 [SMILES: COC1=C(c2c(C)cc(B3OC(C)(C)C(C)(C)O3)cc2C)C(=O)CC1CC#N]

To a mixture of 2-[3-(4-bromo-2,6-dimethyl-phenyl)-2-methoxy-4-oxo-cyclopent-2-en-1-yl]acetonitrile (10.80 g, 32.3 mmol), 4,4,5,5-tetramethyl-2-(4,4,5,5-tetramethyl-1,3,2-dioxaborolan-2-yl)-1,3,2-dioxaborolane (11.8 g, 45.8 mmol), potassium acetate (4.36 g, 44.4 mmol) and SPhos (1.01 g, 2.39 mmol) in 1,4-dioxane (150 mL) was added tris(dibenzylideneacetone)dipalladium(0) (1.10 g, 1.20 mmol). The mixture was degassed by stirring with nitrogen bubbling for 10 min, then heated at 85° C. for 4 h total, then cooled to room temperature. The solvent was removed under reduced pressure, and the residue was dissolved in ethyl acetate (80 mL) and filtered through celite, rinsing with water (50 mL). The Phases were separated and the aqueous layer was extracted with ethyl acetate (50 mL). The combined organic layers were washed with brine (50 mL), then dried over MgSO$_4$ and concentrated under reduced pressure. The residue was purified by flash chromatography over silica using an EtOAc/hexane gradient and the material obtained was purified further by trituration with EtOAc/hexane to give the desired product (8.78 g, 71%) as a beige solid. $^1$H NMR (400 MHz, CDCl$_3$) δ (delta) 7.52 (s, 1H), 7.50 (s, 1H), 3.53 (s, 3H), 3.21-3.30 (m, 1H), 2.89 (dd, 1H), 2.74-2.85 (m, 2H), 2.50 (dd, 1H), 2.23 (s, 3H), 2.15 (s, 3H), 1.34 (s, 12H).

Step Three: Synthesis of N-[2-[3-[2,6-dimethyl-4-(4,4,5,5-tetramethyl-1,3,2-dioxaborolan-2-yl)phenyl]-2-methoxy-4-oxo-cyclopent-2-en-1-yl]ethyl]pyridine-2-carboxamide

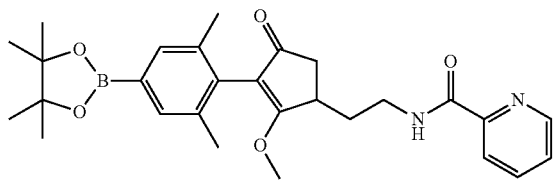 [SMILES: COC1=C(c2c(C)cc(B3OC(C)(C)C(C)(C)O3)cc2C)C(=O)CC1CCNC(=O)c1ccccn1]

An autoclave was charged with Raney Nickel (2800) (7.3 g), (2,3,4,5,6-pentafluorophenyl)pyridine-2-carboxylate (5.70 g, 19.7 mmol), 2-[3-[2,6-dimethyl-4-(4,4,5,5-tetramethyl-1,3,2-dioxaborolan-2-yl)phenyl]-2-methoxy-4-oxo-cyclopent-2-en-1-yl]acetonitrile (5.00 g, 13.1 mmol) in 1,2-dimethoxyethane (125 mL). The mixture was pressurised to 3.5 Bar with hydrogen and stirred vigorously at room temperature, with further Raney Nickel (2800) (2.0 g) being added at 2 h intervals before continuing the reaction under the same conditions. After a total of 6 h, the mixture was filtered through Celite™, rinsing with dimethoxyethane then with methanol. The filtrate was concentrated under reduced pressure and the residue was purified by flash chromatography over silica using an EtOAc/hexane gradient to give the desired product (4.59 g, 71%) as a pale yellow foam. $^1$H NMR (400 MHz, CDCl$_3$) δ (delta) ppm 8.55 (d, 1H), 8.17-8.24 (m, 2H), 7.86 (td, 1H), 7.49 (s, 2H), 7.44 (ddd, 1H), 3.58-3.69 (m, 2H), 3.49 (s, 3H), 3.02 (dddd, 1H), 2.84 (dd, 1H), 2.38 (dd, 1H), 2.22-2.33 (m, 1H), 2.15 (d, 6H), 1.79 (dq, 1H), 1.33 (s, 12H).

Step Four: Synthesis of N-[2-[3-[2,6-dimethyl-4-(2,2,2-trifluoroethoxy)phenyl]-2,4-dioxo-cyclopentyl]ethyl]pyridine-2-carboxamide (compound A126)

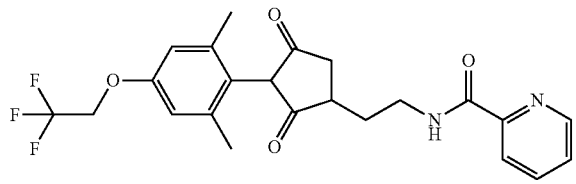 [SMILES: Cc1cc(OCC(F)(F)F)cc(C)c1C1C(=O)CC(CCNC(=O)c2ccccn2)C1=O]

N-[2-[3-[2,6-dimethyl-4-(4,4,5,5-tetramethyl-1,3,2-dioxaborolan-2-yl)phenyl]-2-methoxy-4-oxo-cyclopent-2-en-1-yl]ethyl]pyridine-2-carboxamide (100 mg, 0.204 mmol) was combined with copper (II) acetate (78 mg, 0.43 mmol) and triethylamine (0.11 mL, 0.79 mmol) in 2,2,2-trifluoroethanol (1.5 mL). The resulting slurry was sealed in a microwave vial and heated at 70° C. for 40 min then concentrated under reduced pressure. The residue was partitioned between 0.5M aqueous tetrasodium EDTA (10 mL, 5 mmol) and ethyl acetate (10 mL). The phases were separated and the organic layer was washed with 0.5M aqueous tetrasodium EDTA (10 mL, 5 mmol), water (10 mL) and brine (5 mL). The organic layer was then dried over MgSO$_4$ and concentrated under reduced pressure. The residue was purified by flash chromatography over silica using an EtOAc/hexane gradient to give a mixture of the desired product and protodeborylated starting material, which was taken into the next step without further purification. The crude product (60 mg) was dissolved in a mixture of acetone (2 mL) and 2M aqueous HCl (2 mL) and heated under reflux for 2 h, then cooled to room temperature and concentrated under reduced pressure to remove acetone. The pH of the aqueous mixture was adjusted to 4-5 by addition of saturated aqueous NaHCO$_3$, then extracted with EtOAc (3×5 mL). The combined organic layers were dried over MgSO$_4$ and concentrated under reduced pressure, and the residue was purified by mass-directed Fraction preparative HPLC to give the desired product (21 mg, 23% over two steps) as a colourless gum. $^1$H NMR (400 MHz, CDCl$_3$) δ (delta) 8.64 (br. s., 1H), 8.59 (d, 1H), 8.16 (d, 1H), 7.89 (td, 1H), 7.50 (dd, 1H), 6.64 (s, 2H), 4.29 (q, 2H), 3.81-4.16 (m, 1H), 3.35-3.57 (m, 1H), 2.82-3.00 (m, 2H), 2.26 (d, 1H), 2.02-2.19 (m, 7H), 1.83-2.02 (m, 1H).

General Note on Mass Directed Preparative HPLC

Compounds purified by mass directed prep HPLC using ES+ on a Waters Fraction Lynx system comprising a 2767 injector/collector with a 2545 gradient pump, two 515 isocratic pumps, SFO, 2998 photodiode array, 2424 ELSD and 3100 mass spectrometer. A Waters XBridge dC18 5 micron 19×10 mm guard column was used with an ACT ACE C18-AR, 5 micron 30×100 mm preparative column.

The preparative HPLC was conducted using a 11.4 minute run time using at column dilution, according to the following gradient table:

| For P2_10min_Foc2_0 | | | |
| --- | --- | --- | --- |
| Time (mins) | Solvent A (%) | Solvent B (%) | Flow (ml/mn) |
| 0.00 | 85 | 15 | 33 |
| 1.50 | 85 | 15 | 33 |

-continued

| For P2_10min_Foc2_0 | | | |
|---|---|---|---|
| Time (mins) | Solvent A (%) | Solvent B (%) | Flow (ml/mn) |
| 1.51 | 50 | 50 | 33 |
| 7.0 | 30 | 70 | 33 |
| 7.3 | 0 | 100 | 33 |
| 9.2 | 0 | 100 | 33 |
| 9.8 | 95 | 5 | 33 |
| 11.35 | 95 | 5 | 33 |
| 11.40 | 95 | 5 | 33 |

515 pump 2 ml/min CH$_3$CN with 0.05% TFA
515 pump 2 ml/min 90% MeOH/10% H$_2$O (make up pump)
Solvent A: H$_2$O with 0.05% TFA
Solvent B: CH$_3$CN with 0.05% TFA

Example 9

Synthesis of Compound A142

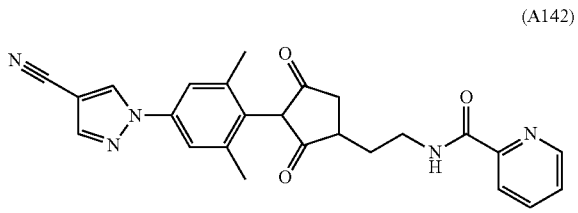 [SMILES: Cc1cc(-n2cc(C#N)cn2)cc(C)c1C1C(=O)CC(CCNC(=O)c2ccccn2)C1=O]

(A142)

Step One: Synthesis of N-[2-[3-[4-(4-cyanopyrazol-1-yl)-2,6-dimethyl-phenyl]-2-methoxy-4-oxo-cyclopent-2-en-1-yl]ethyl]pyridine-2-carboxamide

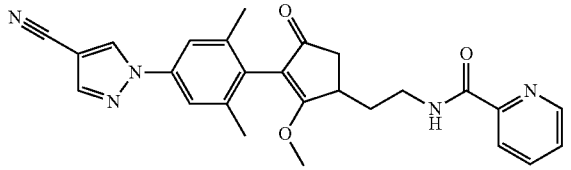 [SMILES: COC1=C(c2c(C)cc(-n3cc(C#N)cn3)cc2C)C(=O)CC1CCNC(=O)c1ccccn1]

N-[2-[3-[2,6-dimethyl-4-(4,4,5,5-tetramethyl-1,3,2-dioxaborolan-2-yl)phenyl]-2-methoxy-4-oxo-cyclopent-2-en-1-yl]ethyl]pyridine-2-carboxamide (200 mg, 0.408 mmol) was combined with copper (II) acetate (230 mg, 1.27 mmol), potassium carbonate (90 mg, 0.64 mmol) and 1H-pyrazole-4-carbonitrile hydrochloride (78 mg, 0.60 mmol) in pyridine (3 mL). The mixture was heated at 80° C. under nitrogen for 5 hours in total, then cooled to room temperature and concentrated under reduced pressure. The residue was partitioned between EtOAc (10 mL) and 0.5M aqueous tetrasodium EDTA (10 mL, 5 mmol) and the mixture was filtered through Celite. The phases were separated and the organic layer was washed with 0.5M tetrasodium EDTA (5 mL, 2.5 mmol), then dried over MgSO$_4$ and concentrated under reduced pressure. The residue was partially purified by flash chromatography over silica using an EtOAc/hexane gradient. The impure material obtained was redissolved in 1:1 EtOAc/ether and washed with 2M aqueous NaOH (3×10 mL) then brine (10 mL). The organic layers were dried over MgSO$_4$ and concentrated under reduced pressure to give the desired product (28 mg, 14%) as a colourless gum. $^1$H NMR (500 MHz, CDCl$_3$) δ (delta) 8.55 (d, 1H), 8.29 (s, 1H), 8.17-8.27 (m, 2H), 7.96 (s, 1H), 7.81-7.92 (m, 1H), 7.45 (dd, 1H), 7.37 (s, 2H), 3.59-3.74 (m, 2H), 3.57 (s, 3H), 3.04-3.14 (m, 1H), 2.87 (dd, 1H), 2.42 (dd, 1H), 2.25-2.38 (m, 1H), 2.22 (s, 6H), 1.72-1.90 (m, 1H).

Step Two: Synthesis of N-[2-[3-[4-(4-cyanopyrazol-1-yl)-2,6-dimethyl-phenyl]-2,4-dioxo-cyclopentyl]ethyl]pyridine-2-carboxamide (compound A142)

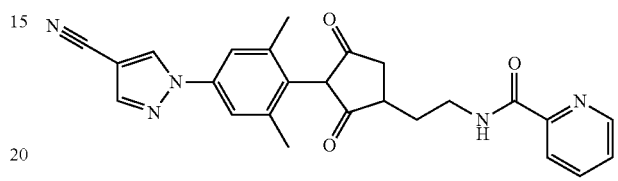

Prepared according to the same procedure used to prepare A1 (step 5) to give the desired product (26 mg, 96%) as a colourless glass. $^1$H NMR (500 MHz, d$_4$-methanol) δ (delta) 8.84 (s, 1H), 8.62 (br.s, 1H), 8.10 (d, 1H), 8.07 (s, 1H), 7.95 (t, 1H), 7.54 (d, 1H), 7.48 (s, 2H), 3.54-3.68 (m, 2H), 2.99 (dd, 1H), 2.81-2.90 (m, 1H), 2.55 (dd, 1H), 2.20-2.27 (m, 1H), 2.18 (s, 6H), 1.79 (ddt, 1H).

Example 10

Synthesis of Compound A111

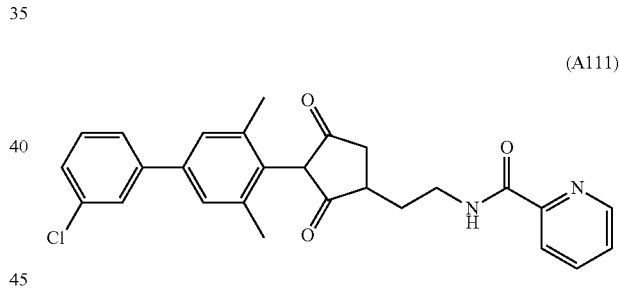

(A111)

Step One: Synthesis of N-[2-[3-[4-(3-chlorophenyl)-2,6-dimethyl-phenyl]-2-methoxy-4-oxo-cyclopent-2-en-1-yl]ethyl]pyridine-2-carboxamide

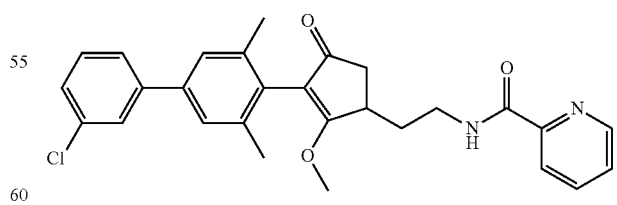

N-[2-[3-[2,6-dimethyl-4-(4,4,5,5-tetramethyl-1,3,2-dioxaborolan-2-yl)phenyl]-2-methoxy-4-oxo-cyclopent-2-en-1-yl]ethyl]pyridine-2-carboxamide (50 mg, 0.10 mmol) was combined with dicloro[1,1'-bis(diphenylphosphino)ferrocene]palladium(II) (7.5 mg, 0.010 mmol), tripotassium phosphate (87 mg, 0.41 mmol) and 1-bromo-3-chloro-benzene (29 mg, 0.15 mmol) in a mixture of 1,2-dimethoxyethane (1 mL) and water (0.3 mL) in a microwave vial. The mixture was stirred rapidly and degassed by nitrogen bubbling for 2 min, then the vial was sealed and heated in the microwave at 150° C. for 30 min. The mixture was partitioned between dichloromethane (10 mL) and water (5 mL) and then the mixture was passed through a PTFE frit to collect the dichloromethane extract. This was concentrated under reduced pressure and the residue was purified by flash chromatography over silica using an EtOAc/hexane gradient to give the desired product (32 mg, 66%) as a pink gum. $^1$H NMR (400 MHz, CDCl$_3$) δ 8.55 (d, 1H), 7.17-8.28 (m, 2H), 7.87 (td, 1H), 7.55 (t, 1H), 7.41-7.47 (m, 2H), 7.31-7.37 (m, 1H), 7.27-7.31 (m, 1H), 7.24 (s, 2H), 3.61-3.69 (m, 2H), 3.58 (s, 3H), 3.02-3.10 (m, 1H), 2.87 (dd, 1H), 2.41 (dd, 1H), 2.25-2.36 (m, 1H), 2.21 (s, 6H), 1.72-1.89 (m, 1H).

Step Two: Synthesis of N-[2-[3-[4-(3-chlorophenyl)-2,6-dimethyl-phenyl]-2,4-dioxo-cyclopentyl]ethyl]pyridine-2-carboxamide (compound A111)

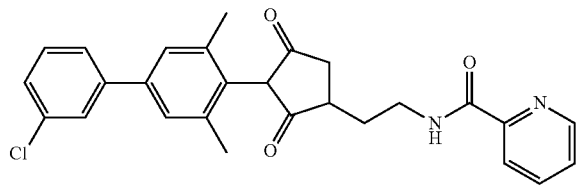 [SMILES: Cc1cc(-c2cccc(Cl)c2)cc(C)c1C1C(=O)CC(CCNC(=O)c2ccccn2)C1=O]

N-[2-[3-[4-(3-chlorophenyl)-2,6-dimethyl-phenyl]-2-methoxy-4-oxo-cyclopent-2-en-1-yl]ethyl]pyridine-2-carboxamide (30 mg, 0.063) was dissolved in morpholine (0.5 mL, 6 mmol) and the mixture was heated under nitrogen at 105° C. for 75 min. The mixture was cooled to room temperature then partitioned between ether (5 mL) and water (10 mL) and the biphasic mixture was filtered through celite. After separation of the phases the aqueous layer pH was adjusted to 5 by dropwise addition of 2M aqueous hydrochloric acid HCl(aq), then extracted with EtOAc (3×5 mL). The combined EtOAc layers were dried over MgSO$_4$ and concentrated under reduced pressure. The residue was purified by flash chromatography over silica using an EtOAc/hexane gradient to give the desired product (27 mg, 93%) as a brown gum. $^1$H NMR (400 MHz, CDCl$_3$) δ (delta) 8.62 (br.s, 1H), 8.58 (d, 1H), 8.17 (d, 1H), 7.88 (t, 1H), 7.53 (s, 1H), 7.49 (dd, 1H), 7.43 (d, 1H), 7.29-7.36 (m, 1H), 7.28 (s, 1H), 7.24 (s, 2H), 4.01 (br.s, 1H), 3.37-3.57 (m, 1H), 2.81-3.03 (m, 2H), 2.26-2.34 (m, 1H), 2.24 (s, 3H), 2.21 (s, 3H), 2.10 (br.s, 1H), 1.98 (br.s, 1H).

Example 11

Synthesis of Compound A170

(A170)

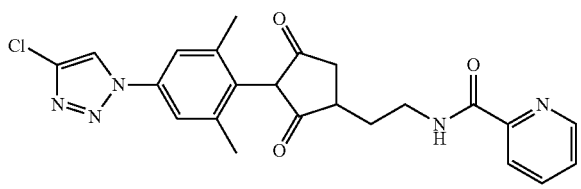

Step One: Synthesis of N-[2-[3-(4-azido-2,6-dimethyl-phenyl)-2-methoxy-4-oxo-cyclopent-2-en-1-yl]ethyl]pyridine-2-carboxamide

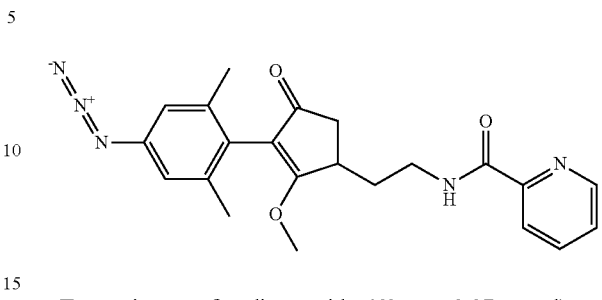

To a mixture of sodium azide (63 mg, 0.97 mmol) and N-[2-[3-[2,6-dimethyl-4-(4,4,5,5-tetramethyl-1,3,2-dioxaborolan-2-yl)phenyl]-2-methoxy-4-oxo-cyclopent-2-en-1-yl]ethyl]pyridine-2-carboxamide (500 mg, 1.02 mmol) in methanol (5 mL) was added copper (II) acetate (18 mg, 0.10 mmol). The resulting mixture was stirred open to air at 55° C. for 6 h in total then cooled to room temperature. The mixture was partitioned between 0.5M aqueous tetrasodium EDTA (50 mL, 25 mmol) and ethyl acetate (50 mL). The phases were separated and the aqueous layer was extracted with ethyl acetate (2×25 mL). The combined organic layers were washed sequentially with 0.5M aqueous tetrasodium EDTA (25 mL, 12.5 mmol), water (25 mL) then brine (25 mL), then dried over MgSO$_4$ and concentrated under reduced pressure. The residue was purified by flash chromatography over silica using an EtOAc/hexane gradient to give the desired product (330 mg, 84%) as a pale yellow gum. $^1$H NMR (400 MHz, CDCl$_3$) δ 8.55 (d, 1H), 8.15-8.25 (m, 2H), 7.87 (td, 1H), 7.45 (ddd, 1H), 6.73 (s, 2H), 3.64 (qd, 2H), 3.54 (s, 3H), 2.98-3.07 (m, 1H), 2.84 (dd, 1H), 2.38 (dd, 1H), 2.23-2.33 (m, 1H), 2.13 (s, 6H), 1.72-1.84 (m, 1H).

Step Two: Synthesis of N-[2-[3-[2,6-dimethyl-4-(4-trimethylsilyltriazol-1-yl)phenyl]-2-methoxy-4-oxo-cyclopent-2-en-1-yl]ethyl]pyridine-2-carboxamide

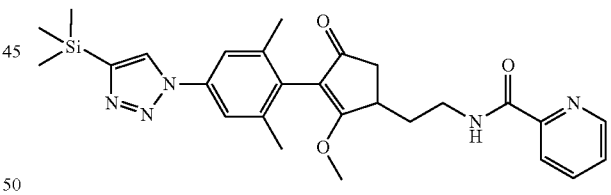

A mixture of N-[2-[3-(4-azido-2,6-dimethyl-phenyl)-2-methoxy-4-oxo-cyclopent-2-en-1-yl]ethyl]pyridine-2-carboxamide (93 mg, 0.23 mmol), N,N-diisopropylethylamine (0.13 mL, 0.75 mmol) and cuprous iodide (7 mg, 0.04 mmol) in THF (2 mL) in a microwave vial was degassed by nitrogen bubbling for 2 min. Ethynyl(trimethyl)silane (0.70 mL, 5.0 mmol) was then added and the mixture was heated in the microwave at 120° C. for 45 min. The mixture was concentrated under reduced pressure, then the residue purified by flash chromatography over silica using an EtOAc/hexane gradient to give the desired product (48 mg, 42%) as a pale yellow glass. $^1$H NMR (400 MHz, CDCl$_3$) δ (delta) 8.56 (d, 1H), 8.16-8.28 (m, 2H), 7.82-7.93 (m, 2H), 7.45 (dd, 1H), 7.43 (s, 2H), 3.61-3.72 (m, 2H), 3.57 (s, 3H), 3.02-3.13 (m, 1H), 2.88 (dd, 1H), 2.42 (dd, 1H), 2.26-2.37 (m, 1H), 2.23 (s, 6H), 1.78-1.87 (m, 1H), 0.37 (s, 9H).

Step Three: Synthesis of N-[2-[3-[4-(4-chlorotri-azol-1-yl)-2,6-dimethyl-phenyl]-2-methoxy-4-oxo-cyclopent-2-en-1-yl]ethyl]pyridine-2-carboxamide

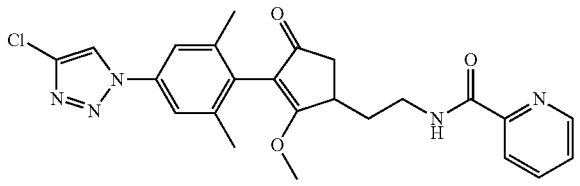 [SMILES: COC1=C(c2c(C)cc(-n3cc(Cl)nn3)cc2C)C(=O)CC1CCNC(=O)c1ccccn1]

N-[2-[3-[2,6-dimethyl-4-(4-trimethylsilyltriazol-1-yl) phenyl]-2-methoxy-4-oxo-cyclopent-2-en-1-yl]ethyl]pyridine-2-carboxamide (61 mg, 0.12 mmol) was combined with N-chlorosuccinimide (97 mg, 0.73 mmol) and silica gel (255 mg, 4.24 mmol) in acetonitrile (1 mL). The mixture was heated under reflux for 90 min, then cooled to room temperature. Celite™ (200 mg) was added and the mixture was dry loaded onto silica and purified by flash chromatography over silica using an EtOAc/hexane gradient to give the desired compound (33 mg, 58%) as a pale yellow gum. $^1$H NMR (400 MHz, CDCl$_3$) δ (delta) 8.56 (d, 1H), 8.14-8.31 (m, 2H), 7.91 (s, 1H), 7.88 (td, 1H), 7.46 (ddd, 1H), 7.40 (s, 2H), 3.65 (dd, 2H), 3.58 (s, 3H), 3.03-3.14 (m, 1H), 2.88 (dd, 1H), 2.43 (dd, 1H), 2.27-2.37 (m, 1H), 2.24 (s, 6H), 1.76-1.87 (m, 1H).

Step Four: Synthesis of N-[2-[3-[4-(4-chlorotriazol-1-yl)-2,6-dimethyl-phenyl]-2,4-dioxo-cyclopentyl] ethyl]pyridine-2-carboxamide (compound A170)

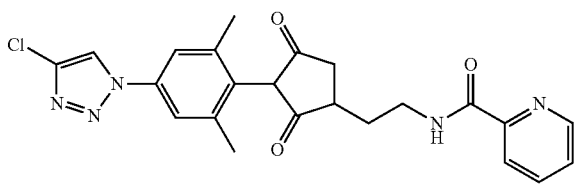 [SMILES: Cc1cc(-n2cc(Cl)nn2)cc(C)c1C1C(=O)CC(CCNC(=O)c2ccccn2)C1=O]

Prepared according to the same procedure used to prepare A1 (step 5) to give the desired product (33 mg, 100%) as a pale yellow gum. $^1$H NMR (500 MHz, d4 methanol) δ (delta) 8.61 (d, 1H), 8.58 (s, 1H), 8.09 (d, 1H), 7.94 (t, 1H), 7.52 (dd, 1H), 7.49 (s, 2H), 3.56-3.67 (m, 2H), 3.00 (dd, 1H), 2.83-2.91 (m, 1H), 2.56 (dd, 1H), 2.20-2.28 (m, 1H), 2.18 (s, 6H), 1.74-1.86 (m, 1H).

Example 12

Synthesis of Compound A34

(A34)

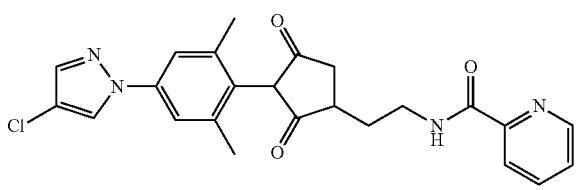

Step One: Synthesis of pyridine-2-carbonyl chloride hydrochloride

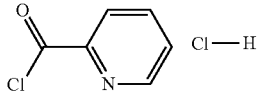

DMF (13 mmol, 0.94 g, 1 mL) was added to a suspension of pyridine-2-carboxylic acid (181.14 mmol, 22.3 g) in thionyl chloride (60 mL) and stirred for 3 hours. The excess thionyl chloride was removed under reduced pressure to give a dark purple solid.

Step Two: Synthesis of (2,3,4,5,6-pentafluorophenyl)pyridine-2-carboxylate

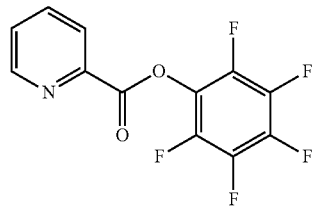 [SMILES: O=C(Oc1c(F)c(F)c(F)c(F)c1F)c1ccccn1]

To a suspension of pyridine-2-carbonyl chloride hydrochloride (182.8 mmol, 32.54 g) in THF (1000 mL), under nitrogen, was added 2,3,4,5,6-pentafluorophenol (182.8 mmol, 33.65 g) followed by the dropwise addition of N,N-diethylethanamine (548.4 mmol, 55.49 g, 76.4 mL). After stirring at room temperature for 2 hours the solid was filtered off through celite and washed with ethyl acetate, the organic layers were concentrated under reduced pressure to leave a brown oil which was purified by flash chromatography (gradient elution: 0-30% ethyl acetate in hexane). The resulting material was further purified by recrystallization from hexane to give the desired product (42.44 g, 80% over 2 steps) as a white solid. $^1$H NMR (400 MHz, CDCl$_3$) δ ppm 7.63 (ddd, 1H), 7.97 (td, 1H), 8.30 (d, 1H), 8.88 (dt, 1H).

Step Three: Synthesis of 2-[4-(4-chloropyrazol-1-yl)-2,6-dimethyl-phenyl]-3-methoxy-cyclopent-2-en-1-one

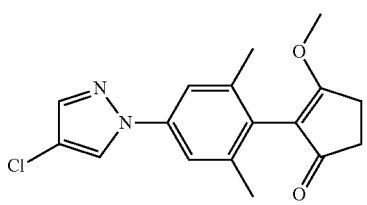 [SMILES: COC1=C(c2c(C)cc(-n3cc(Cl)cn3)cc2C)C(=O)CC1]

A flask charged with 2-(4-bromo-2,6-dimethyl-phenyl)-3-methoxy-cyclopent-2-en-1-one (2 g, 6.7755 mmol), 4-chloro-1H-pyrazole (1.39 g, 13.551 mmol), potassium carbonate (2.83 g, 20.3265 mmol) and Copper (I) Iodide (0.658 g, 3.3878 mmol) was evacuated and purged with nitrogen. Chlorobenzene (10 mL) was added, follow'd by N,N'-dimethylenediamine (0.737 mL, 6.775 mmol), and the reaction was refluxed (131° C.) for 1 hour. The reaction was allowed to cool to ambient temperature, diluted with chloroform (25 mL) and washed with saturated aqueous ammonium chloride (25 mL). The aqueous layer was acidified to pH 5 with 2N HCl and re-extracted with chloroform. The combined organic layers were filtered through a PTFE frit, concentrated in vacuo and diluted with acetone (10 mL). Potassium carbonate (1.89 g, 13.55 mmol) and iodomethane (0.844 mL, 13.55 mmol) were added to the above solution, and the reaction was stirred for 4 hours at ambient temperature. The reaction was diluted with chloroform (25 mL), washed with saturated aqueous ammonium chloride (25 mL) and filtered through a PTFE frit. The filtrate was dry loaded onto silica, purified by flash chromatography (gradient elution: 20-100% EtOAc in hexane) to give 2-[4-(4-chloropyrazol-1-yl)-2,6-dimethyl-phenyl]-3-methoxy-cyclopent-2-en-1-one (1.61 g, 5.08 mmol, 75.0% Yield) as a white solid. $^1$H NMR (400 MHz, Chloroform) δ=7.87 (s, 1H), 7.61 (s, 1H), 7.34 (s, 2H), 3.78 (s, 3H), 2.93-2.79 (m, 2H), 2.73-2.61 (m, 2H), 2.20 (s, 6H).

Step Four: Synthesis of 2-[3-[4-(4-chloropyrazol-1-yl)-2,6-dimethyl-phenyl]-2-methoxy-4-oxo-cyclopent-2-en-1-yl]acetonitrile

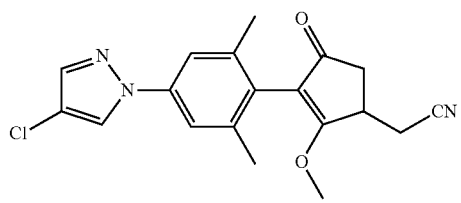 [SMILES: COC1=C(c2c(C)cc(-n3cc(Cl)cn3)cc2C)C(=O)CC1CC#N]

An oven-dried 3-neck flask was charged with 2-[4-(4-chloropyrazol-1-yl)-2,6-dimethyl-phenyl]-3-methoxy-cyclopent-2-en-1-one (869 mg, 2.74 mmol), purged with nitrogen, and THF (8.69 mL) was added. The reaction is cooled to −65° C. and LiHMDS (1M in THF) (3.0175 mL, 3.0175 mmol) was added dropwise over a period of 2 minutes and the reaction was allowed to stir for 20 minutes. A solution of 2-bromoacetonitrile (395 mg, 3.2918 mmol) in THF (1.738 mL) was then added dropwise, and the reaction was allowed to stir for a further 60 minutes, before being allowed to warm to ambient temperature over a period of 40 minutes. The reaction was quenched by the addition of saturated aqueous ammonium chloride solution (25 ml) and the reaction was allowed to stir for a further 10 minutes. The reaction was extracted with EtOAc (2×25 mL). The combined organic layers were filtered through a PTFE frit, dry loaded onto silica and purified by flash chromatography (0-100% EtOAc in hexane) to give 2-[3-[4-(4-chloropyrazol-1-yl)-2,6-dimethyl-phenyl]-4-methoxy-2-oxo-cyclopent-3-en-1-yl]acetonitrile (854 mg, 2.40 mmol, 87.5% yield) as a beige solid. $^1$H NMR (400 MHz, CDCl$_3$) δ (delta) ppm 2.21 (s, 3H), 2.30 (s, 3H), 2.52 (dd, 1H), 2.76-2.95 (m, 3H), 3.28 (dd, 1H), 3.60 (s, 3H), 7.36 (s, 2H), 7.62 (s, 1H), 7.89 (s, 1H).

Step Five: Synthesis of N-[2-[3-[4-(4-chloropyrazol-1-yl)-2,6-dimethyl-phenyl]-2-methoxy-4-oxo-cyclopent-2-en-1-yl]ethyl]pyridine-2-carboxamide

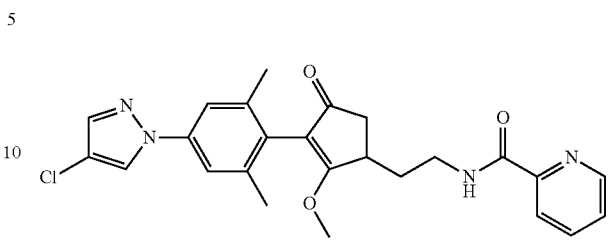

A glass pressure vessel was charged with Raney Nickel (2400) (45.615 mmol, 4 g) which was washed with distilled water (3×10 mL), and the excess water was decanted off. 2-[3-[4-(4-chloropyrazol-1-yl)-2,6-dimethyl-phenyl]-2-methoxy-4-oxo-cyclopent-2-en-1-yl]acetonitrile (2 g, 5.621 mmol), (2,3,4,5,6-pentafluorophenyl)pyridine-2-carboxylate (2.276 g, 7.870 mmol), and 1,2-dimethoxyethane (20 mL) were then added. The vessel was sealed, purged with nitrogen and then hydrogen, and then stirred vigorously at room temperature under 4 Bar of hydrogen for 3 hours. The reaction was filtered through a pad of celite, dry loaded onto silica and purified by flash chromatography (gradient elution: 10-100% EtOAc in hexane) to give N-[2-[3-[4-(4-chloropyrazol-1-yl)-2,6-dimethyl-phenyl]-4-methoxy-2-oxo-cyclopent-3-en-1-yl]ethyl]pyridine-2-carboxamide (1.939 g, 4.171 mmol, 74.2% yield) as a white solid. $^1$H NMR (400 MHz, CDCl$_3$) δ (delta) ppm 1.74-1.87 (m, 1H), 2.21 (s, 6H), 2.26-2.36 (m, 1H), 2.41 (dd, 1H), 2.86 (dd, 1H), 3.01-3.10 (m, 1H), 3.56 (s, 3H), 3.65 (qd, 2H), 7.33 (s, 2H), 7.45 (ddd, 1H), 7.62 (s, 1H), 7.83-7.93 (m, 2H), 8.21 (d, 2H), 8.52-8.59 (m, 1H).

Step Six: Synthesis of N-[2-[3-[4-(4-chloropyrazol-1-yl)-2,6-dimethyl-phenyl]-4-methoxy-2-oxo-cyclopent-3-en-1-yl]ethyl]pyridine-2-carboxamide (compound A34)

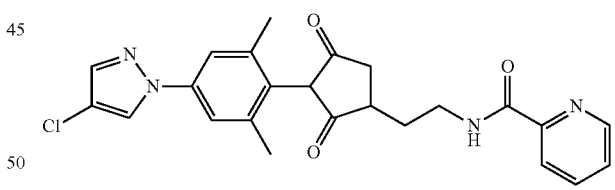

To a solution of N-[2-[3-[4-(4-chloropyrazol-1-yl)-2,6-dimethyl-phenyl]-2-methoxy-4-oxo-cyclopent-2-en-1-yl]ethyl]pyridine-2-carboxamide (11.2 g, 24.1 mmol) in acetone (112 mL) was added 2N HCl (112 mL), and the reaction was heated to 60° C. for 17 hours. The reaction was allowed to cool to ambient temperature, concentrated in vacuo to remove excess acetone, and the pH adjusted to 4.5 using 2N NaOH. The aqueous layer was extracted with EtOAc (2×250 mL). The combined organic layers were dried over Mg$_2$SO$_4$, filtered through a PTFE frit and concentrated to give N-[2-[3-[4-(4-chloropyrazol-1-yl)-2,6-dimethyl-phenyl]-2,4-dioxo-cyclopentyl]ethyl]pyridine-2-carboxamide (10.75 g, 23.84 mmol, 98.76% Yield) as a white solid. $^1$H NMR (400 MHz, Chloroform) δ=12.56 (br. s., 1H), 8.71 (br. s., 1H), 8.61 (d, 1H), 8.21 (d, 1H), 7.91 (t, 1H), 7.87 (s, 1H), 7.61 (s, 1H), 7.57-7.49 (m, 1H), 7.34 (s, 2H), 4.24-4.09 (m, 1H), 3.46 (br. s., 1H), 3.06-2.84 (m, 2H), 2.26 (s, 3H), 2.22 (s, 3H), 2.20-2.15 (m, 2H), 1.89 (br. s., 1H).

Example 13

Synthesis of Compound A120

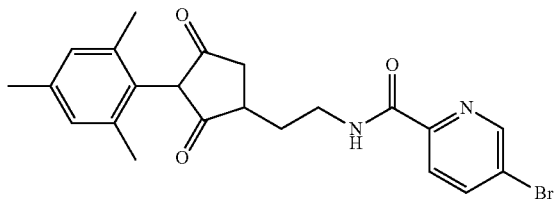

(A120)

Step One: Synthesis of 2-[2-methoxy-4-oxo-3-(2,4, 6-trimethylphenyl)cyclopent-2-en-1-yl]acetonitrile

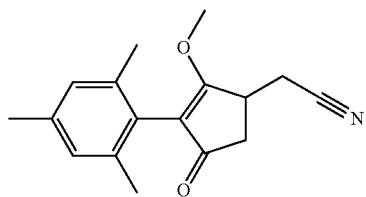 [SMILES: COC1=C(c2c(C)cc(C)cc2C)C(=O)CC1CC#N]

To a solution of 3-methoxy-2-(2,4,6-trimethylphenyl)cyclopent-2-en-1-one (43.420 mmol, 10.0 g) in THF (100 mL), under nitrogen at −78° C., LiHMDS (1M in THF, 47.762 mL, 47.762 mmol) was added dropwise. The temperature of the reaction was maintained below −55° C. during the dropwise addition of LiHMDS. After stirring for 15 minutes at −78° C., 2-bromoacetonitrile (52.1 mmol, 6.25 g, 3.63 mL) in THF (20 mL) was added over a period of 15 minutes. Stirring was continued at −78° C. for 40 minutes then the reaction was warmed to room temperature. After quenching the reaction with saturated ammonium chloride the solvent was removed under reduced pressure and the crude material was dissolved in dichloromethane and water. The phases were separated and the aqueous layer was extracted with dichloromethane. The combined organic layers were washed with water and brine then dried over MgSO$_4$ and the solvent was removed under reduced pressure to leave a brown oil. The crude material was purified by flash chromoatography (gradient elution: 0-100% ethyl acetate in hexane) to give the desired product (11.136 g, 95%) as a brown oil. $^1$H NMR (400 MHz, CDCl$_3$) δ (delta) ppm 6.88 (d, 2H), 3.57 (s, 3H), 3.14-3.32 (m, 1H), 2.88 (dd, 1H), 2.75-2.82 (m, 2H), 2.48 (dd, 1H), 2.23-2.34 (m, 3H), 2.14-2.22 (m, 3H), 2.06-2.14 (m, 3H).

Step Two: Synthesis of tert-butyl N-[2-[2-methoxy-4-oxo-3-(2,4,6-trimethylphenyl)cyclopent-2-en-1-yl]ethyl]carbamate

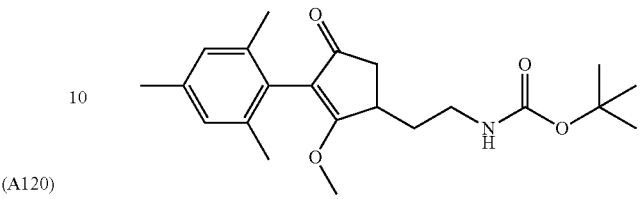

To a solution of 2-[2-methoxy-4-oxo-3-(2,4,6-trimethylphenyl)cyclopent-2-en-1-yl]acetonitrile (3.713 mmol, 1.00 g) in methanol (28 mL) under nitrogen was added tert-butoxycarbonyl tert-butyl carbonate (7.43 mmol, 1.62 g) and nickel (II) chloride (0.668 mmol, 0.0867 g). The mixture was cooled to −5° C. in an acetone/dry ice bath before the sodium borohydride (22.28 mmol, 0.8601 g) was added portionwise over 30 minutes. After stirring for 1 hour at −5° C. the reaction was allowed to warm to room temperature then stirred for a further 3.5'hours. N'-(2-aminoethyl)ethane-1,2-diamine (3.713 mmol, 0.3909 g, 0.409 mL) was added and the mixture left to stir at room temperature for 1 hour. After diluting with saturated sodium bicarbonate and ethyl acetate, the phases were separated and the aqueous layer was extracted with ethyl acetate. The combined organic layers were washed with water and brine then dried over MgSO$_4$ and the solvent was removed under reduced pressure to leave a brown oil. The crude material was purified by flash chromoatography (gradient elution: 0-75% ethyl acetate in hexane) to give the desired product (1.167 g, 84%) as a colourless oil. $^1$H NMR (400 MHz, CDCl$_3$) δ (delta) ppm 6.78-6.95 (m, 2H), 4.60 (br. s., 1H), 3.44-3.63 (m, 3H), 3.14-3.36 (m, 2H), 2.86-3.04 (m, 1H), 2.68-2.85 (m, 1H), 2.22-2.37 (m, 4H), 2.01-2.16 (m, 6H), 1.36-1.71 (m, 10H).

Step Three: Synthesis of 2-[2-methoxy-4-oxo-3-(2, 4,6-trimethylphenyl)cyclopent-2-en-1-yl]ethylammonium chloride

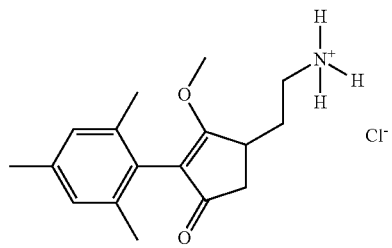 [SMILES: COC1=C(c2c(C)cc(C)cc2C)C(=O)CC1CC[NH3+] ; [Cl-]]

To a solution of tert-butyl N-[2-[2-methoxy-4-oxo-3-(2, 4,6-trimethylphenyl)cyclopent-2-en-1-yl]ethyl]carbamate (15.06 mmol, 5.624 g) in dichloromethane (30 mL) at room temperature was added hydrogen chloride (4M HCl in 1,4-dioxane, 40 mmol, 10 mL). After stirring at room temperature for 4 hours the solvent was removed to leave an off white solid which was carried on directly to the next stage of the synthesis.

Step Four: Synthesis of (2,3,4,5,6-pentafluorophenyl) 5-bromopyridine-2-carboxylate

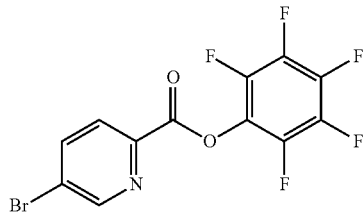 [SMILES: O=C(Oc1c(F)c(F)c(F)c(F)c1F)c1ccc(Br)cn1]

To a suspension of 5-bromopyridine-2-carboxylic acid (2.48 mmol, 0.500 g) in dichloromethane (15 mL) at room temperature was added 2,3,4,5,6-pentafluorophenol (3.09 mmol, 0.569 g) then 3-(ethyliminomethyleneamino)-N,N-dimethyl-propan-1-amine hydrochloride (3.09 mmol, 0.593 g). After 2 hours the solvent was removed under reduced pressure and the yellow residue was diluted with ethyl acetate and water. The two resulting phases were separated and the aqueous layered was extracted with ethyl acetate. The combined organic layers were washed with water, sodium bicarbonate (saturated) and brine then dried over MgSO$_4$. The solvent was removed under reduced pressure to give the desired product (0.894 g, 98%) as a yellow solid. $^1$H NMR (400 MHz, CDCl$_3$) δ (delta) ppm 8.92 (d, 1H), 8.16 (s, 1H), 8.07-8.14 (m, 1H).

Step Five: Synthesis of 5-bromo-N-{2-[2-methoxy-4-oxo-3-(2,4,6-trimethylphenyl)cyclopent-2-en-1-yl]ethyl}pyridine-2-carboxamide

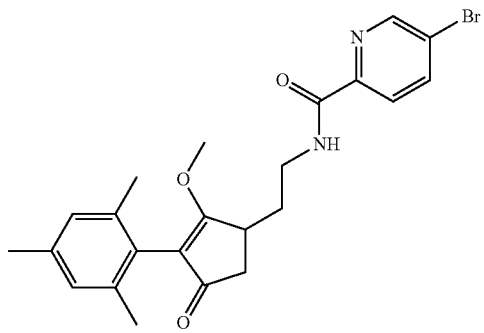 [SMILES: COC1=C(c2c(C)cc(C)cc2C)C(=O)CC1CCNC(=O)c1ccc(Br)cn1]

To a solution of 2-[2-methoxy-4-oxo-3-(2,4,6-trimethylphenyl)cyclopent-2-en-1-yl]ethylammonium trifluoroacetate (7.502 mmol, 2.906 g) in dichloromethane (35 mL) at room temperature was added (2,3,4,5,6-pentafluorophenyl) 5-bromopyridine-2-carboxylate (8.252 mmol, 3.797 g) followed by N,N-diethylethanamine (33.00 mmol, 4.59 mL). After stirring for 3 hours, the solvent was removed under reduced pressure and the crude residue was purified by flash chromatography (gradient elution: 0-85% ethyl acetate in hexane) to give the desired product (3.462 g, 100%) as a brown foam. $^1$H NMR (400 MHz, CDCl$_3$) δ (delta) ppm 1.68 (br. s., 1H), 1.78 (dq, 1H), 2.03-2.16 (m, 6H), 2.22-2.38 (m, 4H), 2.82 (dd, 1H), 3.00 (dddd, 1H), 3.52-3.63 (m, 5H), 6.86 (s, 2H), 7.99 (d, 1H), 8.03-8.13 (m, 2H), 8.60 (d, 1H).

Step Six: Synthesis of 5-bromo-N-{2-[2,4-dioxo-3-(2,4,6-trimethylphenyl)cyclopentyl]ethyl}pyridine-2-carboxamide (compound A120)

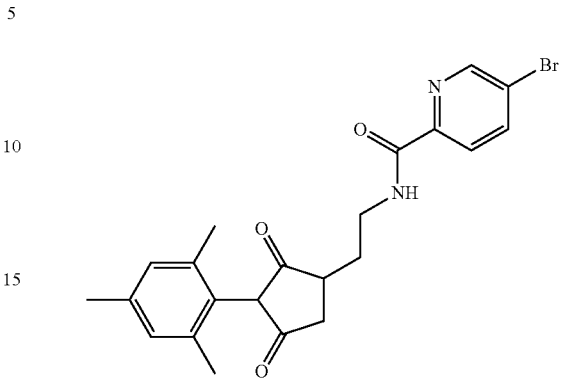

To a solution of 5-bromo-N-{2-[2-methoxy-4-oxo-3-(2,4,6-trimethylphenyl)cyclopent-2-en-1-yl]ethyl}pyridine-2-carboxamide (7.569 mmol, 3.462 g) in acetone (35 mL) was added hydrogen chloride (50 mmol, 25 mL) then the mixture was heated to 65° C. overnight. After cooling to room temperature, the acetone was concentrated under reduced pressure and the resulting yellow solution was extracted with dichloromethane. The organic fractions were concentrated under reduced pressure and purified by flash chromatography (gradient elution: 0-100% ethyl acetate in hexane) to give the desired product (3.18 g, 94%) as a white foam. $^1$H NMR (400 MHz, CDCl$_3$) δ (delta) ppm 1.6-2.25 (m, 11H), 2.74-3.11 (m, 2H), 3.45 (br. s., 1H), 3.52 (m, 1H), 3.97 (br. s., 1H), 6.84 (br. s., 2H), 7.85-8.15 (m, 2H), 8.48-8.7 (m, 2H).

Example 14

Synthesis of Compound P12

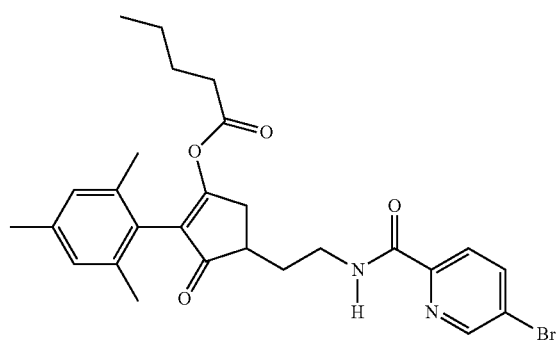

(P12)

To a stirred solution of 5-bromo-N-{2-[2,4-dioxo-3-(2,4,6-trimethylphenyl)cyclopentyl]ethyl}pyridine-2-carboxamide (0.11 mmol, 0.050 g) in dichloromethane (2 mL) at room temperature was added N,N-diethylethanamine (0.12 mmol, 0.013 g) followed by pentanoyl chloride (0.12 mmol, 0.014 g, 0.014 mL). The mixture was left to stir overnight. The reaction mixture was directly purified by flash chromatography (gradient elution: 0-80% ethyl acetate in hexane) to give the desired product (47 mg, 79%) as a colourless oil. $^1$H NMR (400 MHz, CDCl₃) δ (delta) ppm 0.82 (t, 3H), 1.10-1.31 (m, 2H), 1.43-1.58 (m, 2H), 1.78-1.93 (m, 1H), 1.96-2.11 (m, 6H), 2.14-2.41 (m, 6H), 2.67-2.92 (m, 2H), 3.27 (dd, 1H), 3.48-3.88 (m, 2H), 6.86 (s, 2H), 7.90-8.26 (m, 3H), 8.60 (d, 1H).

Example 15

Synthesis of Compound P3

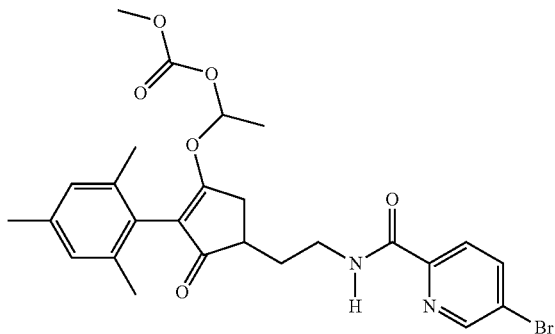
(P3)

To a solution of 5-bromo-N-{2-[2,4-dioxo-3-(2,4,6-trimethylphenyl)cyclopentyl]ethyl}pyridine-2-carboxamide (0.11 mmol, 0.050 g) in DMF (13 mmol, 0.94 g, 1 mL) at room temperature was added potassium carbonate (0.23 mmol, 0.031 g) and 1-chloroethyl methyl carbonate (0.23 mmol, 0.031 g). The mixture was left to stir at room temperature for 4 days. The mixture was diluted with water and extracted with ethyl acetate, the combined organic layers were washed with water and brine and dried over MgSO₄, filtered and concentrated under reduced pressure. The resulting residue was purified by flash chromatography (gradient elution: 0-100% ethyl acetate in hexane) to give the desired product (50 mg, 81%) as a colourless oil. ¹H NMR (400 MHz, CDCl3) δ (delta) ppm 8.47-8.70 (m, 1H), 7.88-8.23 (m, 3H), 6.73-6.95 (m, 2H), 5.71-6.32 (m, 1H), 3.52-3.83 (m, 4H), 2.33-3.30 (m, 3H), 2.27 (s, 4H), 1.98-2.10 (m, 6H), 1.67-1.91 (m, 2H), 1.30-1.57 (m, 3H).

Example 16

Synthesis of Compound P22

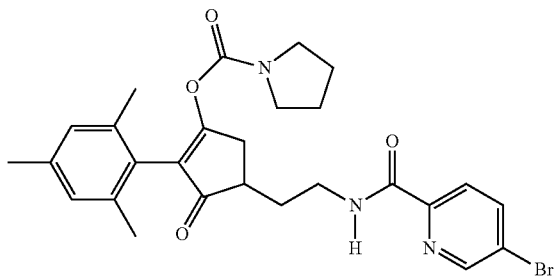
(P22)

To a solution of 5-bromo-N-{2-[2,4-dioxo-3-(2,4,6-trimethylphenyl)cyclopentyl]ethyl}pyridine-2-carboxamide (0.11 mmol, 0.050 g) in dichloromethane (2 mL) at room temperature in a microwave vial was added pyrrolidine-1-carbonyl chloride (0.23 mmol, 0.030 g) and the phosphazine base, P2tBu (1-tert-butyl-2,2,4,4,4-pentakis(dimethylamino)-2λ⁵,4λ⁵-catenadi(phosphazene)) (2M in THF, 0.10 mmol, 0.050 mL). The reaction was heated to 100° C. for 30 minutes. The reaction mixture was directly purified by flash chromatography (gradient elution: 0-80% ethyl acetate in hexane) to give the desired product (22 mg, 36%) as a colourless oil. ¹H NMR (400 MHz, CDCl3) δ (delta) ppm 1.86 (d, 4H), 2.01-2.14 (m, 6H), 2.26 (s, 4H), 2.67-3.12 (m, 2H), 3.14-3.50 (m, 6H), 3.52-3.84 (m, 2H), 6.86 (s, 2H), 7.85-8.23 (m, 3H), 8.60 (d, 1H).

Example 16A

Synthesis of Compound A126B

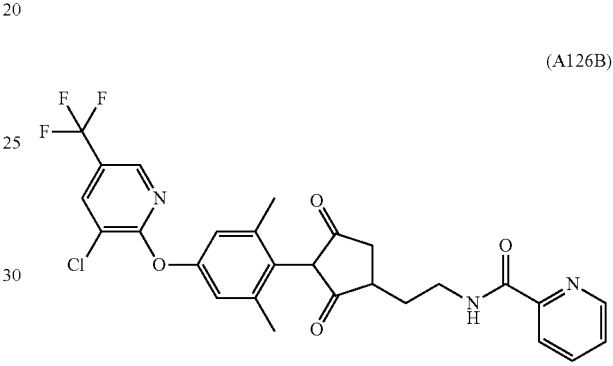
(A126B)

Step One: Synthesis of N-{2-[3-(4-hydroxy-2,6-dimethyl-phenyl)-2-methoxy-4-oxo-cyclopent-2-en-1-yl]ethyl}pyridine-2-carboxamide

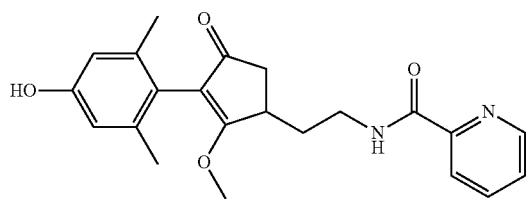 [SMILES: COC1=C(c2c(C)cc(O)cc2C)C(=O)CC1CCNC(=O)c1ccccn1]

An aqueous solution of hydrogen peroxide (1.1 g, 9.7 mmol, 30 mass %) was added to a stirred suspension of N-[2-[3-[2,6-dimethyl-4-(4,4,5,5-tetramethyl-1,3,2-dioxaborolan-2-yl)phenyl]-2-methoxy-4-oxo-cyclopent-2-en-1-yl]ethyl]pyridine-2-carboxamide (500 mg, 1.02 mmol) in methanol (10 mL). After 20 hours, a solution of sodium metabisulfite (20 mL, 10 mmol, 0.5 mol/L) was added dropwise to the rapidly-stirred reaction mixture. The methanol was removed under reduced pressure, then the mixture was partitioned with ethyl acetate (20 mL). The phases were separated, then the aqueous layer was extracted with ethyl acetate (2×10 mL). The combined organic extracts were washed with brine (10 mL), then dried over MgSO₄ and concentrated under reduced pressure. The residue was purified by flash chromatography over silica using an EtOAc/hexane gradient to give the desired product (360 mg, 93%) as a white foam. ¹H NMR (400 MHz, CDCl₃) δ (delta) 8.49-8.61 (m, 1H), 8.15-8.28 (m, 2H), 7.8 (td, 1H), 7.44

(dddd, 1H), 6.44 (s, 1H), 3.60-3.69 (m, 2H), 3.53 (s, 3H), 3.01 (dddd, 1H), 2.85 (dd, 1H), 2.39 (dd, 1H), 2.22-2.32 (m, 1H), 2.03 (s, 6H), 1.73-1.84 (m, 1H).

Step Two: Synthesis of N-[2-[3-[4-[[3-chloro-5-(trifluoromethyl)-2-pyridyl]oxy]-2,6-dimethyl-phenyl]-2-methoxy-4-oxo-cyclopent-2-en-1-yl]ethyl]pyridine-2-carboxamide

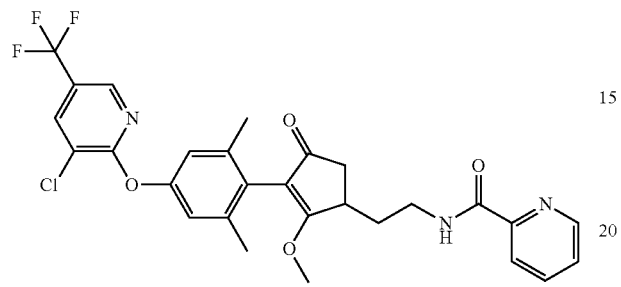

N-{2-[3-(4-hydroxy-2,6-dimethyl-phenyl)-2-methoxy-4-oxo-cyclopent-2-en-1-yl]ethyl}pyridine-2-carboxamide (101 mg, 0.266 mmol) was combined with 3-chloro-2-fluoro-5-(trifluoromethyl)pyridine (66 mg, 0.33 mmol) and potassium carbonate (74 mg, 0.53 mmol) in dimethyl sulfoxide (1 mL). The mixture was heated at 60° C. with stirring for 30 min then cooled to room temperature. The mixture was partitioned between ethyl acetate (15 mL) and water (10 mL). The phases were separated and the aqueous layer was extracted with ethyl acetate (5 mL). The combined organic layers were washed with water (2×5 mL), then brine (5 mL), then filtered through a PTFE frit and concentrated under reduced pressure. The residue was purified by flash chromatography over silica using an EtOAc/hexane gradient to give the desired product (141 mg, 95%) as a colourless gum. $^1$H NMR (400 MHz, CDCl$_3$) δ (delta) 8.56 (d, 1H), 8.17-8.25 (m, 2H), 7.96 (d, 1H), 7.87 (td, 1H), 7.45 (ddd, 1H), 6.87 (s, 2H), 3.65 (qd, 2H), 3.59 (s, 3H), 3.05 (dddd, 1H), 2.85 (dd, 1H), 2.40 (dd, 1H), 2.25-2.36 (m, 1H), 2.16 (s, 6H), 1.73-1.85 (m, 1H).

Step Three: Synthesis of N-[2-[3-[4-[[3-chloro-5-(trifluoromethyl)-2-pyridyl]oxy]-2,6-dimethyl-phenyl]-2,4-dioxo-cyclopentyl]ethyl]pyridine-2-carboxamide (compound A126B)

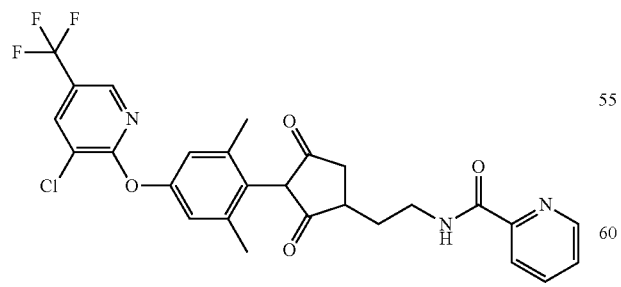

The above compound was prepared from N-[2-[3-[4-[[3-chloro-5-(trifluoromethyl)-2-pyridyl]oxy]-2,6-dimethyl-phenyl]-2-methoxy-4-oxo-cyclopent-2-en-1-yl]ethyl]pyridine-2-carboxamide, according a procedure substantially similar to that used to prepare compound A1 (Example 1, step 5) to give the desired product (103 mg, 91%) as a colourless foam. 1H NMR (400 MHz, CDCl$_3$) δ (delta) 8.69 (br.s, 1H), 8.60 (br.s, 1H), 8.27 (br.s, 1H), 8.22 (d, 1H), 7.87-7.99 (m, 2H), 7.52 (br.s, 1H), 6.87 (s, 2H), 4.13 (d, 1H), 3.45 (d, 1H), 2.98 (br.s, 1H), 2.89 (dd, 1H), 2.10-2.29 (m, 8H), 1.91 (t, 1H).

Example 16B

Synthesis of Compound P1

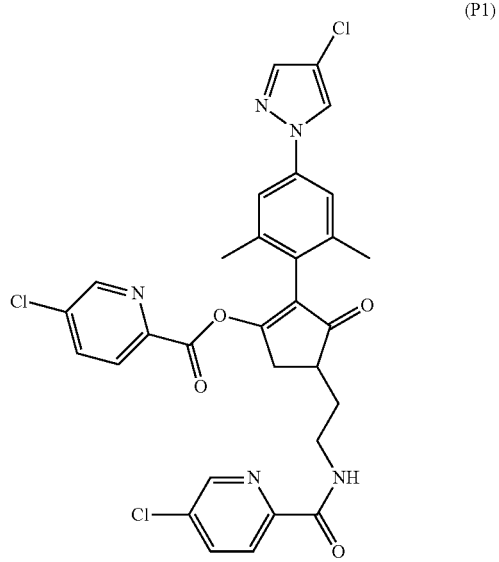 [SMILES: Cc1cc(-n2cc(Cl)cn2)cc(C)c1C1=C(OC(=O)c2ccc(Cl)cn2)CC(CCNC(=O)c2ccc(Cl)cn2)C1=O]

(P1)

Step One: Synthesis of tert-butyl N-[2-[3-[4-(4-chloropyrazol-1-yl)-2,6-dimethyl-phenyl]-2-methoxy-4-oxo-cyclopent-2-en-1-yl]ethyl]carbamate

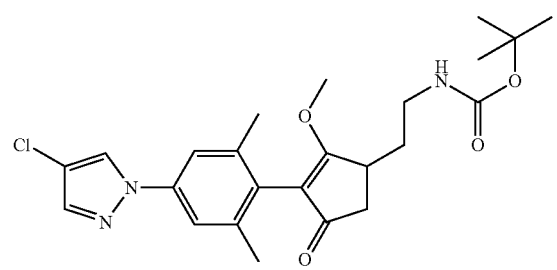 [SMILES: COC1=C(c2c(C)cc(-n3cc(Cl)cn3)cc2C)C(=O)CC1CCNC(=O)OC(C)(C)C]

Prepared from 2-[3-[4-(4-chloropyrazol-1-yl)-2,6-dimethyl-phenyl]-2-methoxy-4-oxo-cyclopent-2-en-1-yl]acetonitrile according to substantially the same procedure used to prepare A120 (step 2) to give the desired product (194 mg, 30%) as a pale yellow gum. $^1$H NMR (500 MHz, CDCl$_3$ and a few drops of d4-methanol) δ (delta) 7.88 (m, 1H), 7.62 (s, 1H), 7.34 (s, 2H), 4.59-4.75 (m, 1H), 3.57 (s, 5H), 3.03-3.19 (m, 1H), 2.65-2.80 (m, 1H), 2.33-2.48 (m, 1H), 2.22 (d, 6H), 1.45 (s, 10H).

Step Two: Synthesis of 2-[3-[4-(4-chloropyrazol-1-yl)-2,6-dimethyl-phenyl]-2,4-dioxo-cyclopentyl]ethylammonium chloride (Intermediate 3)

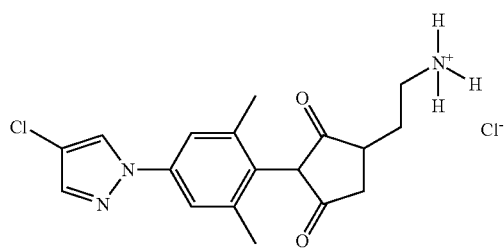 [SMILES: Cc1cc(-n2cc(Cl)cn2)cc(C)c1C1C(=O)CC(CC[NH3+])C1=O ; [Cl-]]

To a solution of tert-butyl N-[2-[3-[4-(4-chloropyrazol-1-yl)-2,6-dimethyl-phenyl]-2-methoxy-4-oxo-cyclopent-2-en-1-yl]ethyl]carbamate (0.100 g, 0.224 mmol) in acetone (2 mL) was added 2M HCl (2 mL). The reaction mixture was heated to 120° C. under microwave irradiation for 20 minutes after which it was diluted with dichloromethane and the phases were separated. The aqueous phase was evaporated to dryness to give the desired product (Intermediate 3) (0.085 g, 99%) as an off white glass. $^1$H NMR (500 MHz, D$_2$O) δ (delta) ppm 7.89 (s, 1H), 7.58 (s, 1H), 7.09 (m, 2H), 3.11 (m, 2H), 3.00 (m, 1H), 2.88 (m, 1H), 2.50 (m, 1H), 2.11 (m, 1H), 1.99 (s, 6H), 1.86 (m, 1H).

Note: The above-shown HCl salt of the amine (R—NH$_3^+$ Cl$^-$) (Intermediate 3), produced in the above process, can be converted to the corresponding free amine (R—NH$_2$) if desired, e.g. via an ion exchange column.

Step Three: Synthesis of [2-[4-(4-chloropyrazol-1-yl)-2,6-dimethyl-phenyl]-4-[2-[(5-chloropyridine-2-carbonyl)amino]ethyl]-3-oxo-cyclopenten-1-yl]5-chloropyridine-2-carboxylate (compound P1)

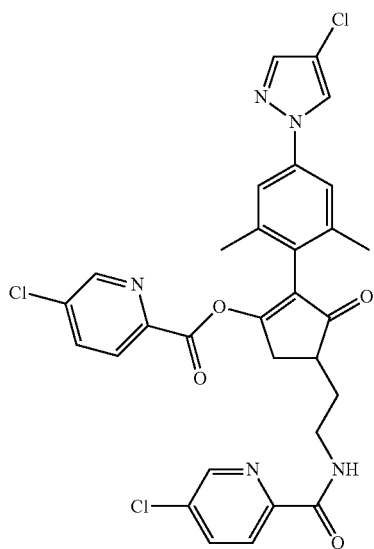 [SMILES: Cc1cc(-n2cc(Cl)cn2)cc(C)c1C1=C(OC(=O)c2ccc(Cl)cn2)CC(CCNC(=O)c2ccc(Cl)cn2)C1=O]

To a solution of 2-[3-[4-(4-chloropyrazol-1-yl)-2,6-dimethyl-phenyl]-2,4-dioxo-cyclopentyl]ethylammonium chloride (e.g. Intermediate 3) (0.172 mmol, 0.066 g) in dichloromethane (5 mL) was added triethylamine (1.7 mmol, 0.98 mL) and 5-chloropyridine-2-carbonyl chloride (1.1 mmol, 0.19 g). After stirring for 1 hour at room temperature the reaction was absorbed onto silica and purified by flash chromoatography (gradient elution: 0-100% ethyl acetate in hexane) to give the desired product (0.059 g, 55%) as an orange oil. $^1$H NMR (500 MHz, CDCl$_3$) δ (delta) ppm 8.39-8.74 (m, 2H), 8.04-8.23 (m, 2H), 7.48-7.98 (m, 5H), 7.20-7.42 (m, 2H), 3.32-3.88 (m, 3H), 2.88-3.21 (m, 2H), 2.06-2.37 (m, 7H), 1.84-2.00 (m, 1H).

Intermediate 4

Synthesis of 2-[3-(2,4,6-trimethyl-phenyl)-2,4-dioxo-cyclopentyl]ethylammonium chloride

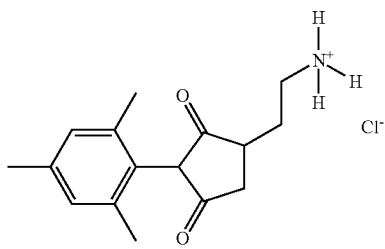 [SMILES: Cc1cc(C)c(C2C(=O)CC(CC[NH3+])C2=O)c(C)c1 ; [Cl-]]

Using similar procedures to those described in Example 16B steps 1 and 2 to prepare Intermediate 3, the above-shown intermediate compound (Intermediate 4) can be prepared from tert-butyl N-{2-[3-(2,4,6-trimethyl-phenyl)-2-methoxy-4-oxo-cyclopent-2-en-1-yl]ethyl}carbamate.

Note: The above-shown HCl salt of the amine (R—NH$_3^+$ Cl$^-$) (Intermediate 4) can optionally be converted to the corresponding free amine (R—NH$_2$) if desired, e.g. via an ion exchange column.

FURTHER CHIRAL HPLC EXAMPLES

Example 17

Neutralization and the Removal of Trifluoroacetate Salt Introduced into A98 During Chiral HPLC N-[2-[(1R)-3-[4-(4-chloropyrazol-1-yl)-2,6-dimethyl-phenyl]-2,4-dioxo-cyclopentyl]ethyl]pyridinium-2-carboxamide trifluoroacetate (54.36 g) was suspended in water (500 mL) and EtOAc (50 mL). Sodium bicarbonate was carefully added portionwise to the mixture until pH 5.0 was achieved. The solution was extracted with EtOAc (500 mL). The aqueous layer was re-acidified to pH 5.0 using 2N HCl and extracted with EtOAc (500 mL). The combined organic layers were dried over MgSO$_4$, filtered through a PTFE frit and concentrated in vacuo to give beige solid N-[2-[(1R)-3-[4-(4-chloropyrazol-1-yl)-2,6-dimethyl-phenyl]-2,4-dioxo-cyclopentyl]ethyl]pyridine-2-carboxamide (43.63 g, 96.76 mmol).

Example 18

Chiral HPLC Separation of Enantiomers of Compound A120 (to Compounds A120A and A120B)

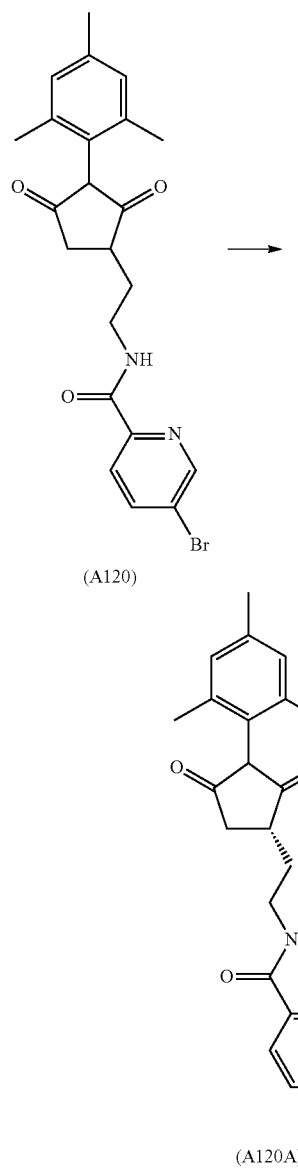

(A120)

(A120A)  (A120B)

Compound A120 (racemic), was separated into the enantiomer compounds A120A and A120B and using a chiral SFC column, by the following method and under the following conditions.

The chiral SFC column used was a Chiralpak® AD—5 micron—20 mm×250 mm SFC column, manufactured by Daicel. In this column, the chiral stationary phase is amylose tris(3,5-dimethylphenylcarbamate)

The solvent system used as an eluent for the column was a 30:70 (by volume) mixture of Solvent A and Solvent B, in which:

Solvent A is methanol
Solvent B is supercritical carbon dioxide.

Other conditions were as follows:
Flow rate through column: 50 ml/minute.
Loading (compound loaded onto column): 20 mg/ml in methanol:acetonitrile (50:50).
Volume of sample (compound) injected per run=1.0 ml
Number of injections of compound=17.
Length of run=6 minutes
Detection wavelength=245 nm Chiral SFC on a total of 340 mg of compound A120 under the above conditions gave 126 mg of compound A120A (100% enantiomeric excess (e.e.), retention time 2.57 minutes under the above conditions) and 84 mg of compound A120B (98.5% enantiomeric excess (e.e.), retention time 3.18 minutes under the above conditions).

Abbreviation: SFC=Supercritical fluid chromatography

Example 19

Chiral HPLC Separation of Enantiomers of Compound A23 (to Compounds A127 and A128)

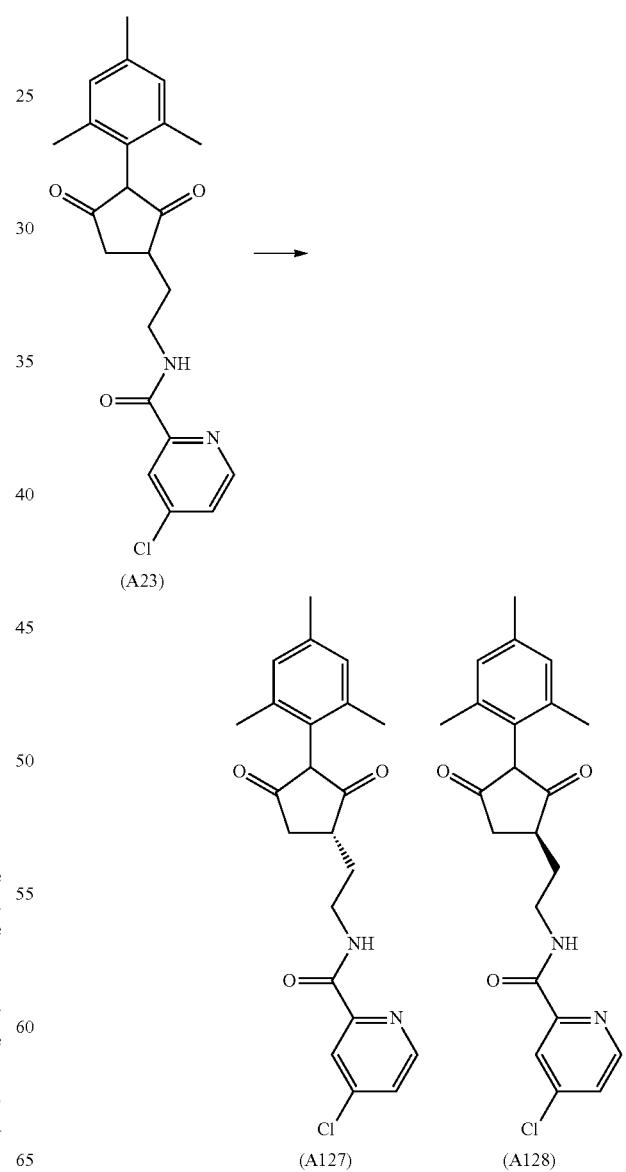

(A23)

(A127)  (A128)

Compound A23 (racemic), was separated into the enantiomer compounds A127 and A128 using a chiral HPLC column, by the following method and under the following conditions.

The chiral HPLC column used was a (s,s)WhelkO1—5 micron—20 mm×250 mm HPLC column, manufactured by Regis Technologies Inc. In this column, the chiral stationary phase is (S,S) 1-(3-5-dinitrobenzamido)-1,2,3,4-tetrahydrophenanthrene.

The solvent system used as an eluent for the column was a 50:50 (by volume) mixture of Solvent A and Solvent B, in which:

Solvent A is isohexane containing 1.0% v/v of isopropanol and 0.1% v/v of trifluoroacetic acid (TFA), and Solvent B is an 80:20 v/v mixture of ispropanol:methanol Other conditions were as follows:

Flow rate through column: 50 ml/minute.

Loading (compound loaded onto column): 53 mg/ml in isopropanol.

Volume of sample (compound) injected per run=1.0 ml

Number of injections of compound=6

Length of run=15 minutes

Chiral HPLC on a total of 320 mg of compound A23 under the above conditions gave 186 mg of the trifluoroacetate salt of compound A127 (100% enantiomeric excess (e.e.), retention time 9.31 minutes under the above conditions) and 192 mg of the trifluoroacetate salt of compound A128 (99.7% enantiomeric excess (e.e.), retention time 12.11 minutes under the above conditions).

Example 20

Chiral HPLC Separation of Enantiomers of Compound A89 (to Compounds A112 and A113)

(A89)

-continued (A112)     (A113)

Compound A89 (racemic), was separated into the enantiomer compounds A112 and A113 using a chiral HPLC column, by the following method and under the following conditions.

The chiral HPLC column used was a (s,s)WhelkO1—5 micron—20 mm×250 mm HPLC column, manufactured by Regis Technologies Inc. In this column, the chiral stationary phase is (S,S) 1-(3-5-dinitrobenzamido)-1,2,3,4-tetrahydrophenanthrene.

The solvent system used as an eluent for the column was a 40:60 (by volume) mixture of Solvent A and Solvent B, in which:

Solvent A is isohexane

Solvent B is isopropanol

Other conditions were as follows:

Flow rate through column: 23 ml/minute from 0 to 14 minutes increasing to 27 ml/minute from 14.5 minutes to the end of the run.

Loading (compound loaded onto column): 40 mg/ml in isopropanol.

Volume of sample (compound) injected per run=0.4 ml

Number of injections of compound=16

Length of run=20 minutes

Chiral HPLC on a total of 400 mg of compound A89 under the above conditions gave 111 mg of compound A112 (98.8% enantiomeric excess (e.e.), retention time 8.07 minutes under the above conditions) and 97 mg of compound A113 (98.4% enantiomeric excess (e.e.), retention time 9.75 minutes under the above conditions).

Additional compounds in Tables A1, A2 and A3 below illustrate the present invention, and are particular embodiments of the compounds of formula (I) according to the present invention. For the most part, these compounds can generally be prepared by methods similar to those shown in the Examples and/or in the process section hereinabove using appropriate starting materials and with any appropriate and/or necessary process changes. It should be noted that certain compounds of the invention exist as a mixture of isomers, including atropisomers, noted above, under the conditions used to obtain the $^1$H NMR data. Where this has occurred, the characterising data are reported for all isomers present at ambient temperature in the specified solvent. Unless otherwise stated, proton NMR spectra were recorded at ambient temperature.

TABLE A1

| Compound No. | Structure | Data |
|---|---|---|
| A1 | 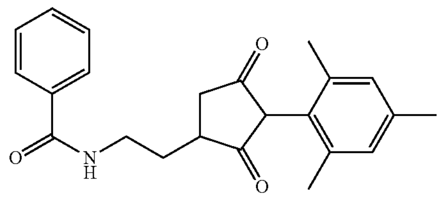 [SMILES: Cc1cc(C)c(C2C(=O)CC(CCNC(=O)c3ccccc3)C2=O)c(C)c1] | ¹H NMR (400 MHz, d4-Methanol) δ (delta) 7.86-7.80 (m, 2H), 7.56-7.50 (m, 1H), 7.49-7.42 (m, 2H), 6.86 (s, 2H), 3.55 (t, 2H), 2.95 (dd, 1H), 2.85-2.76 (m, 1H), 2.49 (dd, 1H), 2.24 (s, 3H), 2.22-2.13 (m, 1H), 2.04 (s, 6H), 1.74 (tdd, 1H). |
| A2 | 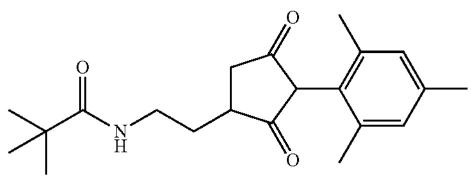 [SMILES: Cc1cc(C)c(C2C(=O)CC(CCNC(=O)C(C)(C)C)C2=O)c(C)c1] | 1H NMR (400 MHz, d-4 methanol) δ (delta) 6.85 (s, 2H), 3.35-3.30 (m, 2H), 2.90 (dd, 1H), 2.75-2.70 (m, 1H), 2.40 (d, 1H), 2.25 (s, 3H), 2.05 (s, 6H), 2.05-2.00 (m, 1H), 1.65-1.55 (m, 1H), 1.20 (s, 9H) |
| A3 | 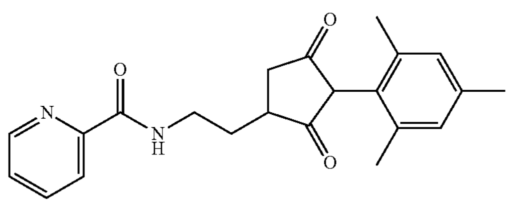 [SMILES: Cc1cc(C)c(C2C(=O)CC(CCNC(=O)c3ccccn3)C2=O)c(C)c1] | 1H NMR (400 MHz, d-4 methanol) δ (delta) 8.65 (d, 1H), 8.10 (d, 1H), 7.95 (dd, 1H), 7.55 (dd, 1H), 6.85 (s, 2H), 3.65-3.55 (m, 2H), 2.90 (dd, 1H), 2.80-2.75 (m, 1H), 2.50 (d, 1H), 2.25 (s, 3H), 2.25-2.20 (m, 1H), 2.05 (s, 6H), 1.80-1.70 (m, 1H) |
| A4 | 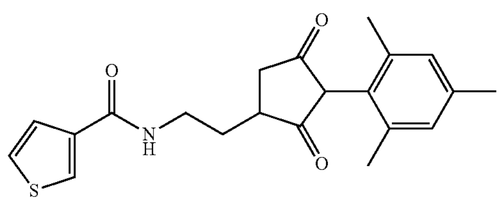 [SMILES: Cc1cc(C)c(C2C(=O)CC(CCNC(=O)c3ccsc3)C2=O)c(C)c1] | 1H NMR (400 MHz, d-4 methanol) δ 8.05 (s, 1H), 7.50 (d, 1H), 7.45 (d, 1H), 6.85 (s, 2H), 3.55-3.50 (m, 2H), 2.90 (dd, 1H), 2.80-2.75 (m, 1H), 2.45 (d, 1H), 2.25 (s, 3H), 2.20-2.15 (m, 1H), 2.05 (s, 6H), 1.75-1.70 (m, 1H) |
| A5 | 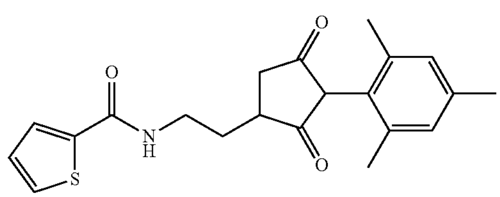 | 1H NMR (400 MHz, d-4 methanol) δ (delta) 7.70 (d, 1H), 7.65 (d, 1H), 7.25-7.20 (m, 1H), 6.85 (s, 2H), 3.55-3.50 (m, 2H), 2.95 (dd, 1H), 2.80-2.75 (m, 1H), 2.45 (dd, 1H), 2.25 (s, 3H), 2.20-2.15 (m, 1H), 2.05 (s, 6H), 1.75-1.70 (m, 1H) |
| A6 | 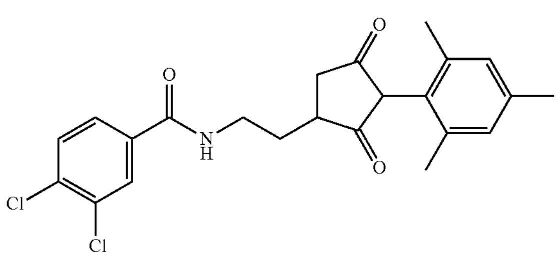 [SMILES: Cc1cc(C)c(C2C(=O)CC(CCNC(=O)c3ccc(Cl)c(Cl)c3)C2=O)c(C)c1] | 1H NMR (400 MHz, d-4 methanol) δ 7.55 (s, 1H), 7.45 (d, 1H), 7.40 (d, 1H), 6.85 (s, 2H), 3.60-3.45 (m, 2H), 2.95 (dd, 1H), 2.85-2.80 (m, 1H), 2.50 (d, 1H), 2.25 (s, 3H), 2.25-2.15 (m, 1H), 2.05 (s, 6H), 1.75-1.65 (m, 1H) |
| A7 | 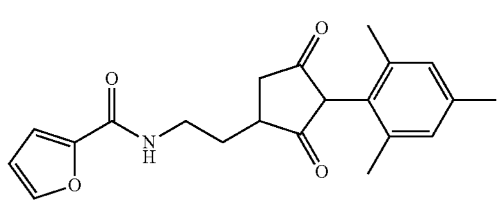 [SMILES: Cc1cc(C)c(C2C(=O)CC(CCNC(=O)c3ccco3)C2=O)c(C)c1] | 1H NMR (400 MHz, d-4 methanol) δ (delta) 1.65-1.75 (1H, m), 2.02-2.06 (6H, s), 2.11-2.21 (1H, m), 2.23-2.26 (3H, s), 2.44-2.51 (1H, m), 2.73-2.81 (1H, m), 2.88-2.97 (1H, m), 3.47-3.54 (2H, m), 6.55-6.57 (1H, m), 6.84-6.87 (2H, s), 7.08-7.12 (1H, m), 7.63-7.66 (1H, m) |

TABLE A1-continued

| Compound No. | Structure | Data |
|---|---|---|
| A8 | 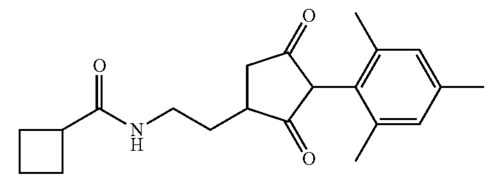 [SMILES: Cc1cc(C)c(C2C(=O)CC(CCNC(=O)C3CCC3)C2=O)c(C)c1] | 1H NMR (400 MHz, d-4 methanol) δ (delta) 1.56-1.68 (2H, m), 1.82-1.93 (1H, m), 1.94-2.11 (8H, m), 2.11-2.21 (1H, m), 2.22-2.34 (5H, m), 2.41-2.49 (1H, m), 2.70-2.79 (1H, m), 2.87-2.96 (1H, m), 3.07-3.17 (1H, m), 3.31-3.38 (2H, m), 6.87-6.91 (2H, s) |
| A9 | 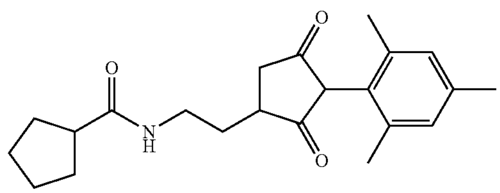 [SMILES: Cc1cc(C)c(C2C(=O)CC(CCNC(=O)C3CCCC3)C2=O)c(C)c1] | 1H NMR (400 MHz, d-4 methanol) δ (delta) 1.54-1.65 (3H, m), 1.66-1.79 (4H, m), 1.81-1.91 (2H, m), 2.00-2.10 (7H, m), 2.22-2.26 (3H, s), 2.39-2.46 (1H, m), 2.57-2.66 (1H, m), 2.67-2.76 (1H, m), 2.84-2.92 (1H, m), 3.28-3.35 (2H, m), 6.84-6.88 (2H, s) |
| A10 | 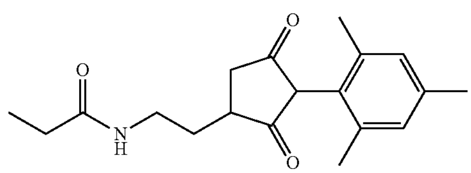 [SMILES: CCC(=O)NCCC1CC(=O)C(c2c(C)cc(C)cc2C)C1=O] | 1H NMR (400 MHz, d-4 methanol) δ (delta) 1.13-1.19 (3H, t), 1.57-1.69 (1H, m), 2.03-2.14 (7H, m), 2.20-2.30 (5H, m), 2.42-2.50 (1H, m), 2.72-2.80 (1H, m), 2.88-2.96 (1H, m), 3.32-3.39 (2H, m), 6.88-6.91 (2H, s) |
| A11 | 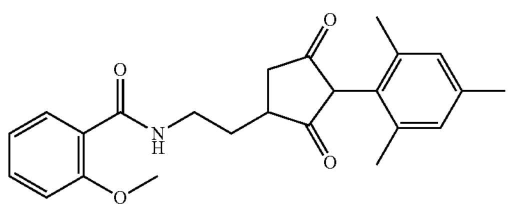 [SMILES: COc1ccccc1C(=O)NCCC1CC(=O)C(c2c(C)cc(C)cc2C)C1=O] | 1H NMR (400 MHz, d-4 methanol) δ (delta) 1.72-1.82 (1H, m), 2.02-2.06 (6H, d), 2.11-2.22 (1H, m), 2.22-2.26 (3H, s), 2.46-2.53 (1H, m), 2.78-2.86 (1H, m), 2.89-2.97 (1H, m), 3.51-3.65 (2H, m), 3.92-3.95 (3H, s), 6.84-6.88 (2H, s), 7.01-7.07 (1H, t), 7.10-7.14 (1H, d), 7.45-7.51 (1H, m), 7.85-7.90 (1H, m) |
| A12 | 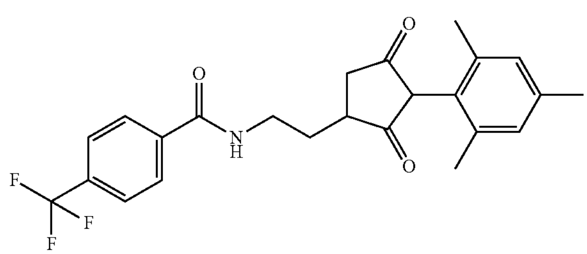 [SMILES: Cc1cc(C)c(C2C(=O)CC(CCNC(=O)c3ccc(C(F)(F)F)cc3)C2=O)c(C)c1] | 1H NMR (400 MHz, d4-methanol) δ (delta) 1.72-1.84 (1H, m), 2.05-2.10 (6H, s), 2.17-2.30 (4H, m), 2.49-2.57 (1H, m), 2.80-2.88 (1H, m), 2.94-3.03 (1H, m), 3.57-3.63 (2H, t), 6.87-6.92 (2H, s), 7.78-7.83 (2H, d), 8.01-8.06 (2H, d) |
| A13 | 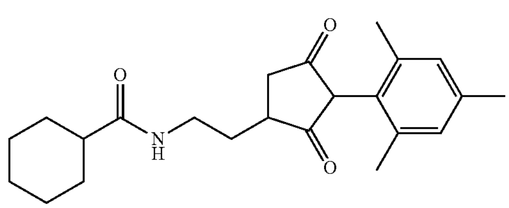 [SMILES: Cc1cc(C)c(C2C(=O)CC(CCNC(=O)C3CCCCC3)C2=O)c(C)c1] | 1H NMR (400 MHz, d-4 methanol) δ (delta) 1.20-1.50 (5H, m), 1.53-1.64 (1H, m), 1.65-1.72 (1H, m), 1.75-1.83 (4H, m), 1.99-2.09 (7H, m), 2.12-2.22 (1H, m), 2.23-2.26 (3H, s), 2.37-2.44 (1H, m), 2.66-2.75 (1H, m), 2.83-2.91 (1H, m), 3.28-3.34 (2H, m), 6.84-6.87 (2H, s). |
| A14 | 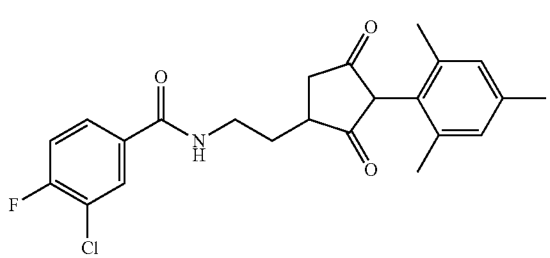 [SMILES: Cc1cc(C)c(C2C(=O)CC(CCNC(=O)c3ccc(F)c(Cl)c3)C2=O)c(C)c1] | 1H NMR (400 MHz, d-4 methanol) δ 1.67-1.78 (1H, m), 2.03-2.06 (6H, s), 2.12-2.22 (1H, m), 2.22-2.26 (3H, s), 2.44-2.52 (1H, m), 2.74-2.82 (1H, m), 2.89-2.98 (1H, m), 3.50-3.57 (2H, t), 6.84-6.88 (2H, s), 7.30-7.37 (1H, t), 7.80-7.85 (1H, m), 7.97-8.01 (1H, m) |

TABLE A1-continued

| Compound No. | Structure | Data |
|---|---|---|
| A15 | 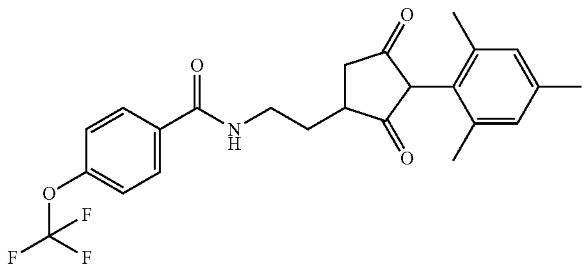 [SMILES: Cc1cc(C)c(C2C(=O)CC(CCNC(=O)c3ccc(OC(F)(F)F)cc3)C2=O)c(C)c1] | 1H NMR (400 MHz, d-4 methanol) δ (delta) 1.69-1.80 (1H, m), 2.02-2.07 (6H, s), 2.13-2.23 (1H, m), 2.23-2.27 (3H, s), 2.46-2.53 (1H, m), 2.76-2.84 (1H, m), 2.90-2.99 (1H, m), 3.52-3.58 (2H, t), 6.84-6.88 (2H, s), 7.33-7.39 (2H, d), 7.91-7.97 (2H, m) |
| A16 | 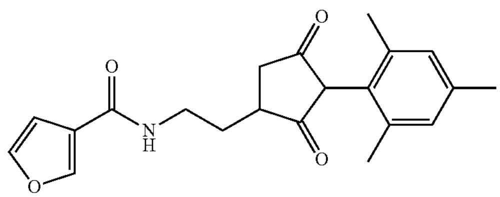 | 1H NMR (400 MHz, d-4 methanol) δ (delta) 1.65-1.75 (1H, m), 2.02-2.06 (6H, s), 2.09-2.21 (1H, m), 2.22-2.26 (3H, s), 2.43-2.51 (1H, m), 2.72-2.82 (1H, m), 2.88-2.97 (1H, m), 3.45-3.52 (2H, t), 6.78-6.81 (1H, m), 6.84-6.87 (2H, s), 7.54-7.57 (1H, m), 8.04-8.06 (1H, m) |
| A17 | 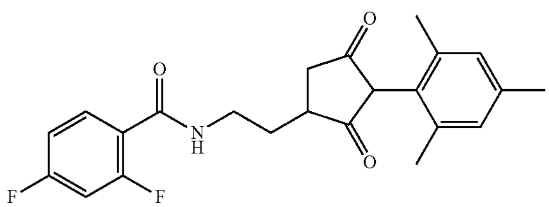 [SMILES: Cc1cc(C)c(C2C(=O)CC(CCNC(=O)c3ccc(F)cc3F)C2=O)c(C)c1] | 1H NMR (400 MHz, d-4 methanol) δ (delta) 1.66-1.77 (1H, m), 2.02-2.07 (6H, s), 2.13-2.23 (1H, m), 2.23-2.26 (3H, s), 2.45-2.53 (1H, m), 2.76-2.84 (1H, m), 2.89-2.98 (1H, m), 3.51-3.58 (2H, m), 6.84-6.88 (2H, s), 7.03-7.11 (2H, m), 7.75-7.83 (1H, m) |
| A18 | 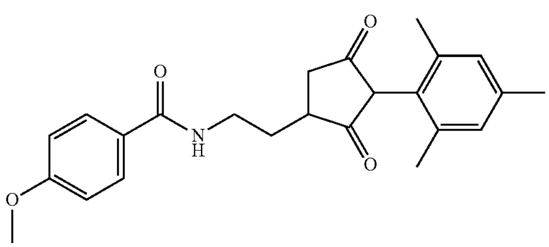 [SMILES: COc1ccc(C(=O)NCCC2CC(=O)C(c3c(C)cc(C)cc3C)C2=O)cc1] | 1H NMR (400 MHz, d-4 methanol) δ (delta) 1.68-1.78 (1H, m), 2.02-2.06 (6H, s), 2.11-2.21 (1H, m), 2.23-2.26 (3H, s), 2.44-2.51 (1H, m), 2.74-2.83 (1H, m), 2.88-2.97 (1H, m), 3.50-3.56 (2H, t), 3.82-3.86 (3H, s), 6.84-6.88 (2H, s), 6.95-6.70 (2H, m), 7.78-7.84 (2H, m) |
| A19 | 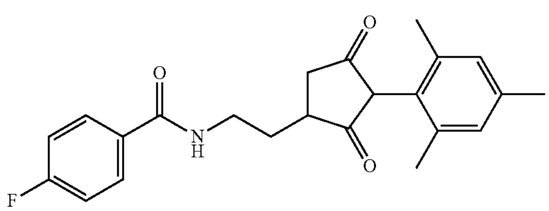 [SMILES: Cc1cc(C)c(C2C(=O)CC(CCNC(=O)c3ccc(F)cc3)C2=O)c(C)c1] | 1H NMR (400 MHz, d-4 methanol) δ (delta) 1.68-1.79 (1H, m), 2.02-2.06 (6H, s), 2.12-2.22 (1H, m), 2.22-2.26 (3H, s), 2.45-2.53 (1H, m), 2.75-2.84 (1H, m), 2.90-2.99 (1H, m), 3.50-3.57 (2H, t), 6.84-6.88 (2H, s), 7.14-7.22 (2H, m), 7.86-7.92 (2H, m) |
| A20 | 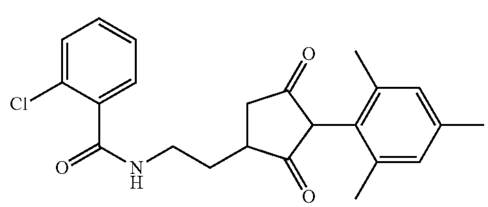 [SMILES: Cc1cc(C)c(C2C(=O)CC(CCNC(=O)c3ccccc3Cl)C2=O)c(C)c1] | 1H NMR (400 MHz, d-chloroform) δ (delta) broad signals 1.87-2.10 (8H, m), 2.21-2.27 (3H, s), 2.38-2.48 (1H, d), 2.94-3.07 (2H, m), 3.42-3.54 (1H, m), 3.71-3.83 (1H, m), 6.82-6.87 (2H, s), 7.25-7.41 (2H, m), 7.52-7.66 (2H, m) |
| A21 | 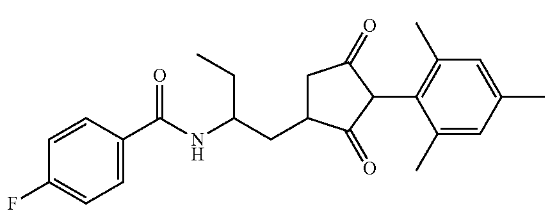 [SMILES: CCC(CC1CC(=O)C(c2c(C)cc(C)cc2C)C1=O)NC(=O)c1ccc(F)cc1] | (As a mixture of diastereoisomers) $^1$H NMR (400 MHz, d4-methanol) δ (delta) 0.99-1.01 (3H, m), 1.17 (1H, t), 1.50-1.83 (3H, m), 2.00 (3H, s), 2.04 (3H, s), 2.11-2.20 (1H, m), 2.24 (3H, s), 2.45-2.55 (1H, m), 2.80-2.90 (1H, m), 3.55-3.65 (1H, m), 4.10-4.25 (1H, m), 6.82-6.87 (2H, m), 7.16-7.23 (2H, m), 7.88-7.95 (2H, m). |

TABLE A1-continued

| Compound No. | Structure | Data |
|---|---|---|
| A22 | 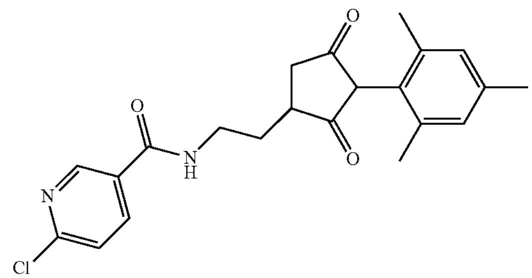 [SMILES: Cc1cc(C)c(C2C(=O)CC(CCNC(=O)c3ccc(Cl)nc3)C2=O)c(C)c1] | 1H NMR (400 MHz, d-4 methanol) δ (delta) 1.68-1.80 (1H, m), 2.01-2.06 (6H, s), 2.13-2.22 (1H, m), 2.22-2.26 (3H, s), 2.45-2.53 (1H, m), 2.76-2.84 (1H, m), 2.90-2.99 (1H, m), 3.52-3.58 (2H, t), 6.83-6.88 (2H, s), 7.52-7.57 (1H, d), 8.17-8.23 (1H, m), 8.78-8.82 (1H, d) |
| A23 | 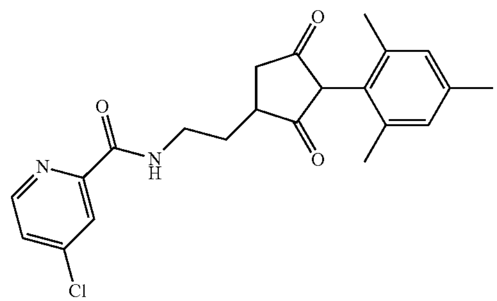 [SMILES: Cc1cc(C)c(C2C(=O)CC(CCNC(=O)c3cc(Cl)ccn3)C2=O)c(C)c1] | 1H NMR (400 MHz, d-4 methanol) δ (delta) 1.68-1.80 (1H, m), 2.02-2.06 (6H, s), 2.14-2.26 (4H, m), 2.45-2.53 (1H, m), 2.76-2.84 (1H, m), 2.89-2.97 (1H, m), 3.55-3.62 (2H, m), 6.84-6.87 (2H, s), 7.59-7.63 (1H, m), 8.08-8.11 (1H, d), 8.55-8.59 (1H, d) |
| A24 | 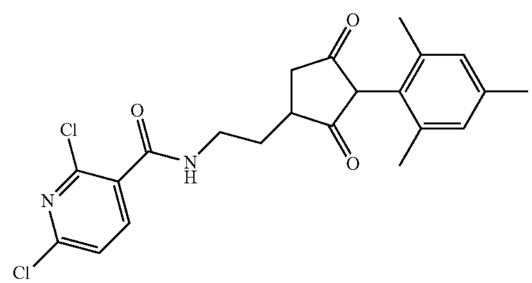 [SMILES: Cc1cc(C)c(C2C(=O)CC(CCNC(=O)c3ccc(Cl)nc3Cl)C2=O)c(C)c1] | 1H NMR (400 MHz, d-4 methanol) δ (delta) 1.66-1.77 (1H, m), 2.02-2.07 (6H, s), 2.14-2.27 (4H, m), 2.46-2.53 (1H, m), 2.79-2.88 (1H, m), 2.90-2.99 (1H, m), 3.50-3.56 (2H, m), 6.85-6.88 (2H, s), 7.48-7.52 (1H, d), 7.88-7.92 (1H, d) |
| A25 | 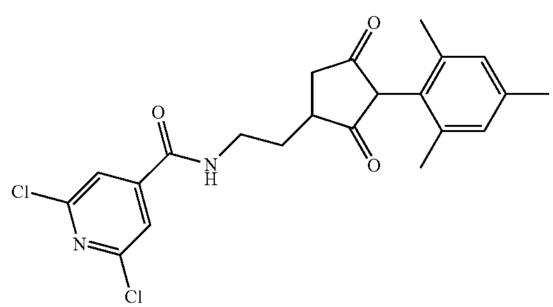 [SMILES: Cc1cc(C)c(C2C(=O)CC(CCNC(=O)c3cc(Cl)nc(Cl)c3)C2=O)c(C)c1] | 1H NMR (400 MHz, d-4 methanol) δ (delta) 1.67-1.78 (1H, m), 2.02-2.06 (6H, d), 2.12-2.22 (1H, m), 2.23-2.26 (3H, s), 2.44-2.51 (1H, m), 2.75-2.83 (1H, m), 2.90-2.98 (1H, m), 3.51-3.56 (2H, m), 6.84-6.88 (2H, s), 7.77-7.79 (1H, s), 7.88-7.90 (1H, s) |
| A26 | 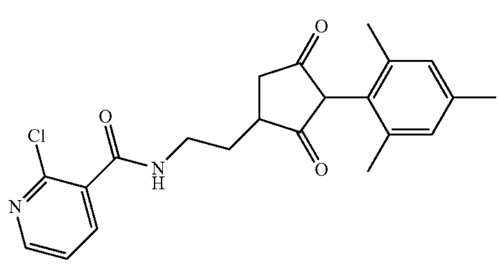 [SMILES: Cc1cc(C)c(C2C(=O)CC(CCNC(=O)c3cccnc3Cl)C2=O)c(C)c1] | 1H NMR (400 MHz, d4-methanol) δ (delta) 1.67-1.78 (1H, m), 2.03-2.07 (6H, s), 2.15-2.26 (4H, m), 2.46-2.54 (1H, m), 2.79-2.90 (1H, m), 2.91-3.00 (1H, m), 3.49-3.58 (2H, m), 6.85-6.88 (2H, s), 7.43-7.47 (1H, m), 7.89-7.93 (1H, m), 8.42-8.45 (1H, m). |

TABLE A1-continued

| Compound No. | Structure | Data |
|---|---|---|
| A27 | 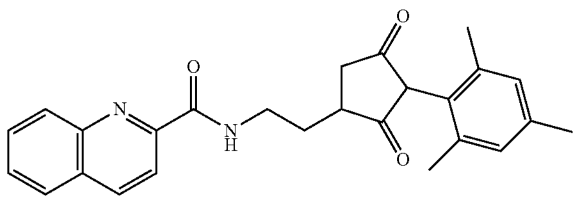 [SMILES: Cc1cc(C)c(C2C(=O)CC(CCNC(=O)c3ccc4ccccc4n3)C2=O)c(C)c1] | 1H NMR (400 MHz, d4-methanol) δ (delta) 1.75-1.86 (1H, m), 2.02-2.07 (6H, m), 2.21-2.31 (4H, m), 2.50-2.57 (1H, m), 2.82-2.90 (1H, m), 2.92-3.00 (1H, m), 3.62-3.70 (2H, m), 6.83-6.88 (2H, s), 7.64-7.71 (1H, t), 7.78-7.85 (1H, t), 7.96-8.01 (1H, d), 8.14-8.22 (2H, t), 8.44-8.49 (1H, d). |
| A28 | 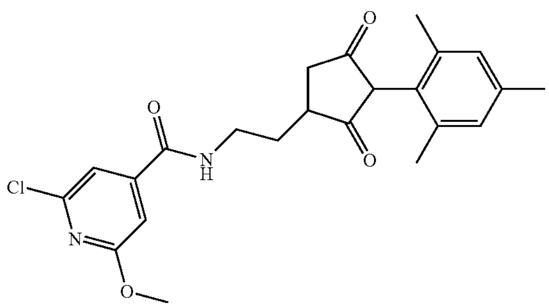 [SMILES: COc1cc(C(=O)NCCC2CC(=O)C(c3c(C)cc(C)cc3C)C2=O)cc(Cl)n1] | 1H NMR (400 MHz, d4-methanol) δ (delta) 1.66-1.77 (1H, m), 2.02-2.06 (6H, m), 2.11-2.22 (1H, m), 2.22-2.27 (3H, s), 2.43-2.52 (1H, m), 2.73-2.83 (1H, m), 2.88-2.98 (1H, m), 3.49-3.55 (2H, m), 3.99 (3H, s), 6.86 (2H, s), 7.10 (1H, d), 7.33 (1H, d). |
| A29 | 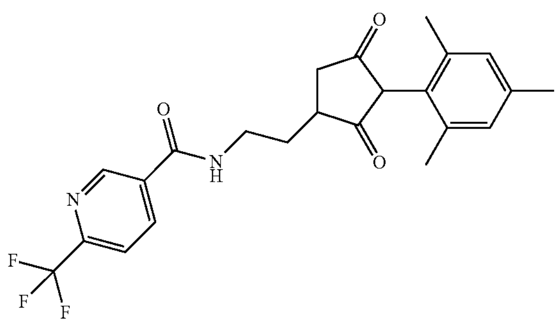 [SMILES: Cc1cc(C)c(C2C(=O)CC(CCNC(=O)c3ccc(C(F)(F)F)nc3)C2=O)c(C)c1] | 1H NMR (400 MHz, d4-methanol) δ (delta) 1.65-1.78 (1H, m), 2.02-2.07 (6H, m), 2.11-2.22 (1H, m), 2.22-2.26 (3H, s), 2.43-2.52 (1H, m), 2.72-2.83 (1H, m), 2.88-2.98 (1H, m), 3.49-3.55 (2H, t), 6.84-6.88 (2H, s), 7.08-7.11 (1H, s), 7.32-7.35 (1H, s), 7.88-7.90 (1H, s). |
| A32 | 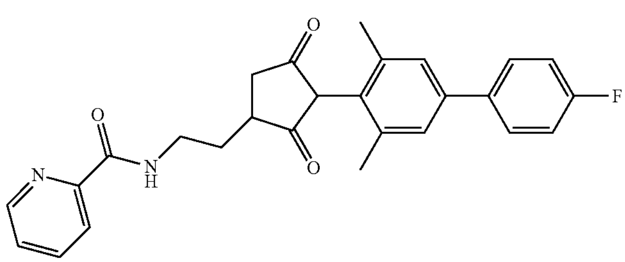 [SMILES: Cc1cc(-c2ccc(F)cc2)cc(C)c1C1C(=O)CC(CCNC(=O)c2ccccn2)C1=O] | 1H NMR (400 MHz, d4-methanol) δ (delta) 1.75-1.89 (1H, m), 2.13-2.18 (6H, s), 2.20-2.32 (1H, m), 2.50-2.60 (1H, m), 2.83-2.93 (1H, m), 2.97-3.09 (1H, m), 3.64-3.70 (2H, t), 7.08-7.16 (2H,t), 7.22-7.26 (2H, s), 7.53-7.60 (2H, m), 8.11-8.18 (1H, t), 8.54-8.61 (1H, m), 8.63-8.71 (1H, t), 8.84-8.90 (1H, bd). |
| A33 | 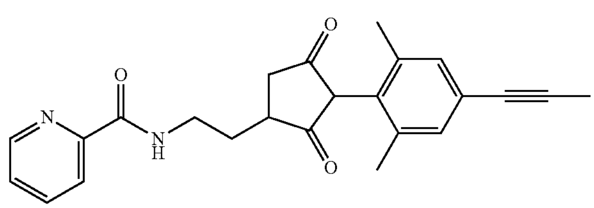 [SMILES: CC#Cc1cc(C)c(C2C(=O)CC(CCNC(=O)c3ccccn3)C2=O)c(C)c1] | 1H NMR (400 MHz, d4-methanol) δ (delta) 1.69-1.82 (1H, m), 1.96-2.00 (3H, s), 2.01-2.09 (6H, s), 2.13-2.25 (1H, m), 2.46-2.55 (1H, m), 2.76-2.85 (1H, m), 2.90-2.99 (1H, m), 3.56-3.63 (2H, m), 7.02-7.07 (2H, s), 7.50-7.57 (1H, m), 7.91-7.98 (1H, t), 8.05-8.13 (1H, m), 8.59-8.66 (1H, m). |
| A34 | 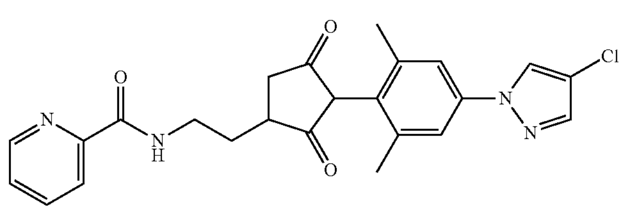 [SMILES: Cc1cc(-n2cc(Cl)cn2)cc(C)c1C1C(=O)CC(CCNC(=O)c2ccccn2)C1=O] | 1H NMR (400 MHz, CDCl$_3$) δ (delta) 1.85-1.95 (1H, m), 2.18-2.21 (6H, s), 2.21-2.29 (3H, m), 2.87-3.05 (2H, m), 3.40-3.52 (1H, m), 7.34-7.38 (2H, m), 7.51-7.58 (1H, m), 7.61-7.64 (1H, s), 7.87-7.90 (1H, s), 7.90-7.97 (1H, t), 8.21-8.26 (1H, d), 8.61-8.65 (1H, d), 8.70-8.77 (1H, m) |

TABLE A1-continued

| Compound No. | Structure | Data |
|---|---|---|
| A35 | 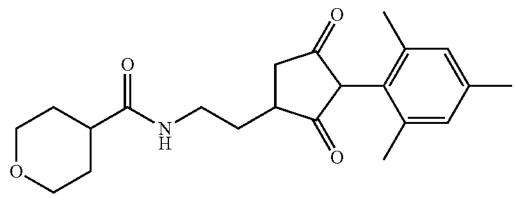 [SMILES: Cc1cc(C)c(C2C(=O)CC(CCNC(=O)C3CCOCC3)C2=O)c(C)c1] | 1H NMR (400 MHz, d4-methanol) δ (delta) 1.61-1.87 (5H, m), 2.04-2.13 (6H, m), 2.25-2.30 (3H, m), 2.49-2.88 (3H, m), 2.96-3.05 (1H, m), 3.14-3.23 (1H, m), 3.35-3.51 (4H, m), 3.89-4.01 (2H, m), 6.86-6.93 (2H, m) |
| A36 | 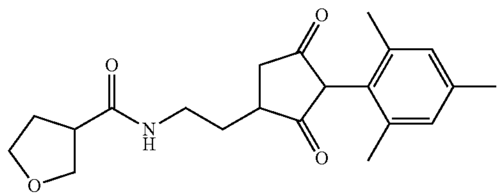 | 1H NMR (400 MHz, d4-methanol) δ (delta) 1.59-1.72 (1H, m), 2.02-2.20 (8H, m), 2.25-2.30 (3H, s), 2.47-2.54 (1H, m), 2.65-2.76 (1H, m), 2.77-2.86 (1H, m), 2.94-3.22 (2H, m), 3.35-3.42 (2H, m), 3.74-4.00 (4H, m), 6.86-6.93 (2H, m) |
| A37 | 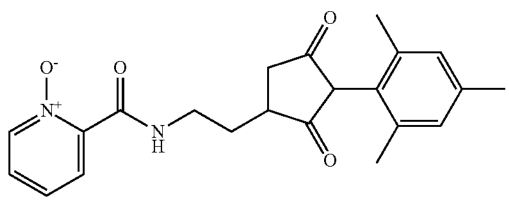 [SMILES: Cc1cc(C)c(C2C(=O)CC(CCNC(=O)c3cccc[n+]3[O-])C2=O)c(C)c1] | 11H NMR (400 MHz, d4-methanol) δ (delta) 1.74-1.86 (1H, m), 2.10-2.20 (6H, s), 2.21-2.32 (4H, m), 2.46-2.57 (1H, m), 2.82-2.88 (1H, m), 2.90-2.98 (1H, m), 3.62-3.72 (2H, t), 6.85-6.88 (2H, s), 7.58-7.70 (2H, m), 8.33-8.42 (2H, m) |
| A38 | 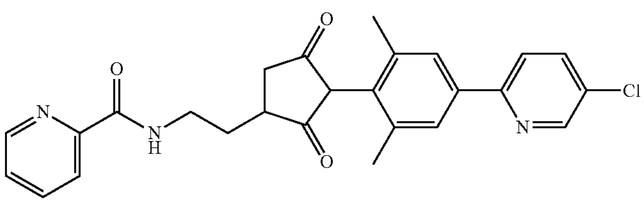 [SMILES: Cc1cc(-c2ccc(Cl)cn2)cc(C)c1C1C(=O)CC(CCNC(=O)c2ccccn2)C1=O] | 1 H NMR (400 MHz, d4-methanol) δ (delta) 1.73-1.85 (1H, m), 2.16-2.28 (7H, m), 2.50-2.59 (1H, m), 2.81-2.89 (1H, m), 2.93-3.03 (1H, m), 3.56-3.66 (2H, m), 7.48-7.62 (1H, bs), 7.64-7.68 (2H, s), 7.81-7.89 (2H, m), 7.93-7.99 (1H, t), 8.01-8.18 (1H, bs), 8.54-8.58 (1H, s), 8.58-8.71 (1H, bs). |
| A39 | trifluoroacetate salt | 1H NMR (400 MHz, d4-methanol) δ (delta) 1.65-1.77 (1H, m), 2.01-2.07 (6H, s), 2.14-2.26 (4H, m), 2.45-2.54 (1H, m), 2.77-2.86 (1H, m), 2.89-2.99 (1H, m), 3.44-3.62 (2H, m), 6.81-6.88 (2H, s), 7.48-7.54 (1H, d), 7.88-7.94 (1H, d), |
| A40 | trifluoroacetate salt | 1H NMR (400 MHz, d4-methanol) δ (delta) 1.66-1.77 (1H, m), 2.03-2.07 (6H, s), 2.16-2.26 (4H, m), 2.47-2.54 (1H, m), 2.81-2.88 (1H, m), 2.91-2.99 (1H, m), 3.47-3.63 (2H, m), 6.84-6.88 (2H, s), 7.43-7.47 (1H, d), 8.08-8.12 (1H, d) |
| A41 | trifluoroacetate salt | 1H NMR (400 MHz, d4-methanol) δ (delta) 1.68-1.79 (1H, m), 2.02-2.06 (6H, s), 2.12-2.22 (1H, m), 2.22-2.26 (3H, s), 2.45-2.52 (1H, m), 2.78-2.85 (1H, m), 2.88-2.97 (1H, m), 3.51-3.57 (2H, t), 6.84-6.87 (2H, s), 7.18-7.26 (2H, m), 7.84-7.86 (1H, m) |

TABLE A1-continued

| Compound No. | Structure | Data |
|---|---|---|
| A43 | 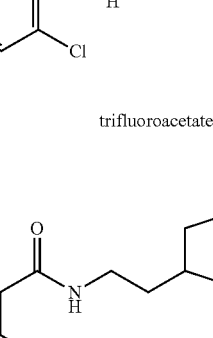 trifluoroacetate salt | 1H NMR (400 MHz, d4-methanol) δ (delta) 1.71-1.82 (1H, m), 2.05-2.12 (6H, s), 2.20-2.31 (4H, m), 2.51-2.59 (1H, m), 2.84-2.92 (1H, m), 2.94-3.03 (1H, m), 3.53-3.69 (2H, m), 6.87-6.92 (2H, s), 8.38-8.41 (1H, s), 8.86-8.90 (1H, s) |
| A44 | 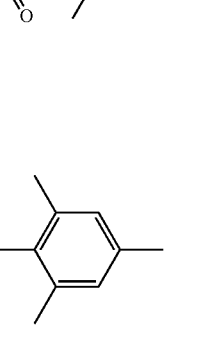 trifluoroacetate salt | 1H NMR (400 MHz, d4-methanol) δ (delta) 1.67-1.78 (1H, m), 2.03-2.07 (6H, s), 2.16-2.27 (4H, m), 2.47-2.55 (1H, m), 2.81-2.90 (1H, m), 2.91-2.99 (1H, m), 3.49-3.64 (2H, m), 6.84-6.88 (2H, s), 7.47-7.52 (1H, m), 7.94-7.98 (1H, m), 8.50-8.54 (1H, m) |
| A45 | 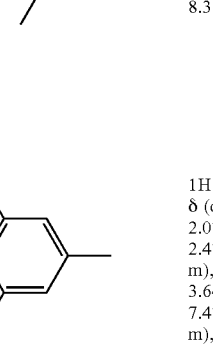 trifluoroacetate salt | 1H NMR (400 MHz, d4-methanol) δ (delta) 1.59-1.71 (1H, m), 2.01-2.16 (7H, m), 2.22-2.36 (3H, s), 2.39-2.47 (1H, m), 2.73-2.80 (1H, m), 2.86-2.95 (1H, m), 3.36-3.43 (2H, m), 4.87-4.94 (2H, s), 6.84-6.88 (2H, s), 7.94-7.99 (2H, m), 8.51-8.57 (1H, m), 8.72-8.77 (1H, m) |
| A46 | 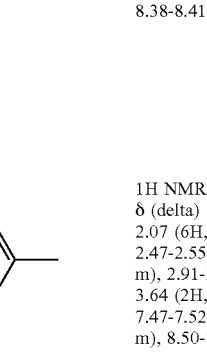 trifluoroacetate salt | 1H NMR (400 MHz, d4-methanol) δ (delta) 1.71-1.81 (1H, m), 2.06-2.10 (6H, s), 2.20-2.31 (4H, m), 2.51-2.58 (1H, m), 2.86-2.93 (1H, m), 2.96-3.03 (1H, m), 3.52-3.67 (2H, m), 6.88-6.91 (2H, s), 7.41-7.46 (1H, m), 8.14-8.18 (1H, m), 8.56-8.59 (1H, m) |
| A47 | 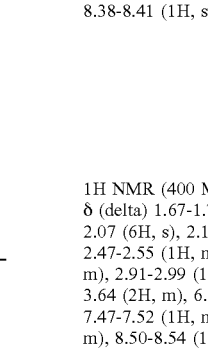 trifluoroacetate salt | 1H NMR (400 MHz, d4-methanol) δ (delta) 1.67-1.78 (1H, m), 2.02-2.06 (6H, s), 2.15-2.27 (4H, m), 2.45-2.52 (1H, m), 2.75-2.83 (1H, m), 2.89-2.97 (1H, m), 3.51-3.64 (2H, m), 6.83-6.87 (2H, s), 7.58-7.62 (1H, m), 7.93-7.99 (1H, t), 8.03-8.07 (1H, d) |
| A48 | 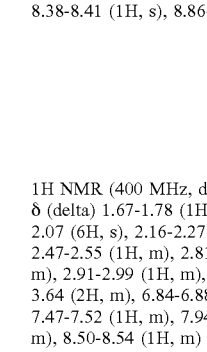 trifluoroacetate salt | 1H NMR (400 MHz, d4-methanol) δ (delta) 1.67-1.78 (1H, m), 2.02-2.06 (6H, s), 2.14-2.26 (4H, m), 2.45-2.52 (1H, m), 2.76-2.83 (1H, m), 2.89-2.97 (1H, m), 3.51-3.64 (2H, m), 6.83-6.87 (2H, m), 7.72-7.77 (1H, d), 7.82-7.88 (1H, t), 8.06-8.09 (1H, d) |

TABLE A1-continued

| Compound No. | Structure | Data |
|---|---|---|
| A50 | 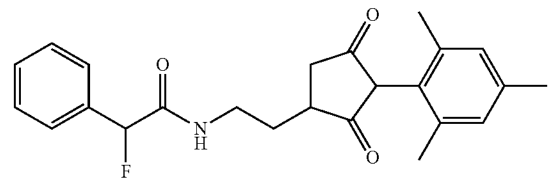 [SMILES: Cc1cc(C)c(C2C(=O)CC(CCNC(=O)C(F)c3ccccc3)C2=O)c(C)c1] | 1H NMR (400 MHz, d4-methanol) δ (delta) 1.57-1.68 (1H, m), 2.01-2.05 (6H, d), 2.06-2.17 (1H, m), 2.22-2.26 (3H, s), 2.38-2.46 (1H, m), 2.63-2.74 (1H, m), 2.80-2.91 (1H, m), 3.35-3.50 (2H, m), 5.70-5.85 (1H, m), 6.84-6.88 (2H, s), 7.37-7.50 (5H, m) |
| A51 | 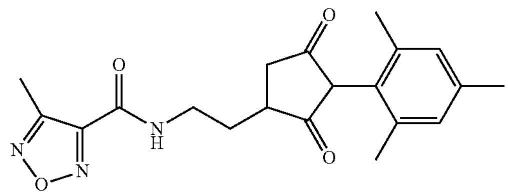 | 1H NMR (400 MHz, d4-methanol) δ (delta) 1.67-1.76 (1H, m), 2.02-2.08 (6H, s), 2.15-2.26 (4H, m), 2.45-2.51 (1H, m), 2.52-2.56 (3H, s), 2.76-2.83 (1H, m), 2.90-2.97 (1H, m), 3.50-3.58 (2H, m), 6.84-6.88 (2H, s) |
| A52 | 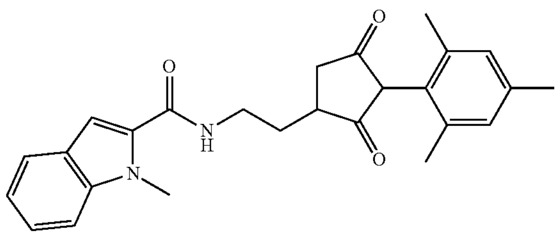 [SMILES: Cc1cc(C)c(C2C(=O)CC(CCNC(=O)c3cc4ccccc4n3C)C2=O)c(C)c1] | 1H NMR (400 MHz, d4-methanol) δ 1.68-1.79 (1H, m), 2.03-2.06 (6H, s), 2.14-2.25 (4H, m), 2.47-2.54 (1H, m), 2.77-2.85 (1H, m), 2.91-2.99 (1H, m), 3.49-3.56 (2H, t), 3.97-3.99 (3H, s), 6.84-6.87 (2H, s), 7.00-7.02 (1H, s), 7.06-7.11 (1H, t), 7.24-7.30 (1H, t), 7.39-7.44 (1H, t), 7.57-7.61 (1H, d) |
| A53 | 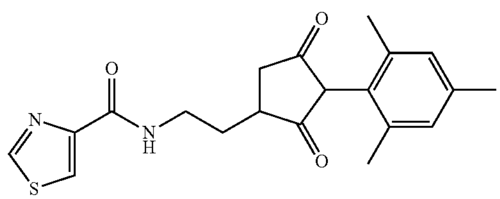 | 1H NMR (400 MHz, d4-methanol) δ (delta) 1.68-1.79 (1H, m), 2.02-2.06 (6H, s), 2.13-2.25 (4H, m), 2.45-2.52 (1H, m), 2.76-2.83 (1H, m), 2.88-2.96 (1H, m), 3.52-3.61 (2H, m), 6.83-6.87 (2H, s), 8.22-8.24 (1H, m), 8.97-8.98 (1H, m) |
| A54 | 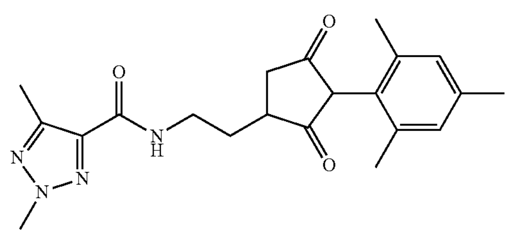 [SMILES: Cc1cc(C)c(C2C(=O)CC(CCNC(=O)c3nn(C)nc3C)C2=O)c(C)c1] | 1H NMR (400 MHz, d4-methanol) δ (delta) 1.64-1.75 (1H, m), 2.02-2.06 (6H, s), 2.10-2.21 (1H, m), 2.22-2.25 (3H, s), 2.44-2.50 (4H, m), 2.75-2.82 (1H, m), 2.88-2.96 (1H, m), 3.47-3.52 (2H, t), 4.10-4.12 (3H, s), 6.84-6.87 (2H, s) |
| A55 | trifluoroacetate salt | 1H NMR (400 MHz, d4-methanol) δ (delta) 1.69-1.81 (1H, m), 2.02-2.06 (6H, s), 2.15-2.26 (4H, m), 2.46-2.53 (1H, m), 2.76-2.84 (1H, m), 2.89-2.98 (1H, m), 3.53-3.67 (2H, m), 6.82-6.86 (2H, s), 8.64-8.67 (1H, m), 8.74-8.76 (1H, m), 9.21-9.23 (1H, m) |
| A56 | trifluoroacetate salt | 1H NMR (400 MHz, d4-methanol) δ (delta) 1.68-1.79 (1H, m), 2.01-2.05 (6H, s), 2.14-2.26 (4H, m), 2.46-2.53 (1H, m), 2.61-2.64 (3H, s), 2.76-2.83 (1H, m), 2.89-2.97 (1H, m), 3.52-3.66 (2H, m), 6.83-6.88 (2H, s), 8.56-8.58 (1H, s), 9.06-9.09 (1H, s). |

TABLE A1-continued

| Compound No. | Structure | Data |
|---|---|---|
| A57 | 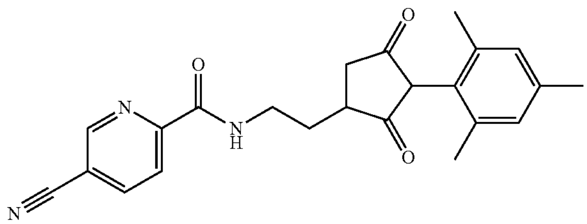 [SMILES: Cc1cc(C)c(C2C(=O)CC(CCNC(=O)c3ccc(C#N)cn3)C2=O)c(C)c1] | 1H NMR (400 MHz, d4-methanol) δ (delta) 1.69-1.80 (1H, m), 2.02-2.05 (6H, s), 2.15-2.25 (4H, m), 2.46-2.52 (1H, m), 2.76-2.83 (1H, m), 2.89-2.97 (1H, m), 3.53-3.66 (2H, m), 6.83-6.86 (2H, s), 8.19-8.24 (1H, d), 8.30-8.34 (1H, m), 8.93-8.95 (1H, m) |
| A57A | trifluoroacetate salt | |
| A58 | 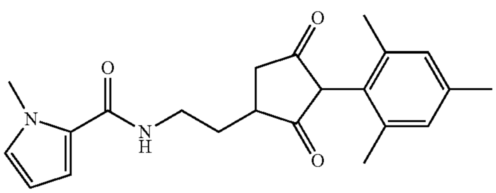 [SMILES: Cc1cc(C)c(C2C(=O)CC(CCNC(=O)c3cccn3C)C2=O)c(C)c1] | 1H NMR (400 MHz, d4-methanol) δ (delta) 1.67-1.78 (1H, m), 2.06-2.09 (6H, s), 2.10-2.21 (1H, m), 2.26-2.29 (3H, s), 2.46-2.53 (1H, m), 2.78-2.85 (1H, m), 2.92-3.00 (1H, m), 3.44-3.52 (2H, m), 3.90-3.92 (3H, s), 6.06-6.09 (1H, m), 6.76-6.79 (1H, m), 6.81-6.84 (1H, m), 6.88-6.91 (2H, s) |
| A59 | trifluoroacetate salt | 1H NMR (400 MHz, d4-methanol) δ (delta) 1.69-1.79 (1H, m), 2.00-2.03 (6H, s), 2.16-2.25 (1H, m), 2.26-2.29 (3H, s), 2.47-2.54 (1H, m), 2.81-2.88 (1H, m), 2.92-3.00 (1H, m), 3.52-3.58 (2H, t), 4.03-4.05 (3H, s), 6.87-6.91 (2H, s), 7.06-7.09 (1H, s), 7.26-7.29 (1H, s) |
| A60 | 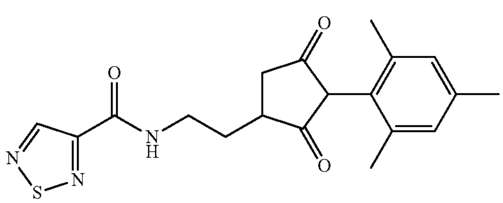 [SMILES: Cc1cc(C)c(C2C(=O)CC(CCNC(=O)c3cnsn3)C2=O)c(C)c1] | 1H NMR (400 MHz, d4-methanol) δ (delta) 1.74-1.88 (1H, m), 2.04-2.10 (6H, s), 2.22-2.32 (4H, m), 2.50-2.57 (1H, m), 2.82-2.90 (1H, m), 2.93-3.02 (1H, m), 3.59-3.72 (2H, m), 6.85-6.89 (2H, s), 9.44-9.47 (1H, s) |
| A61 | 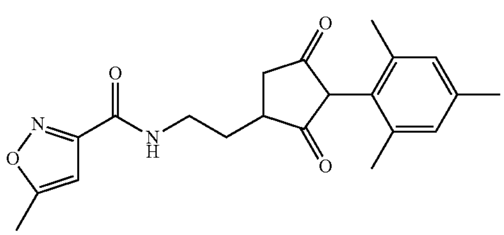 [SMILES: Cc1cc(C)c(C2C(=O)CC(CCNC(=O)c3cc(C)on3)C2=O)c(C)c1] | 1H NMR (400 MHz, d4-methanol) δ (delta) 1.60-1.71 (1H, m), 1.98-2.02 (6H, s), 2.08-2.18 (1H, m), 2.18-2.21 (3H, s), 2.37-2.48 (4H, m), 2.69-2.77 (1H, m), 2.84-2.92 (1H, m), 3.41-3.54 (2H, m), 6.38-6.41 (1H, s), 6.80-6.83 (2H, s). |

TABLE A1-continued

| Compound No. | Structure | Data |
|---|---|---|
| A62 | 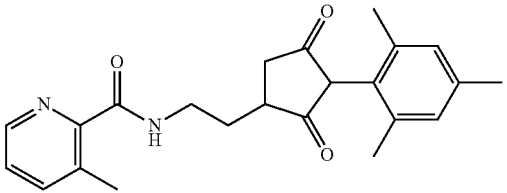<br>trifluoroacetate salt | 1H NMR (400 MHz, d4-methanol) δ (delta) 1.64-1.75 (1H, m), 1.99-2.03 (6H, s), 2.11-2.21 (4H, m), 2.42-2.49 (1H, m), 2.53-2.56 (3H, s), 2.75-2.82 (1H, m), 2.85-2.94 (1H, m), 3.48-3.54 (2H, t), 6.80-6.83 (2H, s), 7.36-7.41 (1H, m), 7.68-7.73 (1H, d), 8.35-8.39 (1H, d) |
| A63 | 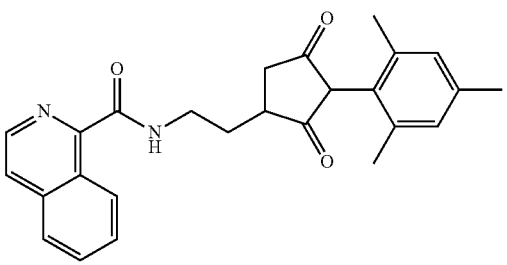<br>trifluoroacetate salt | 1H NMR (400 MHz, d4-methanol) δ 1.76-1.88 (1H, m), 2.05-2.11 (6H, s), 2.22-2.35 (4H, m), 2.52-2.60 (1H, m), 2.86-2.94 (1H, m), 2.96-3.03 (1H, m), 3.63-3.69 (2H, t), 6.84-6.88 (2H, s), 7.67-7.73 (1H, t), 7.75-7.81 (1H, t), 7.89-7.93 (1H, d), 7.93-7.97 (1H, d), 8.45-8.49 (1H, d), 8.93-8.98 (1H, d) |
| A64 | 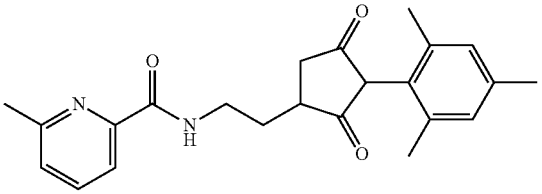<br>trifluoroacetate salt | 1H NMR (400 MHz, d4-methanol) δ (delta) 1.65-1.76 (1H, m), 1.98-2.02 (6H, s), 2.10-2.21 (4H, m), 2.42-2.49 (1H, m), 2.53-2.56 (3H, s), 2.72-2.80 (1H, m), 2.85-2.93 (1H, m), 3.48-3.60 (2H, m), 7.36-7.40 (1H, d), 7.77-7.82 (1H, t), 7.84-7.88 (1H, d) |
| A65 | 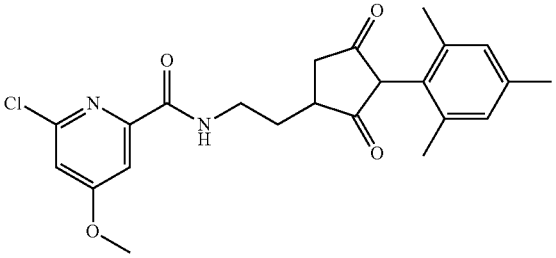<br>trifluoroacetate salt | 1H NMR (400 MHz, d4-methanol) δ (delta) 1.64-1.76 (1H, m), 2.02-2.07 (6H, s), 2.13-2.25 (4H, m), 2.38-2.46 (1H, m), 2.69-2.77 (1H, m), 2.82-2.90 (1H, m), 3.48-3.62 (2H, m), 3.91-3.96 (3H, s), 6.81-6.85 (2H, s), 7.12-7.15 (1H, s), 7.57-7.60 (1H, s) |
| A66 | 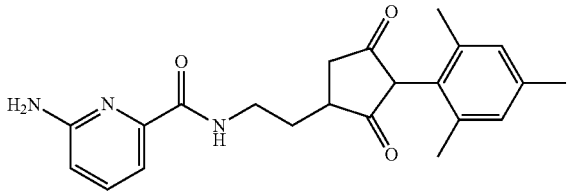<br>trifluoroacetate salt | 1H NMR (400 MHz, d4-methanol) δ (delta) 1.70-1.81 (1H, m), 2.06-2.11 (6H, s), 2.14-2.28 (4H, m), 2.36-2.44 (1H, m), 2.70-2.77 (1H, m), 2.80-2.89 (1H, m), 3.54-3.60 (2H, t), 6.68-6.73 (1H, d), 6.84-6.88 (2H, s), 7.30-7.34 (1H, d), 7.53-7.59 (1H, t) |

TABLE A1-continued

| Compound No. | Structure | Data |
|---|---|---|
| A69 | 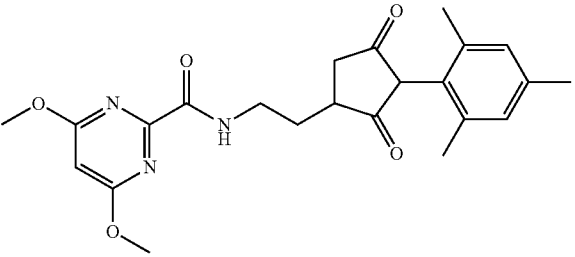<br>trifluoroacetate salt | 1H NMR (400 MHz, d4methanol) δ (delta) 1.64-1.75 (1H, m), 2.00-2.07 (6H, d), 2.08-2.19 (4H, m), 2.20-2.27 (1H, m), 2.53-2.61 (1H, m), 2.63-2.71 (1H, m), 3.47-3.61 (2H, m), 3.94-4.00 (6H, s), 6.18-6.21 (1H, s), 6.73-6.78 (2H, d) |
| A70 | 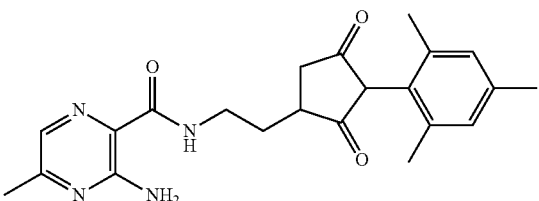<br>trifluoroacetate salt | 1H NMR (400 MHz, d4-methanol) δ (delta) 1.61-1.72 (1H, m), 1.97-2.01 (6H, s), 2.07-2.20 (4H, m), 2.29-2.34 (3H, s), 2.40-2.47 (1H, m), 2.71-2.78 (1H, m), 2.83-2.91 (1H, m), 3.44-3.50 (2H, t), 6.78-6.81 (2H, s), 7.67-7.69 (1H, s) |
| A71 | 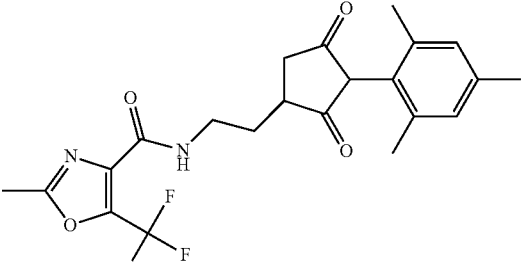<br>trifluoroacetate salt | 1H NMR (400 MHz, d4-methanol) δ (delta) 1.67-1.78 (1H, m), 2.05-2.09 (6H, s), 2.12-2.24 (1H, m), 2.26-2.29 (3H, s), 2.47-2.54 (1H, m), 2.55-2.58 (3H, s), 2.76-2.84 (1H, m), 2.91-2.99 (1H, m), 3.49-3.58 (2H, m), 6.87-6.91 (2H, s) |
| A72 | 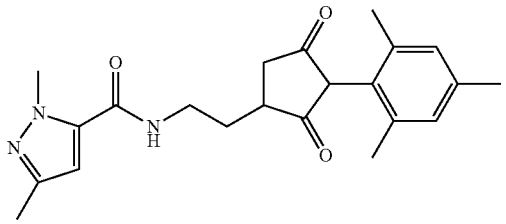<br>trifluoroacetate salt | 1H NMR (400 MHz, d4-methanol) δ (delta) 1.60-1.71 (1H, m), 1.98-2.02 (6H, d), 2.03-2.15 (1H, m), 2.15-2.18 (3H, s), 2.18-2.21 (3H, s), 2.39-2.46 (1H, m), 2.69-2.77 (1H, m), 2.85-2.93 (1H, m), 3.39-3.45 (2H, t), 3.97-3.99 (3H, s), 6.47-6.50 (1H, s), 6.79-6.83 (2H, s) |
| A73 | 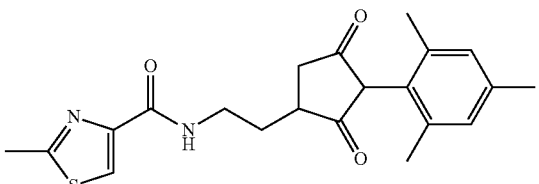<br>trifluoroacetate salt | 1H NMR (400 MHz, d4-methanol) δ (delta) 1.62-1.73 (1H, m), 1.98-2.02 (6H, s), 2.08-2.18 (1H, m), 2.18-2.21 (3H, s), 2.40-2.47 (1H, m), 2.64-2.67 (3H, s), 2.71-2.78 (1H, m), 2.84-2.92 (1H, m), 3.46-3.53 (2H, m), 6.79-6.82 (2H, s), 7.95-7.97 (1H, s) |

TABLE A1-continued

| Compound No. | Structure | Data |
|---|---|---|
| A74 | 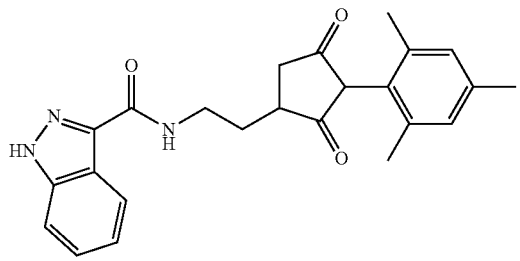<br>trifluoroacetate salt | 1H NMR (400 MHz, d4 methanol) δ 1.64-1.75 (1H, m), 1.98-2.01 (6H, s), 2.12-2.22 (4H, m), 2.42-2.49 (1H, m), 2.75-2.83 (1H, m), 2.85-2.93 (1H, m), 3.52-3.58 (2H, t), 6.76-6.79 (2H, s), 7.16-7.21 (1H, t), 7.31-7.37 (1H, t), 7.47-7.52 (1H, d), 8.16-8.21 (1H, d) |
| A75 | 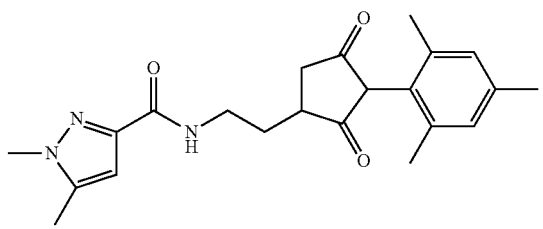<br>trifluoroacetate salt | 1H NMR (400 MHz, d4 methanol) δ (delta) 1.59-1.70 (1H, m), 1.98-2.02 (6H, s), 2.03-2.17 (1H, m), 2.17-2.21 (3H, s), 2.21-2.24 (3H, s), 2.38-2.45 (1H, m), 2.69-2.77 (1H, m), 2.83-2.91 (1H, m), 3.42-3.48 (2H, t), 3.72-3.75 (3H, s), 6.42-6.44 (1H, s), 6.79-6.82 (2H, s) |
| A76 | 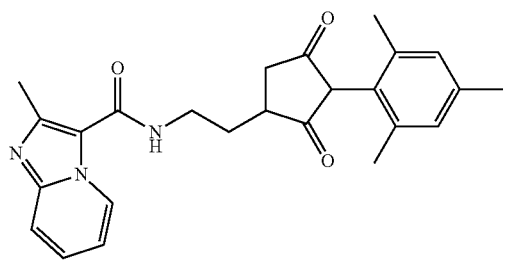<br>trifluoroacetate salt | 1H NMR (400 MHz, d4-methanol) δ 1.75-1.86 (1H, m), 2.07-2.10 (6H, s), 2.20-2.30 (4H, m), 2.41-2.46 (1H, m), 2.64-2.67 (3H, s), 2.75-2.83 (1H, m), 2.85-2.93 (1H, m), 3.59-3.63 (2H, t), 6.81-6.85 (2H, s), 7.01-7.07 (1H, t), 7.42-7.48 (1H, t), 7.51-7.56 (1H, d), 9.02-9.07 (1H, d) |
| A77 | 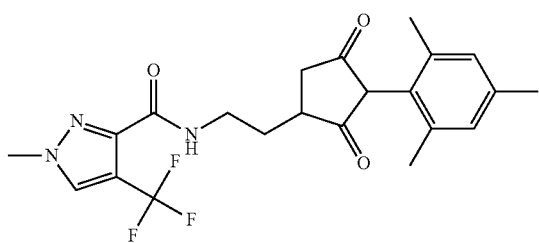<br>trifluoroacetate salt | 1H NMR (400 MHz, d4-methanol) δ (delta) 1.60-1.71 (1H, m), 1.99-2.02 (6H, s), 2.07-2.17 (1H, m), 2.17-2.20 (3H, s), 2.40-2.47 (1H, m), 2.70-2.78 (1H, m), 2.84-2.92 (1H, m), 3.43-3.49 (2H, t), 3.86-3.88 (3H, s), 6.79-6.82 (2H, s), 7.99-8.02 (1H, s) |
| A78 | 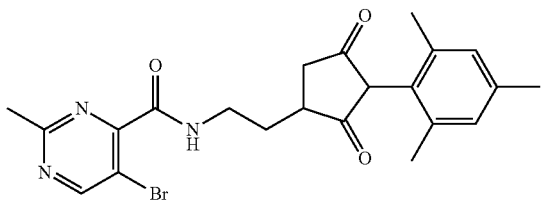<br>trifluoroacetate salt | 1H NMR (400 MHz, d4-methanol) δ (delta) 1.63-1.74 (1H, m), 1.98-2.02 (6H, s), 2.11-2.22 (4H, m), 2.43-2.50 (1H, m), 2.61-2.64 (3H, s), 2.76-2.83 (1H, m), 2.87-2.95 (1H, m), 3.43-3.59 (2H, m), 6.80-6.84 (2H, s), 8.84-8.86 (1H, s) |

TABLE A1-continued

| Compound No. | Structure | Data |
|---|---|---|
| A79 | trifluoroacetate salt | 1H NMR (400 MHz, d4-methanol) δ (delta) 1.61-1.72 (1H, m), 1.98-2.02 (6H, s), 2.05-2.15 (1H, m), 2.19-2.22 (3H, s), 2.40-2.47 (1H, m), 2.52-2.55 (3H, s), 2.62-2.64 (3H, s), 2.69-2.77 (1H, m), 2.85-2.93 (1H, m), 3.41-3.46 (2H, t), 6.80-6.83 (2H, s) |
| A83 | 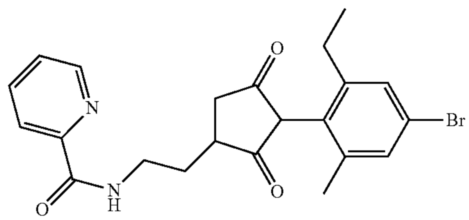 [SMILES: CCc1cc(Br)cc(C)c1C1C(=O)CC(CCNC(=O)c2ccccn2)C1=O] | 1H NMR (400 MHz, d4-methanol) δ (delta) 8.63 (d, 1H), 8.09 (d, 1H), 7.97-7.93 (m, 1H), 7.56-7.52 (m, 1H), 7.22 (s, 2H), 3.66-3.55 (m, 2H), 2.97-2.93 (m, 1H), 2.81 (br, 1H), 2.51 (d, 1H), 2.39 (q, 2H), 2.26-2.14 (m, 1H), 2.06 (2, 3H), 1.81-1.68 (m, 1H), 1.07-1.03 (m, 3H). |
| A84 | 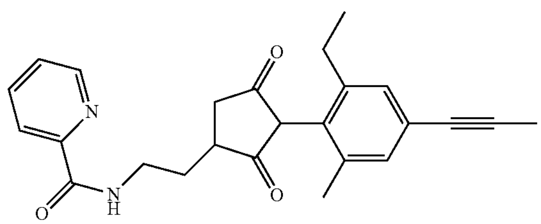 [SMILES: CC#Cc1cc(C)c(C2C(=O)CC(CCNC(=O)c3ccccn3)C2=O)c(CC)c1] | (As a mixture of atropisomers) 1H NMR (400 MHz, CDCl$_3$) δ (delta) 1.12 (dt, 3H), 1.78-1.94 (m, 2H), 2.04 (s, 3H), 2.11 (s, 1.5H), 2.15 (s, 1.5H), 2.18 (d, 1H), 2.44 (dt, 2H), 2.81-3.04 (m, 2H), 3.35-3.53 (m, 1H), 4.04-4.25 (m, 1H), 7.05-7.19 (m, 2H), 7.46-7.60 (m, 1H), 7.91 (t, 1H), 8.22 (d, 1H), 8.61 (d, 1H), 8.69 (br. s., 1H), 12.25 (br. s., 1H). |
| A85 | 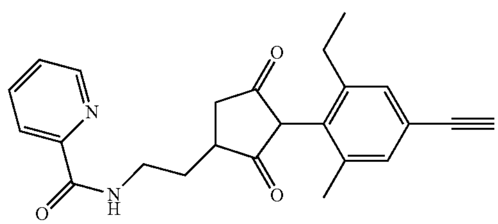 [SMILES: C#Cc1cc(C)c(C2C(=O)CC(CCNC(=O)c3ccccn3)C2=O)c(CC)c1] | 1H NMR (400 MHz, CDCl$_3$) δ (delta) 1.05-1.18 (m, 3H), 1.87 (t, 1H), 2.10-2.23 (m, 4H), 2.40-2.56 (m, 2H), 2.83-3.00 (m, 2H), 3.01 (s, 1H), 3.43 (d, 1H), 4.08-4.21 (m, 1H), 7.20-7.26 (m, 2H), 7.42-7.50 (m, 1H), 7.92 (t, 1H), 8.22 (d, 1H), 8.61 (d, 1H), 8.71 (br. s., 1H). |
| A86 | 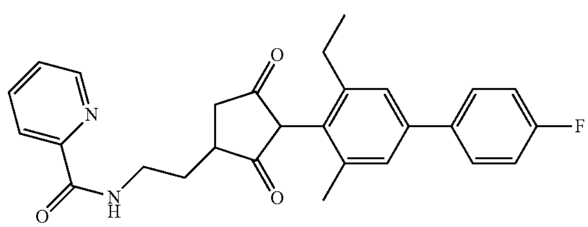 [SMILES: CCc1cc(-c2ccc(F)cc2)cc(C)c1C1C(=O)CC(CCNC(=O)c2ccccn2)C1=O] | (As a mixture of atropisomers) 1H NMR (400 MHz, CDCl$_3$) δ (delta) 12.35 (br, 1H), 8.71 (br, 1H), 8.62 (d, 1H), 8.23 (d, 1H), 7.96-7.88 (m, 1H), 7.57-7.49 (m, 3H), 7.26 (s, 2H), 7.10 (t, 2H), 4.18 (d, 1H), 3.44 (d, 1H), 3.04-2.96 (m, 1H), 2.96-2.88 (m, 1H), 2.58-2.54 (m, 2H), 2.26 (s, 1.5H), 2.22 (s, 1.5H), 2.26-2.17 (m, 2H), 1.89 (t, 1H), 1.20-1.16 (m, 3H) |
| A87 | 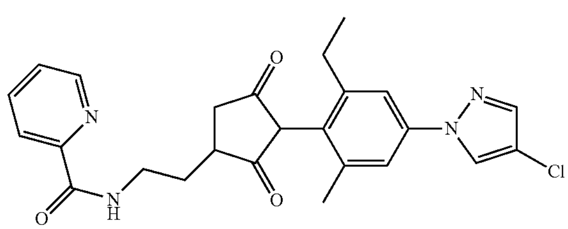 [SMILES: CCc1cc(-n2cc(Cl)cn2)cc(C)c1C1C(=O)CC(CCNC(=O)c2ccccn2)C1=O] | 1H NMR (400 MHz, CDCl$_3$) δ (delta) 8.71 (br, 1H), 8.61 (d, 1H), 8.22 (d, 1H), 8.01-7.84 (m, 2H), 7.62 (s, 1H), 7.57-7.49 (m, 1H), 7.46-7.32 (m, 2H), 4.25-4.11 (m, 1H), 3.46 (br, 1H), 3.05-2.83 (m, 2H), 2.56-2.52 (m, 2H), 2.25-2.20 (m, 5H), 1.88 (br, 1H), 1.23-1.11 (m, 3H) |
| A88 | 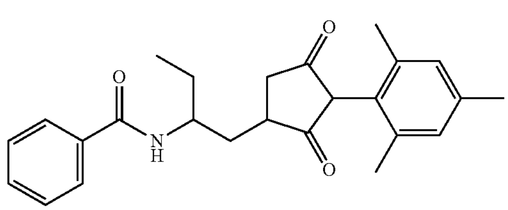 [SMILES: CCC(CC1CC(=O)C(c2c(C)cc(C)cc2C)C1=O)NC(=O)c1ccccc1] | (As a mixture of diastereoisomers) 1H NMR (400 MHz, d4-methanol) δ (delta) 0.96-1.03 (3H, m), 1.14-1.20 (1H, t), 1.55-1.82 (3H, m), 2.00-2.03 (3H, s), 2.03-2.06 (3H, s), 2.12-2.21 (1H, m), 2.22-2.25 (3H, s), 2.46-2.55 (1H, m), 2.82-2.92 (1H, m), 3.56-3.63 (1H, q), 4.13-4.23 (1H, m), 6.83-6.87 (2H, d), 7.43-7.49 (2H, m), 7.50- |

TABLE A1-continued

| Compound No. | Structure | Data |
|---|---|---|
| | | 7.56 (1H, m), 7.83-7.88 (2H, m) |
| A89 | 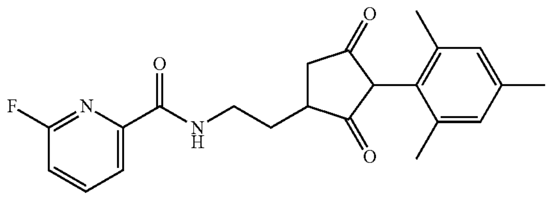 [SMILES: Cc1cc(C)c(C2C(=O)CC(CCNC(=O)c3cccc(F)n3)C2=O)c(C)c1] | 1H NMR (400 MHz, d4-methanol) δ (delta) 1.70-1.81 (1H, m), 2.05-2.09 (6H, s), 2.17-2.28 (4H, m), 2.48-2.55 (1H, m), 2.78-2.86 (1H, m), 2.91-3.00 (1H, m), 3.53-3.68 (2H, m), 6.86-6.90 (2H, s), 7.24-7.29 (1H, m), 8.01-8.05 (1H, m), 8.08-8.16 (1H, m) |
| A89A | trifluoroacetate salt | |
| A91 | trifluoroacetate salt | 1H NMR (400 MHz, d4-methanol) δ (delta) 1.70-1.81 (1H, m), 1.97-2.02 (6H, d), 2.08-2.18 (1H, m), 2.18-2.22 (3H, s), 2.42-2.49 (1H, m), 2.72-2.80 (1H, m), 2.86-2.94 (1H, m), 3.49-3.63 (2H, m), 3.91-3.94 (3H, s), 6.79-6.83 (2H, d), 6.88-6.92 (1H, d), 7.61-7.65 (1H, d), 7.72-7.78 (1H, t). |
| A92 | trifluoroacetate salt | 1H NMR (400 MHz, d4-methanol) δ (delta) 1.35-1.42 (3H, t), 1.78-1.89 (1H, m), 2.04-2.09 (6H, d), 2.13-2.24 (1H, m), 2.25-2.29 (3H, s), 2.49-2.56 (1H, m), 2.79-2.87 (1H, m), 2.93-3.01 (1H, m), 3.56-3.69 (2H, m), 4.39-4.50 (2H, m), 6.86-6.90 (2H, d), 6.92-6.97 (1H, d), 7.66-7.71 (1H, d), 7.78-7.85 (1H, t). |
| A93 | trifluoroacetate salt | 1H NMR (400 MHz, d4-methanol) δ (delta) 1.75-1.86 (1H, m), 2.01-2.06 (6H, s), 2.13-2.25 (4H, m), 2.47-2.54 (1H, m), 2.77-2.86 (1H, m), 2.90-2.98 (1H, m), 3.57-3.70 (2H, m), 6.80-6.86 (2H, d), 7.38-7.51 (3H, m), 7.94-8.18 (5H, m) |
| A94 | trifluoroacetate salt | 1H NMR (400 MHz, d4-methanol) δ (delta) 1.69-1.80 (1H, m), 2.01-2.06 (6H, s), 2.16-2.26 (4H, m), 2.46-2.53 (1H, m), 2.75-2.83 (1H, m), 2.89-2.97 (1H, m), 3.53-3.69 (2H, m), 6.82-6.86 (2H, s), 7.94-7.99 (1H, d), 8.18-8.24 (1H, t), 8.32-8.36 (1H, d) |

TABLE A1-continued

| Compound No. | Structure | Data |
|---|---|---|
| A96 | 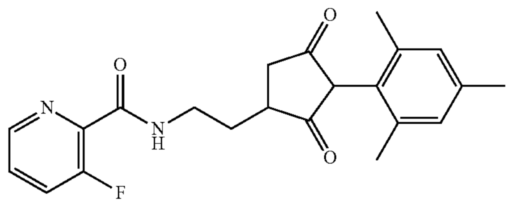 [SMILES: Cc1cc(C)c(C2C(=O)CC(CCNC(=O)c3ncccc3F)C2=O)c(C)c1] | 1H NMR (400 MHz, d4-methanol) δ (delta) 1.70-1.82 (1H, m), 2.05-2.09 (6H, s), 2.17-2.28 (4H, m), 2.49-2.56 (1H, m), 2.80-2.88 (1H, m), 2.92-3.01 (1H, m), 3.53-3.68 (2H, m), 6.86-6.90 (2H, s), 7.59-7.65 (1H, m), 7.70-7.78 (1H, t), 8.45-8.50 (1H, d) |
| A97 | 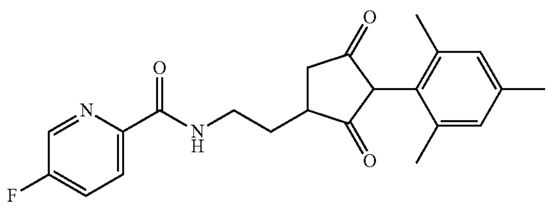 [SMILES: Cc1cc(C)c(C2C(=O)CC(CCNC(=O)c3ccc(F)cn3)C2=O)c(C)c1] | 1H NMR (400 MHz, d4-methanol) δ (delta) 1.71-1.82 (1H, m), 2.05-2.08 (6H, s), 2.16-2.28 (4H, m), 2.47-2.55 (1H, m), 2.78-2.86 (1H, m), 2.91-2.99 (1H, m), 3.56-3.65 (2H, m), 7.71-7.79 (1H, m), 8.15-8.21 (1H, m), 8.52-8.55 (1H, d) |
| A98 | 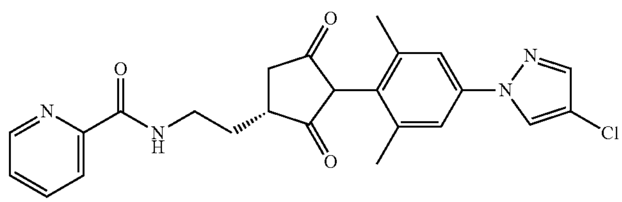 [SMILES: Cc1cc(-n2cc(Cl)cn2)cc(C)c1C1C(=O)C[C@@H](CCNC(=O)c2ccccn2)C1=O] | 1H NMR (400 MHz, d4-methanol) δ (delta) 1.73-1.84 (1H, m), 2.12-2.27 (7H, m), 2.51-2.58 (1H, m), 2.81-2.89 (1H, m), 2.94-3.02 (1H, m), 3.57-3.67 (2H, m), 7.42-7.45 (2H, s), 7.55-7.61 (1H, t), 7.64-7.66 (1H, s), 7.97-8.03 (1H, t), 8.10-8.15 (1H, d), 8.31-8.34 (1H, s), 8.63-8.67 (1H, d) |
| A99 | 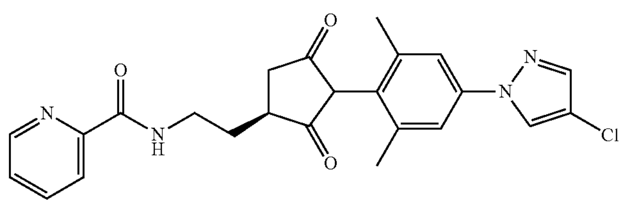 [SMILES: Cc1cc(-n2cc(Cl)cn2)cc(C)c1C1C(=O)C[C@H](CCNC(=O)c2ccccn2)C1=O] | 1H NMR (400 MHz, d4-methanol) δ (delta) 1.73-1.84 (1H, m), 2.12-2.27 (7H, m), 2.51-2.58 (1H, m), 2.81-2.89 (1H, m), 2.94-3.02 (1H, m), 3.57-3.67 (2H, m), 7.42-7.45 (2H, s), 7.55-7.61 (1H, t), 7.64-7.66 (1H, s), 7.97-8.03 (1H, t), 8.10-8.15 (1H, d), 8.31-8.34 (1H, s), 8.63-8.67 (1H, d) |
| A100 | 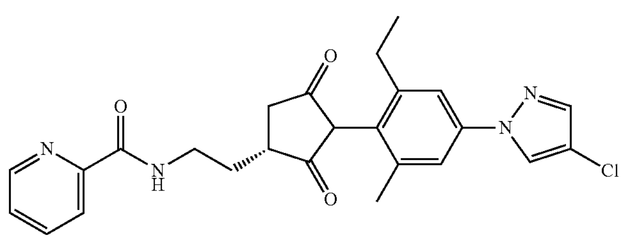 [SMILES: CCc1cc(-n2cc(Cl)cn2)cc(C)c1C1C(=O)C[C@@H](CCNC(=O)c2ccccn2)C1=O] | 1H NMR (400 MHz, CDCl$_3$) δ (delta) 8.71 (br, 1H), 8.61 (d, 1H), 8.22 (d, 1H), 8.01-7.84 (m, 2H), 7.62 (s, 1H), 7.57-7.49 (m, 1H), 7.46-7.32 (m, 2H), 4.25-4.11 (m, 1H), 3.46 (br, 1H), 3.05-2.83 (m, 2H), 2.56-2.52 (m, 2H), 2.25-2.20 (m, 5H), 1.88 (br, 1H), 1.23-1.11 (m, 3H) |
| A101 | 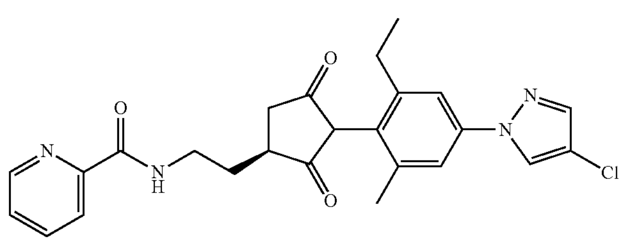 [SMILES: CCc1cc(-n2cc(Cl)cn2)cc(C)c1C1C(=O)C[C@H](CCNC(=O)c2ccccn2)C1=O] | 1H NMR (400 MHz, CDCl$_3$) δ (delta) 8.71 (br, 1H), 8.61 (d, 1H), 8.22 (d, 1H), 8.01-7.84 (m, 2H), 7.62 (s, 1H), 7.57-7.49 (m, 1H), 7.46-7.32 (m, 2H), 4.25-4.11 (m, 1H), 3.46 (br, 1H), 3.05-2.83 (m, 2H), 2.56-2.52 (m, 2H), 2.25-2.20 (m, 5H), 1.88 (br, 1H), 1.23-1.11 (m, 3H) |

The following compound is also one embodiment of the present invention:

A1A

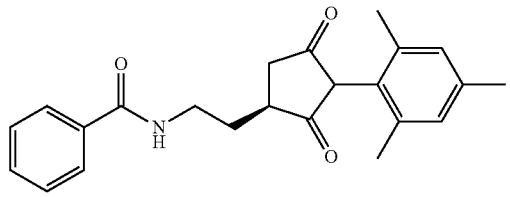

Additional compounds in Table A2 below illustrate the present invention, and are particular embodiments of the compounds of formula (I) according to the present invention. For the most part (in particular for the $R^1=R^3=$methyl compounds, e.g. compounds A102, A103 and A104), these compounds are thought to be preparable, for example by methods similar to those shown in the Examples and/or in the process section hereinabove using appropriate starting materials and with any appropriate and/or necessary process changes.

TABLE A2

| Compound number | Structure | Data |
|---|---|---|
| A102 | 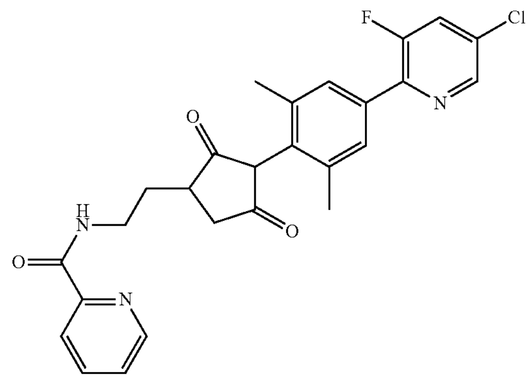 [SMILES: Cc1cc(-c2ncc(Cl)cc2F)cc(C)c1C1C(=O)CC(CCNC(=O)c2ccccn2)C1=O] | 1H NMR (400 MHz, CDCl$_3$) δ (delta) 1.99 (s, 3H), 2.08-2.42 (m, 7H), 2.91 (br. s., 1H), 3.50 (br. s., 1H), 3.89 (br. s., 1H), 7.39-7.51 (m, 2H), 7.57 (br. s., 2H), 7.85 (t, 1H), 8.14 (d, 1H), 8.42 (s, 1H), 8.55 (d, 2H) |
| A103 | 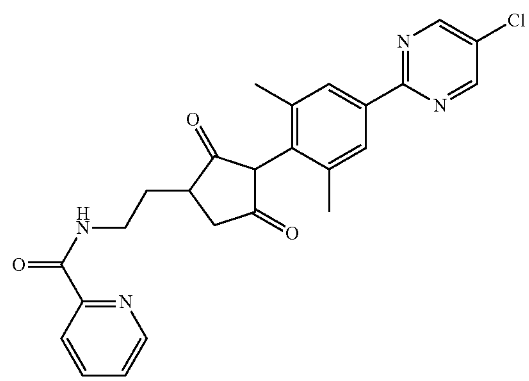 [SMILES: Cc1cc(-c2ncc(Cl)cn2)cc(C)c1C1C(=O)CC(CCNC(=O)c2ccccn2)C1=O] | |
| A104 | 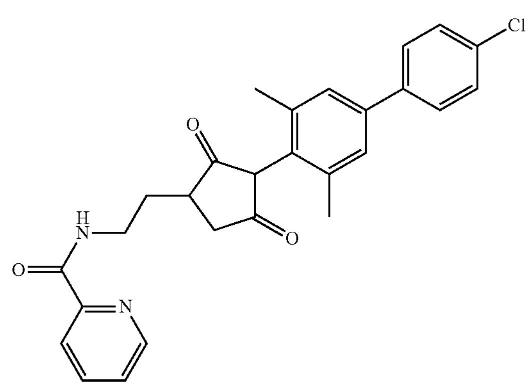 | 1H NMR (400 MHz, CDCl$_3$) δ (delta) 1.84-1.95 (m, 1H), 2.15-2.25 (m, 5H), 2.28 (s, 3H), 2.85-2.96 (m, 1H), 2.96-3.06 (m, 1H), 3.37-3.48 (m, 1H), 4.15-4.26 (m, 1H), 7.24-7.28 (m, 2H), 7.37 (d, 2H), 7.46-7.56 (m, 3H), 7.92 (td, 1H), 8.23 (d, 1H), 8.62 (d, 1H), 8.71 (br. s., 1H). |

TABLE A2-continued

| Compound number | Structure | Data |
|---|---|---|
| A105 | 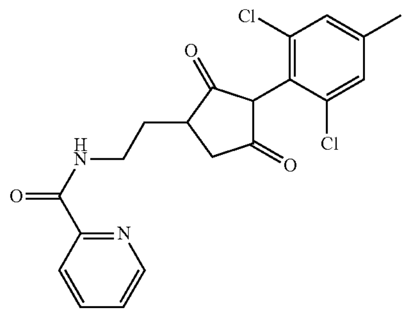 [SMILES: Cc1cc(Cl)c(C2C(=O)CC(CCNC(=O)c3ccccn3)C2=O)c(Cl)c1] | 1H NMR (500 MHz, D$_2$O) δ (delta) 1.79-1.95 (m, 1H), 2.34 (s, 5H), 2.86-2.96 (m, 1H), 2.98-3.15 (m, 1H), 3.56-3.77 (m, 2H), 7.23-7.28 (m, 1H), 7.24 (s, 2H), 8.12-8.30 (m, 1H), 8.56-8.67 (m, 1H), 8.70-8.81 (m, 1H), 8.86-9.07 (m, 1H) |
| A106 | 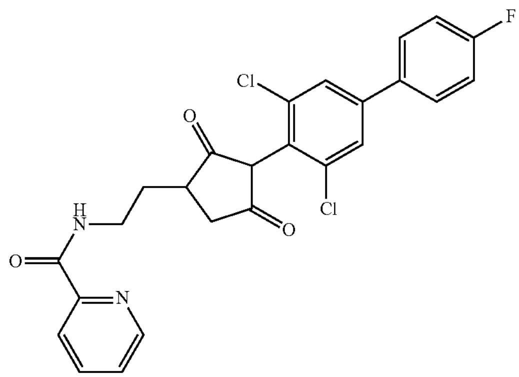 [SMILES: O=C(NCCC1CC(=O)C(c2c(Cl)cc(-c3ccc(F)cc3)cc2Cl)C1=O)c1ccccn1] | 1H NMR (400 MHz, d4-methanol) δ (delta) 1.82 (br. s., 1H), 2.14-2.35 (m, 1H), 2.50-2.70 (m, 1H), 2.84-3.21 (m, 2H), 3.25-3.42 (m, 1H), 3.53-3.76 (m, 1H), 7.20 (s, 2H), 7.54-7.73 (m, 3H), 7.54-7.73 (m, 2H), 7.85-8.01 (m, 1H), 8.31-8.47 (m, 1H), 8.66-9.01 (m, 1H) |
| A107 | 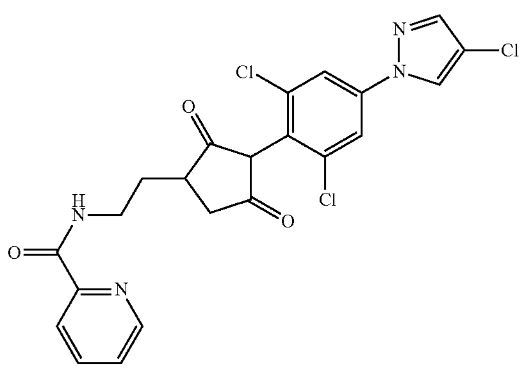 [SMILES: O=C(NCCC1CC(=O)C(c2c(Cl)cc(-n3cc(Cl)cn3)cc2Cl)C1=O)c1ccccn1] | |
| A108 | 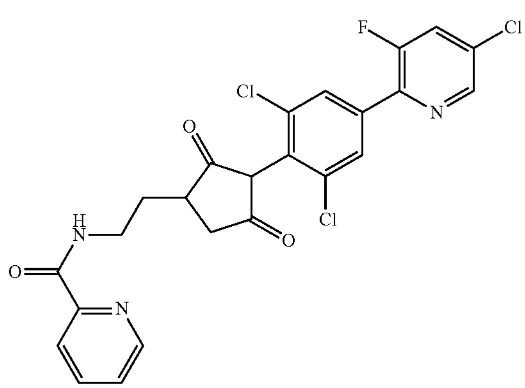 [SMILES: O=C(NCCC1CC(=O)C(c2c(Cl)cc(-c3ncc(Cl)cc3F)cc2Cl)C1=O)c1ccccn1] | |

Additional compounds in Table A3 below illustrate the present invention, and are particular embodiments of the compounds of formula (I) according to the present invention. For the most part, these compounds can generally be prepared by methods similar to those shown in the Examples and/or in the process section hereinabove using appropriate starting materials and with any appropriate and/or necessary process changes.

It should be noted that certain compounds of the invention exist as a mixture of isomers, including atropisomers, noted above, under the conditions used to obtain the $^1$H NMR data. Where this has occurred, the characterising data are reported for all isomers present at ambient temperature in the specified solvent. Unless otherwise stated, proton ($^1$H) NMR spectra were recorded at ambient temperature.

TABLE A3

| Compound number | Structure | Data |
|---|---|---|
| A109 | 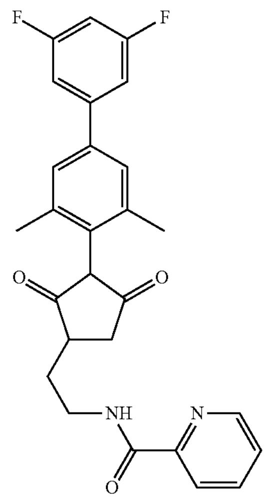 | $^1$H NMR (400 MHz, CDCl$_3$) δ (delta) 2.00 (s, 2H), 2.04-2.15 (m, 1H), 2.16-2.36 (m, 6H), 2.91 (m, 2H), 3.48 (d, 1H), 4.00 (br. s., 1H), 6.65-6.80 (m, 1H), 7.06 (d, 2H), 7.22 (s, 2H), 7.49 (m, 1H), 7.74-8.01 (m, 1H), 8.16 (d, 1H), 8.58 (d, 1H), 8.63 (br. s., 1H) |
| A110 | 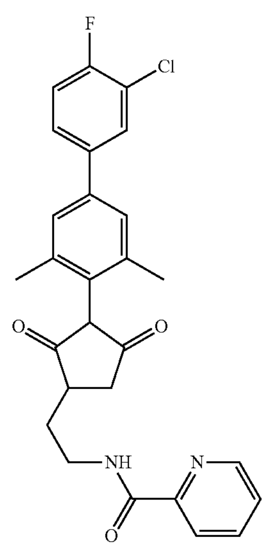 [SMILES: Cc1cc(-c2ccc(F)c(Cl)c2)cc(C)c1C1C(=O)CC(CCNC(=O)c2ccccn2)C1=O] | $^1$H NMR (400 MHz, CDCl$_3$) δ (delta) 1.83-1.99 (m, 1H), 2.10-2.39 (m, 8H), 2.77-3.14 (m, 2H), 3.32-3.58 (m, 1H), 3.82-4.47 (m, 1H), 7.15 (t, 1H), 7.20 (s, 2H), 7.35-7.43 (m, 1H), 7.49 (br. s., 1H), 7.53-7.64 (m, 1H), 7.76-7.99 (m, 1H), 8.17 (br. s., 1H), 8.49-8.64 (m, 1H), 8.64-8.84 (m, 1H) |

TABLE A3-continued

| Compound number | Structure | Data |
|---|---|---|
| A111 | 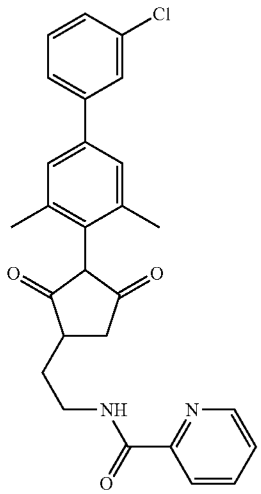 [SMILES: Cc1cc(-c2cccc(Cl)c2)cc(C)c1C1C(=O)CC(CCNC(=O)c2ccccn2)C1=O] | 1H NMR (400 MHz, CDCl$_3$) δ (delta) 1.98 (br. s., 1H), 2.10 (br. s., 1H), 2.21 (s, 3H), 2.24 (s, 3H), 2.26-2.34 (m, 1H), 2.81-3.03 (m, 2H), 3.37-3.57 (m, 1H), 4.01 (br. s., 1H), 7.24 (s, 2H), 7.28 (s, 1H), 7.29-7.36 (m, 1H), 7.43 (d, 1H), 7.49 (dd, 1H), 7.53 (s, 1H), 7.88 (t, 1H), 8.17 (d, 1H), 8.58 (d, 1H), 8.62 (br. s., 1H) |
| A112 | 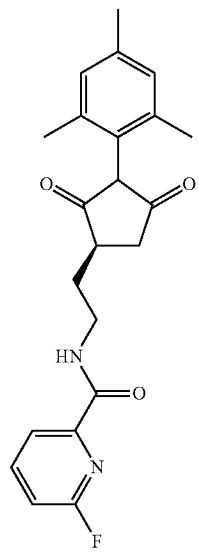 [SMILES: Cc1cc(C)c(C2C(=O)C[C@@H](CCNC(=O)c3cccc(F)n3)C2=O)c(C)c1] | 1H NMR (400 MHz, CDCl$_3$) δ (delta) 1.79-2.50 (m, 13H), 2.88 (d, 2H), 3.29-3.53 (m, 1H), 6.89 (s, 2H), 7.05-7.22 (m, 1H), 7.81-8.19 (m, 2H), 8.19-8.39 (m, 1H) |
| A113 | 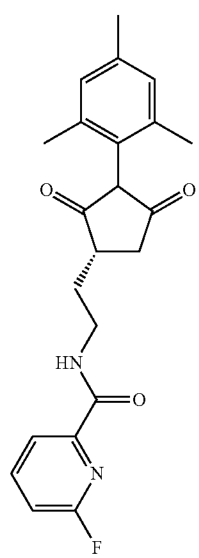 [SMILES: Cc1cc(C)c(C2C(=O)C[C@H](CCNC(=O)c3cccc(F)n3)C2=O)c(C)c1] | 1H NMR (400 MHz, CDCl$_3$) δ (delta) 1.79-2.50 (m, 13H), 2.88 (d, 2H), 3.29-3.53 (m, 1H), 6.89 (s, 2H), 7.05-7.22 (m, 1H), 7.81-8.19 (m, 2H), 8.19-8.39 (m, 1H) |

TABLE A3-continued

| Compound number | Structure | Data |
|---|---|---|
| A114 | 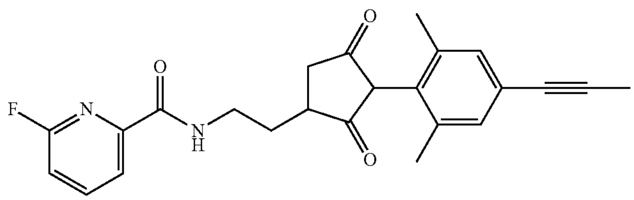 [SMILES: CC#Cc1cc(C)c(C2C(=O)CC(CCNC(=O)c3cccc(F)n3)C2=O)c(C)c1] | 1H NMR (400 MHz, CDCl$_3$) δ (delta) 1.80-2.16 (m, 11H), 2.16-2.33 (m, 1H), 2.71-2.93 (m, 2H), 3.38-3.57 (m, 1H), 3.64-3.90 (m, 1H), 6.95-7.22 (m, 3H), 7.86-8.11 (m, 2H), 8.21 (br. s., 1H) |
| A115 | 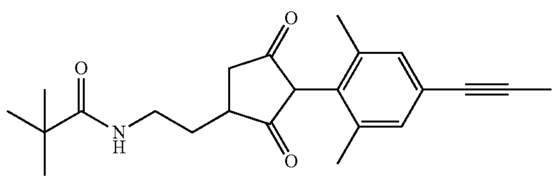 [SMILES: CC#Cc1cc(C)c(C2C(=O)CC(CCNC(=O)C(C)(C)C)C2=O)c(C)c1] | 1H NMR (400 MHz, CDCl$_3$) δ (delta) 1.27 (d, 9H), 1.91-2.22 (m, 11H), 2.86 (s, 2H), 3.09-3.23 (m, 1H), 3.85-4.06 (m, 1H), 6.18-6.37 (m, 1H), 7.09 (br. s., 1H), 7.16-7.24 (m, 1H) |
| A116 | 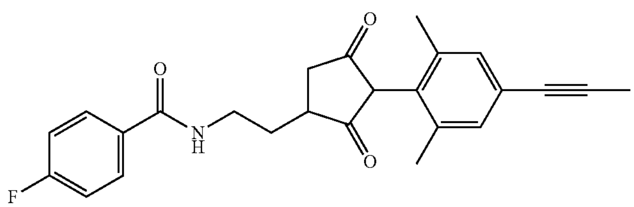 [SMILES: CC#Cc1cc(C)c(C2C(=O)CC(CCNC(=O)c3ccc(F)cc3)C2=O)c(C)c1] | 1H NMR (400 MHz, CDCl$_3$) δ (delta) 1.76-2.12 (m, 11H), 2.13-2.37 (m, 1H), 2.66-2.98 (m, 2H), 3.16-3.41 (m, 1H), 3.70 (d, 1H), 6.91-7.17 (m, 4H), 7.75 (ddd, 2H), 7.86 (br. s., 1H) |
| A117 | 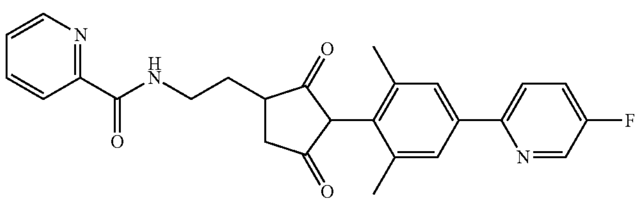 [SMILES: Cc1cc(-c2ccc(F)cn2)cc(C)c1C1C(=O)CC(CCNC(=O)c2ccccn2)C1=O] | 1H NMR (400 MHz, CDCl$_3$) δ (delta) 1.90-2.09 (m, 2H), 2.12-2.36 (m, 7H), 2.73-3.05 (m, 2H), 3.36-3.61 (m, 1H), 3.66-4.17 (m, 1H), 7.36-7.49 (m, 2H), 7.53 (br. s., 2H), 7.63 (dd, 1H), 7.85 (t, 1H), 8.15 (d, 1H), 8.45 (br. s., 1H), 8.48-8.67 (m, 2H) |
| A118 | 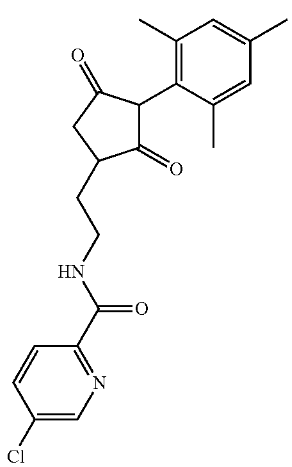 [SMILES: Cc1cc(C)c(C2C(=O)CC(CCNC(=O)c3ccc(Cl)cn3)C2=O)c(C)c1] | 1H NMR (400 MHz, CDCl$_3$) δ (delta) 1.61-3.03 (m, 13H), 3.20-3.77 (m, 2H), 3.77-4.06 (m, 1H), 6.83 (s, 2H), 7.65-8.63 (m, 4H) |

TABLE A3-continued
| Compound number | Structure | Data |
|---|---|---|
| A119 | 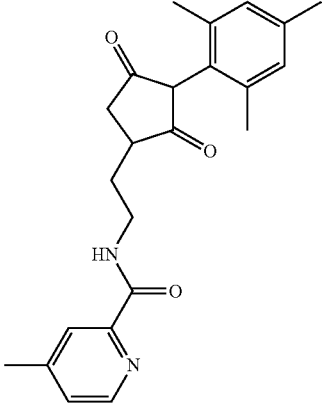 | 1H NMR (400 MHz, CDCl$_3$) δ (delta) 1.65-3.11 (m, 17H), 3.24-3.69 (m, 1H), 3.88-4.30 (m, 1H), 6.86 (s, 2H), 7.26 (s, 1H), 7.89-8.20 (m, 1H), 8.42 (d, 1H), 8.48-8.79 (m, 1H) |
| A120 | 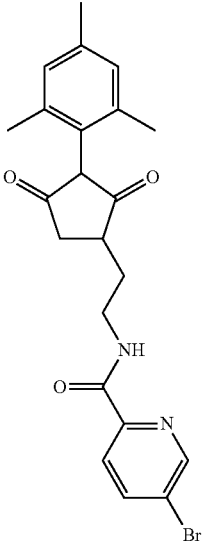 [SMILES: Cc1cc(C)c(C2C(=O)CC(CCNC(=O)c3ccc(Br)cn3)C2=O)c(C)c1] | 1H NMR (400 MHz, CDCl$_3$) δ (delta) 1.83-2.4 (m, 11H), 2.74-3.11 (m, 2H), 3.45-3.52 (m, 2H), 3.97 (br. s., 1H), 6.84 (br. s., 2H), 7.9-8.09 (m, 2H), 8.48-8.7 (m, 2H) |
| A120A | 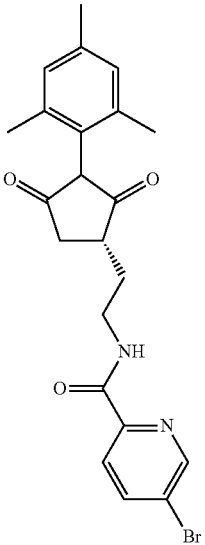 [SMILES: Cc1cc(C)c(C2C(=O)C[C@@H](CCNC(=O)c3ccc(Br)cn3)C2=O)c(C)c1] | 1H NMR (400 MHz, CDCl$_3$) δ (delta) 1.83-2.4 (m, 11H), 2.74-3.11 (m, 2H), 3.45-3.52 (m, 2H), 3.97 (br. s., 1H), 6.84 (br. s., 2H), 7.9-8.09 (m, 2H), 8.48-8.7 (m, 2H) |

TABLE A3-continued
| Compound number | Structure | Data |
|---|---|---|
| A120B | 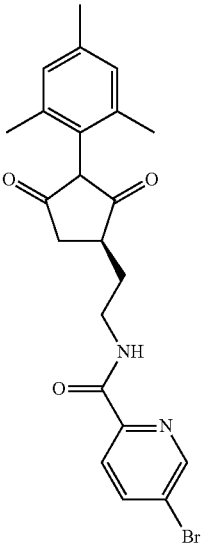 | 1H NMR (400 MHz, CDCl₃) δ (delta) 1.83-2.4 (m, 11H), 2.74-3.11 (m, 2H), 3.45-3.52 (m, 2H), 3.97 (br. s., 1H), 6.84 (br. s., 2H), 7.9-8.09 (m, 2H), 8.48-8.7 (m, 2H) |
| A121 | 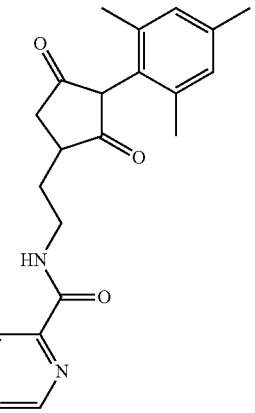 | 1H NMR (400 MHz, CDCl₃) δ (delta) 1.48-2.30 (m, 11H), 2.75-3.08 (m, 2H), 3.29-3.69 (m, 2H), 3.97 (br. s., 1H), 6.84 (br. s., 2H), 7.33-7.81 (m, 1H), 7.90-8.71 (m, 3H) |
| A122 | 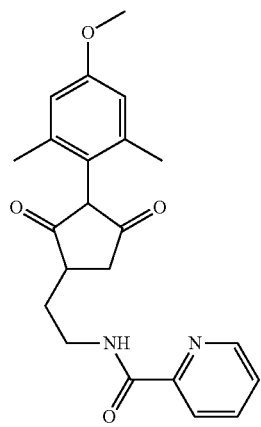 [SMILES: COc1cc(C)c(C2C(=O)CC(CCNC(=O)c3ccccn3)C2=O)c(C)c1] | 1H NMR (400 MHz, CDCl₃) δ (delta) 1.87-2.05 (m, 2H), 2.10 (s, 3H), 2.12 (s, 3H), 2.18-2.33 (m, 1H), 2.74-2.97 (m, 2H), 3.39-3.57 (m, 1H), 3.73 (s, 3H), 3.91 (br. s., 1H), 6.59 (s, 2H), 7.36-7.57 (m, 1H), 7.87 (t, 1H), 8.14 (d, 1H), 8.40-8.72 (m, 2H) |

TABLE A3-continued

| Compound number | Structure | Data |
|---|---|---|
| A123 | 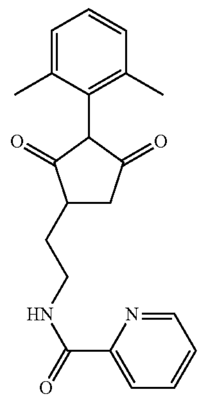 [SMILES: Cc1cccc(C)c1C1C(=O)CC(CCNC(=O)c2ccccn2)C1=O] | 1H NMR (400 MHz, d6-DMSO) δ (delta) 1.51-1.64 (m, 1H), 2.01 (s, 3H), 2.02 (s, 3H), 2.04-2.14 (m, 1H), 2.38 (dd, 1H), 2.57-2.71 (m, 1H), 2.78-2.93 (m, 1H), 3.35-3.50 (m, 2H), 6.96-7.03 (m, 2H), 7.03-7.12 (m, 1H), 7.61 (ddd, 1H), 7.94-8.11 (m, 2H), 8.65 (d, 1H), 8.94 (t, 1H) |
| A124 | 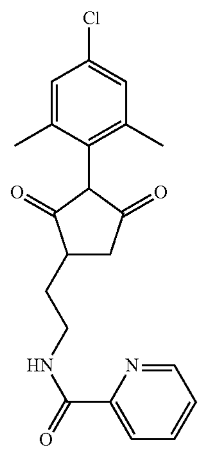 [SMILES: Cc1cc(Cl)cc(C)c1C1C(=O)CC(CCNC(=O)c2ccccn2)C1=O] | 1H NMR (400 MHz, CDCl$_3$) δ (delta) 1.81-1.90 (m, 1H), 2.08 (d, 1H), 2.14 (s, 3H), 2.18 (s, 3H), 2.19-2.25 (m, 1H), 2.84-2.92 (m, 1H), 2.92-3.00 (m, 1H), 3.37-3.47 (m, 1H), 4.13-4.23 (m, 1H), 7.07 (s, 2H), 7.48-7.58 (m, 1H), 7.92 (td, 1H), 8.22 (d, 1H), 8.61 (d, 1H), 8.71 (br. s., 1H), 12.52 (br. s., 1H) |
| A125 | 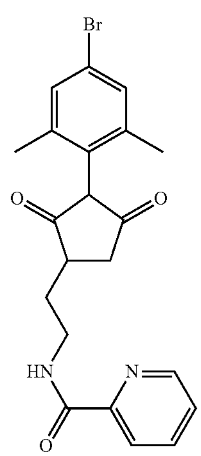 [SMILES: Cc1cc(Br)cc(C)c1C1C(=O)CC(CCNC(=O)c2ccccn2)C1=O] | 1H NMR (400 MHz, CDCl$_3$) δ (delta) 1.85 (t, 1H), 2.09-2.12 (m, 1H), 2.14 (s, 3H), 2.18 (s, 3H), 2.20-2.29 (m, 1H), 2.82-3.04 (m, 2H), 3.42 (d, 1H), 4.14-4.25 (m, 1H), 7.22 (s, 2H), 7.54 (d, 1H), 7.92 (t, 1H), 8.22 (d, 1H), 8.61 (d, 1H), 8.71 (br. s., 1H), 12.53 (br. s., 1H) |

TABLE A3-continued

| Compound number | Structure | Data |
|---|---|---|
| A126 | 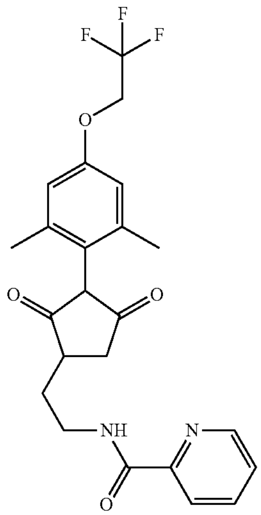 [SMILES: Cc1cc(OCC(F)(F)F)cc(C)c1C1C(=O)CC(CCNC(=O)c2ccccn2)C1=O] | 1H NMR (400 MHz, CDCl$_3$) δ (delta) 1.83-2.02 (m, 1H), 2.02-2.19 (m, 7H), 2.26 (d, 1H), 2.82-3.00 (m, 2H), 3.35-3.57 (m, 1H), 3.81-4.16 (m, 1H), 4.29 (q, 2H), 6.64 (s, 2H), 7.50 (dd, 5.20 1H), 7.89 (td, 1H), 8.16 (d, 1H), 8.59 (d, 1H), 8.64 (br. s., 1H) |
| A126A | 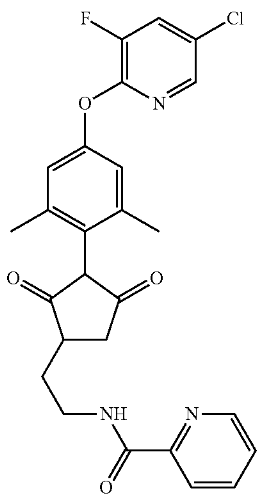 [SMILES: Cc1cc(Oc2ncc(Cl)cc2F)cc(C)c1C1C(=O)CC(CCNC(=O)c2ccccn2)C1=O] | 1H NMR (400 MHz, CDCl$_3$) δ (delta) 1.84-1.97 (m, 1H), 2.09-2.28 (m, 8H), 2.84-2.93 (m, 1H), 2.97 (d, 1H), 3.44 (d, 1H), 4.05-4.23 (m, 1H), 6.85 (s, 2H), 7.46-7.58 (m, 2H), 7.87-7.96 (m, 2H), 8.22 (d, 1H), 8.61 (d, 1H), 8.64-8.72 (m, 1H) |
| A126B | 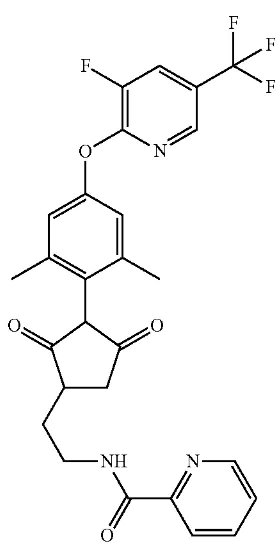 [SMILES: Cc1cc(Oc2ncc(C(F)(F)F)cc2F)cc(C)c1C1C(=O)CC(CCNC(=O)c2ccccn2)C1=O] | 1H NMR (400 MHz, CDCl$_3$) δ (delta) 1.91 (t, 1H), 2.10-2.29 (m, 8H), 2.89 (dd, 6.72 1H), 2.98 (br. s., 1H), 3.45 (d, 1H), 4.13 (d, 1H), 6.87 (s, 2H), 7.52 (br. s., 1H), 7.87-7.99 (m, 2H), 8.22 (d, 1H), 8.27 (br. s., 1H), 8.60 (br. s., 1H), 8.69 (br. s., 1H) |

… TABLE A3-continued
| Compound number | Structure | Data |
|---|---|---|
| A127 | 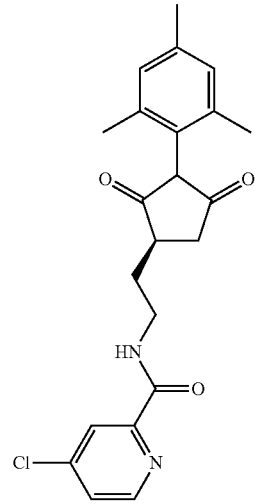 [SMILES: Cc1cc(C)c(C2C(=O)C[C@@H](CCNC(=O)c3cc(Cl)ccn3)C2=O)c(C)c1] | 1H NMR (400 MHz, CDCl₃) δ (delta) 1.77-2.43 (m, 12H), 2.67-3.17 (m, 2H), 3.26-3.87 (m, 2H), 6.89 (s, 2H), 7.45-7.57 (m, 1H), 8.07-8.68 (m, 3H) |
| A128 | 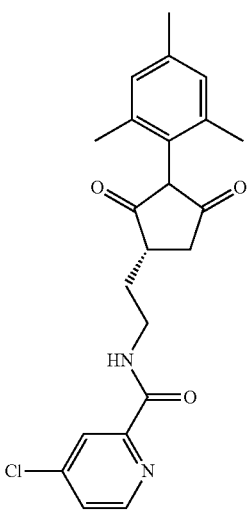 [SMILES: Cc1cc(C)c(C2C(=O)C[C@H](CCNC(=O)c3cc(Cl)ccn3)C2=O)c(C)c1] | 1H NMR (500 MHz, CDCl₃) δ (delta) 1.77-2.43 (m, 12H), 2.67-3.17 (m, 2H), 3.26-3.87 (m, 2H), 6.89 (s, 2H), 7.45-7.57 (m, 1H), 8.07-8.68 (m, 3H) |
| A129 | 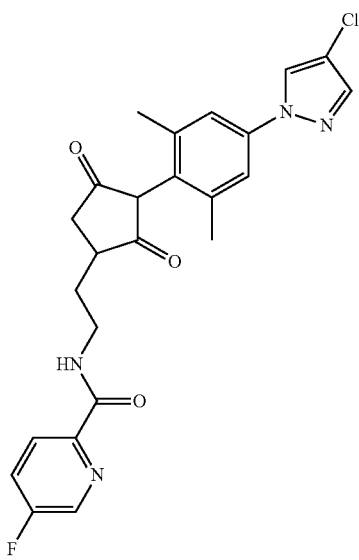 [SMILES: Cc1cc(-n2cc(Cl)cn2)cc(C)c1C1C(=O)CC(CCNC(=O)c2ccc(F)cn2)C1=O] | 1H NMR (500 MHz, CDCl₃) δ (delta) 1.67-2.47 (m, 9H), 2.67-3.09 (m, 2H), 3.37-3.62 (m, 1H), 3.79-4.08 (m, 1H), 7.27 (d, 2H), 7.45-7.66 (m, 2H), 7.84 (s, 1H), 8.19 (br. s., 1H), 8.28-8.64 (m, 1.5H), 11.5-13 (br. s., 0.5H). |

TABLE A3-continued
| Compound number | Structure | Data |
|---|---|---|
| A130 | 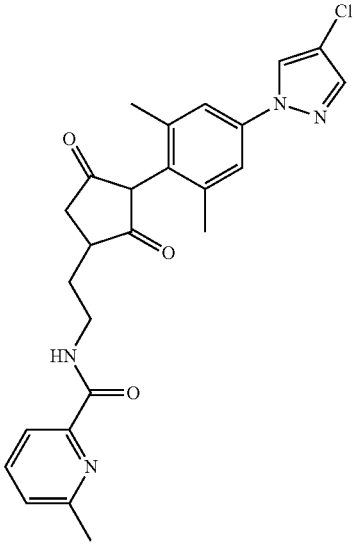 [SMILES: Cc1cccc(C(=O)NCCC2CC(=O)C(c3c(C)cc(-n4cc(Cl)cn4)cc3C)C2=O)n1] | 1H NMR (500 MHz, CDCl$_3$) δ (delta) 1.76-1.99 (m, 1H), 2.08-2.43 (m, 8H), 2.60 (s, 3H), 2.75-3.10 (m, 2H), 3.47 (d, 1H), 4.12 (q, 1H), 7.28-7.42 (m, 3H), 7.60 (s, 1H), 7.67-8.06 (m, 3H), 8.71 (br. s., 1H) |
| A131 | 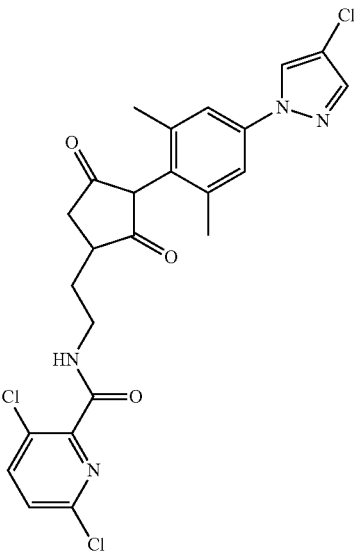 [SMILES: Cc1cc(-n2cc(Cl)cn2)cc(C)c1C1C(=O)CC(CCNC(=O)c2nc(Cl)ccc2Cl)C1=O] | 1H NMR (500 MHz, CDCl$_3$) δ (delta) 1.76-1.95 (m, 1H), 1.95-2.18 (m, 7H), 2.18-2.43 (m, 1H), 2.65-2.99 (m, 2H), 3.36-3.55 (m, 1H), 3.54-3.83 (m, 1H), 7.18 (s, 2H), 7.36 (d, 1H), 7.54 (s, 1H), 7.65-7.86 (m, 2H), 7.96-8.33 (m, 1H) |

TABLE A3-continued
| Compound number | Structure | Data |
|---|---|---|
| A132 | 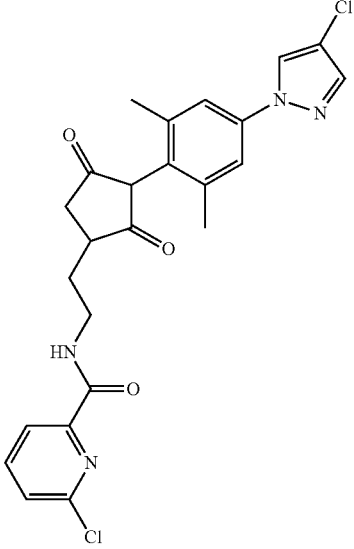 [SMILES: Cc1cc(-n2cc(Cl)cn2)cc(C)c1C1C(=O)CC(CCNC(=O)c2cccc(Cl)n2)C1=O] | 1H NMR (500 MHz, CDCl₃) δ (delta) 1.55-2.47 (m, 9H), 2.61-3.06 (m, 2H), 3.27-3.60 (m, 1H), 3.60-4.06 (m, 1H), 7.23 (s, 2H), 7.40-8.13 (m, 5H), 8.14-8.65 (m, 1H) |
| A133 | 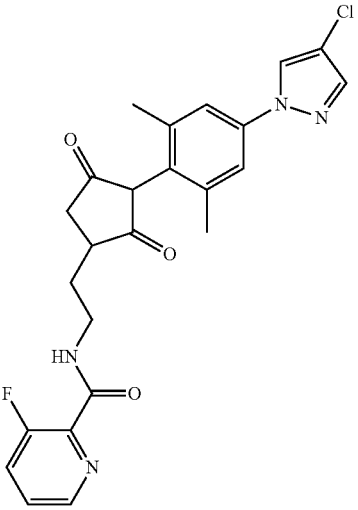 [SMILES: Cc1cc(-n2cc(Cl)cn2)cc(C)c1C1C(=O)CC(CCNC(=O)c2ncccc2F)C1=O] | 1H NMR (500 MHz, CDCl₃) δ (delta) 1.77-2.22 (m, 8H), 2.22-2.48 (m, 1H), 2.92 (m, 2H), 3.40-3.59 (m, 1H), 3.58-4.00 (m, 1H), 7.20 (d, 2H), 7.31-7.63 (m, 3H), 7.81 (s, 1H), 8.15-8.53 (m, 2H) |

TABLE A3-continued
| Compound number | Structure | Data |
|---|---|---|
| A134 | 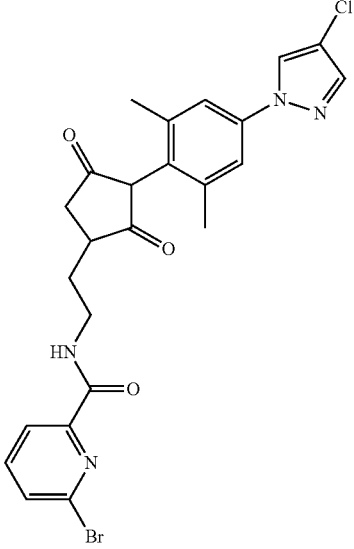 [SMILES: Cc1cc(-n2cc(Cl)cn2)cc(C)c1C1C(=O)CC(CCNC(=O)c2cccc(Br)n2)C1=O] | 1H NMR (500 MHz, CDCl₃) δ (delta) 1.82-2.42 (m, 9H), 2.87 (m, 2H), 3.32-3.59 (m, 1H), 3.69-4.05 (m, 1H), 7.25-7.4 (s, 2H), 7.54-7.94 (m, 4H), 8.10 (d, 1H), 8.20-8.54 (m, 1H) |
| A135 | 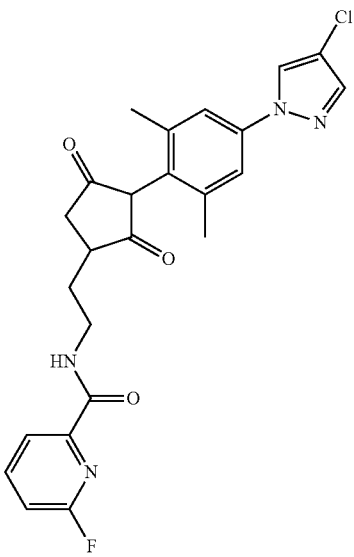 [SMILES: Cc1cc(-n2cc(Cl)cn2)cc(C)c1C1C(=O)CC(CCNC(=O)c2cccc(F)n2)C1=O] | 1H NMR (500 MHz, CDCl₃) δ (delta) 1.87-2.02 (m, 2H), 2.07-2.47 (m, 7H), 2.69-3.05 (m, 2H), 3.48 (d, 1H), 3.64-4.01 (m, 1H), 6.84-7.37 (m, 3H), 7.57 (s, 1H), 7.72-8.45 (m, 4H) |

| Compound number | Structure | Data |
|---|---|---|
| A136 | 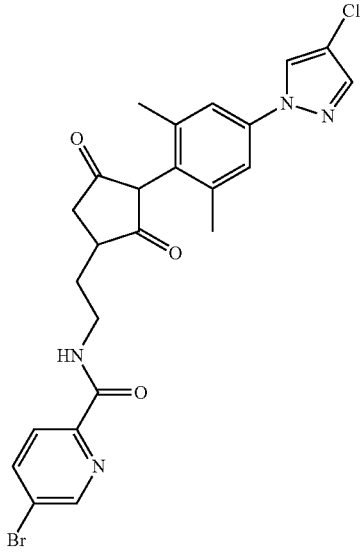 | 1H NMR (500 MHz, CDCl$_3$) δ (delta) 1.52-2.57 (m, 8H), 2.57-3.19 (m, 2H), 3.19-3.80 (m, 2H), 3.80-4.22 (m, 1H), 6.97-7.46 (m, 1H), 7.57 (s, 1H), 7.83 (s, 1H), 7.88-8.35 (m, 2H), 8.35-8.85 (m, 2H), 11.84-12.62 (m, 1H) |
| A137 | 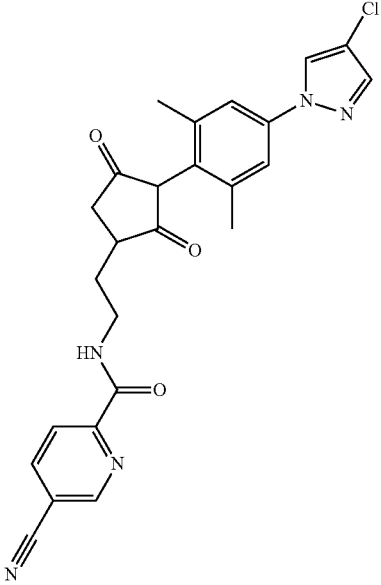 [SMILES: Cc1cc(-n2cc(Cl)cn2)cc(C)c1C1C(=O)CC(CCNC(=O)c2ccc(C#N)cn2)C1=O] | 1H NMR (500 MHz, CDCl$_3$) δ (delta) 1.56-2.7 (m, 8H), 2.7-3.02 (br. s., 2H), 3.54 (br. s., 2H), 3.74-4.06 (m, 1H), 7.03-7.33 (m, 2H), 7.56 (s, 1H), 7.81 (s, 1H), 7.97-9.02 (m, 3.5H), 11.89 (br. s., 0.5H) |

TABLE A3-continued
| Compound number | Structure | Data |
|---|---|---|
| A138 | 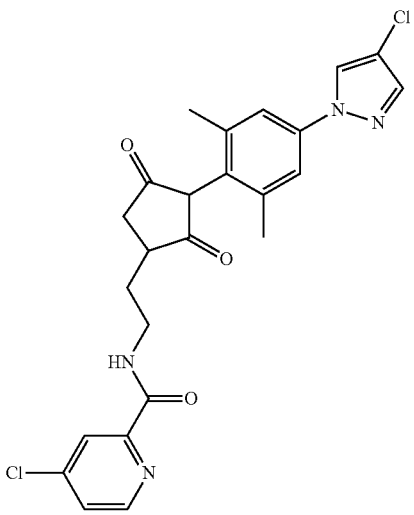 [SMILES: Cc1cc(-n2cc(Cl)cn2)cc(C)c1C1C(=O)CC(CCNC(=O)c2cc(Cl)ccn2)C1=O] | 1H NMR (500 MHz, CDCl₃) δ (delta) 1.58-2.57 (m, 9H), 2.89 (dd, 2H), 3.25-4.30 (m, 2H), 7.2-7.3 (s, 2H), 7.40-7.70 (m, 2H), 7.74-7.97 (m, 1H), 8.16 (br. s., 1H), 8.36-8.73 (m, 1.5H), 11.52-12.52 (m, 0.5H) |
| A139 | 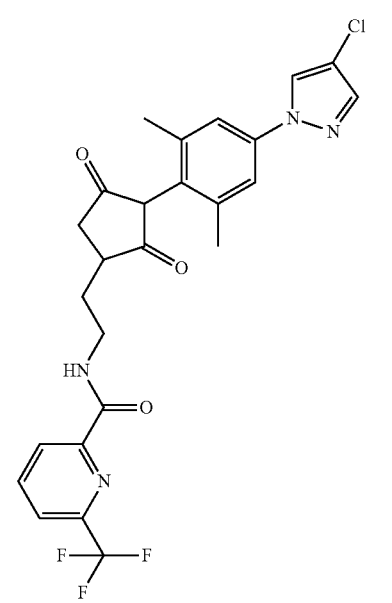 [SMILES: Cc1cc(-n2cc(Cl)cn2)cc(C)c1C1C(=O)CC(CCNC(=O)c2cccc(C(F)(F)F)n2)C1=O] | 1H NMR (500 MHz, CDCl₃) δ (delta) 1.51-2.58 (m, 9H), 2.62-3.20 (m, 2H), 3.28-3.82 (m, 1H), 3.84-4.29 (m, 1H), 7.2-7.3 (m, 2H), 7.47-7.67 (m, 1H), 7.68-7.96 (m, 2H), 8.10 (br. s., 1H), 8.38 (br. s., 1H), 8.55 (br. s., 0.5H), 11.49-12.53 (m, 0.5H) |

TABLE A3-continued
| Compound number | Structure | Data |
|---|---|---|
| A140 | 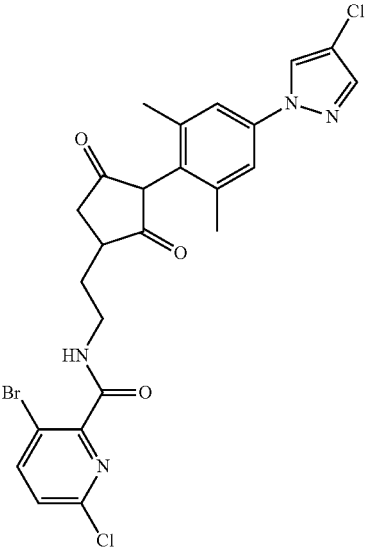 [SMILES: Cc1cc(-n2cc(Cl)cn2)cc(C)c1C1C(=O)CC(CCNC(=O)c2nc(Cl)ccc2Br)C1=O] | 1H NMR (500 MHz, CDCl₃) δ (delta) 1.72-2.52 (m, 9H), 2.60-3.10 (m, 2H), 3.47 (m, 1H), 3.62-3.90 (m, 1H), 6.99-7.38 (m, 3H), 7.55 (s, 1H), 7.81 (s, 1H), 7.89-8.04 (m, 1H), 8.08-8.32 (m, 1H) |
| A141 | 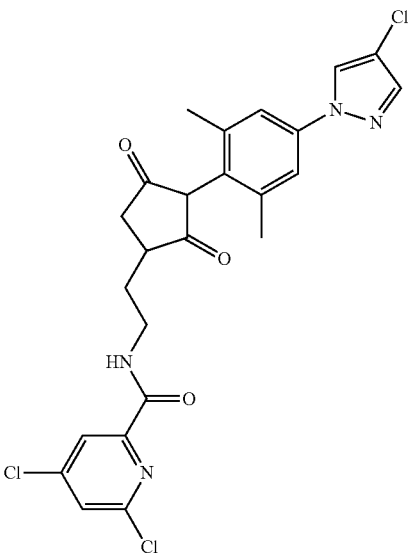 [SMILES: Cc1cc(-n2cc(Cl)cn2)cc(C)c1C1C(=O)CC(CCNC(=O)c2cc(Cl)cc(Cl)n2)C1=O] | 1H NMR (400 MHz, CDCl₃) δ (delta) 1.68-2.50 (m, 9H), 2.73-3.10 (m, 2H), 3.38-3.62 (m, 1H), 3.86-4.27 (m, 1H), 7.12-7.42 (m, 2H), 7.45-7.60 (s, 2H), 7.85 (s, 1H), 8.00-8.19 (m, 1H), 8.21-8.54 (m, 0.5H), 11.5-13.5 (m, 0.5H). |

TABLE A3-continued

| Compound number | Structure | Data |
|---|---|---|
| A141A | 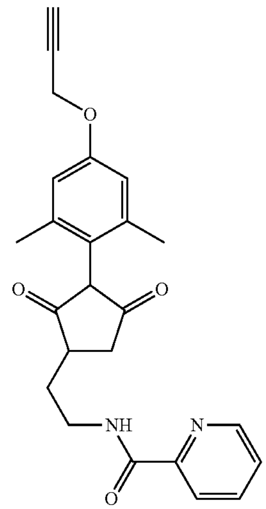 [SMILES: C#CCOc1cc(C)c(C2C(=O)CC(CCNC(=O)c3ccccn3)C2=O)c(C)c1] | 1H NMR (500 MHz, CDCl₃) δ (delta) 1.93-2.07 (m, 2H), 2.11 (s, 3H), 2.13 (s, 3H), 2.18-2.33 (m, 1H), 2.50 (t, 1H), 2.75-3.03 (m, 2H), 3.37-3.59 (m, 1H), 3.92 (br. s., 1H), 4.62 (s, 2H), 6.66 (s, 2H), 7.37-7.59 (m, 1H), 7.87 (t, 1H), 8.15 (d, 1H), 8.57 (d, 2H) |
| A142 | 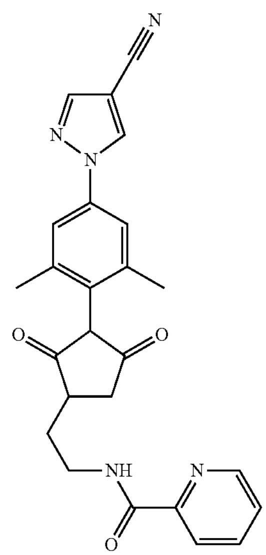 [SMILES: Cc1cc(-n2cc(C#N)cn2)cc(C)c1C1C(=O)CC(CCNC(=O)c2ccccn2)C1=O] | 1H NMR (500 MHz, d4-methanol) δ (delta) 1.79 (ddt, 1H), 2.18 (s, 6H), 2.20-2.27 (m, 1H), 2.55 (dd, 1H), 2.81-2.90 (m, 1H), 2.99 (dd, 1H), 3.54-3.68 (m, 2H), 7.48 (s, 2H), 7.54 (d, 1H), 7.95 (t, 1H), 8.07 (s, 1H), 8.10 (d, 1H), 8.62 (br. s., 1H), 8.84 (s, 1H). |
| A143 | 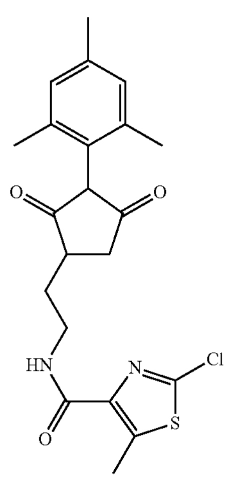 [SMILES: Cc1cc(C)c(C2C(=O)CC(CCNC(=O)c3nc(Cl)sc3C)C2=O)c(C)c1] | 1H NMR (400 MHz, d4-methanol) δ (delta) 6.76 (2H, s), 3.39 (2H, t), 2.86-2.78 (1H, m), 2.72-2.62 (1H, m), 2.65 (3H, s), 2.37 (1H, d) 2.14 (3H, s), 2.10-2.02 (1H, m), 1.94 (6H, s), 1.64-1.55 (1H, m) |

TABLE A3-continued

| Compound number | Structure | Data |
|---|---|---|
| A144 | 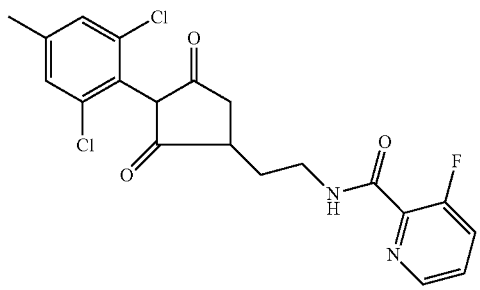 [SMILES: Cc1cc(Cl)c(C2C(=O)CC(CCNC(=O)c3ncccc3F)C2=O)c(Cl)c1] | 1H NMR (500 MHz, D₂O) δ (delta) 1.70-1.85 (m, 1H), 2.08-2.21 (m, 1H), 2.29 (s, 4H), 2.65-2.82 (m, 2H), 3.45-3.61 (m, 2H), 7.14-7.39 (m, 3H), 7.82-7.96 (m, 1H), 8.01-8.25 (m, 1H) |
| A145 | 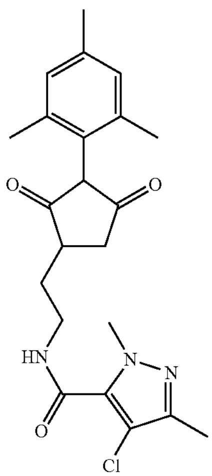 | 1H NMR (500 MHz, d4-methanol) δ (delta) 6.74 (2H, s), 3.72 (3H, s), 3.45-3.33 (2H, m), 2.87-2.78 (1H, m), 2.72-2.65 (1H, m), 2.38 (1H, m), 2.18 (3H, s), 2.14 (3H, s), 2.09-2.02 (1H, m), 1.94 (6H, s), 1.65-1.54 (1H, m) |
| A146 | 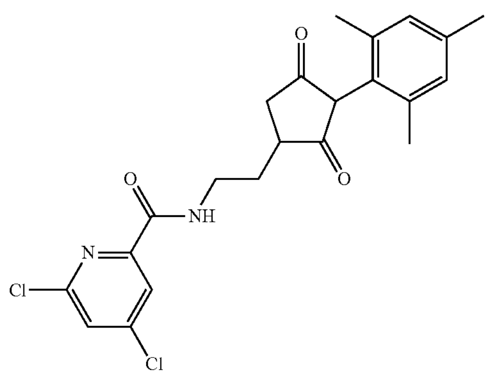 [SMILES: Cc1cc(C)c(C2C(=O)CC(CCNC(=O)c3cc(Cl)cc(Cl)n3)C2=O)c(C)c1] | 1H NMR (500 MHz, CDCl₃) δ (delta) 2.00-2.35 (m, 12H), 2.90 (s, 2H), 3.38-3.53 (m, 1H), 4.12 (d, 1H), 6.89 (s, 2H), 7.41-7.63 (m, 1H), 8.04-8.20 (m, 1H), 8.25-8.43 (m, 1H) |
| A147 | 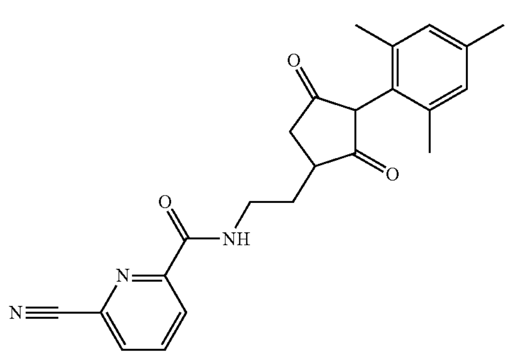 [SMILES: Cc1cc(C)c(C2C(=O)CC(CCNC(=O)c3cccc(C#N)n3)C2=O)c(C)c1] | 1H NMR (500 MHz, CDCl₃) δ (delta) 1.85-2.16 (m, 8H), 2.23 (s, 4H), 2.85 (d, 2H), 3.36-3.68 (m, 1H), 3.68-3.99 (m, 1H), 6.84 (s, 2H), 8.05 (s, 4H) |

TABLE A3-continued
| Compound number | Structure | Data |
|---|---|---|
| A148 | 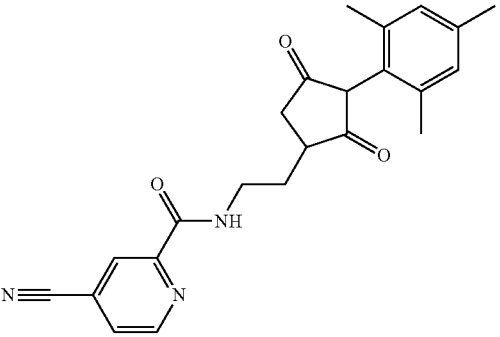 [SMILES: Cc1cc(C)c(C2C(=O)CC(CCNC(=O)c3cc(C#N)ccn3)C2=O)c(C)c1] | 1H NMR (500 MHz, CDCl₃) δ (delta) 1.82-2.16 (m, 8H), 2.22 (s, 4H), 2.64-2.95 (m, 2H), 3.42-3.67 (m, 1H), 3.68-3.96 (m, 1H), 6.73-6.96 (m, 2H), 7.60-7.76 (m, 1H), 8.25-8.51 (m, 2H), 8.69-8.83 (m, 1H) |
| A149 | 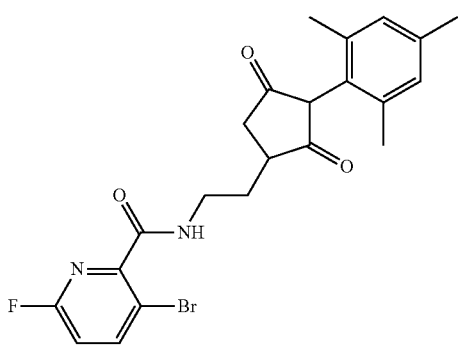 [SMILES: Cc1cc(C)c(C2C(=O)CC(CCNC(=O)c3nc(F)ccc3Br)C2=O)c(C)c1] | 1H NMR (500 MHz, CDCl₃) δ (delta) 1.75-1.95 (m, 1H), 1.95-2.13 (m, 7H), 2.22 (s, 4H), 2.81 (d, 2H), 3.30-3.53 (m, 1H), 3.53-3.81 (m, 1H), 6.82 (s, 2H), 6.96 (dd, 1H), 8.07 (dd, 2H) |
| A150 | 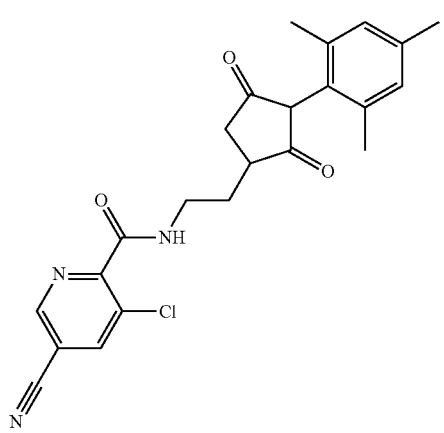 [SMILES: Cc1cc(C)c(C2C(=O)CC(CCNC(=O)c3ncc(C#N)cc3Cl)C2=O)c(C)c1] | 1H NMR (500 MHz, CDCl₃) δ (delta) 1.62-1.93 (m, 1H), 1.93-2.09 (m, 7H), 2.19 (s, 4H), 2.56-2.85 (m, 2H), 3.37-3.71 (m, 2H), 6.78 (s, 2H), 8.05 (d, 1H), 8.18-8.36 (m, 1H), 8.61 (d, 1H) |
| A151 | 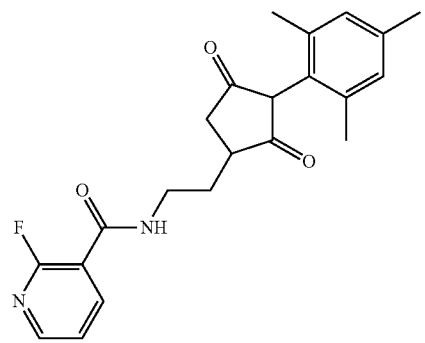 [SMILES: Cc1cc(C)c(C2C(=O)CC(CCNC(=O)c3cccnc3F)C2=O)c(C)c1] | 1H NMR (500 MHz, CDCl₃) δ (delta) 1.70-2.39 (m, 12H), 2.57-2.98 (m, 2H), 3.33-3.66 (m, 1H), 3.70-4.01 (m, 1H), 6.83 (s, 2H), 7.30-7.41 (m, 1H), 7.41-7.58 (m, 1H), 8.18-8.38 (m, 1H), 8.39-8.59 (m, 1H) |

TABLE A3-continued

| Compound number | Structure | Data |
|---|---|---|
| A152 | 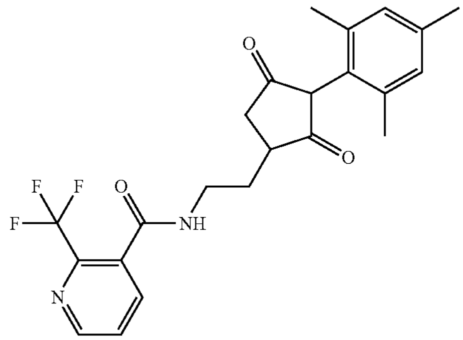 [SMILES: Cc1cc(C)c(C2C(=O)CC(CCNC(=O)c3cccnc3C(F)(F)F)C2=O)c(C)c1] | 1H NMR (500 MHz, CDCl₃) δ (delta) 1.68-2.10 (m, 8H), 2.22-2.35 (s, 4H), 2.57-2.98 (m, 2H), 3.21-3.52 (m, 1H), 3.52-3.69 (m, 1H), 6.82 (s, 2H), 7.29-7.82 (m, 3H), 8.52-8.75 (m, 1H) |
| A153 | 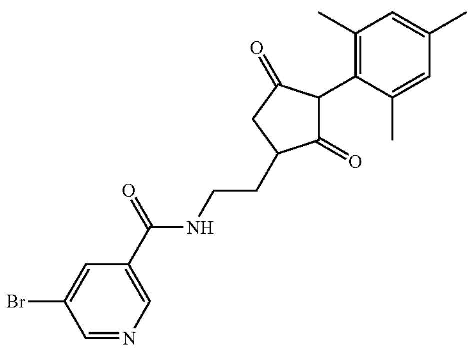 | 1H NMR (500 MHz, CDCl₃) δ (delta) 1.81-2.25 (m, 11H), 2.25-2.48 (m, 1H), 2.73-2.88 (m, 1H), 2.88-3.05 (m, 1H), 3.25-3.51 (m, 1H), 3.63-3.85 (m, 1H), 6.79 (d, 2H), 8.07-8.48 (m, 3H), 8.80 (d, 1H) |
| A154 | 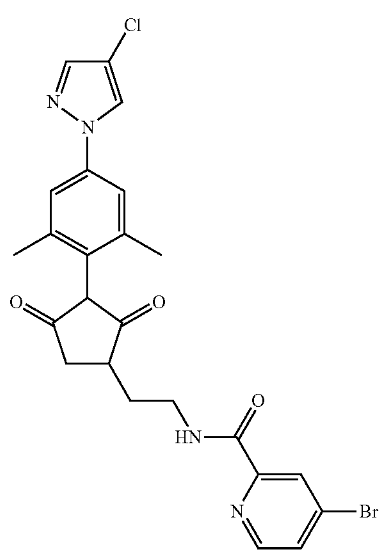 [SMILES: Cc1cc(-n2cc(Cl)cn2)cc(C)c1C1C(=O)CC(CCNC(=O)c2cc(Br)ccn2)C1=O] | 1H NMR (500 MHz, CDCl₃) δ (delta) 1.60-2.56 (m, 8H), 2.58-3.12 (m, 2H), 3.29-3.69 (m, 2H), 3.87-4.27 (m, 1H), 7.29 (br. s., 2H), 7.59 (s, 2H), 7.85 (s, 1H), 8.24-8.47 (m, 2H), 8.47-8.78 (m, 1H) |

TABLE A3-continued
| Compound number | Structure | Data |
|---|---|---|
| A155 | 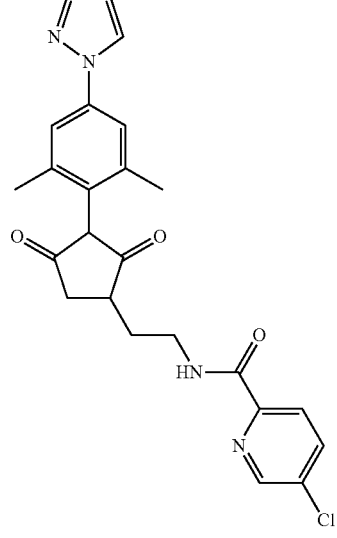 | 1H NMR (500 MHz, CDCl₃) δ (delta) 1.56-2.33 (m, 9H), 2.56-3.05 (m, 2H), 3.4-3.6 (br. s., 1.5H), 3.76-4.07 (m, 0.5H), 7.07-7.36 (m, 2H), 7.56 (s, 1H), 7.66-7.89 (m, 2H), 8.09 (d, 1H), 8.33-8.76 (m, 2H) |
| A156 | 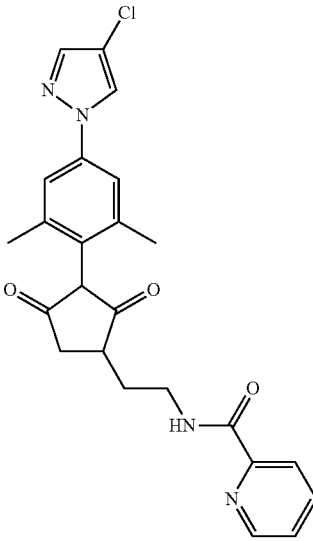 | 1H NMR (400 MHz, CDCl₃) δ (delta) 1.68-2.4 (m, 9H), 2.4-2.6 (s, 3H), 2.97 (d, 2H), 3.26-3.65 (m, 1H), 3.86-4.18 (m, 1H), 7.15-7.49 (m, 3H), 7.61 (br. s., 1H), 7.86 (br. s., 1H), 8.04 (br. s., 1H), 8.25-8.63 (m, 1H), 8.63-8.98 (m, 1H) |
| A157 | 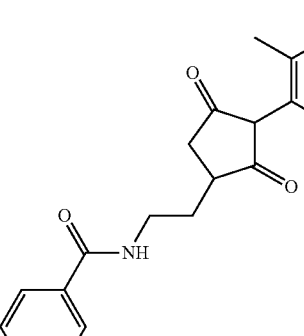 | 1H NMR (500 MHz, CDCl₃) δ (delta) 1.76-1.97 (m, 2H), 1.97-2.10 (m, 6H), 2.18 (s, 3H), 2.24-2.50 (m, 1H), 2.59-3.09 (m, 2H), 3.16-3.58 (m, 1H), 3.59-3.73 (m, 1H), 6.76 (d, 2H), 7.92-8.58 (m, 3H), 8.74 (d, 1H) |

TABLE A3-continued
| Compound number | Structure | Data |
|---|---|---|
| A158 | 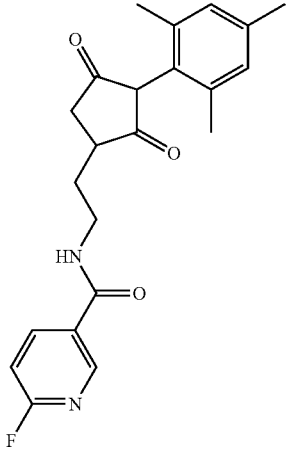 [SMILES: Cc1cc(C)c(C2C(=O)CC(CCNC(=O)c3ccc(F)nc3)C2=O)c(C)c1] | 1H NMR (500 MHz, CDCl$_3$) δ (delta) 1.54-2.53 (m, 12H), 2.55-3.18 (m, 2H), 3.18-3.67 (m, 1H), 3.63-3.89 (m, 1H), 6.83 (d, 2H), 6.87-6.95 (m, 1H), 8.17-8.32 (m, 1H), 8.58-8.00 (m, 1H) |
| A159 | 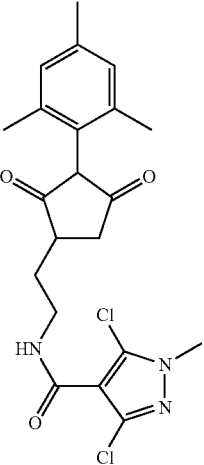 | 1H NMR (500 MHz, d4-methanol) δ (delta) 6.89 (2H, s), 3.87 (3H, s), 3.61-3.99 (2H, m), 3.01-2.92 (1H, m), 2.88 (1H, br), 2.51 (1H, d) 2.28 (3H, s), 2.24-2.14 (1H, m), 2.07 (6H, s), 1.79-1.69 (1H, m) |
| A160 | 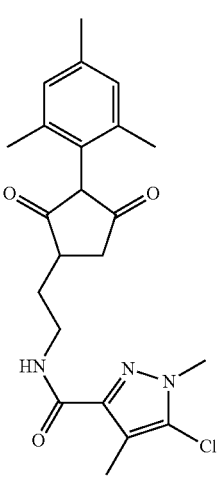 [SMILES: Cc1cc(C)c(C2C(=O)CC(CCNC(=O)c3nn(C)c(Cl)c3C)C2=O)c(C)c1] | 1H NMR (500 MHz, d4-methanol) δ (delta) 6.74 (2H, s), 3.76 (3H, s), 3.39 (t, 2H), 2.87-2.78 (1H, m), 2.73-2.64 (br. m, 1H), 2.38 (1H, d) 2.15 (3H, s), 2.12 (3H, s), 2.09-2.02 (1H, m), 1.94 (6H, s), 1.64-1.06 (1H, m) |

TABLE A3-continued

| Compound number | Structure | Data |
|---|---|---|
| A161 | 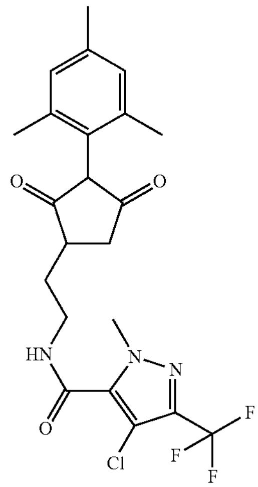 [SMILES: Cc1cc(C)c(C2C(=O)CC(CCNC(=O)c3c(Cl)c(C(F)(F)F)nn3C)C2=O)c(C)c1] | 1H NMR (500 MHz, d4-methanol) δ (delta) 6.74 (2H, s), 3.92 (3H, s), 3.51-3.41 (2H, m), 2.88-2.80 (1H, m), 2.75-2.68 (1H, br. m), 2.38 (1H, d), 2.14 (3H, s), 2.13-2.04 (1H, m), 1.93 (6H, s), 1.68-1.58 (1H, m) |
| A162 | 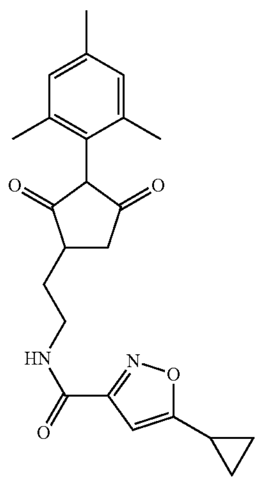 [SMILES: Cc1cc(C)c(C2C(=O)CC(CCNC(=O)c3cc(C4CC4)on3)C2=O)c(C)c1] | 1H NMR (500 MHz, d4-methanol) δ (delta) 6.74 (2H, s), 6.26 (1H, s), 3.47-3.34 (2H, m), 2.86-2.77 (1H, m), 2.70-2.62 (1H, br. m), 2.37 (1H, d), 2.13 (3H, s), 2.10-2.00 (2H, m), 1.93 (6H, s), 1.63-1.53 (1H, m), 1.04-0.98 (2H, m), 0.88-0.81 (2H, m) |
| A163 | 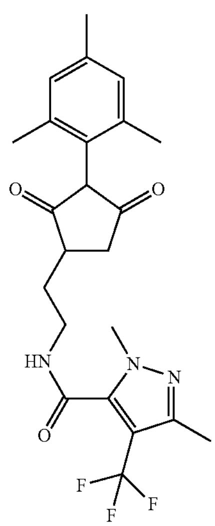 | 1H NMR (500 MHz, d4-methanol) δ (delta) 6.77 (2H, s), 3.70 (3H, s), 3.49-3.37 (2H, m), 2.87-2.79 (1H, m), 2.72-2.65 (1H, br. m), 2.38 (1H, d), 2.19 (3H, s), 2.15 (3H, s), 2.12-2.02 (1H, m), 1.94 (6H, s), 1.65-1.55 (1H, m) |

TABLE A3-continued
| Compound number | Structure | Data |
|---|---|---|
| A164 | 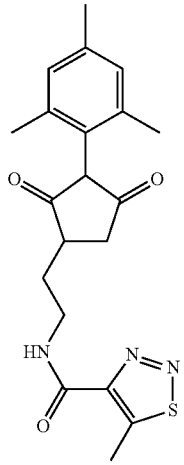 [SMILES: Cc1cc(C)c(C2C(=O)CC(CCNC(=O)c3nnsc3C)C2=O)c(C)c1] | 1H NMR (500 MHz, d4-methanol) δ (delta) 6.74 (2H, s), 3.49 (2H, t), 2.88-2.81 (1H, m), 2.79 (3H, s), 2.76-2.69 (1H, br. m), 2.40 (1H, d) 2.17-2.08 (1H, m), 2.13 (3H, s), 1.93 (6H, s), 1.70-1.61 (1H, m) |
| A165 | 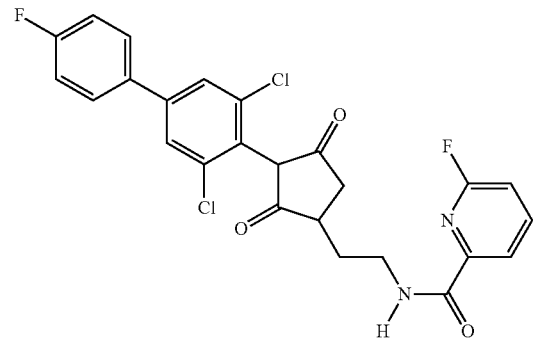 [SMILES: O=C(NCCC1CC(=O)C(c2c(Cl)cc(-c3ccc(F)cc3)cc2Cl)C1=O)c1cccc(F)n1] | 1H NMR (500 MHz, CDCl$_3$) δ (delta) 1.89-2.03 (m, 1H), 2.17 (br. s., 2H), 2.84-3.05 (m, 2H), 3.33-3.55 (m, 1H), 4.12-4.28 (m, 1H), 7.13 (s, 2H), 7.51 (s, 4H), 7.96-8.21 (m, 3H), 8.28-8.48 (m, 1H) |
| A166 | 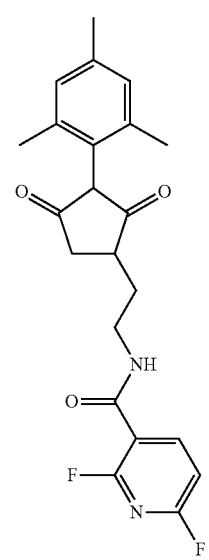 [SMILES: Cc1cc(C)c(C2C(=O)CC(CCNC(=O)c3ccc(F)nc3F)C2=O)c(C)c1] | 1H NMR (500 MHz, CDCl$_3$) δ (delta) 1.71-1.89 (m, 1H), 1.89-2.27 (m, 10H), 2.42 (dd, 1H), 2.65-2.99 (m, 2H), 3.50-3.66 (m, 2H), 6.86 (s, 2H), 6.97 (dd, 1H), 7.77-7.97 (m, 1H), 8.50 (d, 1H) |

TABLE A3-continued
| Compound number | Structure | Data |
|---|---|---|
| A167 | 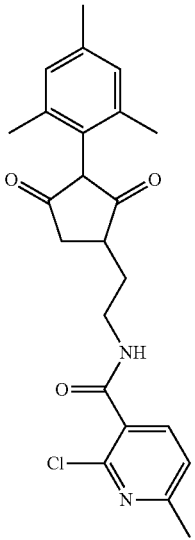 | 1H NMR (500 MHz, CDCl₃) δ (delta) 1.73-2.02 (m, 8H), 2.11-2.35 (m, 4H), 2.42-2.60 (m, 3H), 2.61-2.93 (m, 2H), 3.25-3.74 (m, 2H), 6.79 (s, 2H), 7.06 (d, 1H), 7.62-7.85 (m, 2H) |
| A168 | 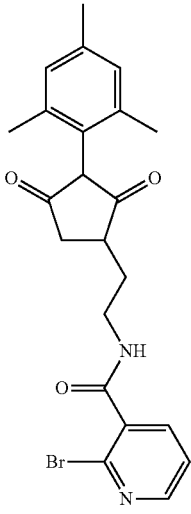 [SMILES: Cc1cc(C)c(C2C(=O)CC(CCNC(=O)c3cccnc3Br)C2=O)c(C)c1] | 1H NMR (500 MHz, CDCl₃) δ (delta) 2.00 (d, 8H), 2.20 (s, 4H), 2.60-2.93 (m, 2H), 3.29-3.49 (m, 1H), 3.49-3.73 (m, 1H), 6.79 (s, 2H), 7.20 (dd, 1H), 7.78 (d, 2H), 8.29 (dd, 1H) |

| Compound number | Structure | Data |
|---|---|---|
| A169 | 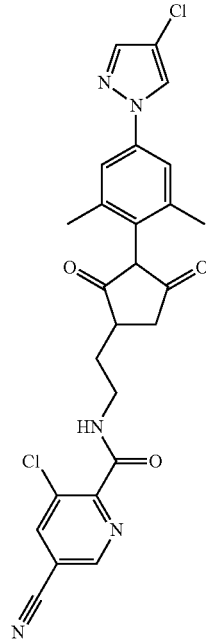 [SMILES: Cc1cc(-n2cc(Cl)cn2)cc(C)c1C1C(=O)CC(CCNC(=O)c2ncc(C#N)cc2Cl)C1=O] | 1H NMR (500 MHz, CDCl₃) δ (delta) 1.90-2.54 (m, 9H), 2.81-3.10 (m, 2H), 3.39-4.06 (m, 2H), 7.19-7.40 (m, 2H), 7.59 (s, 1H), 7.78-7.90 (m, 1H), 7.93-8.46 (m, 2H), 8.58-8.88 (m, 1H) |
| A170 | 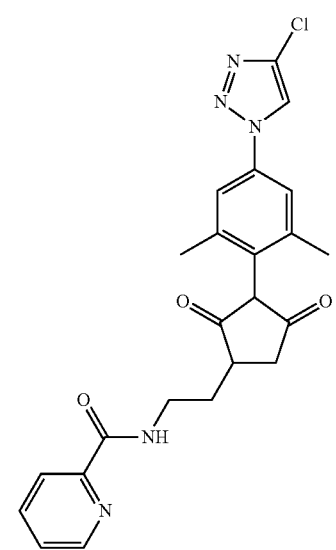 [SMILES: Cc1cc(-n2cc(Cl)nn2)cc(C)c1C1C(=O)CC(CCNC(=O)c2ccccn2)C1=O] | 1H NMR (500 MHz, d4-methanol) δ (delta) 1.74-1.86 (m, 1H), 2.18 (s, 6H), 2.20-2.28 (m, 1H), 2.56 (dd, 1H), 2.83-2.91 (m, 1H), 3.00 (dd, 1H), 3.56-3.67 (m, 2H), 7.49 (s, 2H), 7.52 (dd, 1H), 7.94 (t, 1H), 8.09 (d, 1H), 8.58 (s, 1H), 8.61 (d, 1H) |

TABLE A3-continued

| Compound number | Structure | Data |
|---|---|---|
| A171 | 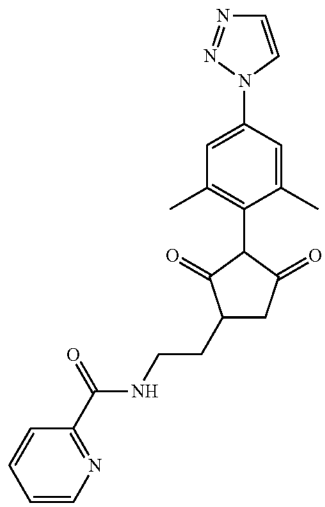 [SMILES: Cc1cc(-n2ccnn2)cc(C)c1C1C(=O)CC(CCNC(=O)c2ccccn2)C1=O] | 1H NMR (500 MHz, d4-methanol) δ (delta) 1.75-1.85 (m, 1H), 2.20 (s, 6H), 2.22-2.28 (m, 1H), 2.51-2.60 (m, 1H), 2.81-2.91 (m, 1H), 2.95-3.05 (m, 1H), 3.57-3.67 (m, 2H), 7.51-7.57 (m, 3H), 7.87 (d, 1H), 7.95 (td, 1H), 8.10 (d, 1H), 8.49 (d, 1H), 8.63 (d, 1H) |
| A172 | 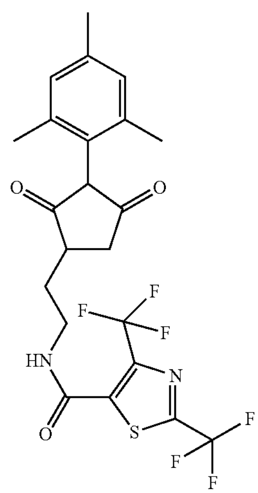 [SMILES: Cc1cc(C)c(C2C(=O)CC(CCNC(=O)c3sc(C(F)(F)F)nc3C(F)(F)F)C2=O)c(C)c1] | 1H NMR (500 MHz, d4-methanol) δ (delta) 6.75 (2H, s), 3.52-3.38 (2H, m), 2.89-2.79 (1H, m), 2.74-2.65 (1H, br. m), 2.38 (1H, d), 2.14 (3H, s), 2.12-2.02 (1H, m), 1.95 (6H, s), 1.69-1.57 (1H, m) |
| A173 | 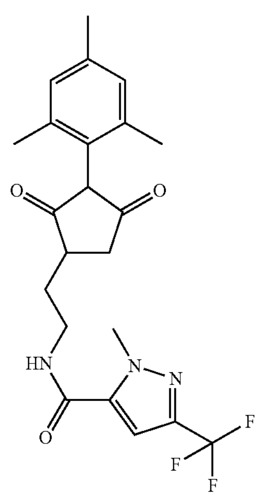 [SMILES: Cc1cc(C)c(C2C(=O)CC(CCNC(=O)c3cc(C(F)(F)F)nn3C)C2=O)c(C)c1] | 1H NMR (500 MHz, d4-methanol) δ (delta) 6.97 (1H, s), 6.73 (2H, s), 4.04 (3H, s), 3.38 (2H, t), 2.88-2.78 (1H, m), 2.72-2.63 (1H, br. m), 2.37 (1H, d), 2.13 (3H, s), 2.11-2.01 (1H, m), 1.93 (6H, s), 1.68-1.53 (1H, m) |

TABLE A3-continued
| Compound number | Structure | Data |
|---|---|---|
| A174 | 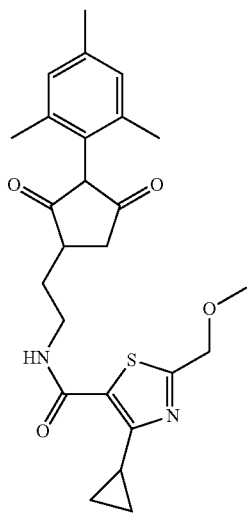 | 1H NMR (500 MHz, d4-methanol) δ (delta) 6.74 (2H, s), 4.49 (2H, s), 3.39 (2H, t), 3.34 (3H, s), 2.88-2.78 (1H, m), 2.72-2.62 (1H, m), 2.62-2.52 (1H, m), 2.37 (1H, d) 2.13 (3H, s), 2.10-2.01 (1H, m), 1.94 (6H, s), 1.68-1.56 (1H, m), 0.89 (4H, d) |
| A175 | 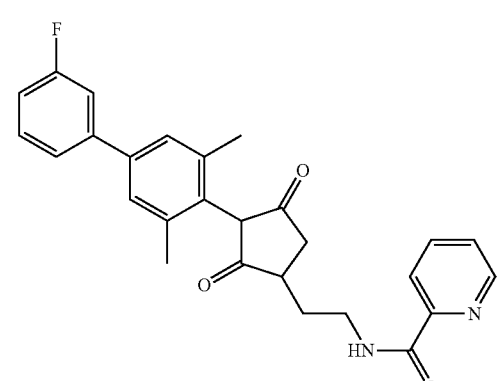 | 1H NMR (400 MHz, d4-methanol) δ (delta) 1.66-1.84 (m, 2H), 2.24 (d, 6H), 2.73 (s, 2H), 3.27-3.39 (m, 1H), 3.55-3.65 (m, 2H), 6.95-7.10 (m, 1H), 7.29 (br. s., 3H), 7.37-7.48 (m, 2H), 7.50-7.68 (m, 1H), 7.89-7.99 (m, 1H), 8.06-8.24 (m, 1H), 8.49-8.79 (m, 1H) |
| A176 | 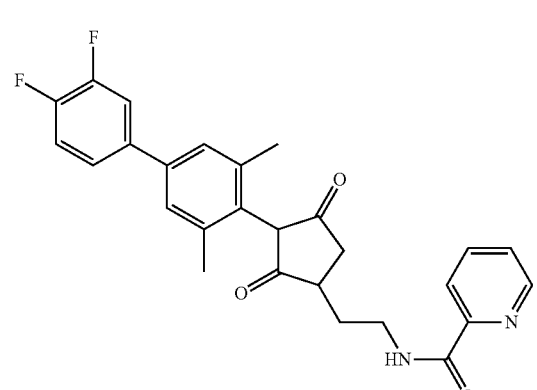 | 1H NMR (500 MHz, d4-methanol) δ (delta) 1.77 (ddt, 1H), 2.19 (s, 7H), 2.42 (dd, 1H), 2.63-2.96 (m, 2H), 3.55-3.75 (m, 3H), 7.18-7.63 (m, 6H), 7.86-8.01 (m, 1H), 8.10 (d, 1H), 8.50-8.78 (m, 1H) |

TABLE A3-continued
| Compound number | Structure | Data |
|---|---|---|
| A177 | 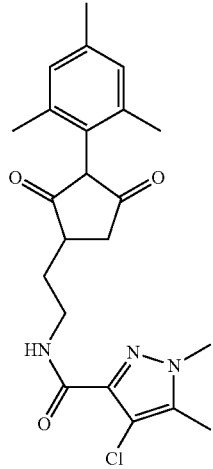 | 1H NMR (400 MHz, d4-methanol) δ (delta) 6.73 (2H, s), 3.72 (3H, s), 3.43-3.35 (2H, m), 2.87-2.79 (1H, m), 2.73-2.64 (1H, br. m), 2.38 (1H, d), 2.17 (3H, s), 2.13 (3H, s), 2.09-2.00 (1H, m), 1.93 (6H, s), 1.65-1.54 (1H, m) |
| A178 | 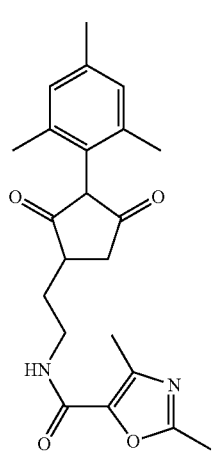 | 1H NMR (400 MHz, d4-methanol) δ (delta) 6.74 (2H, s), 3.38 (2H, t), 2.87-2.78 (1H, m), 2.72-2.63 (1H, br. s), 2.38 (1H, d), 2.37 (3H, s), 2.29 (3H, s), 2.13 (3H, s), 2.10-2.00 (1H, m), 1.92 (6H, s), 1.66-1.53 (1H, m) |
| A179 | 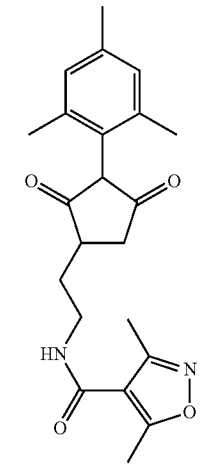 [SMILES: Cc1cc(C)c(C2C(=O)CC(CCNC(=O)c3c(C)noc3C)C2=O)c(C)c1] | |

| Compound number | Structure | Data |
|---|---|---|
| A180 | 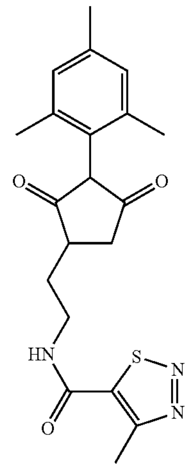 [SMILES: Cc1cc(C)c(C2C(=O)CC(CCNC(=O)c3snnc3C)C2=O)c(C)c1] | |
| A181 | 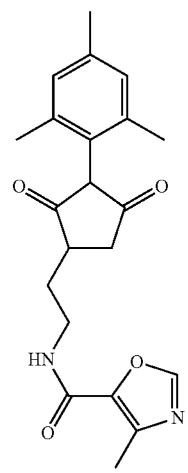 [SMILES: Cc1cc(C)c(C2C(=O)CC(CCNC(=O)c3ocnc3C)C2=O)c(C)c1] | 1H NMR (400 MHz, d4-methanol) δ 8.02 (1H, s), 6.72 (2H, s), 3.38 (2H, t), 2.87-2.77 (1H, m), 2.72-2.61 (1H, m), 2.36 (1H, d), 2.33 (3H, s), 2.12 (3H, s), 2.08-1.99 (1H, m), 1.92 (6H, s), 1.64-1.52 (1H, m) |
| A182 | 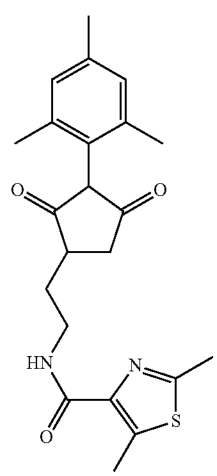 | 1H NMR (400 MHz, d4-methanol) δ 6.73 (2H, s), 3.35 (2H, t), 2.87-2.78 (1H, m), 2.70-2.61 (1H, m), 2.53 (3H, s), 2.45 (3H, s), 2.36 (1H, d), 2.12 (3H, s), 2.07-1.98 (1H, m), 1.93 (6H, s), 1.65-1.53 (1H, m) |

TABLE A3-continued
| Compound number | Structure | Data |
|---|---|---|
| A183 | 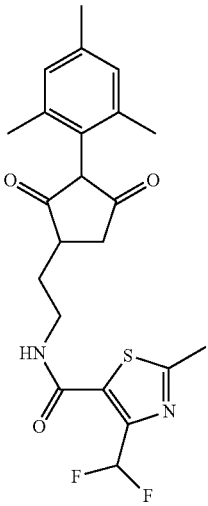 | 1H NMR (400 MHz, d4-methanol) δ 7.33 (1H, t), 6.88 (2H, s), 3.51 (2H, t), 3.00-2.90 (1H, m), 2.83-2.72 (1H, m), 2.74 (3H, s), 2.49 (1H, d), 2.26 (3H, s), 2.22-2.11 (1H, m), 2.04 (6H, s), 1.79-1.67 (1H, m) |
| A184 | 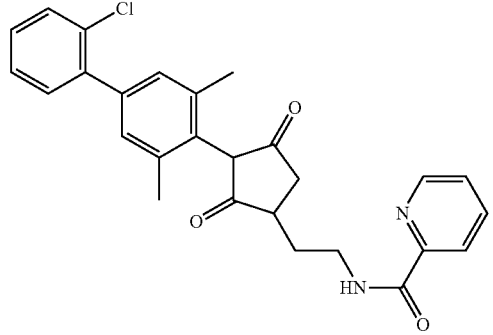 [SMILES: Cc1cc(-c2ccccc2Cl)cc(C)c1C1C(=O)CC(CCNC(=O)c2ccccn2)C1=O] | 1H NMR (400 MHz, CD$_3$OD) δ 1.66-1.86 (m, 1H), 2.19-2.26 (m, 6H), 2.33 (dd, 1H), 2.61-2.79 (m, 2H), 3.33 (dt, 1H), 3.63 (t, 2H), 7.10 (s, 2H), 7.26-7.37 (m, 3H), 7.43-7.49 (m, 1H), 7.54 (ddd, 1H), 7.96 (td, 1H), 8.11 (d, 1H), 8.65 (d, 1H) |
| A185 | 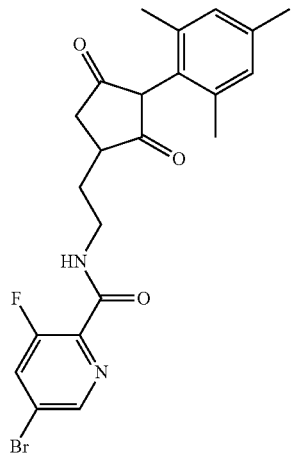 | 1H NMR (400 MHz, CD$_3$CN) δ 1.68-1.86 (m, 1H), 1.91-2.12 (m, 7H), 2.24 (s, 4H), 2.68-2.92 (m, 2H), 3.35-3.68 (m, 2H), 6.85 (s, 2H), 7.95 (dd, 1H), 8.13-8.34 (m, 1H), 8.46-8.60 (m, 1H) |

TABLE A3-continued

| Compound number | Structure | Data |
|---|---|---|
| A186 | 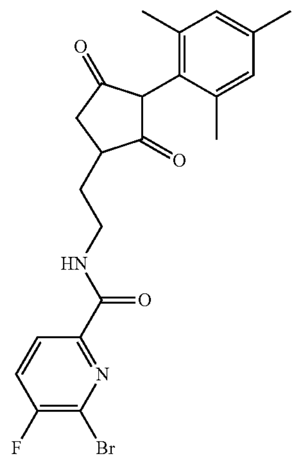 [SMILES: Cc1cc(C)c(C2C(=O)CC(CCNC(=O)c3ccc(F)c(Br)n3)C2=O)c(C)c1] | 1H NMR (400 MHz, CD₃CN) δ 1.73-1.90 (m, 1H), 1.93-2.13 (m, 7H), 2.26 (s, 4H), 2.67-2.92 (m, 2H), 3.37-3.74 (m, 2H), 6.87 (s, 2H), 7.74 (t, 1H), 8.10 (d, 1H), 8.21-8.53 (m, 1H) |
| A187 | 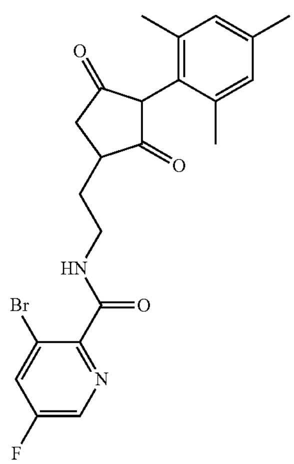 | 1H NMR (400 MHz, CDCl₃) δ 1.80 (m, 1H), 1.90-2.47 (m, 11H), 2.65-2.98 (m, 2H), 3.50 (s, 2H), 6.89 (s, 2H), 7.98 (dd, 2H), 8.48 (d, 1H) |
| A188 | 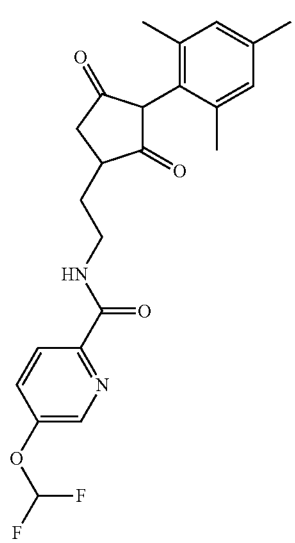 [SMILES: Cc1cc(C)c(C2C(=O)CC(CCNC(=O)c3ccc(OC(F)F)cn3)C2=O)c(C)c1] | 1H NMR (400 MHz, CD₃CN) δ 8.47 (d, 2H), 8.15 (d, 1H), 7.70 (dd, 1H), 6.69-7.19 (m, 3H), 3.58-3.80 (m, 1H), 3.39-3.58 (m, 1H), 2.80 (br. s., 2H), 2.26 (s, 4H), 1.73-2.13 (m, 8H) |

TABLE A3-continued

| Compound number | Structure | Data |
|---|---|---|
| A189 | 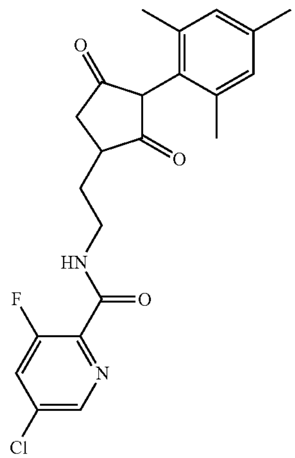 | 1H NMR (400 MHz, CD$_3$CN) δ 8.36-8.54 (m, 1H), 8.13-8.36 (m, 1H), 7.73-7.89 (m, 1H), 6.85 (s, 2H), 3.26-3.73 (m 2H), 2.63-2.92 (m, 2H), 2.24 (s, 4H), 1.93-2.11 (m, 7H), 1.70-1.86 (m, 1H) |
| A190 | 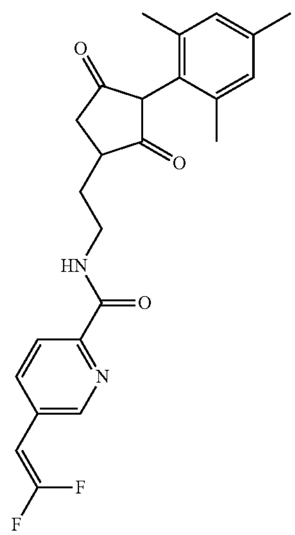 [SMILES: Cc1cc(C)c(C2C(=O)CC(CCNC(=O)c3ccc(C=C(F)F)cn3)C2=O)c(C)c1] | 1H NMR (400 MHz, CDCl$_3$) δ 8.48 (s, 2H), 8.13 (d, 1H), 7.84 (dd, 1H), 6.86 (s, 2H), 5.25-5.48 (m, 1H), 3.73-4.06 (m, 1H), 3.48 (br. s., 1H), 2.74-2.97 (m, 2H), 1.74-2.37 (m, 12H) |
| A191 | 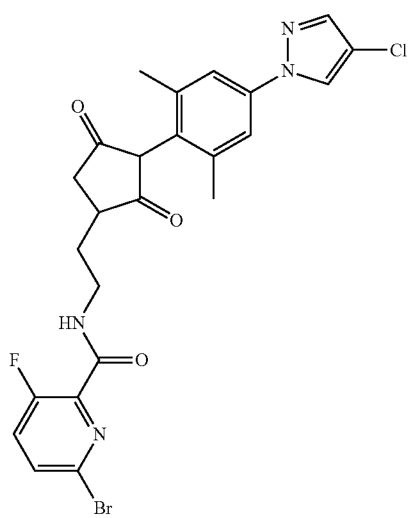 [SMILES: Cc1cc(-n2cc(Cl)cn2)cc(C)c1C1C(=O)CC(CCNC(=O)c2nc(Br)ccc2F)C1=O] | 1H NMR (400 MHz, CDCl$_3$) δ 8.28 (s, 1H), 7.93 (d, 1H), 7.79 (s, 1H), 7.45-7.65 (m, 2H), 7.14 (s, 2H), 3.30-3.81 (m, 2H), 2.87 (dd, 2H), 2.28 (d, 1H), 1.80-2.14 (m, 8H) |

TABLE A3-continued

| Compound number | Structure | Data |
|---|---|---|
| A192 | 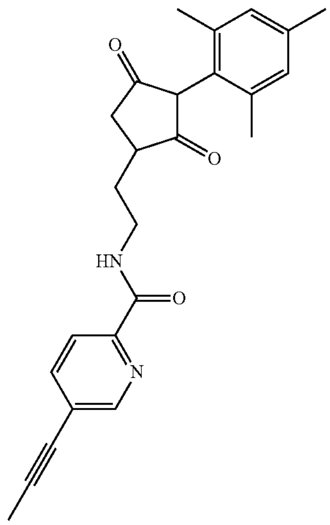 [SMILES: CC#Cc1ccc(C(=O)NCCC2CC(=O)C(c3c(C)cc(C)cc3C)C2=O)nc1] | 1H NMR (400 MHz, CDCl₃) δ 8.34-8.79 (m, 2H), 7.55-8.19 (m, 2H), 6.61-6.97 (m, 2H), 2.54-4.07 (m, 4H), 1.61-2.35 (m, 15H) |
| A193 | 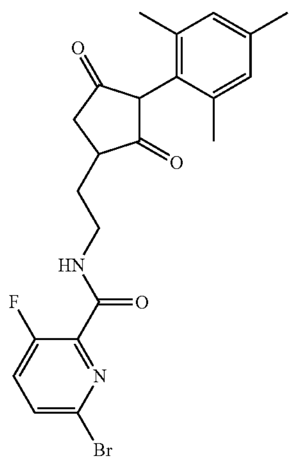 [SMILES: Cc1cc(C)c(C2C(=O)CC(CCNC(=O)c3nc(Br)ccc3F)C2=O)c(C)c1] | 1H NMR (400 MHz, CD₃OD) δ 8.38 (d, 1H), 7.80 (d, 1H), 6.84 (s, 2H), 3.41-3.63 (m, 2H), 2.86-3.03 (m, 1H), 2.70-2.86 (m, 1H), 2.34-2.56 (m, 1H), 2.23 (s, 4H), 2.04 (d, 6H), 1.61-1.83 (m, 1H) |
| A194 | 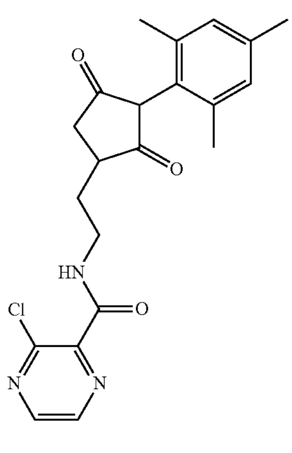 [SMILES: Cc1cc(C)c(C2C(=O)CC(CCNC(=O)c3nccnc3Cl)C2=O)c(C)c1] | 1H NMR (400 MHz, CDCl₃) δ 8.32-8.57 (m, 2H), 8.05-8.26 (m, 1H), 6.79 (s, 2H), 3.57-3.84 (m, 1H), 3.36-3.57 (m, 1H), 2.62-2.89 (m, 2H), 2.20 (m, 4H), 1.94-2.14 (m, 7H), 1.88 (m, 1H) |

TABLE A3-continued

| Compound number | Structure | Data |
|---|---|---|
| A195 | 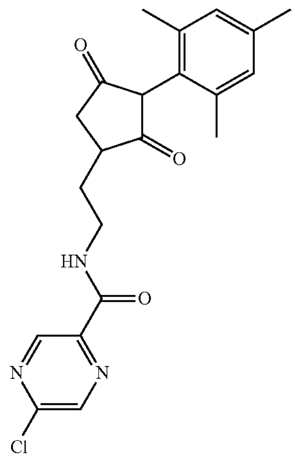 [SMILES: Cc1cc(C)c(C2C(=O)CC(CCNC(=O)c3cnc(Cl)cn3)C2=O)c(C)c1] | 1H NMR (400 MHz, CDCl₃) δ 9.07 (d, 1H), 8.51 (d, 1H), 8.01-8.29 (m, 1H), 6.82 (s, 2H), 3.63-3.81 (m, 1H), 3.46-3.63 (m, 1H), 2.65-2.92 (m, 2H), 2.23-2.35 (m, 1H), 2.21 (s, 3H), 2.05 (d, 7H), 1.75-1.97 (m, 1H) |
| A196 | 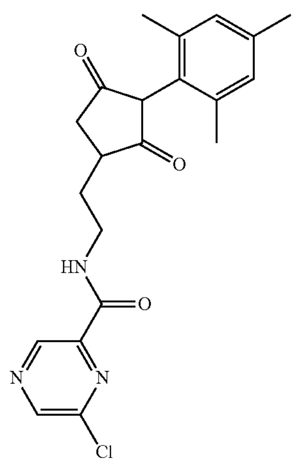 [SMILES: Cc1cc(C)c(C2C(=O)CC(CCNC(=O)c3cncc(Cl)n3)C2=O)c(C)c1] | 1H NMR (400 MHz, CDCl₃) δ 9.16 (s, 1H), 8.65 (s, 1H), 7.90-8.22 (m, 1H), 6.81 (s, 2H), 3.48-3.75 (m, 2H), 2.64-2.94 (m, 2H), 2.25-2.39 (m, 1H), 2.20 (s, 3H), 2.05 (s, 7H), 1.70-1.92 (m, 1H) |
| A197 | 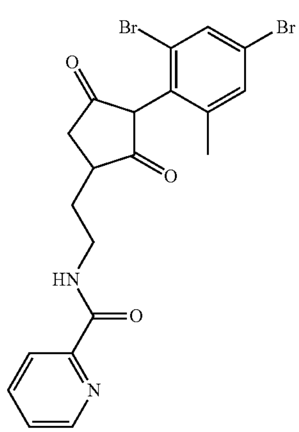 [SMILES: Cc1cc(Br)cc(Br)c1C1C(=O)CC(CCNC(=O)c2ccccn2)C1=O] | 1H NMR (400 MHz, CDCl₃) δ 1.79-1.89 (m, 1H), 2.11-2.28 (m, 5H), 2.80-3.02 (m, 2H), 3.43 (d, 1H), 4.15 (s, br, 1H), 7.34 (d, 1H), 7.53 (dd, 1H), 7.62 (s, 1H), 7.88-7.98 (m, 1H), 8.21 (d, 1H), 1.85 (m, 1H), 8.72 (br. s., 1H) |

TABLE A3-continued

| Compound number | Structure | Data |
|---|---|---|
| A198 | 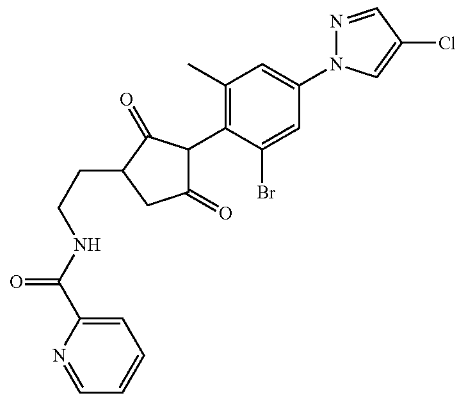 [SMILES: Cc1cc(-n2cc(Cl)cn2)cc(Br)c1C1C(=O)CC(CCNC(=O)c2ccccn2)C1=O] | 1H NMR (400 MHz, CDCl$_3$) δ 8.70-8.53 (m, 2H), 8.26-8.13 (m, 1H), 7.91 (dd, 1H), 7.60-7.44 (m, 4H), 4.14-3.95 (m, 1H), 3.88-3.70 (m, 1H), 3.50-3.27 (m, 1H), 2.80 (d, 1H), 2.27 (d, 1H), 2.22 (s, 3H), 2.18-2.00 (m, 2H) |
| A199 | 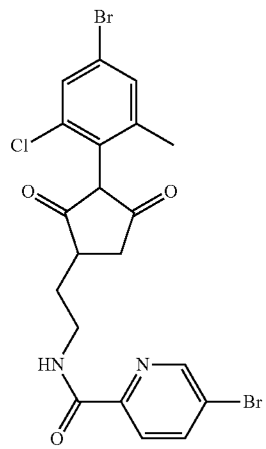 [SMILES: Cc1cc(Br)cc(Cl)c1C1C(=O)CC(CCNC(=O)c2ccc(Br)cn2)C1=O] | 1H NMR (400 MHz, d4-methanol) δ 8.57 (s, 1H), 8.00 (d, 1H), 7.88 (d, 1H), 7.31 (s, 1H), 7.21 (s, 1H), 3.53-3.41 (m, 2H), 2.90-2.77 (m, 1H), 2.76-2.68 (m, 1H), 2.46-2.37 (m, 1H), 2.14-2.01 (m, 1H), 2.02 (s, 3H), 1.74-1.58 (m, 1H) |
| A200 | 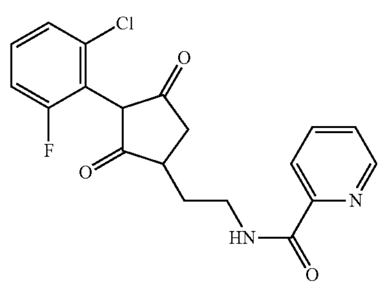 [SMILES: O=C(NCCC1CC(=O)C(c2c(F)cccc2Cl)C1=O)c1ccccn1] | 1H NMR (400 MHz, CD$_3$OD) δ 1.64-1.90 (m, 1H), 2.14-2.38 (m, 2H), 2.61-2.82 (m, 2H), 3.55-3.65 (m, 2H), 6.93-7.07 (m, 1H), 7.22 (d, 2H), 7.47-7.61 (m, 1H), 7.90-8.01 (m, 1H), 8.05-8.15 (m, 1H), 8.57-8.74 (m, 1H) |
| A201 | 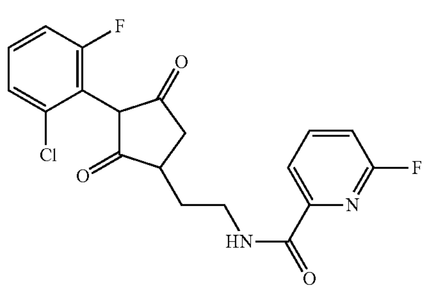 [SMILES: O=C(NCCC1CC(=O)C(c2c(F)cccc2Cl)C1=O)c1cccc(F)n1] | 1H NMR (400 MHz, CD$_3$OD) δ 1.68-1.89 (m, 1H), 2.10-2.22 (m, 1H), 2.24-2.36 (m, 1H), 2.58-2.81 (m, 2H), 3.79-3.85 (m, 2H), 6.89-7.08 (m, 2H), 7.15-7.28 (m, 2H), 7.43 (d, 1H), 7.69 (dd, 1H) |

TABLE A3-continued

| Compound number | Structure | Data |
|---|---|---|
| A202 | (2-bromo-6-chloro-4-bromophenyl substituted cyclopentane-1,3-dione with ethyl picolinamide side chain); trifluoroacetate salt | 1H NMR (400 MHz, CD$_3$OD) δ 8.62 (s, 1H), 8.12 (d, 1H), 8.00 (t, 1H), 7.76 (d, 1H), 7.71-7.53 (m, 2H), 3.68-3.53 (m, 2H), 3.03-2.40 (m, 1H), 2.40-2.80 (m, 1H), 2.53 (d, 1H), 2.27-2.13 (m, 1H), 1.89-1.73 (m, 1H) |
| A203 | (3,5-dichlorobiphenyl-2,6-dimethyl substituted cyclopentane-1,3-dione with ethyl picolinamide side chain) | 1H NMR (400 MHz, CD$_3$OD) δ 1.66-1.84 (m, 1H), 2.24 (d, 6H), 2.28-2.39 (m, 1H), 2.58-2.69 (m, 1H), 2.71-2.82 (m, 1H), 3.30-3.34 (m, 1H), 3.62 (t, 2H), 7.28 (s, 2H), 7.36 (t, 1H), 7.48-7.60 (m, 3H), 7.95 (td, 1H), 8.11 (d, 1H), 8.64 (d, 1H) |
| A204 | (4-methylbiphenyl-2,6-dimethyl substituted cyclopentane-1,3-dione with ethyl picolinamide side chain) | 1H NMR (400 MHz, CD$_3$OD) δ 1.66-1.85 (m, 1H), 2.16-2.25 (m, 7H), 2.29-2.42 (m, 3H), 2.60-2.82 (m, 2H), 3.54-3.73 (m, 3H), 7.15-7.63 (m, 7H), 7.96 (td, 1H), 8.11 (d, 1H), 8.65 (d, 1H) |
| A205 | (mesityl substituted cyclopentane-1,3-dione with ethyl pyrimidine-4-carboxamide side chain) | 1H NMR (400 MHz, d4-methanol) δ 9.39-9.27 (m, 1H), 9.13-8.93 (m, 1H), 8.24-8.07 (m, 1H), 6.86 (s, 2H), 3.71-3.53 (m, 2H), 3.03-2.87 (m, 1H), 2.87-2.74 (m, 1H), 2.59-2.44 (m, 1H), 2.25 (s, 4H), 2.04 (s, 7H), 1.85-1.69 (m, 1H) |
| A206 | (mesityl substituted cyclopentane-1,3-dione with ethyl 5-chloropyrimidine-2-carboxamide side chain) | 1H NMR (400 MHz, d4-methanol) δ 8.97 (s, 2H), 6.86 (s, 2H), 3.72-3.51 (m, 2H), 3.02-2.87 (m, 1H), 2.87-2.69 (m, 1H), 2.60-2.40 (m, 1H), 2.25 (s, 4H), 2.09-1.95 (m, 7H), 1.84-1.65 (m, 1H) |

TABLE A3-continued

| Compound number | Structure | Data |
|---|---|---|
| A207 | 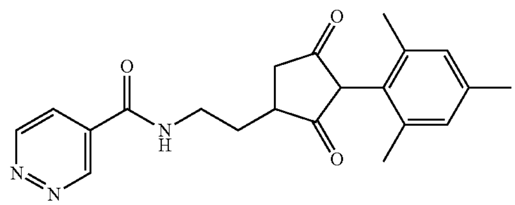 [SMILES: Cc1cc(C)c(C2C(=O)CC(CCNC(=O)c3ccnnc3)C2=O)c(C)c1] | 1H NMR (400 MHz, d4-methanol) δ 9.96-9.83 (m, 1H), 9.75-9.67 (m, 1H), 8.83-8.58 (m, 1H), 6.87 (s, 2H), 3.71-3.54 (m, 2H), 3.08-2.93 (m, 1H), 2.93-2.77 (m, 1H), 2.60-2.40 (m, 1H), 2.25 (s, 4H), 2.12-1.96 (m, 7H), 1.88-1.69 (m, 1H) |
| A208 | 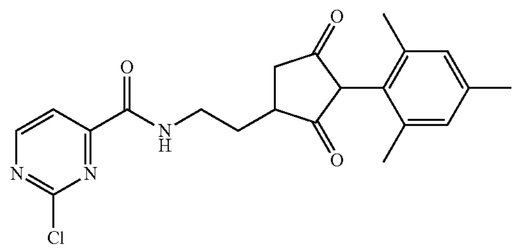 [SMILES: Cc1cc(C)c(C2C(=O)CC(CCNC(=O)c3ccnc(Cl)n3)C2=O)c(C)c1] | 1H NMR (400 MHz, d4-methanol) δ 8.90 (d, 1H), 8.01 (d, 1H), 6.85 (s, 2H), 3.58 (s, 2H), 3.02-2.87 (m, 1H), 2.87-2.68 (m, 1H), 2.56-2.46 (m, 1H), 2.24 (s, 4H), 2.09-1.97 (m, 7H), 1.82-1.67 (m, 1H) |
| A209 | 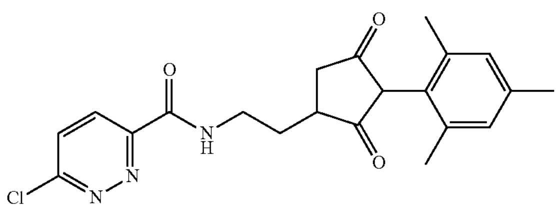 [SMILES: Cc1cc(C)c(C2C(=O)CC(CCNC(=O)c3ccc(Cl)nn3)C2=O)c(C)c1] | 1H NMR (400 MHz, d4-methanol) δ 8.36-8.24 (m, 1H), 8.08-7.73 (m, 1H), 6.88 (s, 2H), 3.73-3.48 (m, 2H), 3.05-2.89 (m, 1H), 2.89-2.72 (m, 1H), 2.63-2.41 (m, 1H), 2.27 (s, 4H), 2.11-1.95 (m, 7H), 1.86-1.68 (m, 1H) |
| A210 | 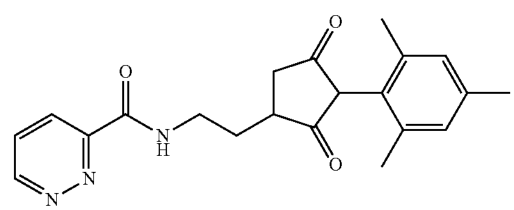 [SMILES: Cc1cc(C)c(C2C(=O)CC(CCNC(=O)c3cccnn3)C2=O)c(C)c1] | 1H NMR (400 MHz, d4-methanol) δ 9.64-9.39 (m, 1H), 8.72-8.55 (m, 1H), 8.43-8.00 (m, 1H), 6.96-6.61 (m, 2H), 3.70-3.60 (m, 2H), 3.02-2.90 (m, 1H), 2.90-2.77 (m, 1H), 2.63-2.42 (m, 1H), 2.25 (s, 4H), 2.12-1.98 (m, 7H), 1.84-1.70 (m, 1H) |
| A211 | 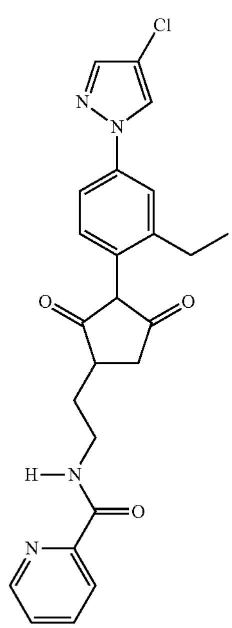 [SMILES: CCc1cc(-n2cc(Cl)cn2)ccc1C1C(=O)CC(CCNC(=O)c2ccccn2)C1=O] | 1H NMR (400 MHz, d4-methanol) δ (delta) 8.86 (d, 1H), 8.60 (dd, 1H), 8.49 (d, 1H), 8.39 (s, 1H), 8.08 (dd, 1H), 7.70 (s, 1H), 7.67 (d, 1H), 7.54 (dd, 1H), 7.14 (d, 1H), 3.73-3.63 (m, 2H), 3.01 (dd, 1H), 2.91-2.80 (m, 1H), 2.58 (dd, 1H), 2.57 (quart, 2H), 2.30-2.20 (m, 1H), 1.93-1.78 (m, 1H), 1.16 (t, 3H) |

TABLE A3-continued

| Compound number | Structure | Data |
|---|---|---|
| A212 | 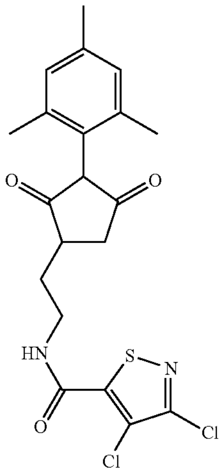 [SMILES: Cc1cc(C)c(C2C(=O)CC(CCNC(=O)c3snc(Cl)c3Cl)C2=O)c(C)c1] | 1H NMR (400 MHz, d4-methanol) δ (delta) 6.76 (2H, s), 3.54-3.42 (2H, m), 2.90-2.77 (1H, m), 2.75-2.66 (1H, m), 2.39 (1H, d), 2.14 (3H, s), 2.12-2.03 (1H, m), 1.95 (6H, s), 1.72-1.61 (1H, m) |
| A213 | 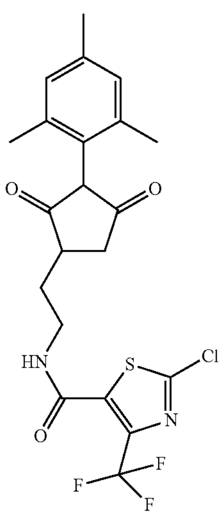 [SMILES: Cc1cc(C)c(C2C(=O)CC(CCNC(=O)c3sc(Cl)nc3C(F)(F)F)C2=O)c(C)c1] | 1H NMR (400 MHz, d-4 methanol) δ (delta) 6.76 (2H, s), 3.47-3.33 (2H, m), 2.85-2.78 (1H, m), 2.71-2.63 (1H, m), 2.35 (1H, d), 2.14 (3H, s), 2.10-2.02 (1H, m), 1.95 (6H, s), 1.64-1.54 (1H, m) |

Additional compounds in Table P1 below illustrate the present invention, and are particular embodiments of the compounds of formula (I) according to the present invention, in which G is not hydrogen. For the most part, these compounds can generally be prepared by methods similar to those shown in the Examples and/or in the process section hereinabove using appropriate starting materials and with any appropriate and/or necessary process changes.

It should be noted that certain compounds of the invention exist as a mixture of isomers, including atropisomers, noted above, under the conditions used to obtain the $^1$H NMR data. Where this has occurred, the characterising data are reported for all isomers present at ambient temperature in the specified solvent. Unless otherwise stated, proton ($^1$H) NMR spectra were recorded at ambient temperature.

TABLE P1
| Compound number | Structure | Data |
|---|---|---|
| P1 | 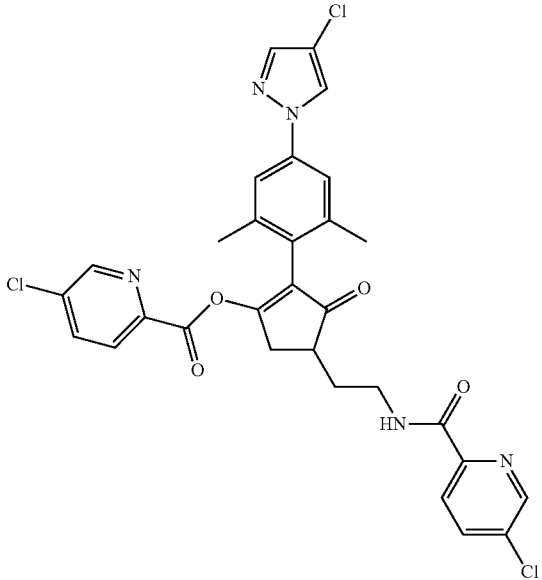 [SMILES: Cc1cc(-n2cc(Cl)cn2)cc(C)c1C1=C(OC(=O)c2ccc(Cl)cn2)CC(CCNC(=O)c2ccc(Cl)cn2)C1=O] | 1H NMR (500 MHz, CDCl₃) δ ppm 1.84-2.02 (m, 1H), 2.06-2.37 (m, 7H), 2.88-3.21 (m, 2H), 3.32-3.88 (m, 3H), 7.20-7.42 (m, 2H), 7.48-7.98 (m, 5H), 8.04-8.23 (m, 2H), 8.39-8.74 (m, 2H) |
| P2 | 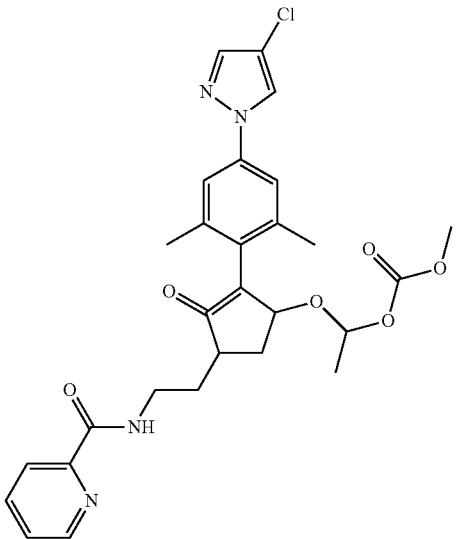 | 1H NMR (400 MHz, CDCl₃) δ ppm 1.28-1.50 (m, 3H), 1.65-1.97 (m, 2H), 2.12-2.28 (m, 7H), 2.54-2.99 (m, 3H), 3.01-3.39 (m, 1H), 3.64-3.81 (m, 4H), 5.56-6.36 (m, 1H), 7.33 (br. s., 3H), 7.88 (s, 2H), 8.20 (s, 2H), 8.44-8.66 (m, 1H) |
| P3 | 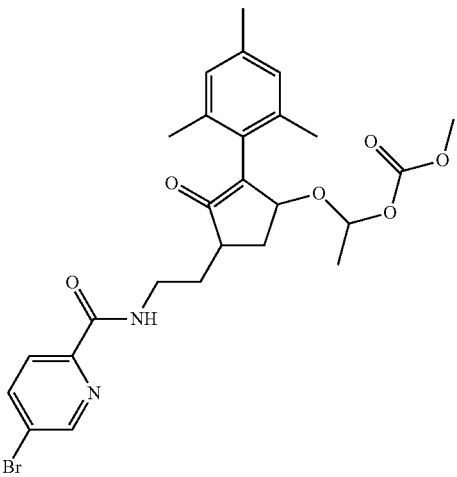 | 1H NMR (400 MHz, CDCl₃) δ ppm 8.47-8.70 (m, 1H), 7.88-8.23 (m, 3H), 6.73-6.95 (m, 2H), 5.71-6.32 (m, 1H), 3.52-3.83 (m, 4H), 2.33-3.30 (m, 3H), 2.27 (s, 4H), 1.98-2.10 (m, 6H), 1.67-1.91 (m, 2H), 1.30-1.57 (m, 3H) |

| Compound number | Structure | Data |
|---|---|---|
| P4 | 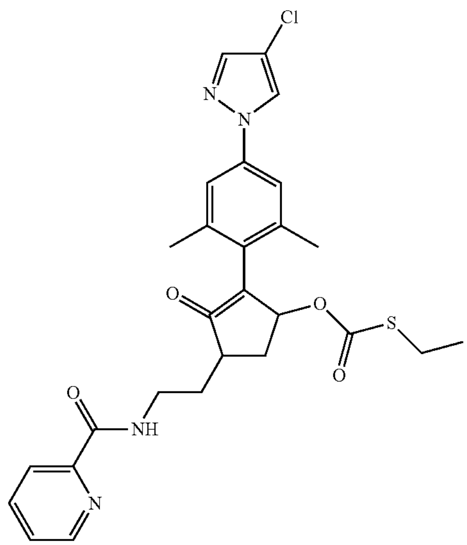 | 1H NMR (400 MHz, CDCl$_3$) δ ppm 8.55 (d, 1H), 8.19 (d, 2H), 7.75-7.95 (m, 2H), 7.61 (s, 1H), 7.39-7.52 (m, 1H), 7.33 (s, 2H), 3.53-3.86 (m, 2H), 3.32-3.53 (m, 1H), 2.77-3.02 (m, 4H), 2.21-2.36 (m, 1H), 2.09-2.21 (m, 6H), 1.83-1.93 (m, 1H), 1.19-1.36 (m, 3H) |
| P5 | 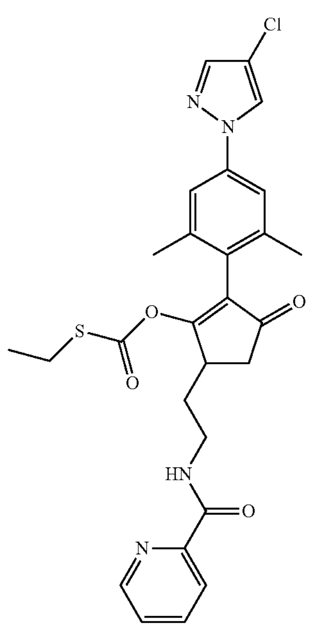 [SMILES: CCSC(=O)OC1=C(c2c(C)cc(-n3cc(Cl)cn3)cc2C)C(=O)CC1CCNC(=O)c1ccccn1] | 1H NMR (400 MHz, CDCl$_3$) δ ppm 8.46-8.60 (m, 1H), 8.09-8.29 (m, 2H), 7.75-7.95 (m, 2H), 7.55-7.68 (m, 1H), 7.41-7.51 (m, 1H), 7.29-7.37 (m, 2H), 3.57-3.75 (m, 2H), 3.32-3.51 (m, 1H), 2.87-3.11 (m, 1H), 2.65-2.81 (m, 2H), 2.45-2.63 (m, 1H), 2.17 (d, 7H), 1.68-1.86 (m, 1H), 1.14 (s, 3H) |

TABLE P1-continued
| Compound number | Structure | Data |
|---|---|---|
| P6 | 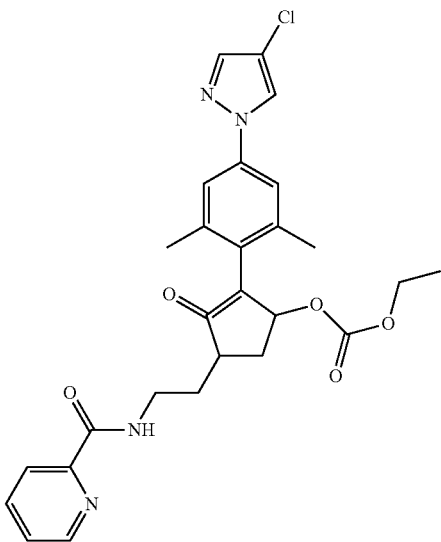 | 1H NMR (400 MHz, CDCl$_3$) δ ppm 8.45-8.64 (m, 1H), 8.19 (d, 2H), 7.77-7.97 (m, 2H), 7.61 (s, 1H), 7.30-7.50 (m, 3H), 4.14-4.26 (m, 2H), 3.54-3.87 (m, 2H), 3.41 (dd, 1H), 2.97 (dd, 2H), 2.09-2.38 (m, 7H), 1.82-1.98 (m, 1H), 1.27 (q, 3H) |
| P7 | 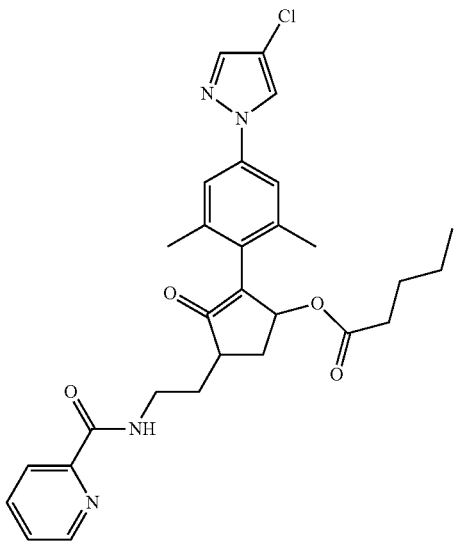 | 1H NMR (400 MHz, CDCl$_3$) δ ppm 8.56 (dd, 1H), 8.19 (d, 2H), 7.75-7.96 (m, 2H), 7.62 (s, 1H), 7.39-7.51 (m, 1H), 7.33 (s, 2H), 3.52-3.88 (m, 2H), 3.20-3.40 (m, 1H), 2.87 (m, 2H), 2.36 (t, 2H), 2.08-2.31 (m, 7H), 1.79-1.96 (m, 1H), 1.43-1.60 (m, 2H), 1.10-1.30 (m, 2H), 0.82 (t, 3H) |

TABLE P1-continued
| Compound number | Structure | Data |
|---|---|---|
| P8 | 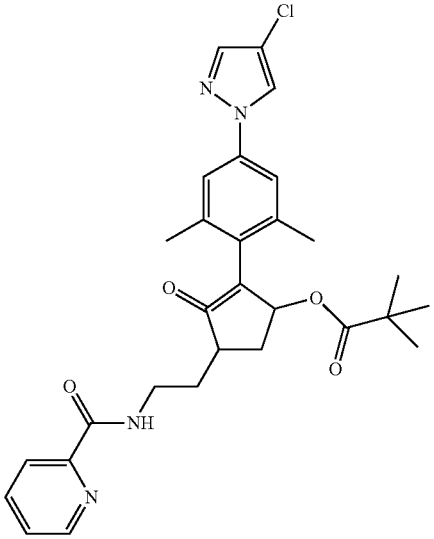 | 1H NMR (400 MHz, CDCl₃) δ ppm 8.49-8.62 (m, 1H), 8.19 (d, 2H), 7.77-7.92 (m, 2H), 7.62 (s, 1H), 7.40-7.51 (m, 1H), 7.33 (s, 2H), 3.50-3.87 (m, 2H), 3.20-3.36 (m, 1H), 2.75-2.95 (m, 2H), 2.21-2.37 (m, 1H), 2.15 (d, 6H), 1.78-1.98 (m, 1H), 1.10 (s, 9H) |
| P9 | 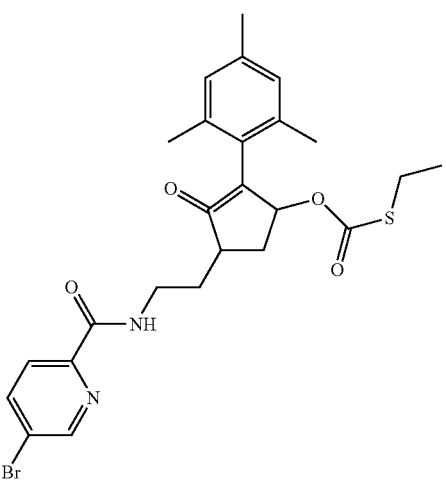 | 1H NMR (400 MHz, CDCl₃) δ ppm 8.53-8.67 (m, 1H), 7.89-8.23 (m, 3H), 6.86 (s, 2H), 3.72 (s, 2H), 3.35 (dd, 1H), 2.73-2.99 (m, 4H), 2.26 (s, 4H), 1.97-2.11 (m, 6H), 1.78-1.94 (m, 1H), 1.18-1.32 (m, 3H) |
| P10 | 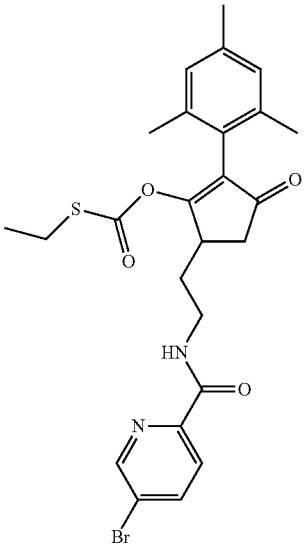 [SMILES: CCSC(=O)OC1=C(c2c(C)cc(C)cc2C)C(=O)CC1CCNC(=O)c1ccc(Br)cn1] | 1H NMR (400 MHz, CDCl₃) δ ppm 8.61 (d, 1H), 7.87-8.18 (m, 3H), 6.85 (s, 2H), 3.51-3.68 (m, 2H), 3.37-3.50 (m, 1H), 2.90-3.05 (m, 1H), 2.75 (m, 2H), 2.41-2.57 (m, 1H), 2.16-2.35 (m, 4H), 1.99-2.14 (m, 6H), 1.66-1.84 (m, 1H), 1.13 (t, 3H) |

TABLE P1-continued
| Compound number | Structure | Data |
|---|---|---|
| P11 | 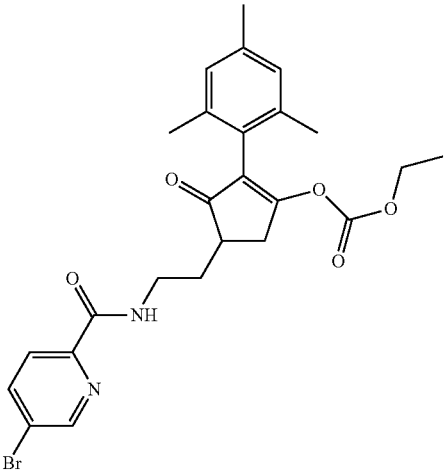 [SMILES: CCOC(=O)OC1=C(c2c(C)cc(C)cc2C)C(=O)C(CCNC(=O)c2ccc(Br)cn2)C1] | 1H NMR (400 MHz, CDCl₃) δ ppm 8.60 (d, 1H), 7.88-8.22 (m, 3H), 6.87 (s, 2H), 4.19 (q, 2H), 3.53-3.83 (m, 2H), 3.36 (dd, 1H), 2.92 (dd, 2H), 2.26 (s, 4H), 1.97-2.15 (m, 6H), 1.79-1.95 (m, 1H), 1.21-1.35 (m, 3H) |
| P12 | 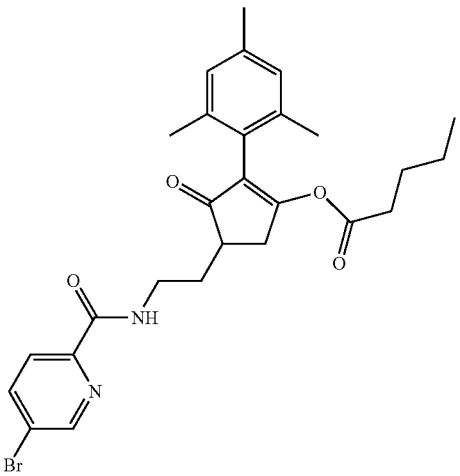 [SMILES: CCCCC(=O)OC1=C(c2c(C)cc(C)cc2C)C(=O)C(CCNC(=O)c2ccc(Br)cn2)C1] | 1H NMR (400 MHz, CDCl₃) δ ppm 8.60 (d, 1H), 7.90-8.26 (m, 3H), 6.86 (s, 2H), 3.48-3.88 (m, 2H), 3.27 (dd, 1H), 2.67-2.92 (m, 2H), 2.14-2.41 (m, 6H), 1.96-2.11 (m, 6H), 1.78-1.93 (m, 1H), 1.43-1.58 (m, 2H), 1.10-1.31 (m, 2H), 0.82 (t, 3H) |
| P13 | 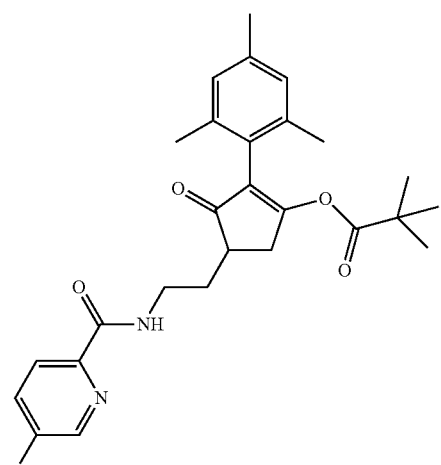 | 1H NMR (400 MHz, CDCl₃) δ ppm 8.54-8.67 (m, 1H), 7.87-8.22 (m, 3H), 6.71-6.90 (m, 2H), 3.47-3.85 (m, 2H), 3.11-3.34 (m, 1H), 2.63-2.92 (m, 2H), 2.25 (m, 4H), 1.97-2.13 (m, 6H), 1.76-1.94 (m, 1H), 1.09 (s, 9H) |

TABLE P1-continued
| Compound number | Structure | Data |
|---|---|---|
| P14 | 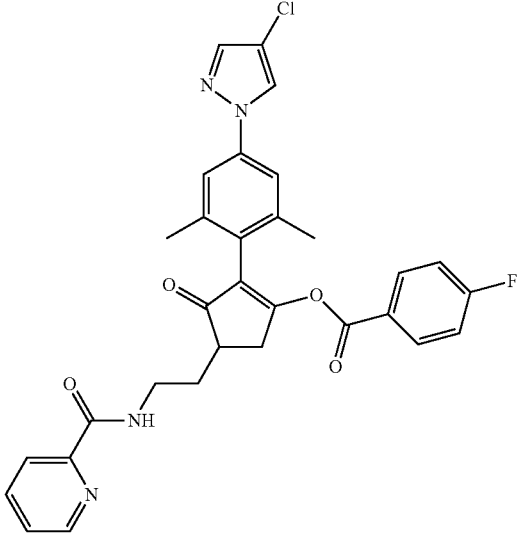 [SMILES: Cc1cc(-n2cc(Cl)cn2)cc(C)c1C1=C(OC(=O)c2ccc(F)cc2)CC(CCNC(=O)c2ccccn2)C1=O] | 1H NMR (400 MHz, CDCl₃) δ ppm 8.45-8.66 (m, 1H), 8.09-8.36 (m, 2H), 7.79-7.98 (m, 4H), 7.61 (s, 1H), 7.39-7.50 (m, 1H), 7.29-7.38 (m, 2H), 7.01-7.18 (m, 2H), 3.40-3.90 (m, 3H), 2.83-3.17 (m, 2H), 2.20 (d, 7H), 1.80-2.01 (m, 1H) |
| P15 | 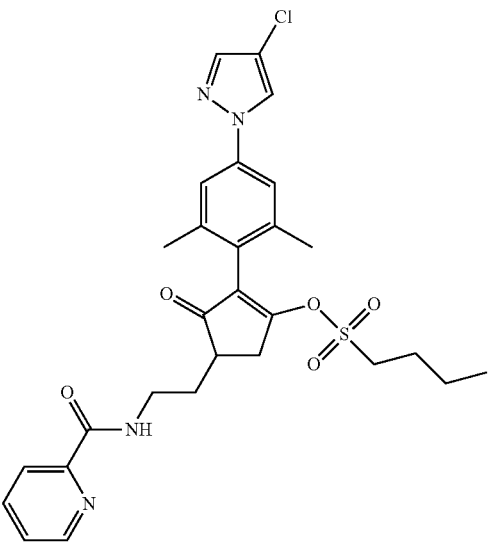 [SMILES: CCCCS(=O)(=O)OC1=C(c2c(C)cc(-n3cc(Cl)cn3)cc2C)C(=O)C(CCNC(=O)c2ccccn2)C1] | 1H NMR (400 MHz, CDCl₃) δ ppm 0.71-0.86 (m, 3H), 1.18-1.40 (m, 2H), 1.55-1.71 (m, 2H), 1.91 (br. s., 1H), 2.07-2.37 (m, 7H), 2.75-3.22 (m, 4H), 3.47 (dd, 1H), 3.56-3.84 (m, 2H), 7.29-7.49 (m, 3H), 7.55-7.65 (s, 1H), 7.77-7.97 (m, 2H), 8.07-8.36 (m, 2H), 8.46-8.62 (m, 1H) |

TABLE P1-continued

| Compound number | Structure | Data |
|---|---|---|
| P16 | 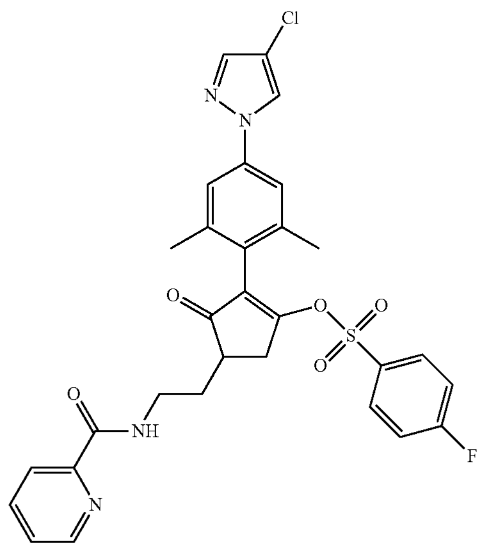 [SMILES: Cc1cc(-n2cc(Cl)cn2)cc(C)c1C1=C(OS(=O)(=O)c2ccc(F)cc2)CC(CCNC(=O)c2ccccn2)C1=O] | 1H NMR (400 MHz, CDCl$_3$) δ ppm 8.46-8.67 (m, 1H), 8.20 (d, 2H), 7.87 (s, 2H), 7.74 (dd, 2H), 7.63 (s, 1H), 7.38-7.49 (m, 1H), 7.26 (d, 2H), 7.03-7.18 (m, 2H), 3.52-3.83 (m, 2H), 3.32-3.52 (m, 1H), 2.79-3.05 (m, 2H), 2.15-2.31 (m, 1H), 1.95-2.08 (m, 6H), 1.80-1.95 (m, 1H) |
| P17 | 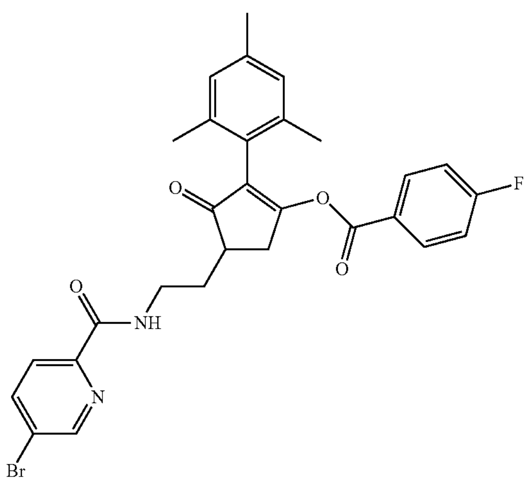 [SMILES: Cc1cc(C)c(C2=C(OC(=O)c3ccc(F)cc3)CC(CCNC(=O)c3ccc(Br)cn3)C2=O)c(C)c1] | 1H NMR (400 MHz, CDCl$_3$) δ ppm 8.60 (d, 1H), 8.02-8.24 (m, 2H), 7.86-8.02 (m, 3H), 7.10 (t, 2H), 6.86 (s, 2H), 3.55-3.87 (m, 2H), 3.35-3.55 (m, 1H), 2.78-3.16 (m, 2H), 2.25 (m, 4H), 2.01-2.19 (m, 6H), 1.84-2.00 (m, 1H) |
| P18 | 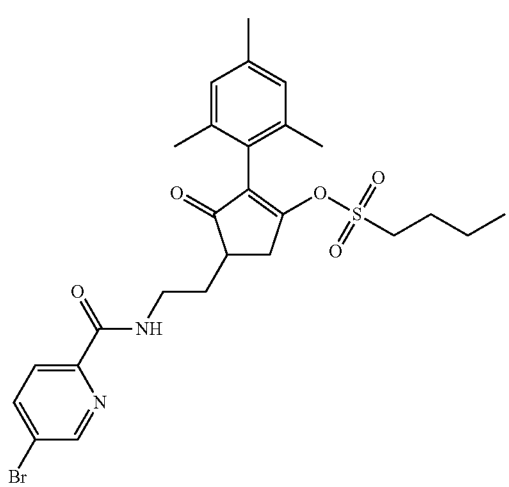 [SMILES: CCCCS(=O)(=O)OC1=C(c2c(C)cc(C)cc2C)C(=O)C(CCNC(=O)c2ccc(Br)cn2)C1] | 1H NMR (400 MHz, CDCl$_3$) δ ppm 8.60 (d, 1H), 7.89-8.22 (m, 3H), 6.88 (s, 2H), 3.50-3.84 (m, 2H), 3.26-3.47 (m, 1H), 2.78-3.05 (m, 4H), 2.27 (s, 4H), 1.97-2.13 (m, 6H), 1.79-1.97 (m, 1H), 1.55 (s, 2H), 1.20 (d, 2H), 0.78 (t, 3H) |

TABLE P1-continued

| Compound number | Structure | Data |
|---|---|---|
| P19 | 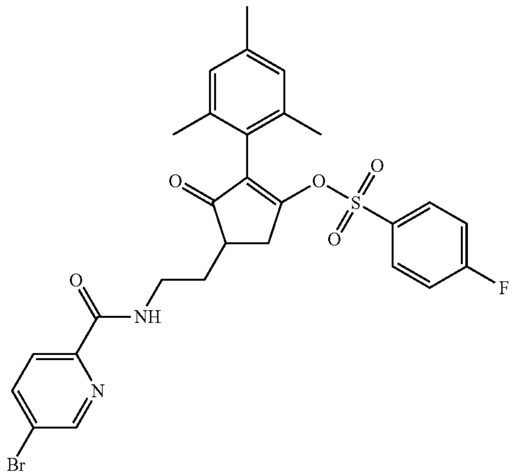 [SMILES: Cc1cc(C)c(C2=C(OS(=O)(=O)c3ccc(F)cc3)CC(CCNC(=O)c3ccc(Br)cn3)C2=O)c(C)c1] | 1H NMR (400 MHz, CDCl₃) δ ppm 8.60 (d, 1H), 8.08 (d, 2H), 7.92-8.04 (m, 1H), 7.65 (dd, 2H), 7.04 (t, 2H), 6.75 (d, 2H), 3.49-3.80 (m, 2H), 3.26-3.44 (m, 1H), 2.71-2.97 (m, 2H), 2.25 (s, 4H), 1.90 (d, 7H) |
| P20 | 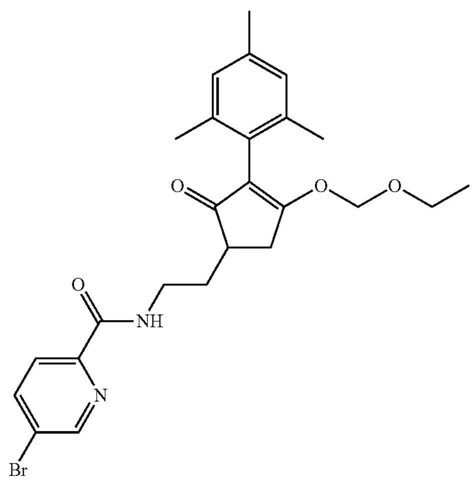 [SMILES: CCOCOC1=C(c2c(C)cc(C)cc2C)C(=O)C(CCNC(=O)c2ccc(Br)cn2)C1] | 1H NMR (400 MHz, CDCl₃) δ ppm 8.50-8.70 (m, 1H), 7.86-8.26 (m, 3H), 6.75-6.92 (m, 2H), 4.96-5.22 (m, 2H), 3.52-3.83 (m, 5H), 3.00-3.26 (m, 1H), 2.68-2.79 (m, 1H), 2.15-2.32 (m, 4H), 1.97-2.13 (m, 6H), 1.70-1.91 (m, 1H), 1.21-1.33 (m, 3H) |
| P21 | 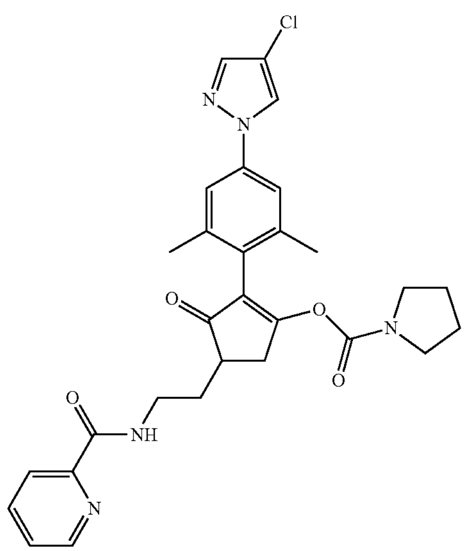 [SMILES: Cc1cc(-n2cc(Cl)cn2)cc(C)c1C1=C(OC(=O)N2CCCC2)CC(CCNC(=O)c2ccccn2)C1=O] | 1H NMR (400 MHz, in solvent) δ ppm 1.68-1.97 (m, 4H), 2.13-2.35 (m, 6H), 2.70-2.91 (m, 1H), 2.97-3.13 (m, 1H), 3.23 (s, 2H), 3.29-3.42 (m, 4H), 3.42-3.82 (m, 3H), 7.33 (m, 3H), 7.55-7.65 (s, 1H), 7.76-7.96 (m, 2H), 8.19 (d, 2H), 8.56 (d, 1H) |

TABLE P1-continued
| Compound number | Structure | Data |
|---|---|---|
| P22 | 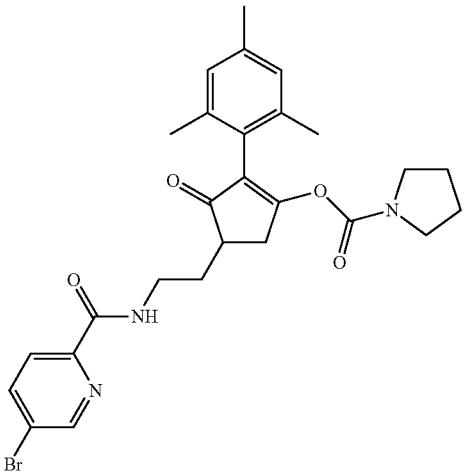 [SMILES: Cc1cc(C)c(C2=C(OC(=O)N3CCCC3)CC(CCNC(=O)c3ccc(Br)cn3)C2=O)c(C)c1] | 1H NMR (400 MHz, CDCl₃) δ ppm 1.86 (d, 4H), 2.01-2.14 (m, 6H), 2.26 (s, 4H), 2.67-3.12 (m, 2H), 3.14-3.50 (m, 6H), 3.52-3.84 (m, 2H), 6.86 (s, 2H), 7.85-8.23 (m, 3H), 8.60 (d, 1H) |
| P23 | 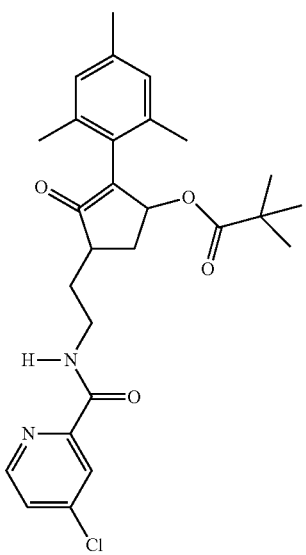 | 1H NMR (400 MHz, CDCl₃) δ 8.49-8.40 (m, 1H), 8.24-8.12 (m, 2H), 7.50-7.39 (m, 1H), 6.88-6.76 (m, 2H), 3.84-3.49 (m, 2H), 3.33-3.13 (m, 1H), 2.93-2.69 (m, 2H), 2.25 (s, 4H), 2.04 (d, 6H), 1.95-1.76 (m, 1H), 1.09 (s, 9H) |
| P24 | 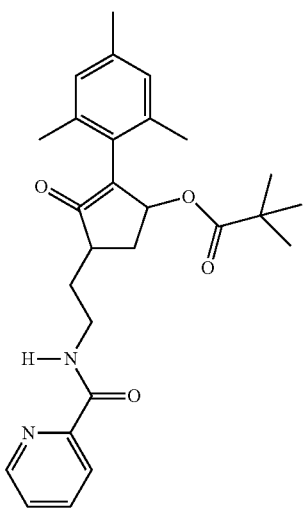 | 1H NMR (400 MHz, CDCl₃) δ 8.60-8.49 (m, 1H), 8.34-8.12 (m, 2H), 7.90-7.73 (m, 1H), 7.49-7.36 (m, 1H), 6.83 (s, 2H), 3.87-3.51 (m, 2H), 3.36-3.15 (m, 1H), 2.96-2.62 (m, 2H), 2.25 (s, 4H), 2.04 (d, 6H), 1.94-1.79 (m, 1H), 1.08 (s, 9H) |

| Compound number | Structure | Data |
|---|---|---|
| P25 | 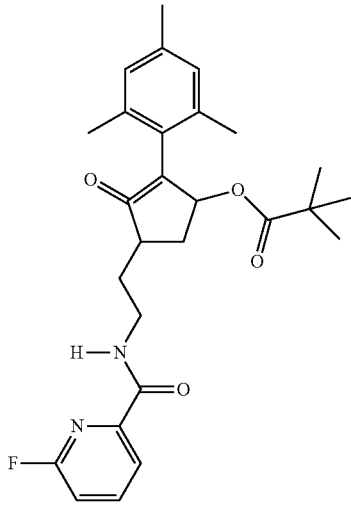 | 1H NMR (400 MHz, CDCl₃) δ 8.18-7.79 (m, 3H), 7.16-6.98 (m, 1H), 6.83 (s, 2H), 3.88-3.50 (m, 2H), 3.34-3.13 (m, 1H), 2.92-2.69 (m, 2H), 2.33-1.68 (m, 11H), 1.14-0.99 (m, 9H) |
| P26 | 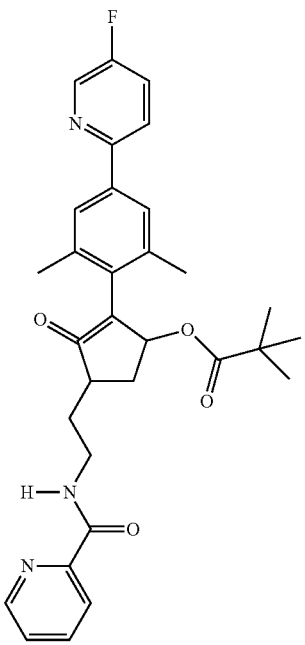 | 1H NMR (400 MHz, CDCl₃) δ 8.56 (d, 1H), 8.52 (d, 1H), 8.29-8.22 (br, 1H), 8.19 (d, 1H), 7.85 (t, 1H), 7.72-7.67 (m, 1H), 7.60 (s, 2H), 7.48-7.41 (m, 2H), 3.83-3.72 (m, 1H), 3.66-3.56 (m, 1H), 3.35-3.26 (m, 1H), 2.92-2.82 (m, 2H), 2.33-2.20 (m, 1H), 2.18 (d, 6H), 1.95-1.82 (m, 1H), 1.09 (s, 9H) |

TABLE P1-continued

| Compound number | Structure | Data |
| --- | --- | --- |
| P27 | 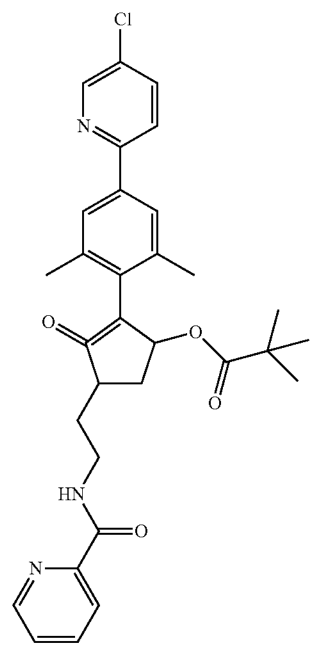 | 1H NMR (400 MHz, CDCl$_3$) δ 8.54 (s, 1H), 8.49 (d, 1H), 8.22-8.15 (br, 1H), 8.12 (d, 1H), 7.79 (t, 1H), 7.66-7.56 (m, 2H), 7.55 (s, 2H), 7.39-7.32 (m, 1H), 3.76-3.64 (m, 1H), 3.61-3.49 (m, 1H), 3.30-3.19 (m, 1H), 2.87-2.75 (m, 2H), 2.28-2.13 (m, 1H), 2.10 (d, 6H), 1.88-1.75 (m, 1H), 1.01 (s, 9H) |
| P28 | 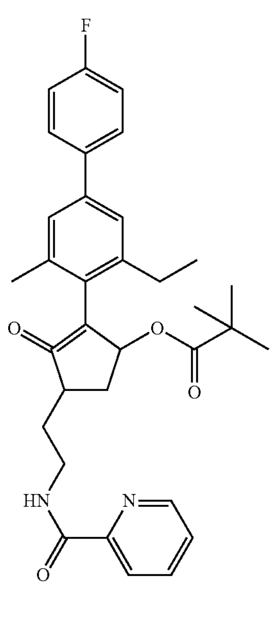 | 1H NMR (400 MHz, CDCl3) δ 8.56 (d, 1H), 8.26 (br. s., 1H), 8.20 (d, 1H), 7.86 (dt, 1H), 7.58-7.50 (m, 2H), 7.48-7.40 (m, 1H), 7.24 (d, 2H), 7.10 (t, 2H), 3.86-3.58 (m, 2H), 3.33 (dd, 1H), 2.96-2.83 (m, 2H), 2.53-2.38 (m, 2H), 2.30 (d, 1H), 2.14 (d, 2H), 1.90 (d, 1H), 1.14-1.04 (m, 12H) |

TABLE P1-continued

| Compound number | Structure | Data |
|---|---|---|
| P29 | 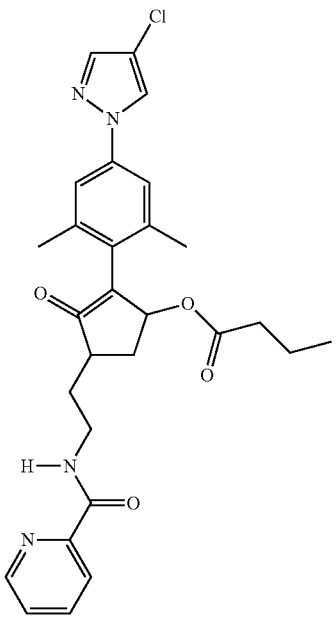 | 1H NMR (400 MHz, CDCl$_3$) δ 8.62-8.48 (m, 1H), 8.19 (d, 2H), 7.94-7.78 (m, 2H), 7.62 (s, 1H), 7.49-7.39 (m, 1H), 7.32 (s, 2H), 3.86-3.68 (m, 1H), 3.68-3.51 (m, 1H), 3.43-3.25 (m, 1H), 2.97-2.72 (m, 2H), 2.34 (t, 3H), 2.15 (d, 6H), 1.97-1.75 (m, 1H), 1.66-1.45 (m, 2H), 0.84 (t, 3H) |
| P30 | 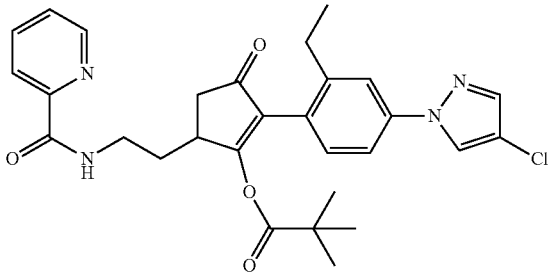 [SMILES: CCc1cc(-n2cc(Cl)cn2)ccc1C1=C(OC(=O)C(C)(C)C)C(CCNC(=O)c2ccccn2)CC1=O] | H NMR (400 MHz, CDCl$_3$) δ 8.55 (d, 1H), 8.30-8.20 (m, 1H), 8.19 (d, 1H), 7.91 (s, 1H), 7.85 (dd, 1H), 7.63 (s, 1H), 7.57 (s, 1H), 7.48-7.38 (m, 2H), 7.07 (d, 1H), 3.82-3.69 (m, 1H), 3.68-3.57 (m, 1H), 3.29 (dd, 1H), 2.92-2.80 (m, 2H), 2.58-2.48 (m, 2H), 2.33-2.22 (m, 1H), 1.96-1.82 (m, 1H), 1.16 (t, 3H), 1.14 (s, 9H) |

BIOLOGICAL EXAMPLES

Biological Example 1A

Test 1A—Glasshouse Assay for Herbicidal Activity

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown under controlled conditions in a glasshouse (at 24/16° C., day/night; 14 hours light; 65% humidity) and watered twice daily. 13 days after application of the test herbicide, for pre- and post-emergence, the test was evaluated visually for percentage phytotoxicity to the plant (where 100%=total damage to plant; 0%=no damage to plant).

Biological Example 1A

Post-emergence Herbicidal Activity

Test Plants:

*Lolium perenne* (LOLPE), *Alopecurus myosuroides* (ALOMY), *Echinochloa crus-galli* (ECHCG), and *Avena fatua* (AVEFA); these are all grassy monocotyledonous weeds.

Biological Example 1A

Table of Post-emergence Herbicidal Activity (% Phytotoxicity)

| Compound No | Application Rate (g/ha) | LOLPE | ALOMY | ECHCG | AVEFA |
|---|---|---|---|---|---|
| A1 | 250 | 100 | 80 | 100 | 90 |
| A2 | 250 | 100 | 90 | 80 | 80 |
| A3 | 250 | 100 | 90 | 100 | 100 |
| A4 | 250 | 80 | 70 | 100 | 60 |

| Compound No | Application Rate (g/ha) | LOLPE | ALOMY | ECHCG | AVEFA |
|---|---|---|---|---|---|
| A5 | 250 | 70 | 50 | 60 | 30 |
| A6 | 250 | 90 | 30 | 90 | 60 |
| A7 | 250 | 60 | 60 | 90 | 50 |
| A8 | 250 | 90 | 60 | 80 | 70 |
| A9 | 250 | 80 | 60 | 70 | 50 |
| A10 | 250 | 70 | 60 | 50 | 70 |
| A11 | 250 | 100 | 70 | 100 | 70 |
| A12 | 250 | 100 | 80 | 100 | 100 |
| A13 | 250 | 90 | 70 | 100 | 70 |
| A14 | 250 | 70 | 60 | 100 | 70 |
| A15 | 250 | 90 | 60 | 100 | 90 |
| A16 | 250 | 60 | 60 | 50 | 50 |
| A17 | 250 | 100 | 80 | 100 | 90 |
| A18 | 250 | 90 | 60 | 100 | 80 |
| A19 | 250 | 100 | 80 | 100 | 70 |
| A20 | 250 | 100 | 70 | 100 | 70 |
| A21 | 250 | 100 | 90 | 100 | 90 |
| A22 | 250 | 80 | 70 | 80 | 80 |
| A23 | 250 | 90 | 90 | 100 | 90 |
| A24 | 250 | 90 | 80 | 80 | 80 |
| A25 | 250 | 60 | 50 | 80 | 40 |
| A26 | 250 | 80 | 80 | 80 | 80 |
| A27 | 250 | 70 | 80 | 100 | 90 |
| A28 | 250 | 70 | 100 | 80 | 50 |
| A29 | 250 | 80 | 80 | 80 | 90 |
| A32 | 250 | 100 | 90 | 100 | 100 |
| A33 | 250 | 100 | 90 | 100 | 100 |
| A34 | 250 | 100 | 90 | 100 | 100 |
| A35 | 250 | 60 | 80 | 40 | 40 |
| A36 | 250 | 80 | 80 | 80 | 70 |
| A37 | 250 | 90 | 100 | 80 | 80 |
| A38 | 250 | 100 | 100 | 100 | 100 |
| A39 | 250 | 100 | 100 | 100 | 100 |
| A40 | 250 | 100 | 100 | 100 | 100 |
| A41 | 250 | 70 | 70 | 60 | 70 |
| A43 | 250 | 100 | 100 | 100 | 100 |
| A44 | 250 | 100 | 100 | 100 | 90 |
| A45 | 250 | 80 | 50 | 60 | 80 |
| A46 | 250 | 100 | 60 | 90 | 70 |
| A47 | 250 | 100 | 80 | 100 | 90 |
| A48 | 250 | 100 | 100 | 100 | 90 |
| A50 | 250 | 100 | 20 | 70 | 70 |
| A51 | 250 | 100 | 100 | 90 | 90 |
| A52 | 250 | 90 | 70 | 100 | 70 |
| A53 | 250 | 100 | 80 | 100 | 90 |
| A54 | 250 | 100 | 100 | 60 | 100 |
| A55 | 250 | 90 | 80 | 90 | 60 |
| A56 | 250 | 100 | 100 | 90 | 90 |
| A57 | 250 | 100 | 100 | 100 | 100 |
| A57A | 250 | 90 | 100 | 90 | 90 |
| A58 | 250 | 80 | 50 | 50 | 30 |
| A59 | 250 | 80 | 60 | 30 | 60 |
| A60 | 250 | 80 | 80 | 70 | 90 |
| A61 | 250 | 100 | 90 | 70 | 60 |
| A62 | 250 | 100 | 100 | 80 | 80 |
| A63 | 250 | 100 | 90 | 90 | 90 |
| A64 | 250 | 80 | 90 | 60 | 80 |
| A65 | 250 | 80 | 100 | 80 | 70 |
| A66 | 250 | 60 | 80 | 70 | 40 |
| A69 | 250 | 60 | 50 | 30 | 70 |
| A70 | 250 | 100 | 100 | 90 | 90 |
| A71 | 250 | 100 | 100 | 80 | 90 |
| A72 | 250 | 90 | 90 | 70 | 90 |
| A73 | 250 | 80 | 90 | 90 | 90 |
| A74 | 250 | 80 | 90 | 70 | 30 |
| A75 | 250 | 90 | 90 | 90 | 90 |
| A76 | 250 | 60 | 70 | 80 | 90 |
| A77 | 250 | 90 | 70 | 90 | 90 |
| A78 | 250 | 60 | 80 | 80 | 80 |
| A79 | 250 | 70 | 80 | 70 | 80 |
| A83 | 250 | 100 | 100 | 100 | 100 |
| A84 | 250 | 100 | 100 | 100 | 100 |
| A85 | 250 | 100 | 90 | 100 | 100 |
| A86 | 250 | 100 | 100 | 100 | 100 |
| A87 | 250 | 100 | 100 | 100 | 100 |
| A88 | 250 | 100 | 80 | 100 | 90 |
| A89 | 250 | 100 | 100 | 100 | 100 |
| A89A | 250 | 100 | 100 | 100 | 100 |
| A91 | 250 | 80 | 80 | 80 | 80 |
| A92 | 250 | 70 | 80 | 70 | 80 |
| A93 | 250 | 70 | 70 | 50 | 40 |
| A94 | 250 | 80 | 90 | 90 | 100 |
| A96 | 250 | 100 | 100 | 100 | 100 |
| A97 | 250 | 100 | 100 | 100 | 100 |
| A102 | 250 | 100 | 100 | 100 | 100 |
| A104 | 250 | 100 | 90 | 100 | 90 |
| A105 test 1 | 250 | 90 | 40 | 100 | 90 |
| A105 test 2 | 250 | 90 | 60 | 100 | 90 |
| A106 | 250 | 100 | 90 | 100 | 100 |
| A109 | 250 | 100 | 100 | 100 | 100 |
| A110 | 250 | 100 | 90 | 100 | 100 |
| A111 | 250 | 100 | 100 | 100 | 100 |
| A114 | 250 | 100 | 100 | 100 | 100 |
| A115 | 250 | 100 | 100 | 100 | 100 |
| A116 | 250 | 100 | 90 | 100 | 100 |
| A117 | 250 | 100 | 100 | 100 | 100 |
| A118 | 250 | 100 | 100 | 100 | 100 |
| A119 | 250 | 90 | 100 | 100 | 90 |
| A120 | 250 | 100 | 100 | 100 | 90 |
| A121 | 250 | 100 | 90 | 100 | 90 |
| A122 | 250 | 100 | 100 | 100 | 90 |
| A123 | 250 | 100 | 100 | 90 | 100 |
| A124 | 250 | 100 | 100 | 100 | 100 |
| A125 | 250 | 100 | 100 | 100 | 100 |
| A126 | 250 | 100 | 100 | 100 | 100 |
| A126A | 250 | 90 | 90 | 90 | 90 |
| A126B | 250 | 90 | 90 | 100 | 90 |
| A129 | 250 | 100 | 100 | 100 | 100 |
| A130 | 250 | 80 | 30 | 80 | 80 |
| A131 | 250 | 100 | 100 | 100 | 100 |
| A132 | 250 | 100 | 100 | 100 | 100 |
| A133 | 250 | 100 | 100 | 100 | 90 |
| A134 | 250 | 100 | 100 | 100 | 100 |
| A135 | 250 | 100 | 100 | 100 | 90 |
| A136 | 250 | 100 | 100 | 100 | 90 |
| A137 | 250 | 80 | 80 | 100 | 70 |
| A138 | 250 | 100 | 100 | 100 | 90 |
| A139 | 250 | 100 | 90 | 90 | 90 |
| A140 | 250 | 100 | 90 | 100 | 100 |
| A141 | 250 | 70 | 60 | 100 | 10 |
| A141A | 250 | 70 | 80 | 80 | 80 |
| A142 | 250 | 100 | 100 | 100 | 90 |
| A143 | 250 | 100 | 90 | 100 | 90 |
| A144 | 250 | 90 | 30 | 100 | 90 |
| A145 | 250 | 90 | 100 | 90 | 90 |
| A146 | 250 | 70 | 60 | 100 | 40 |
| A147 | 250 | 70 | 60 | 60 | 60 |
| A148 | 250 | 90 | 70 | 90 | 90 |
| A149 | 250 | 100 | 100 | 100 | 100 |
| A150 | 250 | 80 | 70 | 80 | 90 |
| A151 | 250 | 90 | 90 | 90 | 90 |
| A152 | 250 | 70 | 80 | 80 | 70 |
| A154 | 250 | 100 | 100 | 100 | 100 |
| A155 | 250 | 100 | 100 | 100 | 100 |
| A156 | 250 | 90 | 50 | 100 | 90 |
| A157 | 250 | 70 | 70 | 90 | 70 |
| A158 | 250 | 80 | 80 | 70 | 90 |
| A159 | 250 | 100 | 100 | 90 | 90 |
| A160 | 250 | 90 | 90 | 100 | 100 |
| A161 | 250 | 100 | 90 | 100 | 100 |
| A162 | 250 | 100 | 70 | 90 | 90 |
| A164 | 250 | 90 | 90 | 100 | 100 |
| A165 | 250 | 100 | 90 | 100 | 100 |
| A166 | 250 | 90 | 80 | 60 | 90 |
| A167 | 250 | 70 | 60 | 90 | 30 |
| A168 | 250 | 70 | 60 | 80 | 80 |
| A169 | 250 | | | | |
| A170 test 1 | 250 | 90 | 90 | 100 | 100 |

-continued

| Compound No | Application Rate (g/ha) | LOLPE | ALOMY | ECHCG | AVEFA |
|---|---|---|---|---|---|
| A170 test 2 | 250 | 80 | 90 | 100 | 90 |
| A171 | 250 | 10 | 0 | 60 | 10 |
| A172 | 250 | 100 | 90 | 100 | 90 |
| A173 test 1 | 250 | 100 | 100 | 100 | 100 |
| A173 test 2 | 250 | 100 | 100 | 100 | 100 |
| A174 test 1 | 250 | 100 | 90 | 90 | 100 |
| A174 test 2 | 250 | 90 | 90 | 90 | 90 |
| A177 | 250 | 90 | 100 | 100 | 90 |
| A178 | 250 | 100 | 70 | 80 | 90 |
| A179 | 250 | 70 | 70 | 80 | 100 |
| A180 | 250 | 80 | 70 | 90 | 80 |
| A181 | 250 | 90 | 80 | 80 | 100 |
| A182 | 250 | 80 | 80 | 90 | 90 |
| A183 | 250 | 90 | 60 | 90 | 60 |
| A184 | 250 | 60 | 10 | 90 | 20 |
| A185 | 250 | 100 | 90 | 100 | 100 |
| A186 | 250 | 100 | 100 | 100 | 90 |
| A187 | 250 | 100 | 90 | 100 | 90 |
| A188 | 250 | 100 | 100 | 100 | 100 |
| A189 | 250 | 100 | 100 | 100 | 100 |
| A190 | 250 | 90 | 80 | 90 | 90 |
| A191 | 250 | 90 | 100 | 100 | 100 |
| A192 | 250 | 100 | 80 | 100 | 90 |
| A193 | 250 | 100 | 90 | 90 | 90 |
| A194 | 250 | 90 | 80 | 100 | 90 |
| A195 | 250 | 60 | 30 | 80 | 30 |
| A196 | 250 | 90 | 80 | 100 | 90 |
| A197 | 250 | 60 | 90 | 100 | 70 |
| A203 | 250 | 80 | 80 | 100 | 100 |
| A204 | 250 | 100 | 90 | 100 | 90 |
| A212 | 250 | 70 | 30 | 70 | 50 |
| A213 | 250 | 60 | 10 | 50 | 10 |
| P2 | 250 | 90 | 80 | 100 | 100 |
| P3 | 250 | 100 | 90 | 100 | 100 |
| P4 | 250 | 100 | 100 | 100 | 100 |
| P6 | 250 | 100 | 100 | 100 | 100 |
| P7 | 250 | 100 | 100 | 100 | 100 |
| P8 | 250 | 100 | 100 | 100 | 100 |
| P9 | 250 | 100 | 100 | 100 | 100 |
| P10 | 250 | 100 | 100 | 100 | 100 |
| P11 | 250 | 100 | 100 | 100 | 100 |
| P12 | 250 | 100 | 100 | 100 | 100 |
| P13 | 250 | 100 | 100 | 100 | 100 |
| P14 | 250 | 100 | 100 | 100 | 100 |
| P15 | 250 | 100 | 100 | 100 | 100 |
| P16 | 250 | 100 | 100 | 100 | 90 |
| P17 | 250 | 100 | 100 | 100 | 100 |
| P18 | 250 | 100 | 100 | 100 | 90 |
| P19 | 250 | 100 | 100 | 100 | 100 |
| P20 | 250 | 100 | 100 | 100 | 100 |
| P21 | 250 | 70 | 80 | 100 | 80 |
| P22 | 250 | 100 | 90 | 100 | 100 |

Note:
a hyphen (-) in the table above indicates that no measurement was made.

Biological Example 1A

Pre-emergence Herbicidal Activity

Test plants: *Lolium perenne* (LOLPE), *Alopecurus myosuroides* (ALOMY), *Echinochloa crus-galli* (ECHCG), and *Avena fatua* (AVEFA); these are all grassy monocotyledonous weeds.

Biological Example 1A

Table of Pre-emergence Herbicidal Activity (% Phytotoxicity)

Positive pre-emergence herbicidal results were obtained for many exemplified compounds of the present invention applied pre-emergence at 250 g/ha; but, for brevity, only some of these results are presented below.

| Compound No | Application Rate (g/ha) | LOLPE | ALOMY | ECHCG | AVEFA |
|---|---|---|---|---|---|
| A1 | 1000 | 100 | 90 | 100 | 70 |
| A2 | 250 | 100 | 90 | 70 | 70 |
| A3 | 250 | 100 | 90 | 100 | 90 |
| A13 | 250 | 90 | 80 | 100 | 80 |
| A19 | 250 | 100 | 90 | 100 | 50 |
| A23 | 250 | 100 | 90 | 100 | 80 |
| A32 | 250 | 100 | 100 | 100 | 80 |
| A33 | 250 | 100 | 90 | 100 | 80 |
| A34 | 250 | 100 | 90 | 100 | 100 |
| A87 | 250 | 100 | 100 | 100 | 90 |
| A89 | 250 | 100 | 100 | 100 | 100 |
| A120 | 250 | 100 | 90 | 100 | 70 |
| A145 | 250 | 100 | 90 | 90 | 40 |
| A159 | 250 | 100 | 90 | 100 | 80 |
| P8 | 250 | 100 | 90 | 100 | 90 |
| P9 | 250 | 100 | 100 | 100 | 90 |

Biological Example 1B

Test 1B—Glasshouse Assay for Post-emergence Herbicidal Activity Against Grassy Monocotyledonous Weeds and Cereal Crops (Wheat and Barley)

Biological Example 1B tests the herbicidal activity of "technical" compounds (i.e. compounds not previously formulated before the test), as the herbicides under test.

An "instant formulation", known as the "IF50", containing 50 g/liter (i.e. 5% w/v) of the "technical" (i.e. unformulated) active ingredient (i.e. the herbicide under test), is prepared by dissolving the active ingredient in a mixture of organic solvents and emulsifier, details of which are provided in the Table below.

TABLE

Composition of the mixture of organic solvents and emulsifier used as a base for the instant formulation (IF50).

| Component | Supplier | Chemical description | CAS Registry number | Amount/ % w/w |
|---|---|---|---|---|
| Emulsogen EL360 ™ | Clariant | castor oil ethoxylate (as emulsifier) | 61791-12-6 | 11.12 |
| N-methyl-pyrrolidone | widely available | 1-methyl-2-pyrrolidone | 872-50-4 | 44.44 |
| Dowanol DPM ™ glycol ether | Dow | dipropylene glycol monomethyl ether | 34590-94-8 | 44.44 |

This IF50 is mixed with a small, variable amount of acetone to aid dissolution, before addition of a 0.5% v/v aqueous solution of the adjuvant Adigor™ (an adjuvant containing rapeseed oil methyl ester, ethoxylated alcohols, and a mixture of heavy aromatic hydrocarbons, e.g. available from Syngenta), as the aqueous diluent, to form an aqueous spray solution which contains a predetermined concentration of the active ingredient (which varies depending on the application rate of the active ingredient to the plants) and 0.5% v/v of the adjuvant Adigor™. This aqueous spray solution is suitable for spraying onto plants.

Seeds of a variety of test species are sown in standard soil in pots. After cultivation for 14 days under controlled conditions in a glasshouse (at 22/16° C., day/night; 16 hours light; 65% humidity), the plants are sprayed post-emergence with the above-mentioned aqueous spray solution containing inter alia the "technical" active ingredient (i.e. the herbicide under test) and the adjuvant Adigor™.

The test plants are then grown on under controlled conditions in the glasshouse (at 22/16° C., day/night; 16 hours light; 65% humidity) and are watered twice daily. 14 days after application of the test herbicide, the test is evaluated visually for percentage phytotoxicity to the plant (where 100%=total damage to plant; 0%=no damage to plant).

More specifically, post-emergence herbicidal activity (phytotoxicity) data, on certain tested grassy monocotyledonous weeds (and/or plants of the type Gramineae) and cereal crops in the glasshouse, are measured 14 days after application of the herbicide (14 DAA), typically for inter alia one or more of the following application rates:

(a) a post-emergence application rate of 60 g/ha of the test herbicide with or without 50 g/ha of cloquintocet-mexyl safener, and
(b) a post-emergence application rate of 90 g/ha of the test herbicide with 50 g/ha of cloquintocet-mexyl safener, and
(c) a post-emergence application rate of 120 g/ha of the test herbicide with 50 g/ha of cloquintocet-mexyl safener.

The cloquintocet-mexyl, when used, is present in the formulation containing the herbicide under test dissolved in acetone plus IF50.

The range of herbicide application rates tested sometimes includes application rates other than those shown above, and the rates can vary depending on the herbicide under test.

Herbicidal activity (phytotoxicity) is evaluated visually, and an assessed percentage phytotoxicity score is given for each herbicidal application on each plant species (with 100%=total damage to plant; 0%=no damage to plant; the assessment is recorded in increments of 1%). Two replicates are made for each experiment, and the mean herbicidal activity (phytotoxicity) data is reported.

A selection of the results obtained in Biological Example 1B, using substantially the above-described test method, for Compounds A34, A98, A99, A87, A100, A101, A89, A120, A120A, A120B, A23, A127, A128, A89, A112 and A113 are shown below.

For compounds A34, A98, A99, A87, A100, A101, A89, A120, A120A, A120B, A23, A127, A128, A89, A112 and A113 the tested weeds were as follows: *Avena fatua* (AVEFA), *Lolium multiflorum* (LOLMU), *Setaria viridis* (SETVI), *Poa annua* (POAAN), *Alopecurus myosuroides* (ALOMY). All five of these are grassy monocotyledonous weeds. Except for SETVI, these are all "cool-season" grassy monocotyledonous weeds.

Biological Example 1B

Post-emergence Herbicidal Activity Against Grassy Weeds—Results (Percentage Phytotoxicity)

Abbreviations: T1=herbicidal test result no. 1, for each of compounds A98 and A99. T2=herbicidal test result no. 2, for each of compounds A98 and A99.

| Compound number (herbicide) | Herbicide application Rate (g/ha) | Cloquintocet-mexyl application rate (g/ha) | AVEFA | LOLMU | SETVI | POAAN | ALOMY |
|---|---|---|---|---|---|---|---|
| A34 | 60 | 0 | 100 | 83 | 80 | 78 | 65 |
| A34 | 60 | 50 | 100 | 90 | 85 | 75 | 73 |
| A98 | 60 | 0 | 100 (T1) | 95 (T1) | 94 (T1) | 78 (T1) | 80 (T1) |
| A98 | 60 | 50 | 100 (T1); 100 (T2) | 95 (T1); 100 (T2) | 97 (T1); 100 (T2) | 75 (T1); 75 (T2) | 80 (T1); 78 (T2) |
| A98 | 90 | 50 | 100 (T2) | 100 (T2) | 100 (T2) | 78 (T2) | 88 (T2) |
| A98 | 120 | 50 | 100 (T2) | 100 (T2) | 100 (T2) | 83 (T2) | 97 (T2) |
| A99 | 60 | 0 | 50 (T1) | 35 (T1) | 10 (T1) | 70 (T1) | 50 (T1) |
| A99 | 60 | 50 | 40 (T1); 48 (T2) | 35 (T1); 55 (T2) | 8 (T1); 33 (T2) | 73 (T1); 70 (T2) | 35 (T1); 38 (T2) |
| A99 | 90 | 50 | 60 (T2) | 65 (T2) | 68 (T2) | 73 (T2) | 58 (T2) |
| A99 | 120 | 50 | 78 (T2) | 78 (T2) | 75 (T2) | 75 (T2) | 73 (T2) |
| A87 | 60 | 0 | 100 | 100 | 93 | 83 | 97 |
| A87 | 60 | 50 | 100 | 100 | 95 | 83 | 95 |
| A87 | 30 | 50 | 100 | 100 | 73 | 75 | 70 |
| A100 | 60 | 0 | 100 | 100 | 99 | 80 | 83 |
| A100 | 60 | 50 | 100 | 100 | 99 | 78 | 78 |
| A100 | 45 | 50 | 100 | 100 | 99 | 78 | 75 |
| A100 | 30 | 50 | 100 | 100 | 95 | 73 | 55 |
| A101 | 60 | 0 | 90 | 88 | 53 | 48 | 55 |
| A101 | 60 | 50 | 88 | 83 | 53 | 38 | 55 |
| A101 | 45 | 50 | 88 | 83 | 35 | 15 | 43 |
| A101 | 30 | 50 | 73 | 68 | 15 | 5 | 25 |
| A89 | 60 | 0 | 90 | 100 | 100 | 25 | 98 |
| A89 | 60 | 50 | 90 | 100 | 100 | 15 | 98 |
| A89 | 45 | 50 | 85 | 99 | 100 | 3 | 97 |
| A89 | 30 | 50 | 83 | 90 | 100 | 0 | 88 |

| Compound number (herbicide) | Herbicide application Rate (g/ha) | Cloquintocet-mexyl application rate (g/ha) | AVEFA | LOLMU | SETVI | POAAN | ALOMY |
|---|---|---|---|---|---|---|---|
| A120 | 60 | 0 | 85 | 100 | 100 | 10 | 85 |
| A120 | 60 | 50 | 78 | 99 | 100 | 3 | 80 |
| A120 | 45 | 50 | 78 | 99 | 100 | 3 | 80 |
| A120 | 30 | 50 | 75 | 98 | 100 | 3 | 75 |
| A120A | 60 | 0 | 97 | 100 | 100 | 30 | 95 |
| A120A | 60 | 50 | 97 | 100 | 100 | 10 | 90 |
| A120A | 45 | 50 | 95 | 100 | 100 | 5 | 88 |
| A120A | 30 | 50 | 90 | 97 | 100 | 3 | 80 |
| A120B | 60 | 0 | 38 | 83 | 68 | 4 | 73 |
| A120B | 60 | 50 | 48 | 73 | 68 | 4 | 70 |
| A120B | 45 | 50 | 10 | 73 | 65 | 0 | 58 |
| A120B | 30 | 50 | 3 | 58 | 40 | 0 | 43 |
| A23 | 60 | 0 | 80 | 90 | 99 | 0 | 75 |
| A23 | 60 | 50 | 70 | 83 | 99 | 0 | 78 |
| A23 | 30 | 50 | 13 | 48 | 95 | 0 | 28 |
| A127 | 60 | 0 | 85 | 97 | 100 | 0 | 78 |
| A127 | 60 | 50 | 90 | 83 | 100 | 0 | 68 |
| A127 | 45 | 50 | 80 | 83 | 99 | 0 | 63 |
| A127 | 30 | 50 | 55 | 65 | 97 | 0 | 48 |
| A128 | 60 | 0 | 18 | 85 | 55 | 5 | 48 |
| A128 | 60 | 50 | 10 | 78 | 63 | 0 | 35 |
| A128 | 45 | 50 | 3 | 63 | 43 | 0 | 25 |
| A128 | 30 | 50 | 0 | 43 | 23 | 0 | 3 |
| A89 | 60 | 0 | 97 | 100 | 99 | 15 | 99 |
| A89 | 60 | 50 | 93 | 95 | 100 | 3 | 98 |
| A89 | 30 | 50 | 85 | 93 | 95 | 0 | 80 |
| A112 | 60 | 0 | 98 | 100 | 100 | 40 | 99 |
| A112 | 60 | 50 | 97 | 100 | 100 | 13 | 98 |
| A112 | 45 | 50 | 94 | 100 | 100 | 0 | 97 |
| A112 | 30 | 50 | 93 | 98 | 100 | 0 | 97 |
| A113 | 60 | 0 | 5 | 45 | 53 | 8 | 20 |
| A113 | 60 | 50 | 3 | 23 | 55 | 0 | 25 |
| A113 | 45 | 50 | 3 | 20 | 40 | 0 | 18 |
| A113 | 30 | 50 | 1 | 3 | 5 | 0 | 0 |

Biological Example 1B

Post-emergence Herbicidal Activity Against Cereal Crops (Wheat and Barley)—Results (Percentage Phytotoxicity)

Abbreviations: T1=herbicidal test result no. 1, for each of compounds A98 and A99. T2=herbicidal test result no. 2, for each of compounds A98 and A99.

| Compound number (herbicide) | Herbicide application Rate (g/ha) | Cloquintocet-mexyl application rate (g/ha) | Winter Wheat "Hereward" | Spring Wheat "Teal" | Spring Barley "Harrington" | Winter Barley "Suzuka" |
|---|---|---|---|---|---|---|
| A34 | 60 | 0 | 20 | 43 | 83 | 83 |
| A34 | 60 | 50 | 5 | 10 | 33 | 38 |
| A98 | 60 | 0 | 35 (T1) | 30 (T1) | 33 (T1) | 75 (T1) |
| A98 | 60 | 50 | 13 (T1); 9 (T2) | 10 (T1); 5 (T2) | 10 (T1); 4 (T2) | 13 (T1); 8 (T2) |
| A98 | 90 | 50 | 13 (T2) | 13 (T2) | 5 (T2) | 9 (T2) |
| A98 | 120 | 50 | 23 (T2) | 20 (T2) | 15 (T2) | 40 (T2) |
| A99 | 60 | 0 | 0 (T1) | 2 (T1) | 15 (T1) | 60 (T1) |
| A99 | 60 | 50 | 1 (T1); 0 (T2) | 1 (T1); 5 (T2) | 3 (T1); 3 (T2) | 15 (T1); 14 (T2) |
| A99 | 90 | 50 | 0 (T2) | 5 (T2) | 5 (T2) | 35 (T2) |
| A99 | 120 | 50 | 8 (T2) | 8 (T2) | 8 (T2) | 38 (T2) |
| A87 | 60 | 0 | 43 | 48 | 73 | 83 |
| A87 | 60 | 50 | 33 | 38 | 60 | 60 |
| A87 | 30 | 50 | 23 | 18 | 0 | 3 |
| A100 | 60 | 0 | 60 | 65 | 83 | 93 |
| A100 | 60 | 50 | 40 | 45 | 28 | 53 |
| A100 | 45 | 50 | 30 | 30 | 18 | 30 |
| A100 | 30 | 50 | 15 | 20 | 13 | 10 |
| A101 | 60 | 0 | 43 | 48 | 48 | 75 |
| A101 | 60 | 50 | 38 | 18 | 23 | 40 |

-continued

| Compound number (herbicide) | Herbicide application Rate (g/ha) | Cloquintocet-mexyl application rate (g/ha) | Winter Wheat "Hereward" | Spring Wheat "Teal" | Spring Barley "Harrington" | Winter Barley "Suzuka" |
|---|---|---|---|---|---|---|
| A101 | 45 | 50 | 23 | 13 | 18 | 23 |
| A101 | 30 | 50 | 18 | 10 | 18 | 23 |
| A89 | 60 | 0 | 60 | 75 | 95 | 95 |
| A89 | 60 | 50 | 28 | 50 | 85 | 73 |
| A89 | 45 | 50 | 25 | 20 | 55 | 20 |
| A89 | 30 | 50 | 15 | 13 | 13 | 8 |

| Compound number (herbicide) | Herbicide application Rate (g/ha) | Cloquintocet-mexyl application rate (g/ha) | Winter Wheat "Hereward" | Spring Wheat "Freya" | Spring Barley "Harrington" | Winter Barley "Suzuka" |
|---|---|---|---|---|---|---|
| A120 | 60 | 0 | 68 | 55 | 78 | 88 |
| A120 | 60 | 50 | 50 | 30 | 38 | 40 |
| A120 | 45 | 50 | 50 | 30 | 38 | 40 |
| A120 | 30 | 50 | 38 | 18 | 25 | 15 |
| A120A | 60 | 0 | 73 | NT | 85 | 93 |
| A120A | 60 | 50 | 65 | NT | 73 | 83 |
| A120A | 45 | 50 | 60 | NT | 60 | 75 |
| A120A | 30 | 50 | 53 | NT | 30 | 23 |
| A120B | 60 | 0 | 58 | NT | 53 | 75 |
| A120B | 60 | 50 | 13 | NT | 23 | 13 |
| A120B | 45 | 50 | 10 | NT | 10 | 9 |
| A120B | 30 | 50 | 7 | NT | 3 | 3 |
| A23 | 60 | 0 | 68 | 63 | 75 | 70 |
| A23 | 60 | 50 | 0 | 7 | 5 | 15 |
| A23 | 30 | 50 | 0 | 5 | 1 | 0 |
| A127 | 60 | 0 | 65 | 70 | 83 | 85 |
| A127 | 60 | 50 | 5 | 5 | 8 | 5 |
| A127 | 45 | 50 | 0 | 3 | 0 | 0 |
| A127 | 30 | 50 | 0 | 0 | 0 | 0 |
| A128 | 60 | 0 | 8 | 7 | 48 | 18 |
| A128 | 60 | 50 | 0 | 3 | 0 | 0 |
| A128 | 45 | 50 | 0 | 0 | 0 | 0 |
| A128 | 30 | 50 | 0 | 3 | 0 | 0 |
| A89 | 60 | 0 | 75 | 70 | 88 | 90 |
| A89 | 60 | 50 | 25 | 38 | 43 | 25 |
| A89 | 30 | 50 | 10 | 13 | 13 | 8 |
| A112 | 60 | 0 | 85 | 75 | 93 | 88 |
| A112 | 60 | 50 | 50 | 50 | 73 | 53 |
| A112 | 45 | 50 | 40 | 33 | 45 | 30 |
| A112 | 30 | 50 | 33 | 25 | 30 | 18 |
| A113 | 60 | 0 | 3 | 7 | 33 | 28 |
| A113 | 60 | 50 | 0 | 0 | 8 | 0 |
| A113 | 45 | 50 | 0 | 0 | 0 | 0 |
| A113 | 30 | 50 | 0 | 3 | 0 | 0 |

NT = not tested

The invention claimed is:
1. A compound of formula (I):

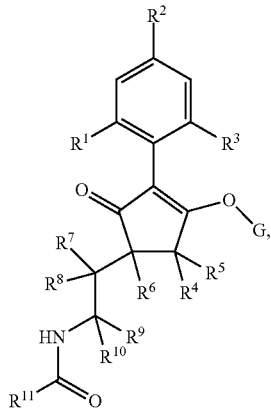

wherein:
R$^1$ is methyl, ethyl, n-propyl, cyclopropyl, trifluoromethyl, vinyl, ethynyl, fluorine, chlorine, bromine, methoxy, ethoxy or fluoromethoxy;
R$^2$ is hydrogen, methyl, ethyl, n-propyl, isopropyl, cyclopropyl, fluoromethyl, fluoroethyl, vinyl, prop-1-enyl, ethynyl, prop-1-ynyl, 2-chloroethynyl, 2-fluoroethynyl, 2-(trifluoromethyl)ethynyl, but-1-ynyl, 2-(cyclopropyl)ethynyl, halogen, methoxy, prop-2-ynyloxy, or (C$_1$-C$_2$ fluoroalkyl)-methoxy-;
or R$^2$ is phenyl optionally substituted by 1, 2 or 3 of, independently, halogen, C$_1$-C$_2$alkyl, C$_1$-C$_2$fluoroalkyl, C$_1$-C$_2$alkoxy, C$_1$-C$_2$fluoroalkoxy, cyano or nitro;
or R$^2$ is monocyclic heteroaryl optionally substituted by 1, 2 or 3 of independently, halogen, C$_1$-C$_2$alkyl, C$_1$-C$_2$fluoroalkyl, C$_1$-C$_2$alkoxy, C$_1$-C$_2$fluoroalkoxy, cyano or nitro;
or R$^2$ is

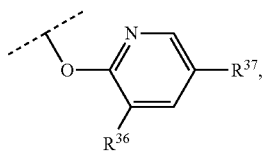

in which R$^{36}$ is fluorine or chlorine, and R$^{37}$ is fluorine, chlorine or C$_1$fluoroalkyl; and
R$^3$ is hydrogen, methyl, ethyl, n-propyl, cyclopropyl, trifluoromethyl, vinyl, ethynyl, fluorine, chlorine, bromine, methoxy, ethoxy, n-propoxy, isopropoxy, C$_1$-C$_2$fluoroalkoxy, C$_1$-C$_2$alkoxy-C$_1$-C$_3$alkoxy-, or C$_1$fluoroalkoxy-C$_1$-C$_3$alkoxy-;
R$^4$, R$^5$ and R$^6$, independently of each other, are hydrogen, C$_1$-C$_5$alkyl, C$_2$-C$_3$alkenyl, C$_2$-C$_3$alkynyl, C$_1$-C$_2$fluoroalkyl or C$_1$-C$_2$alkoxyC$_1$-C$_2$alkyl;
provided that: either (i) at least two of R$^4$, R$^5$ and R$^6$ are hydrogen, or (ii) two of R$^4$, R$^5$ and R$^6$ are methyl and the remaining one of R$^4$, R$^5$ and R$^6$ is hydrogen; and
R$^7$ and R$^8$, independently of each other, are hydrogen, fluorine or C$_1$-C$_3$alkyl; and
R$^9$ and R$^{10}$, independently of each other, are hydrogen, fluorine or C$_1$-C$_3$alkyl;
provided that no more than two of R$^7$, R$^8$, R$^9$ and R$^{10}$ are fluorine;
and provided that at least two of R$^7$, R$^8$, R$^9$ and R$^{10}$ are hydrogen;
and wherein
R$^{11}$ is C$_1$-C$_6$alkyl, C$_3$-C$_7$cycloalkyl, tetrahydro-2H-pyranyl, tetrahydrofuranyl, oxetanyl, tetrahydrothiopheneyl or thietanyl;
or R$^{11}$ is a monocyclic 6-membered-ring heteroaryl, which is carbon-linked, and which is pyridinyl, pyrazinyl, pyrimidinyl, pyridazinyl, 1,3,5-triazinyl or 1,2,4-triazinyl, wherein the monocyclic 6-membered-ring heteroarylisoptionally substituted by 1, 2 or 3 substituents;
wherein the 1, 2 or 3 optional substituents on the monocyclic 6-membered-ring heteroaryl independently are fluorine, chlorine, bromine, iodine, C$_1$-C$_3$alkyl, C$_1$-C$_3$fluoro alkyl, C$_1$-C$_2$alkoxy C$_1$-C$_2$fluoroalkoxy, cyclopropyl, C$_{n1}$alkoxyC$_{n2}$alkyl (wherein n1 is 1 or 2, n2 is 1 or 2, and n1+n2 is 2 or 3), vinyl, C$_2$fluoroalkenyl, C$_2$-C$_3$alkynyl, fluoroethynyl, cyano, amino, or phenyl in which the phenyl is optionally substituted at its meta and/or para position(s) by 1 or 2 fluorines; and
wherein, when R$^{11}$ is pyrazinyl, pyrimidinyl, pyridazinyl, 1,3,5-triazinyl or 1,2,4-triazinyl, then each of these is optionally substituted by 1 or 2 of the substituents on the monocyclic 6-membered-ring heteroaryl, as defined herein;
wherein, when R$^{11}$ is pyridin-3-yl or pyridin-4-yl, then each of these is substituted by 1 or 2 of the substituents on the monocyclic 6-membered-ring heteroaryl, as defined herein,
wherein, when R$^{11}$ is pyridin-2-yl substituted by 3 substituents, then one or more of the optional substituents on the pyridin-2-yl is or are fluorine;
wherein, when R$^{11}$ is monocyclic 6-membered-ring heteroaryl substituted by C$_2$alkyl, C$_2$fluoroalkyl, C$_2$alkoxy or C$_2$fluoroalkoxy, then: the monocyclic 6-membered-ring heteroaryl is substituted by 1 or 2 substituents independently being C$_2$alkyl, C$_2$fluoroalkyl, C$_2$alkoxy or C$_2$fluoroalkoxy, and the monocyclic 6-membered-ring heteroaryl is optionally further substituted by 1 or 2 substituents independently being fluorine, chlorine, bromine, C$_1$alkyl, C$_1$fluoroalkyl, C$_1$alkoxy, C$_1$fluoroalkoxy or cyano; provided that the monocyclic 6-membered-ring heteroaryl is substituted by no more than 2 substituents or in the case of a pyridin-2-yl is substituted by no more than 3 substituents;
wherein, when R$^{11}$ is monocyclic 6-membered-ring heteroaryl substituted by iodine, C$_3$alkyl, C$_3$fluoroalkyl, cyclopropyl, C$_{n1}$alkoxyC$_{n2}$alkyl, vinyl, C$_2$fluoroalkenyl, C$_2$-C$_3$alkynyl or fluoroethynyl, then: the monocyclic 6-membered-ring heteroaryl is pyridin-2-yl substituted by only one iodine, C$_3$alkyl, C$_3$fluoroalkyl, cyclopropyl, C$_{n1}$alkoxyC$_{n2}$alkyl, vinyl, C$_2$fluoroalkenyl, C$_2$-C$_3$alkynyl or fluoroethynyl, and in which the pyridin-2-yl ring is optionally further substituted by 1 or 2 fluorines;
wherein, when R$^{11}$ is monocyclic 6-membered-ring heteroaryl substituted by amino, then: either the monocyclic 6-membered-ring heteroaryl is 6-amino-pyridin-2-yl optionally further substituted by 1 or 2 fluorines; or the monocyclic 6-membered-ring heteroaryl is 3-amino-pyridin-2-yl or 3-amino-pyrazin-2-yl each of which is optionally further substituted at the 5-position of the pyridin-2-yl or pyrazin-2-yl ring by hydrogen, fluorine, methyl or $C_1$fluoroalkyl; and wherein, when $R^{11}$ is monocyclic 6-membered-ring heteroaryl substituted by optionally substituted phenyl, then the monocyclic 6-membered-ring heteroaryl is 6-phenyl-pyridin-2-yl in which the phenyl is optionally substituted at its meta and/or para position(s) by 1 or 2 fluorines, and in which the pyridin-2-yl ring is optionally further substituted by 1 or 2 fluorines;

or $R^{11}$ is a monocyclic 5-membered-ring heteroaryl, which is carbon-linked, and which is pyrrolyl, pyrazolyl, imidazol-2-yl, triazolyl, tetrazolyl, furyl, thiophenyl, oxazolyl, isoxazolyl, thiazolyl, isothiazolyl, oxadiazolyl, or thiadiazolyl, wherein the monocyclic 5-membered-ring heteroaryl is optionally substituted by 1, 2 or 3 substituents;

wherein the 1, 2 or 3 optional substituents on the monocyclic 5-membered-ring heteroaryl are:

1, 2 or 3 optional ring-carbon substituents independently being fluorine, chlorine, bromine, $C_1$-$C_3$alkyl, $C_1$-$C_3$fluoroalkyl, $C_1$-$C_2$alkoxy, $C_1$-$C_2$fluoroalkoxy, cyclopropyl, $C_{n3}$alkoxy$C_{n4}$alkyl (wherein n3 is 1 or 2, n4 is 1 or 2, and n3+n4 is 2 or 3), vinyl, $C_2$fluoroalkenyl, $C_2$-$C_3$alkynyl, fluoroethynyl or cyano; and/or 1 substituent being $C_1$-$C_3$alkyl, $C_1$-$C_3$fluoroalkyl or cyclopropyl, substituted at a ring nitrogen not partaking in a double bond, when the monocyclic 5-membered-ring heteroaryl has a ring nitrogen not partaking in a double bond;

provided that the monocyclic 5-membered-ring heteroaryl has no more than 3 substituents, or has no more than the maximum number of substituents possible for the monocyclic 5-membered-ring heteroaryl in uncharged form if this maximum is less than 3 substituents; and wherein, when $R^{11}$ is a monocyclic 5-membered-ring heteroaryl having a ring nitrogen not partaking in a double bond, then the ring nitrogen not partaking in a double bond is substituted by $C_1$-$C_3$alkyl, $C_1$-$C_3$fluoroalkyl or cyclopropyl; and wherein, when $R^{11}$ is a monocyclic 5-membered-ring heteroaryl, then: the monocyclic 5-membered-ring heteroaryl has no more than one $C_3$fluoroalkyl, vinyl, $C_2$fluoroalkenyl, $C_2$-$C_3$alkynyl or fluoroethynyl substituent; the monocyclic 5-membered-ring heteroaryl has no more than 2 substituents independently being bromine, $C_2$-$C_3$alkyl, $C_2$-$C_3$fluoroalkyl, $C_1$-$C_2$alkoxy, $C_1$-$C_2$fluoroalkoxy, cyclopropyl, $C_{n3}$alkoxy$C_{n4}$alkyl, vinyl, $C_2$fluoroalkenyl, $C_2$-$C_3$alkynyl, fluoroethynyl or cyano; and the monocyclic 5-membered-ring heteroaryl has no more than 2 substituents independently being chlorine or bromine;

or $R^{11}$ is one of the following sub-formulae B, E, F, GG, H, J, Q, R, S, T or U:

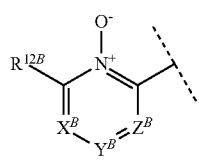
(B)

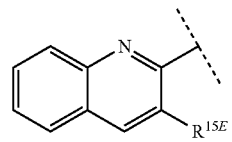
(E)

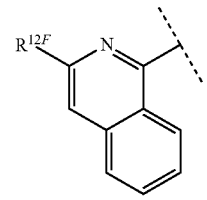
(F)

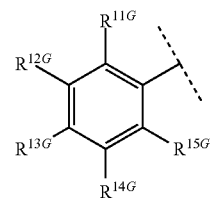
(GG)

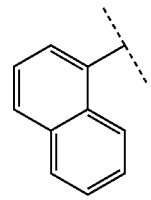
(H)

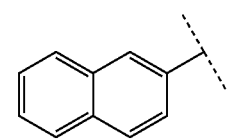
(J)

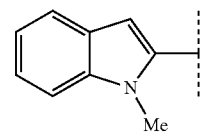
(Q)

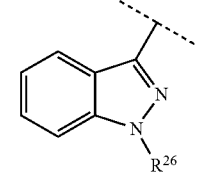
(R)

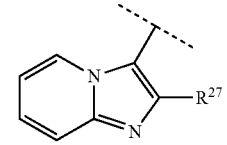
(S)

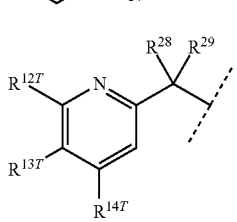
(T)

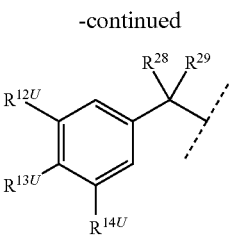

(U)

wherein:

$X^B$ is nitrogen or $CR^{13B}$;
$Y^B$ is nitrogen or $CR^{14B}$;
$Z^B$ is nitrogen or $CR^{15B}$;
provided that no more than one of $X^B$, $Y^B$ and $Z^B$ is nitrogen; and
$R^{12B}$ is hydrogen, fluorine, chlorine or bromine;
$R^{13B}$ is hydrogen, fluorine, chlorine, bromine, methyl, $C_1$fluoroalkyl, cyano, methoxy or $C_1$fluoroalkoxy;
$R^{14B}$ is hydrogen, fluorine or chlorine;
$R^{15B}$ is hydrogen, fluorine, chlorine or bromine;
provided that at least two of $R^{12B}$, $R^{13B}$, $R^{14B}$ and $R^{15B}$ are hydrogen;
and provided that, when $R^{13B}$ is bromine, then $X^A$ is $CR^{13B}$, and $R^{12B}$, $R^{14B}$ and $R^{15B}$ are independently hydrogen or fluorine, provided that at least two of $R^{12B}$, $R^{14B}$ and $R^{15B}$ are hydrogen; and
$R^{15E}$ is hydrogen, fluorine or chlorine;
$R^{12F}$ is hydrogen, fluorine or chlorine;
$R^{11GG}$ is hydrogen, fluorine, methyl or $C_1$fluoroalkyl;
$R^{12GG}$ is hydrogen, fluorine or chlorine;
$R^{13GG}$ is hydrogen, fluorine, chlorine, bromine, $C_1$fluoroalkyl, methoxy or $C_1$fluoroalkoxy;
$R^{14GG}$ is hydrogen or fluorine;
$R^{15GG}$ is hydrogen, fluorine, chlorine, methoxy or $C_1$fluoroalkoxy;
provided that, when $R^{13GG}$ is bromine, then $R^{11GG}$, $R^{12GG}$, $R^{14GG}$ and $R^{15GG}$ are independently hydrogen or fluorine;
provided that, when $R^{11GG}$ is methyl or $C_1$fluoroalkyl, then $R^{12GG}$, $R^{13GG}$, $R^{14GG}$ and $R^{15GG}$ are independently hydrogen or fluorine; and
provided that at least two of $R^{12GG}$, $R^{13GG}$, $R^{14GG}$ and $R^{15GG}$ are hydrogen; and
$R^{26}$ is hydrogen or methyl;
$R^{27}$ is hydrogen or methyl;
$R^{28}$ and $R^{29}$ independently are hydrogen or fluorine;
$R^{12T}$, $R^{13T}$ and $R^{14T}$ are independently hydrogen or fluorine, provided that at least two of $R^{12T}$, $R^{13T}$ and $R^{14T}$ are hydrogen; and
$R^{12U}$, $R^{13U}$ and $R^{14U}$ are independently hydrogen or fluorine, provided that at least two of $R^{12U}$, $R^{13U}$ and $R^{14U}$ are hydrogen;
and wherein:
G is hydrogen; an agriculturally acceptable metal, or an agriculturally acceptable sulfonium or ammonium group; or
G is $-C(X^a)-R^a$, $-C(X^b)-X^c-R^b$, $-C(X^d)-N(R^c)-R^d$, $-SO_2-R^e$, $-P(X^e)(R^f)-R^g$, $-CH_2-X^f-R^h$, or $-CH(Me)-X^f-R^h$; or phenyl-$CH_2-$ or phenyl-$CH(C_1-C_2$alkyl)- (in each of which the phenyl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro), or heteroaryl-$CH_2-$ or heteroaryl-$CH(C_1-C_2$alkyl)- (in each of which the heteroaryl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro), or phenyl-$C(O)-CH_2-$ (wherein the phenyl is optionally substituted by 1, 2 or 3 of, independently, $C_1-C_2$alkyl, $C_1$fluoroalkyl, $C_1-C_2$alkoxy, $C_1$fluoroalkoxy, fluorine, chlorine, bromine, cyano or nitro); or $C_1-C_6$alkoxy-$C(O)-CH_2-$, $C_1-C_6$alkyl-$C(O)-CH_2-$, $C_1-C_6$alkoxy-$C(O)-CH=CH-$, $C_2-C_7$alken-1-yl-$CH_2-$, $C_2-C_7$alken-1-yl-$CH(C_1-C_2$alkyl)-, $C_2-C_4$fluoroalken-1-yl-$CH_2-$, $C_2-C_7$alkyn-1-yl-$CH_2-$, or $C_2-C_7$alkyn-1-yl-$CH(C_1-C_2$alkyl)-;

wherein $X^a$, $X^b$, $X^c$, $X^d$, $X^e$ and $X^f$ are independently of each other oxygen or sulfur; and wherein $R^a$ is H, $C_1-C_{21}$alkyl, $C_2-C_{21}$alkenyl, $C_2-C_{18}$alkynyl, $C_1-C_{10}$fluoroalkyl, $C_1-C_{10}$cyanoalkyl, $C_1-C_{10}$nitroalkyl, $C_1-C_{10}$aminoalkyl, $C_1-C_5$alkylamino$(C_1-C_5)$alkyl, $C_2-C_8$dialkylamino$(C_1-C_5)$alkyl, $C_3-C_7$cycloalkyl$(C_1-C_5)$alkyl, $C_1-C_5$alkoxy$(C_1-C_5)$alkyl, $C_3-C_5$alkenyloxy$(C_1-C_5)$alkyl, $C_3-C_5$alkynyloxy$(C_1-C_5)$alkyl, $C_1-C_5$alkylthio$(C_1-C_5)$alkyl, $C_1-C_5$alkylsulfinyl$(C_1-C_5)$alkyl, $C_1-C_5$alkylsulfonyl$(C_1-C_5)$alkyl, $C_2-C_8$alkylideneaminoxy$(C_1-C_5)$alkyl, $C_1-C_5$alkylcarbonyl$(C_1-C_5)$alkyl, $C_1-C_5$alkoxycarbonyl$(C_1-C_5)$alkyl, aminocarbonyl$(C_1-C_5)$alkyl, $C_1-C_5$alkylaminocarbonyl $(C_1-C_5)$alkyl, $C_2-C_8$dialkylaminocarbonyl$(C_1-C_5)$alkyl, $C_1-C_5$alkylcarbonylamino$(C_1-C_5)$alkyl, $N-(C_1-C_5)$alkylcarbonyl-$N-(C_1-C_5)$alkylamino$(C_1-C_5)$alkyl, $C_3-C_6$trialkylsilyl$(C_1-C_5)$alkyl, phenyl$(C_1-C_5)$alkyl (wherein the phenyl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), heteroaryl$(C_1-C_5)$alkyl (wherein the heteroaryl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), $C_2-C_5$fluoroalkenyl, $C_3-C_8$cycloalkyl; phenyl or phenyl substituted by 1, 2 or 3 of, independently, $C_1-C_3$alkyl, $C_1-C_3$fluoroalkyl, $C_1-C_3$alkoxy, $C_1-C_3$fluoroalkoxy, halogen, cyano or nitro; or heteroaryl or heteroaryl substituted by 1, 2 or 3 of, independently, $C_1-C_3$alkyl, $C_1-C_3$fluoroalkyl, $C_1-C_3$alkoxy, $C_1-C_3$fluoroalkoxy, halogen, cyano or nitro;

$R^b$ is $C_1-C_{18}$alkyl, $C_3-C_{18}$alkenyl, $C_3-C_{18}$alkynyl, $C_2-C_{10}$fluoroalkyl, $C_1-C_{10}$cyanoalkyl, $C_1-C_{10}$nitroalkyl, $C_2-C_{10}$aminoalkyl, $C_1-C_5$alkylamino$(C_1-C_5)$alkyl, $C_2-C_8$dialkylamino$(C_1-C_5)$alkyl, $C_3-C_7$cycloalkyl$(C_1-C_5)$alkyl, $C_1-C_5$alkoxy$(C_1-C_5)$alkyl, $C_3-C_5$alkenyloxy$(C_1-C_5)$alkyl, $C_3-C_5$alkynyloxy$(C_1-C_5)$alkyl, $C_1-C_5$alkylthio$(C_1-C_5)$alkyl, $C_1-C_5$alkylsulfinyl$(C_1-C_5)$alkyl, $C_1-C_5$alkylsulfonyl$(C_1-C_5)$alkyl, $C_2-C_8$alkylideneaminoxy$(C_1-C_5)$alkyl, $C_1-C_5$alkylcarbonyl$(C_1-C_5)$alkyl, aminocarbonyl$(C_1-C_5)$alkyl, $C_1-C_5$alkylaminocarbonyl$(C_1-C_5)$alkyl, $C_2-C_8$dialkylaminocarbonyl$(C_1-C_5)$alkyl, $C_1-C_5$alkylcarbonylamino$(C_1-C_5)$alkyl, $N-(C_1-C_5)$alkylcarbonyl-$N-(C_1-C_5)$alkylamino$(C_1-C_5)$alkyl, $C_3-C_6$trialkylsilyl$(C_1-C_5)$alkyl, phenyl$(C_1-C_5)$alkyl (wherein the phenyl is optionally substituted by 1, 2 or 3 of, independently, $C_1-C_3$alkyl, $C_1-C_3$fluoroalkyl, $C_1-C_3$alkoxy, $C_1-C_3$fluoroalkoxy, $C_1-C_3$alkylthio, $C_1-C_3$alkylsulfinyl, $C_1-C_3$alkylsulfonyl, halogen, cyano, or nitro), heteroaryl$C_1-C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di ($C_3$$C_7$cycloalkyl)amino or $C_3$-$C_7$cycloalkoxy;

or $R^c$ and $R^d$, together with the nitrogen to which they are bonded, form an unsubstituted 4, 5, 6 or 7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino ($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino ($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryl($C_1$-$C_5$)alkyl(wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; $C_1$-$C_6$alkoxy-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present as an agrochemically acceptable salt thereof.

2. A compound as claimed in claim 1, wherein:

$R^{11}$ is $C_1$-$C_6$alkyl, $C_3$-$C_7$cycloalkyl, tetrahydro-2H-pyranyl, tetrahydrofuranyl, oxetanyl, tetrahydrothiophenyl or thietanyl;

or $R^{11}$ is one of the following sub-formulae A, B, C, D, E, F, GG, H, J, K, L, M, N, O, P, Q, R, S, T, U, V, W, X, Y or Z:

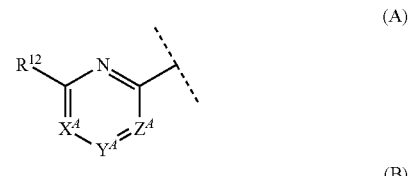

(A)

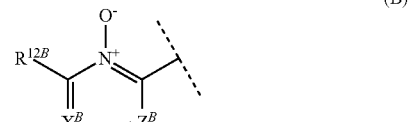

(B)

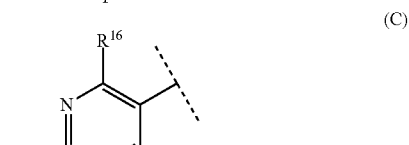

(C)

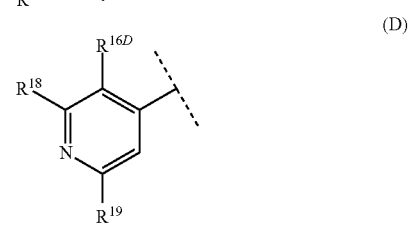

(D)

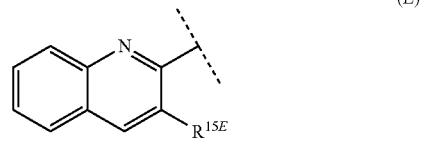

(E)

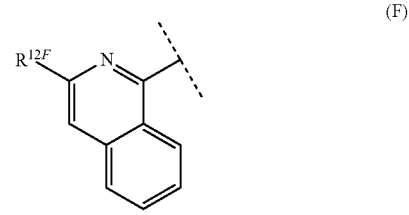

(F)

-continued
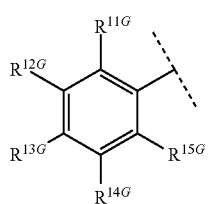 (GG)
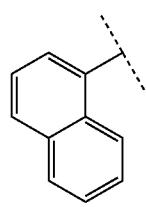 (H)
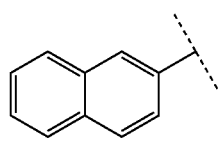 (J)
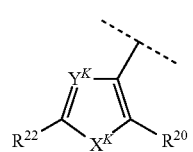 (K)
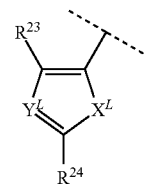 (L)
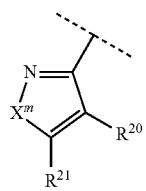 (M)
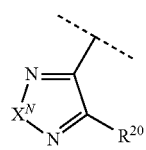 (N)
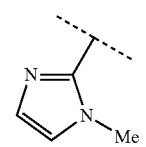 (O)
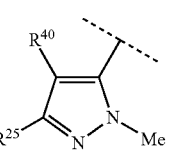 (P)
-continued
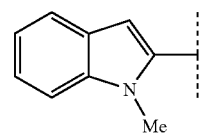 (Q)
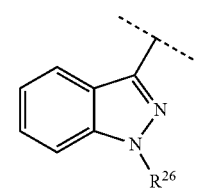 (R)
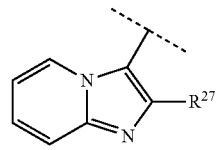 (S)
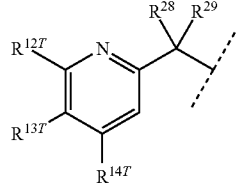 (T)
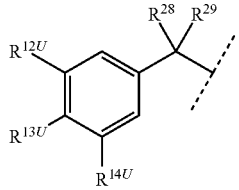 (U)
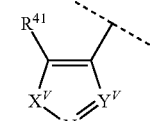 (V)
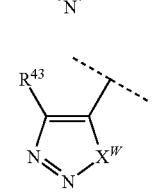 (W)
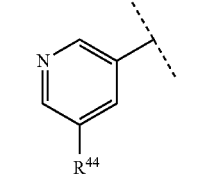 (X)
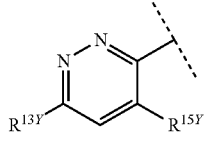 (Y)

-continued

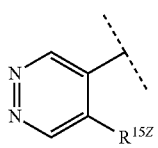
(Z)

wherein:
$X^A$ is nitrogen or $CR^{13}$;
$Y^A$ is nitrogen or $CR^{14}$;
$Z^A$ is nitrogen or $CR^{15}$;
provided that no more than one of $X^A$, $Y^A$ and $Z^A$ is nitrogen; and
$R^{12}$ is hydrogen, fluorine, chlorine, bromine, iodine, $C_1$-$C_2$alkyl, $C_1$-$C_2$fluoroalkyl, $C_1$-$C_2$alkoxy, $C_1$-$C_2$fluoroalkoxy, cyano, amino, or phenyl optionally substituted at meta and/or para position(s) by 1 or 2 fluorine substituents;
$R^{13}$ is hydrogen, fluorine, chlorine, bromine, methyl, ethyl, $C_1$fluoroalkyl, $C_2$fluoroalkyl, vinyl, $C_2$fluoroalkenyl, $C_2$-$C_3$alkynyl, fluoroethynyl, cyano, methoxy, ethoxy, $C_1$fluoroalkoxy, or $C_2$fluoroalkoxy;
$R^{14}$ is hydrogen, fluorine, chlorine, bromine, methoxy, $C_1$fluoroalkoxy, methyl, $C_1$fluoroalkyl or cyano;
$R^{15}$ is hydrogen, fluorine, chlorine, bromine, $C_1$-$C_2$alkyl, $C_1$fluoroalkyl, methoxy, $C_1$fluoroalkoxy, cyano or amino;
provided that at least two of $R^{12}$, $R^{13}$, $R^{14}$ and $R^{15}$ are hydrogen;
and provided that, when $R^{12}$ is iodine, amino, or optionally substituted phenyl, then $X^A$ is $CR^{13}$, $Y^A$ is $CR^{14}$, $Z^A$ is $CR^{15}$, and $R^{13}$, $R^{14}$ and $R^{15}$ are independently hydrogen or fluorine, provided that at least two of $R^{13}$, $R^{14}$ and $R^{15}$ are hydrogen;
and provided that, when $R^{13}$ is bromine, then $X^A$ is $CR^{13}$, and $R^{12}$, $R^{14}$ and $R^{15}$ are independently hydrogen or fluorine, provided that at least two of $R^{12}$, $R^{14}$ and $R^{15}$ are hydrogen;
and provided that, when $R^{13}$ is ethyl, $C_2$fluoroalkyl, vinyl, $C_2$fluoroalkenyl, $C_2$-$C_3$alkynyl, fluoroethynyl, ethoxy or $C_2$fluoroalkoxy, then $X^A$ is $CR^{13}$, $Y^A$ is $CR^{14}$, $Z^A$ is $CR^{15}$, and $R^{12}$, $R^{14}$ and $R^{15}$ are independently hydrogen or fluorine, provided that at least two of $R^{12}$, $R^{14}$ and $R^{15}$ are hydrogen;
and provided that, when $R^{14}$ is bromine or cyano, then $X^A$ is $CR^{13}$, $Y^A$ is $CR^{14}$, $Z^A$ is $CR^{15}$, and of $R^{12}$, $R^{13}$ and $R^{15}$ are independently hydrogen or fluorine, provided that at least two of $R^{12}$, $R^{13}$ and $R^{15}$ are hydrogen;
and provided that, when $R^{15}$ is amino, then $X^A$ is $CR^{13}$, $Y^A$ is nitrogen or $CR^{14}$, $Z^A$ is $CR^{15}$, and $R^{13}$ is hydrogen, methyl or $C_1$fluoroalkyl, and $R^{12}$ and $R^{14}$ are hydrogen;
and wherein:
$X^B$ is nitrogen or $CR^{13B}$;
$Y^B$ is nitrogen or $CR^{14B}$;
$Z^B$ is nitrogen or $CR^{15B}$;
provided that no more than one of $X^B$, $Y^B$ and $Z^B$ is nitrogen; and
$R^{12B}$ is hydrogen, fluorine, chlorine or bromine;
$R^{13B}$ is hydrogen, fluorine, chlorine, bromine, methyl, $C_1$fluoroalkyl, cyano, methoxy or $C_1$fluoroalkoxy;
$R^{14B}$ is hydrogen, fluorine, chlorine or chlorine;
$R^{15B}$ is hydrogen, fluorine, chlorine or bromine;
provided that at least two of $R^{12B}$, $R^{13B}$, $R^{14B}$ and $R^{15B}$ are hydrogen;
and provided that, when $R^{13B}$ is bromine, then $X^A$ is $CR^{13B}$, and $R^{12B}$, $R^{14B}$ and $R^{15B}$ are independently hydrogen or fluorine, provided that at least two of $R^{12B}$, $R^{14B}$ and $R^{15B}$ are hydrogen; and
$R^{16}$ is hydrogen, fluorine, chlorine, bromine, methyl or $C_1$fluoroalkyl;
$R^{17}$ is hydrogen, fluorine, chlorine, methyl or $C_1$fluoroalkyl;
provided that no more than one of $R^{16}$ and $R^{17}$ is hydrogen;
and provided that when $R^{16}$ is bromine then $R^{17}$ is hydrogen or fluorine;
$R^{16D}$ is hydrogen or fluorine;
$R^{18}$ is hydrogen, fluorine or chlorine;
$R^{19}$ is hydrogen, fluorine, chlorine, methoxy, $C_1$fluoroalkoxy, methyl or $C_1$fluoroalkyl;
provided that no more than one of $R^{18}$ and $R^{19}$ is hydrogen;
$R^{15E}$ is hydrogen, fluorine or chlorine;
$R^{12F}$ is hydrogen, fluorine or chlorine;
$R^{11GG}$ is hydrogen, fluorine, methyl or $C_1$fluoroalkyl;
$R^{12GG}$ is hydrogen, fluorine or chlorine;
$R^{13GG}$ is hydrogen, fluorine, chlorine, bromine, $C_1$fluoroalkyl, methoxy or $C_1$fluoroalkoxy;
$R^{14GG}$ is hydrogen or fluorine;
$R^{15GG}$ is hydrogen, fluorine, chlorine, methoxy or $C_1$fluoroalkoxy;
provided that, when $R^{13GG}$ is bromine, then $R^{11GG}$, $R^{12GG}$, $R^{14GG}$ and $R^{15GG}$ are independently hydrogen or fluorine;
provided that, when $R^{11GG}$ is methyl or $C_1$fluoroalkyl, then $R^{12GG}$, $R^{13GG}$, $R^{14GG}$ and $R^{15GG}$ are independently hydrogen or fluorine; and
provided that at least two of $R^{12GG}$, $R^{13GG}$, $R^{14GG}$ and $R^{15GG}$ are hydrogen;
$X^K$ is O or S; and $Y^K$ is C—H or N;
$X^L$ is O, S or N-Me; and $Y^L$ is C—H or N; provided that when $X^L$ is N-Me then $Y^L$ is not N;
$X^m$ is O, S or N-Me;
$X^N$ is O, S or N-Me;
$X^V$ is O, S or N-Me; and $Y^V$ is N or $CR^{42}$; and
$X^W$ is O, S or N-Me;
$R^{20}$ is hydrogen, methyl, $C_1$fluoroalkyl, fluorine or chlorine;
$R^{21}$ is hydrogen, methyl, $C_1$fluoroalkyl, ethyl, cyclopropyl, fluorine or chlorine;
$R^{22}$ is hydrogen, methyl, $C_1$fluoroalkyl, fluorine or chlorine;
$R^{23}$ is hydrogen, methyl, $C_1$fluoroalkyl, ethyl or cyclopropyl;
$R^{24}$ is hydrogen, methyl, $C_1$fluoroalkyl, ethyl or methoxymethyl;
$R^{25}$ is hydrogen, methyl, $C_1$fluoroalkyl, fluorine or chlorine;
$R^{26}$ is hydrogen or methyl; and
$R^{27}$ is hydrogen or methyl; and
$R^{28}$ and $R^{29}$ independently are hydrogen or fluorine;
$R^{40}$ is hydrogen, methyl, $C_1$fluoroalkyl, fluorine or chlorine;
$R^{41}$ is hydrogen, methyl, $C_1$fluoroalkyl, fluorine or chlorine;
$R^{42}$ is hydrogen, methyl, $C_1$fluoroalkyl, fluorine or chlorine;
$R^{43}$ is hydrogen, methyl or $C_1$fluoroalkyl;
$R^{44}$ is fluorine, chlorine or bromine;

$R^{12T}$, $R^{13T}$ and $R^{14T}$ are independently hydrogen or fluorine, provided that at least two of $R^{12T}$, $R^{13T}$ and $R^{14T}$ are hydrogen; and $R^{12U}$, $R^{13U}$ and $R^{14U}$ are independently hydrogen or fluorine, provided that at least two of $R^{12U}$, $R^{13U}$ and $R^{14U}$ are hydrogen; and $R^{13Y}$ is hydrogen, fluorine, chlorine, bromine, $C_1$fluoroalkyl, methoxy or $C_1$fluoroalkoxy;

$R^{15Y}$ is hydrogen, fluorine, chlorine, bromine, methoxy or $C_1$fluoroalkoxy;

provided that one or both of $R^{13Y}$ and $R^{15Y}$ are independently hydrogen or fluorine; and $R^{15Z}$ is hydrogen, fluorine or chlorine;

and wherein the compound of formula (I) is optionally present as an agrochemically acceptable salt thereof.

3. The compound of claim 1, wherein:

$R^2$ is hydrogen, methyl, ethyl, n-propyl, isopropyl, cyclopropyl, fluoromethyl, fluoroethyl, vinyl, prop-1-enyl, ethynyl, prop-1-ynyl, 2-chloroethynyl, 2-fluoroethynyl, 2-(trifluoromethyl)ethynyl, but-1-ynyl, 2-(cyclopropyl)ethynyl, halogen, or ($C_1$-$C_2$fluoroalkyl)-methoxy-;

or $R^2$ is phenyl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro;

or $R^2$ is monocyclic heteroaryl optionally substituted by 1, 2 or 3 of, independently, halogen, $C_1$-$C_2$alkyl, $C_1$-$C_2$fluoroalkyl, $C_1$-$C_2$alkoxy, $C_1$-$C_2$fluoroalkoxy, cyano or nitro; and $R^{11}$ is $C_1$-$C_6$alkyl, $C_3$-$C_7$cycloalkyl, tetrahydro-2H-pyranyl or tetrahydrofuranyl;

or $R^{11}$ is one of the following sub-formulae A, B1, C, D1, E, F, G1, H, J, K, L, M, N, O, P1, Q, R, S, T or U:

-continued

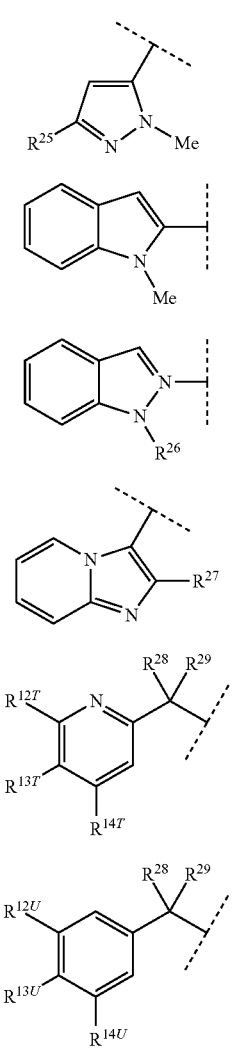

wherein:
X$^A$ is nitrogen or CR$^{13}$;
Y$^A$ is nitrogen or CR$^{14}$;
Z$^A$ is nitrogen or CR$^{15}$;
provided that no more than one of X$^A$, Y$^A$ and Z$^A$ is nitrogen; and
R$^{12}$ is hydrogen, fluorine, chlorine, bromine, iodine, C$_1$-C$_2$alkyl, C$_1$-C$_2$fluoroalkyl, C$_1$-C$_2$alkoxy, C$_1$-C$_2$fluoroalkoxy, cyano, amino, or phenyl optionally substituted at meta and/or para position(s) by 1 or 2 fluorine substituents;
R$^{13}$ is hydrogen, fluorine, chlorine, methyl, C$_1$fluoroalkyl, or cyano;
R$^{14}$ is hydrogen, fluorine, chlorine, methoxy, C$_1$fluoroalkoxy, methyl or C$_1$fluoroalkyl;
R$^{15}$ is hydrogen, fluorine, chlorine, bromine, C$_1$-C$_2$alkyl, C$_1$fluoroalkyl, methoxy, C$_1$fluoroalkoxy, cyano or amino;
provided that at least two of R$^{12}$, R$^{13}$, R$^{14}$ and R$^{15}$ are hydrogen;
and provided that, when R$^{12}$ is iodine, amino, or optionally substituted phenyl, then X$^A$ is CR$^{13}$, Y$^A$ is CR$^{14}$, Z$^A$ is CR$^{15}$, and R$^{13}$, R$^{14}$ and R$^{15}$ are independently hydrogen or fluorine, provided that at least two of R$^{13}$, R$^{14}$ and R$^{15}$ are hydrogen;
and provided that, when R$^{15}$ is amino, then X$^A$ is CR$^{13}$, Y$^A$ is nitrogen or CR$^{14}$, Z$^A$ is CR$^{15}$, and R$^{13}$ is hydrogen, methyl or C$_1$fluoroalkyl, and R$^{12}$ and R$^{14}$ are hydrogen; and
R$^{16}$ is hydrogen, fluorine or chlorine;
R$^{17}$ is hydrogen, fluorine, chlorine, methyl or C$_1$fluoroalkyl; provided that no more than one of R$^{16}$ and R$^{17}$ is hydrogen;
R$^{18}$ is chlorine;
R$^{19}$ is fluorine, chlorine, methoxy, C$_1$fluoroalkoxy, methyl or C$_1$fluoroalkyl;
R$^{15E}$ is hydrogen, fluorine or chlorine;
R$^{12F}$ is hydrogen, fluorine or chlorine;
R$^{12GG}$ is hydrogen, fluorine or chlorine;
R$^{13GG}$ is hydrogen, fluorine, chlorine, C$_1$fluoroalkyl, methoxy or C$_1$fluoroalkoxy;
R$^{14GG}$ is hydrogen or fluorine;
R$^{15GG}$ is hydrogen, fluorine, chlorine, methoxy or C$_1$fluoroalkoxy;
provided that at least two of R$^{12GG}$, R$^{13GG}$, R$^{14GG}$ and R$^{15GG}$ are hydrogen;
X$^K$ is O or S; and Y$^K$ is C—H or N;
X$^L$ is O, S or N-Me; and Y$^L$ is C—H or N; provided that when X$^L$ is N-Me then Y$^L$ is not N;
X$^m$ is O, S or N-Me;
X$^N$ is O, S or N-Me;
R$^{20}$ is hydrogen, methyl or C$_1$fluoroalkyl;
R$^{21}$ is hydrogen, methyl or C$_1$fluoroalkyl;
R$^{22}$ is hydrogen, methyl or C$_1$fluoroalkyl;
R$^{23}$ is hydrogen, methyl or C$_1$fluoroalkyl;
R$^{24}$ is hydrogen, methyl or C$_1$fluoroalkyl;
R$^{25}$ is hydrogen, methyl or C$_1$fluoroalkyl;
R$^{26}$ is hydrogen or methyl; and
R$^{27}$ is hydrogen or methyl; and
R$^{28}$ and R$^{29}$ independently are hydrogen or fluorine;
R$^{12T}$, R$^{13T}$ and R$^{14T}$ are independently hydrogen or fluorine, provided that at least two of R$^{12T}$, R$^{13T}$ and R$^{14T}$ are hydrogen; and
R$^{12U}$, R$^{13U}$ and R$^{14U}$ are independently hydrogen or fluorine, provided that at least two of R$^{12U}$, R$^{13U}$ and R$^{14U}$ are hydrogen;
and wherein:
G is hydrogen; an agriculturally acceptable metal, or an agriculturally acceptable sulfonium or ammonium group; or
G is —C(X$^a$)—R$^a$, —C(X$^b$)—X$^c$—R$^b$, —C(X$^d$)—N(R$^c$)—R$^d$, —SO$_2$—R$^e$, —P(X$^e$)(R$^f$)—R$^g$, or —CH$_2$—X$^f$—R$^h$; or phenyl-CH$_2$— or phenyl-CH(C$_1$-C$_2$alkyl)- (in each of which the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or heteroaryl-CH$_2$— or heteroaryl-CH(C$_1$-C$_2$alkyl)- (in each of which the heteroaryl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or phenyl-C(O)—CH$_2$— (wherein the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro); or C$_1$-C$_6$alkoxy-C(O)—CH$_2$—, C$_1$-C$_6$alkyl-C(O)—CH$_2$—, C$_1$-C$_6$alkoxy-C(O)—CH═CH—, C$_2$-C$_7$alken-1-yl-CH$_2$—, C$_2$-C$_7$alken-1-yl-CH(C$_1$-C$_2$alkyl)-, C$_2$-C$_4$fluoroalken-1-yl-CH$_2$—, C$_2$-C$_7$alkyn-1-yl-CH$_2$—, or C$_2$-C$_7$alkyn-1-yl-CH(C$_1$-C$_2$alkyl)-;

and wherein $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy ($C_1$-$C_5$)alkyl, $C_3$-$C_5$alkynyloxy ($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$$C_5$alkoxycarbonyl ($C_1$-$C_5$)alkyl, aminocarbonyl($C_1$-$C_5$)alkyl, $C_1$-$C_5$alkylaminocarbonyl ($C_1$-$C_5$)alkyl, $C_2$-$C_8$dialkylaminocarbonyl($C_1$-$C_5$)alkyl, $C_1$-$C_5$alkylcarbonylamino ($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present as an agrochemically acceptable salt thereof.

4. The compound of claim 2, wherein G is hydrogen; an agriculturally acceptable metal, or an agriculturally acceptable sulfonium or ammonium group; or G is —C($X^a$)—$R^a$ or —C($X^b$)—$X^c$—$R^b$, wherein $X^a$, $R^a$, $X^b$, $X^c$ and $R^b$ are as defined in claim 2.

5. The compound of claim 4, wherein: when G is —C($X^a$)—$R^a$ or —C($X^b$)—$X^c$—$R^b$, then $X^a$ and $X^b$ are oxygen, $X^c$ is oxygen or sulfur, $R^a$ is $C_1$-$C_{10}$alkyl, $C_2$-$C_6$alkenyl, $C_2$-$C_6$alkynyl, $C_3$-$C_6$cycloalkyl, $C_1$-$C_4$alkoxy$C_1$-$C_4$alkyl, $C_3$-$C_6$cycloalkyl($C_1$-$C_2$)alkyl, or phenyl or phenyl substituted by 1, 2 or 3 of, independently, $C_1$-$C_3$alkyl, $C_1$-$C_2$fluoroalkyl, $C_1$-$C_3$alkoxy, $C_1$-$C_2$fluoroalkoxy, fluorine, chlorine, bromine, cyano or nitro, or a monocyclic 5- or 6-membered heteroaryl or a monocyclic 5- or 6-membered heteroaryl substituted by 1, 2 or 3 of, independently, $C_1$-$C_3$alkyl, $C_1$-$C_2$fluoroalkyl, $C_1$-$C_3$alkoxy, $C_1$-$C_2$fluoroalkoxy, fluorine, chlorine, bromine or cyano; and $R^b$ is $C_1$-$C_{10}$alkyl, $C_2$-$C_5$alkenyl-$CH_2$—, $C_2$-$C_4$alkenyl-CH(Me)-, $C_2$-$C_5$alkynyl-$CH_2$—, $C_2$-$C_4$alkynyl-CH(Me)-, $C_3$-$C_6$cycloalkyl, $C_1$-$C_4$alkoxy$C_1$-$C_4$alkyl, $C_3$-$C_6$cycloalkyl($C_1$-$C_2$)alkyl, or phenyl or phenyl substituted by 1, 2 or 3 of, independently, $C_1$-$C_3$alkyl, $C_1$-$C_2$fluoroalkyl, $C_1$-$C_3$alkoxy, $C_1$-$C_2$fluoroalkoxy, fluorine, chlorine, bromine, cyano or nitro, or a monocyclic 5- or 6-membered heteroaryl or a monocyclic 5- or 6-membered heteroaryl substituted by 1, 2 or 3 of, independently, $C_1$-$C_3$alkyl, $C_1$-$C_2$fluoroalkyl, $C_1$-$C_3$alkoxy, $C_1$-$C_2$fluoroalkoxy, fluorine, chlorine, bromine or cyano.

6. The compound of claim 5, wherein $R^1$ is methyl, ethyl, ethynyl, chlorine, bromine or methoxy.

7. The compound of claim 6, wherein $R^3$ is hydrogen, methyl, ethyl, ethynyl, fluorine, chlorine, bromine, methoxy or fluoromethoxy.

8. The compound of claim 1, wherein:

$R^2$ is methyl, ethynyl, prop-1-ynyl, 2-chloroethynyl, chlorine or bromine;

or $R^2$ is phenyl optionally substituted by 1 or 2 of, independently, halogen, $C_1$-$C_2$alkyl, $C_1$-$C_2$fluoroalkyl or cyano;

or $R^2$ is monocyclic heteroaryl optionally substituted by 1 or 2 of, independently, halogen, $C_1$-$C_2$alkyl, $C_1$-$C_2$fluoroalkyl, cyano or nitro;

or $R^2$ is ($C_1$fluoroalkyl)-methoxy-.

9. The compound as claimed in claim 8, wherein:

when $R^2$ is optionally substituted phenyl, then $R^2$ is

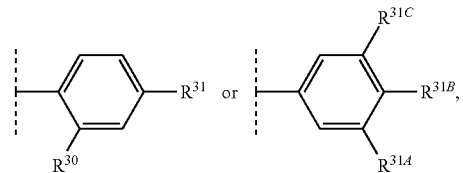

in which:

$R^{30}$ is hydrogen, fluorine, chlorine or $C_1$fluoroalkyl;

$R^{31}$ is fluorine, chlorine, $C_1$fluoroalkyl or methyl;

$R^{31A}$ is fluorine or chlorine;

$R^{31B}$ is hydrogen, fluorine or chlorine; and $R^{31C}$ is hydrogen, fluorine or chlorine;

wherein one or both of $R^{31B}$ and $R^{31C}$ is or are hydrogen; and when $R^2$ is optionally substituted monocyclic heteroaryl, then $R^2$ is

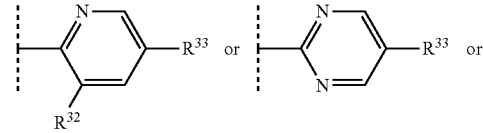

-continued

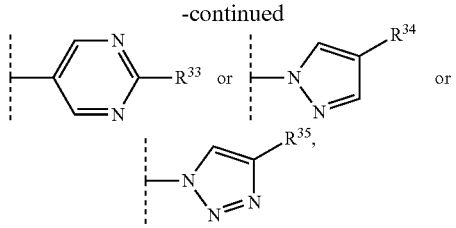

in which:
R³² is hydrogen, fluorine, chlorine or C₁fluoroalkyl; and
R³³ is fluorine, chlorine or C₁fluoroalkyl;
R³⁴ is fluorine, chlorine, bromine, methyl, C₁fluoroalkyl or cyano; and
R³⁵ is fluorine, chlorine, bromine, methyl, C₁fluoroalkyl or cyano.

10. The compound as claimed in claim 1, wherein all of R⁴, R⁵, R⁶, R⁷, R⁸, R⁹ and R¹⁰ are hydrogen.

11. The compound as claimed in claim 1, wherein R¹¹ is sub-formula A, as defined in claim 2.

12. The compound as claimed in claim 11, wherein:
R¹¹ is sub-formula A;
X⁴ is CR¹³;
Y⁴ is CR¹⁴;
Z⁴ is CR¹⁵;
R¹² is hydrogen, fluorine, chlorine or bromine;
R¹³ is hydrogen, fluorine, chlorine, bromine, C₁fluoroalkyl, methoxy or C₁fluoroalkoxy;
R¹⁴ is hydrogen, fluorine or chlorine; and
R¹⁵ is hydrogen, fluorine, chlorine or bromine;
provided that at least two of R¹², R¹³, R¹⁴ and R¹⁵ are hydrogen;
and provided that, when R¹³ is bromine, then R¹², R¹⁴ and R¹⁵ are independently hydrogen or fluorine, provided that at least two of R¹², R¹⁴ and R¹⁵ are hydrogen.

13. The compound as claimed in claim 12, wherein:
R¹², R¹⁴ and R¹⁵ are all hydrogen, and
R¹³ is hydrogen, fluorine, chlorine, bromine or C₁fluoroalkoxy.

14. The compound as claimed in claim 1, wherein the compound of formula (I) is a compound of formula (IC):

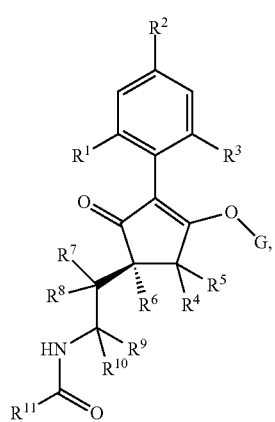

(IC)

wherein R¹, R², R³, R⁴, R⁵, R⁶, R⁷, R⁸, R⁹, R¹⁰, R¹¹, and G are as defined in claim 1,
and wherein 40% or more by molarity of the compound of formula (IC) has the indicated stereochemistry at the ring-carbon atom bonded to R⁶ and —CR⁷R⁸—CR⁹R¹⁰—NHC(O)—R¹¹.

15. The compound as claimed in claim 14, wherein, more than 50% by molarity of the compound of formula (IC) has the indicated stereochemistry at the ring-carbon atom bonded to R⁶ and —CR⁷R⁸—CR⁹R¹⁰—NHC(O)—R¹¹.

16. The compound as claimed in claim 1, wherein the compound is any of compounds A1 thru A108, present either as a free compound and/or present as an agrochemically acceptable salt thereof:

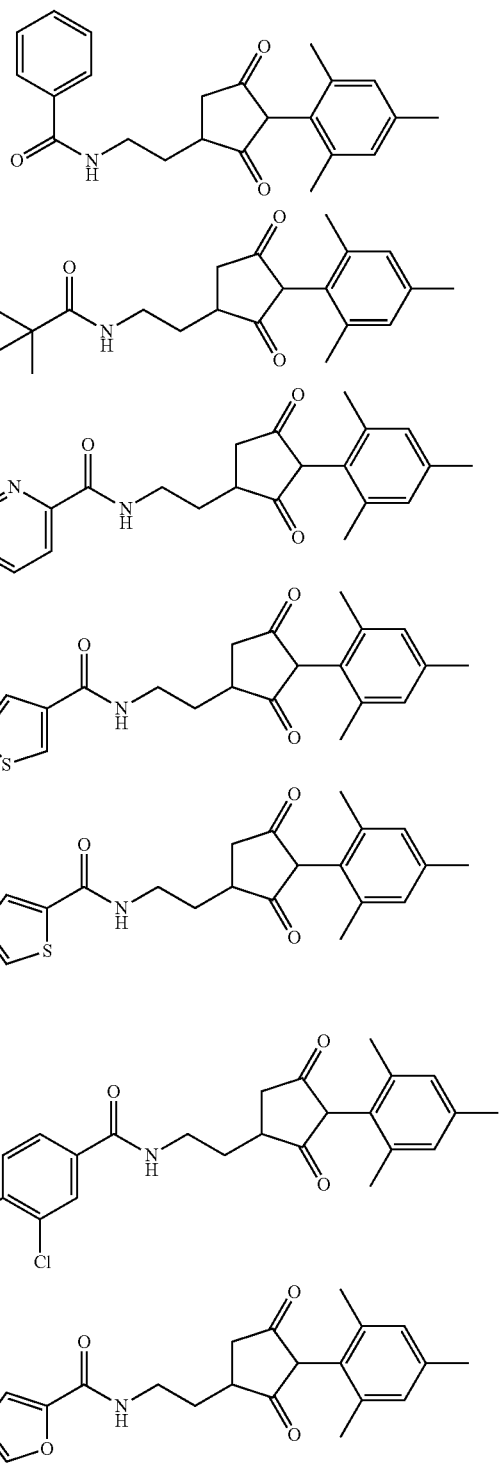

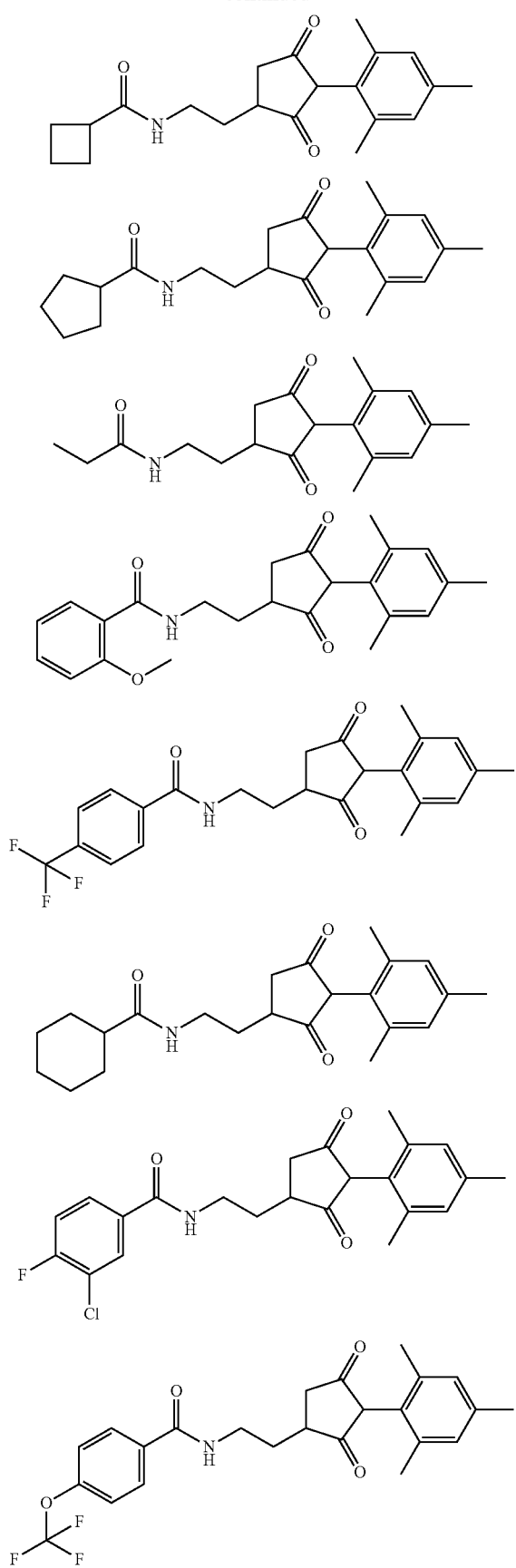
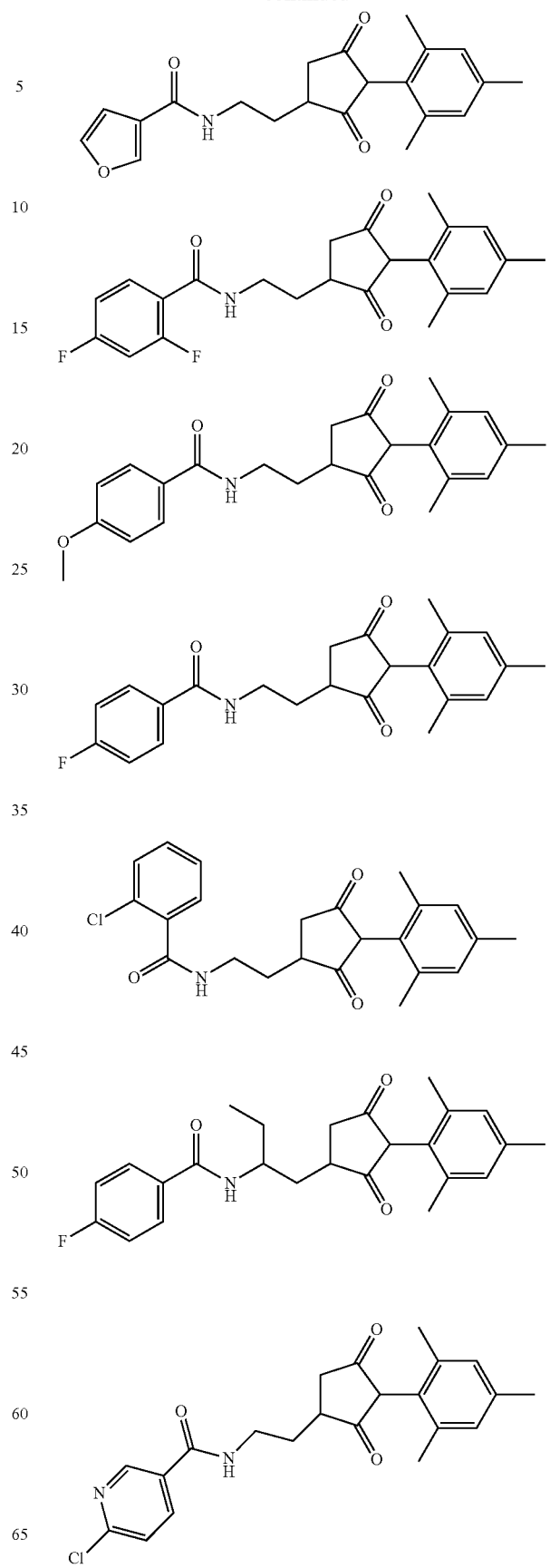

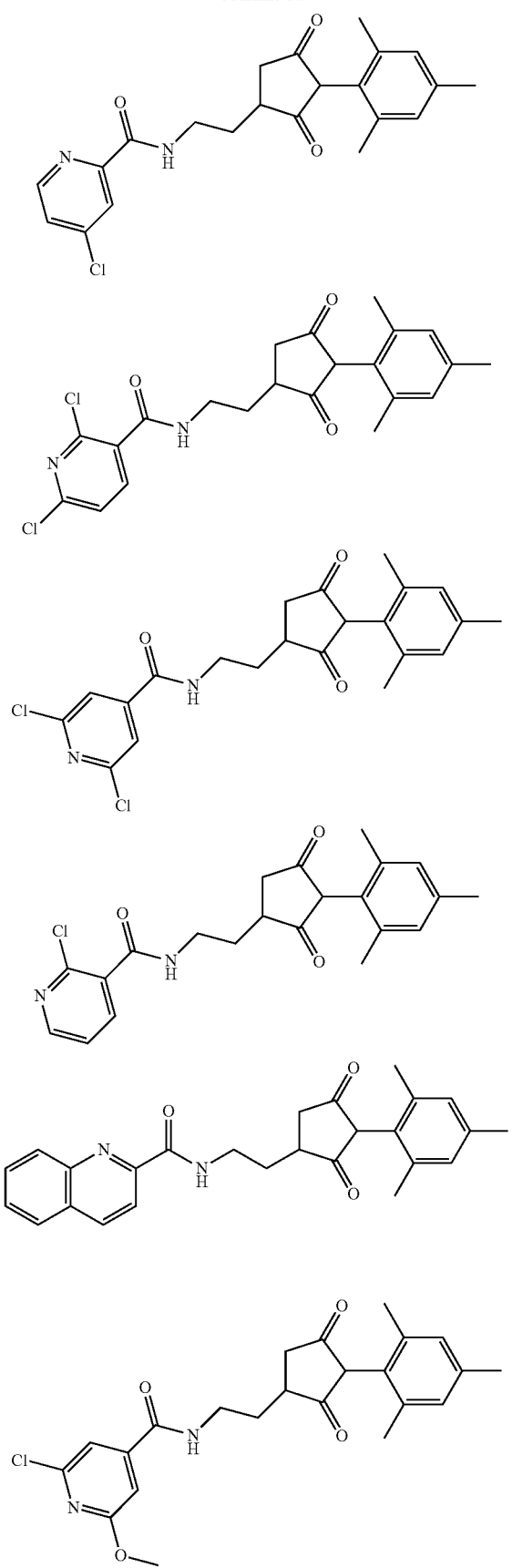
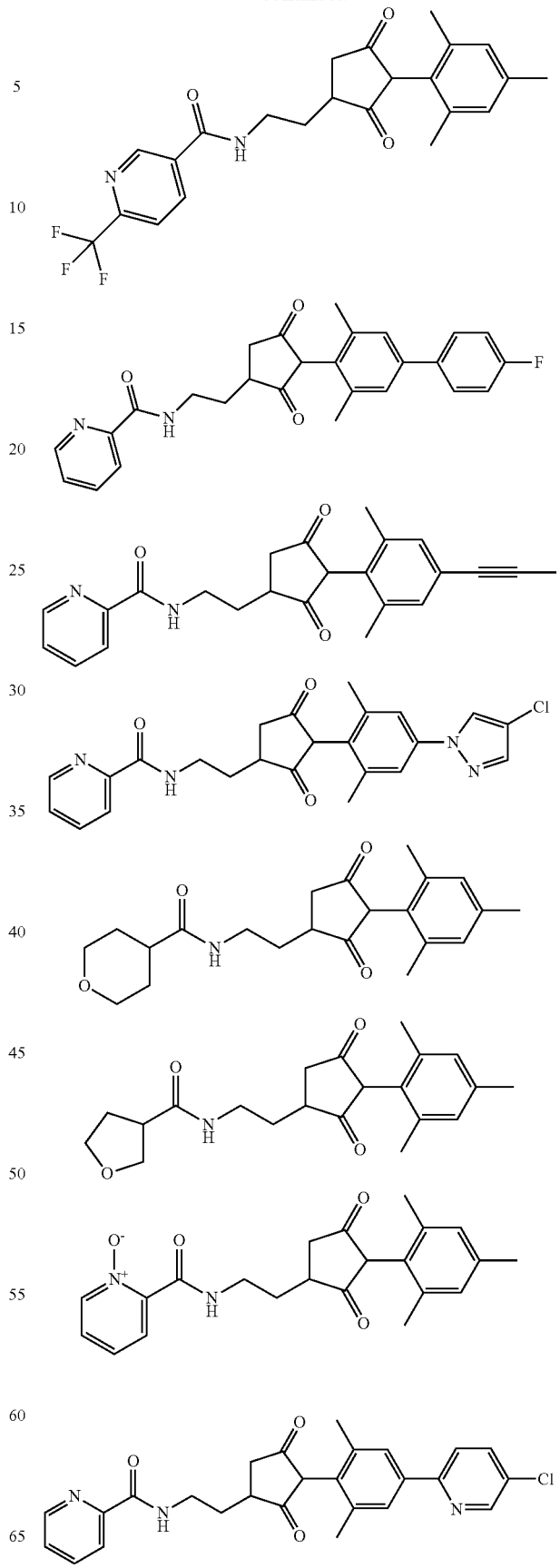

301
-continued
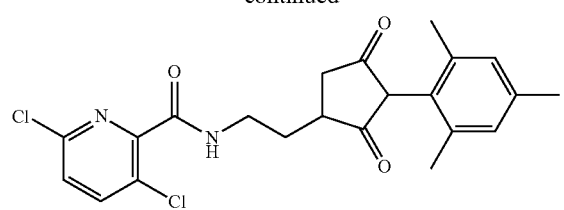
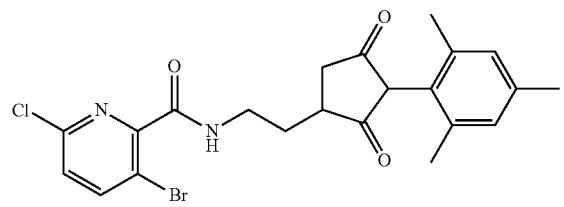
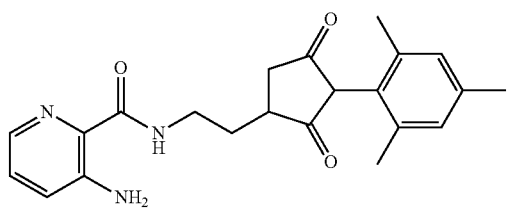
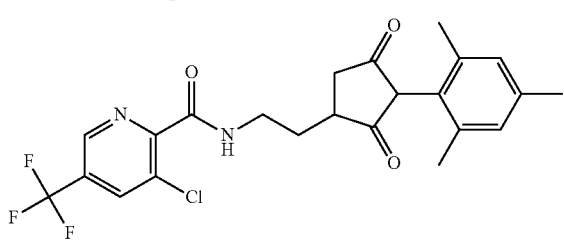
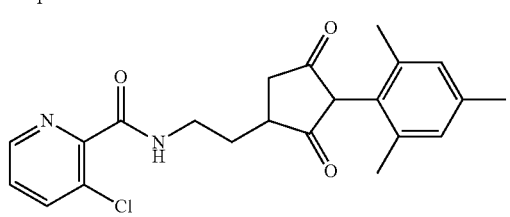
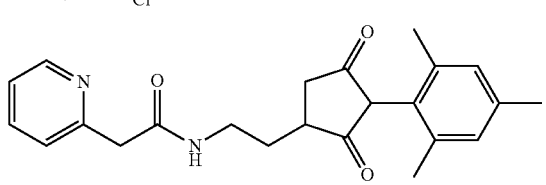
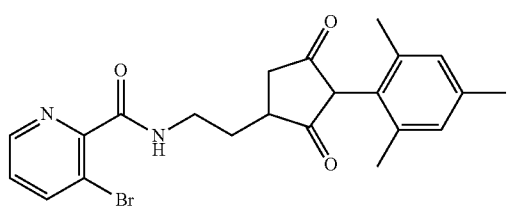
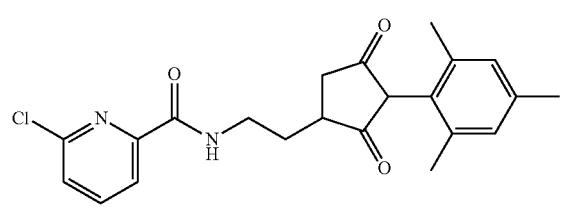
302
-continued
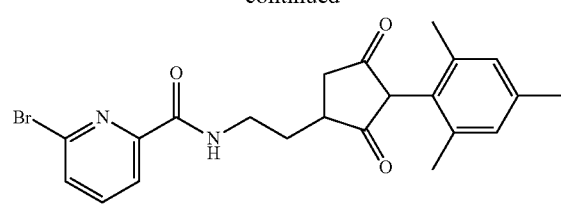
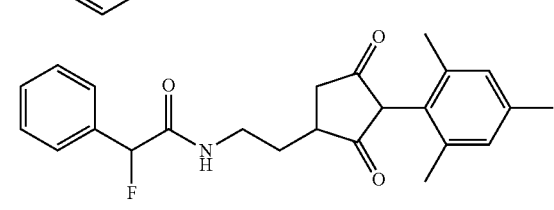
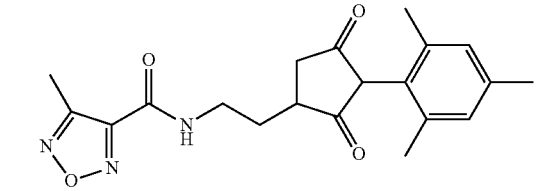
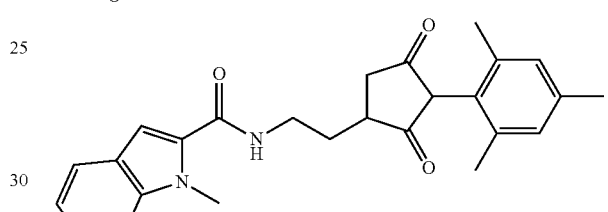
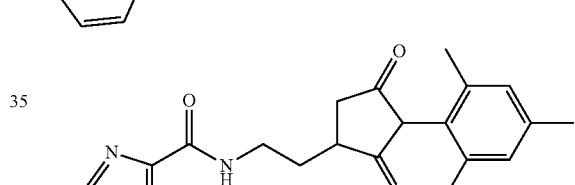
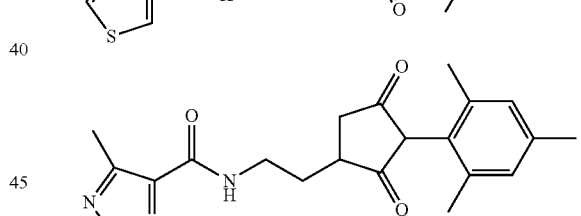
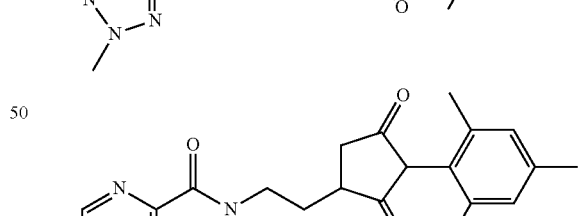
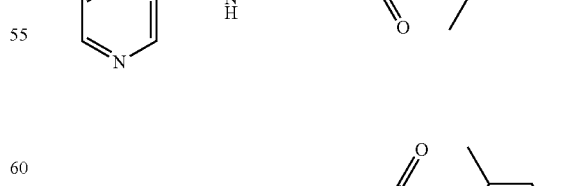
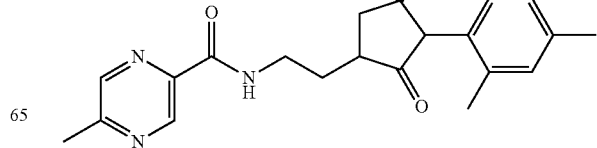

303
-continued
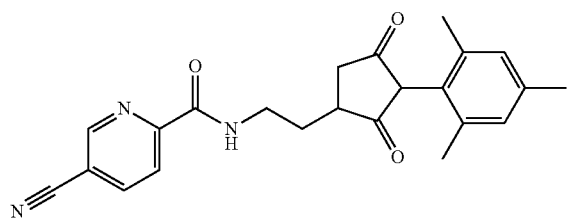
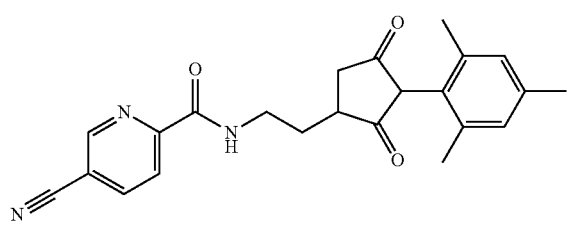
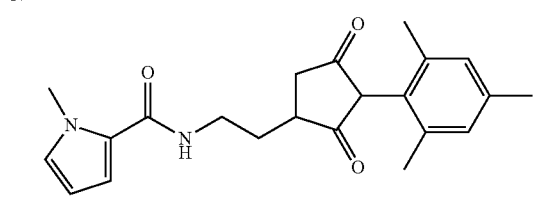
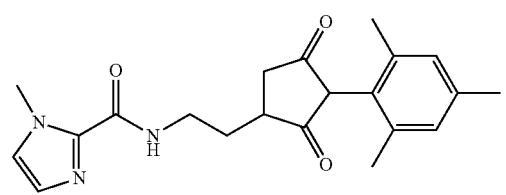
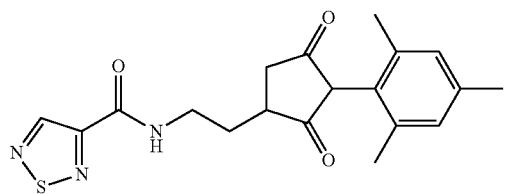
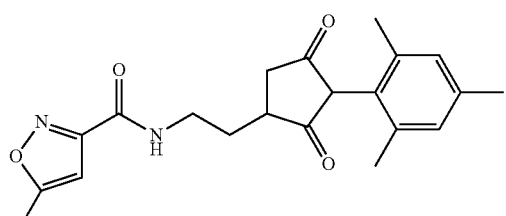
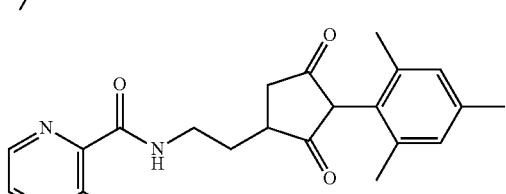
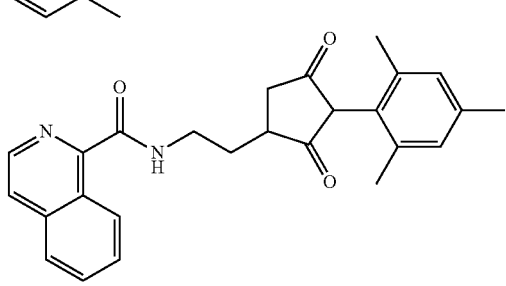
304
-continued
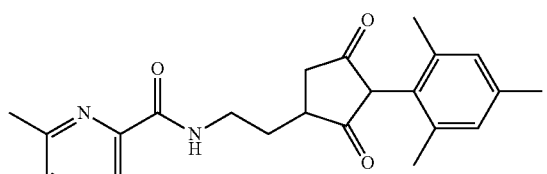
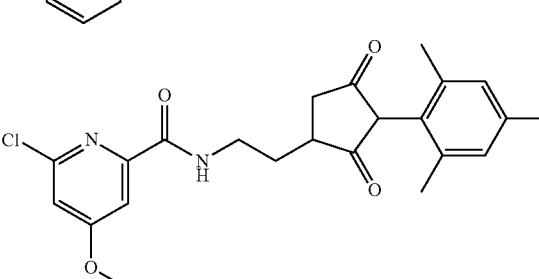
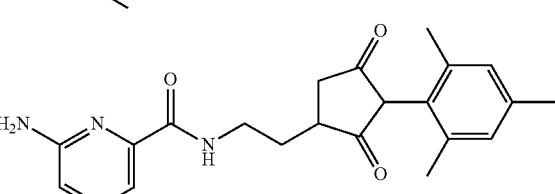
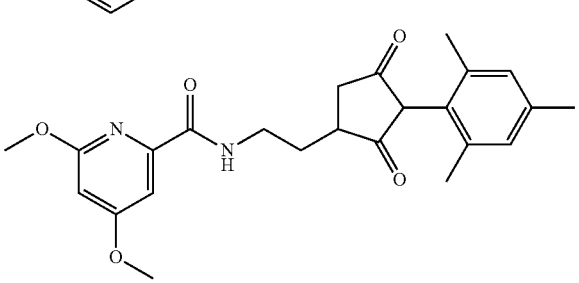
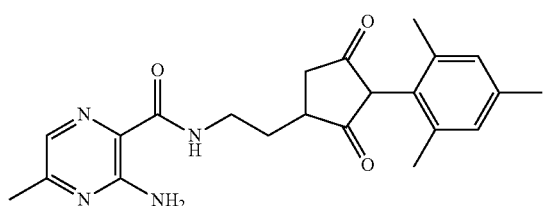
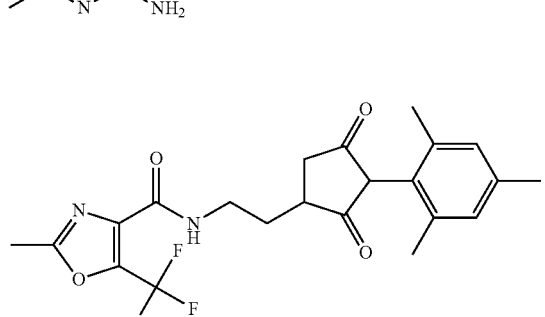
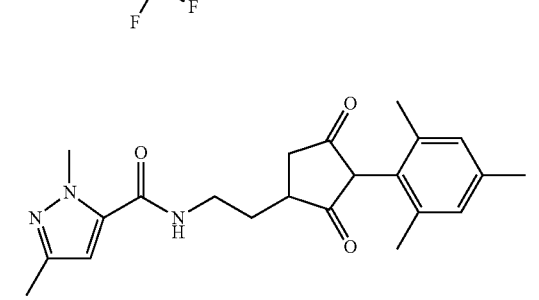

305
-continued
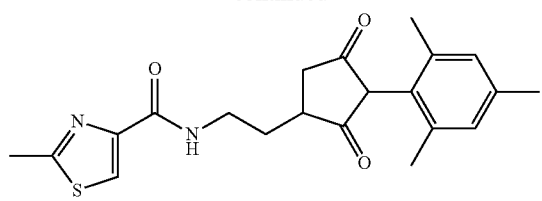
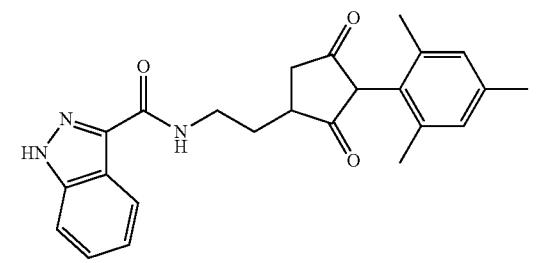
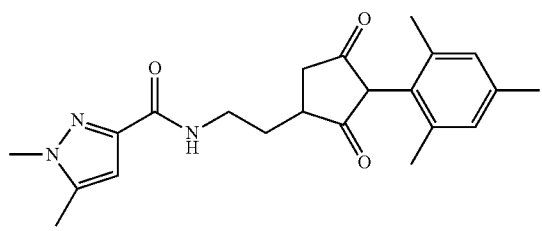
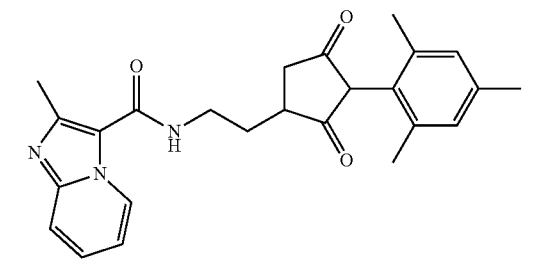
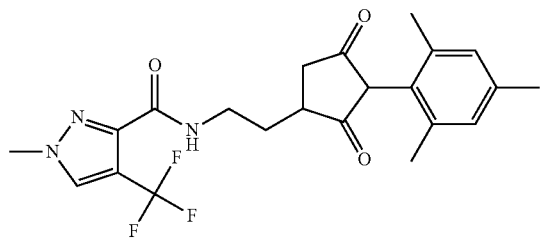
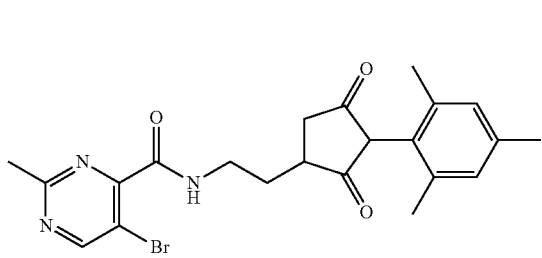
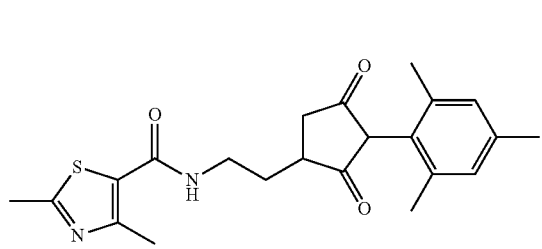
306
-continued
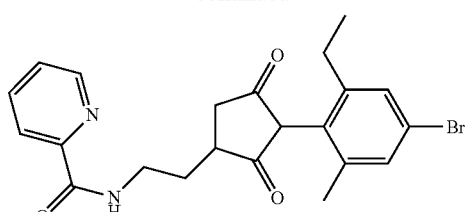
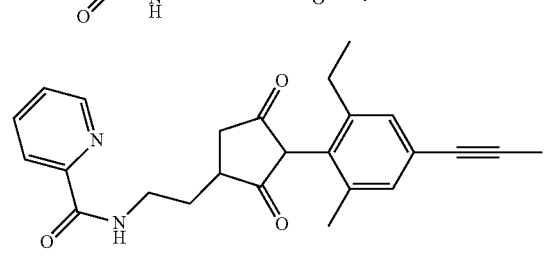
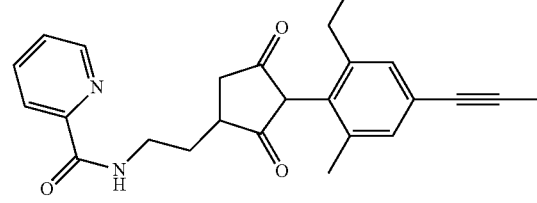
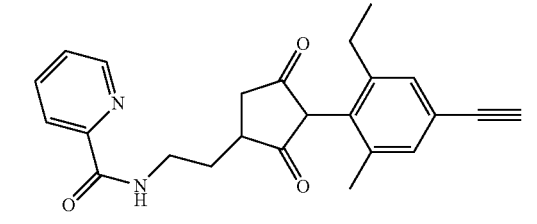
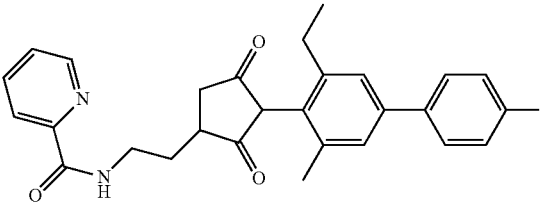
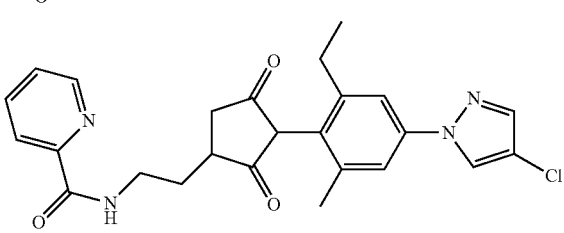
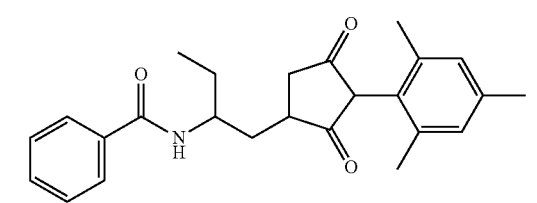
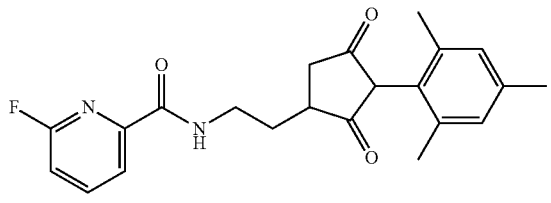
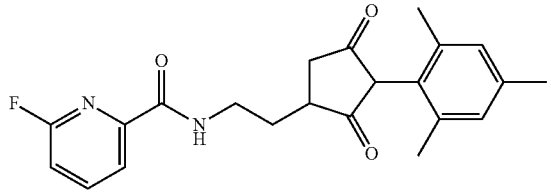

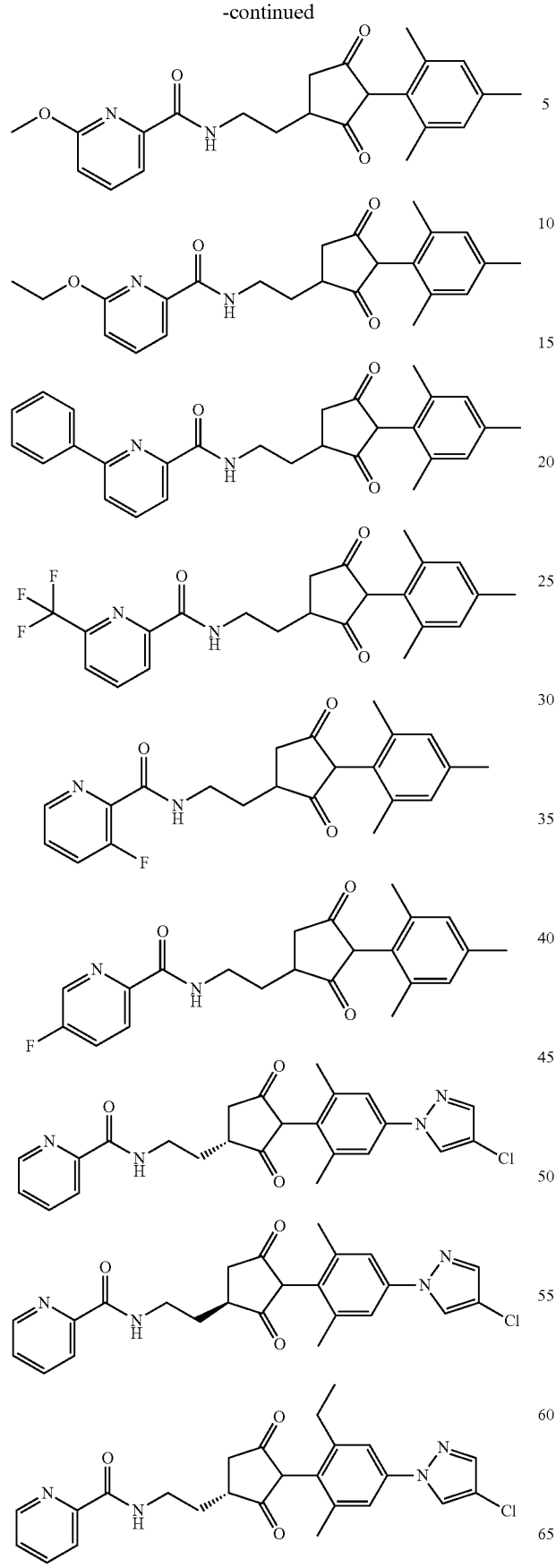
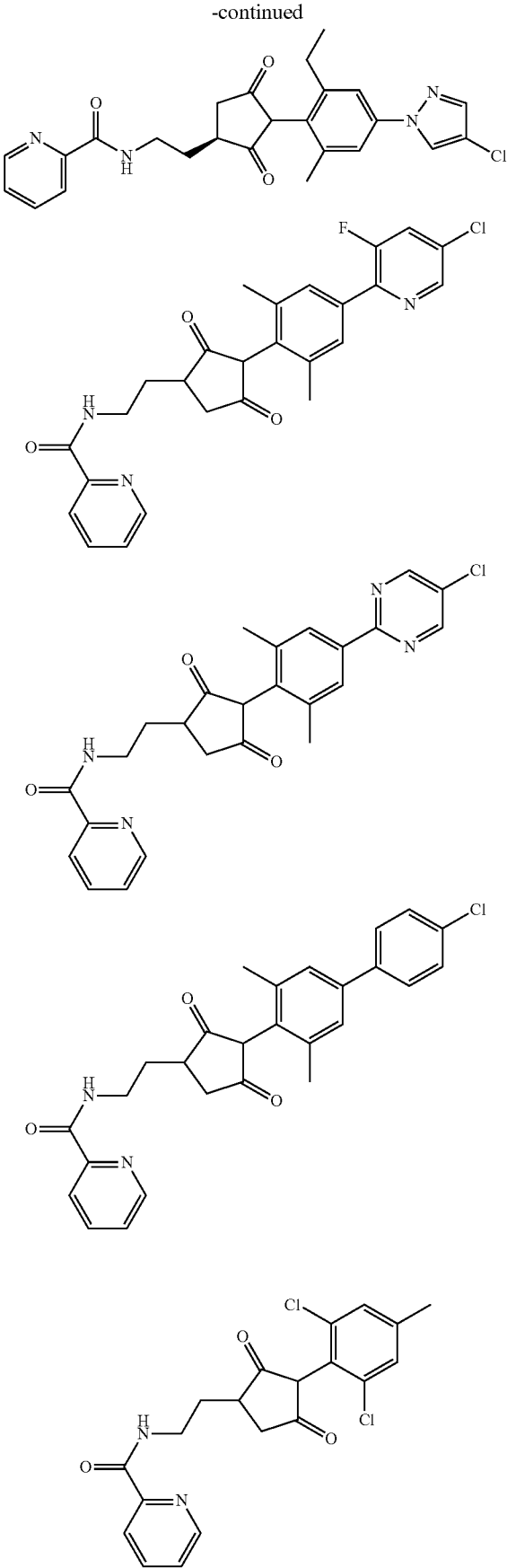

309
-continued
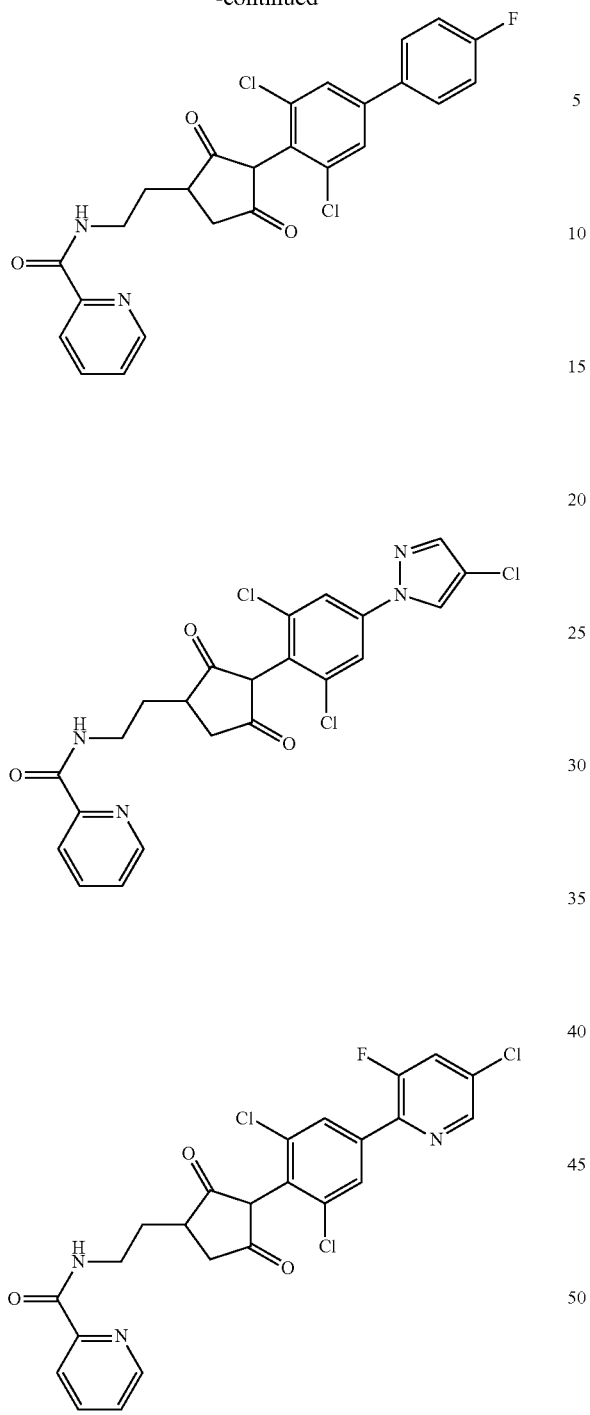
310
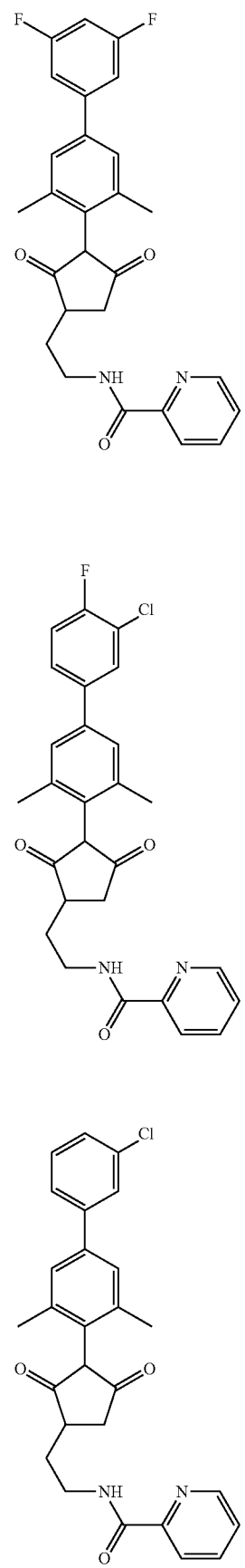
17. The compound as claimed in claim 1, wherein the compound is any of compounds A109 to A211 or any of compounds P1 to P30 present either as a free compound and/or present as an agrochemically acceptable salt thereof:

311
-continued
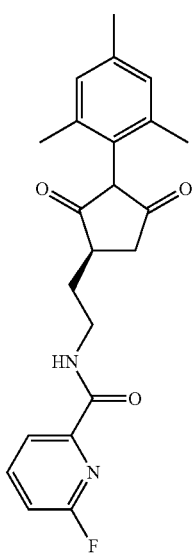
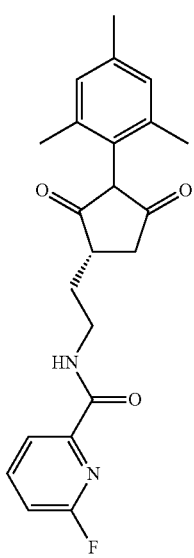
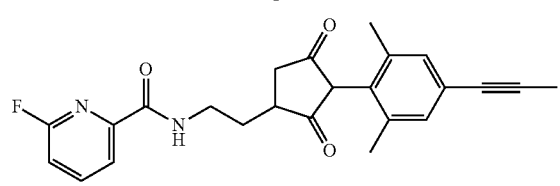
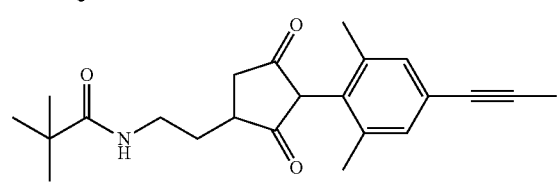
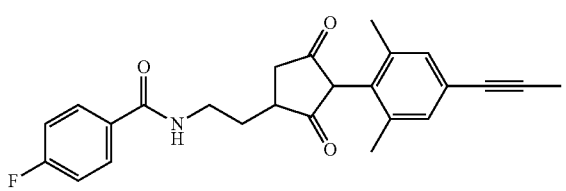
312
-continued
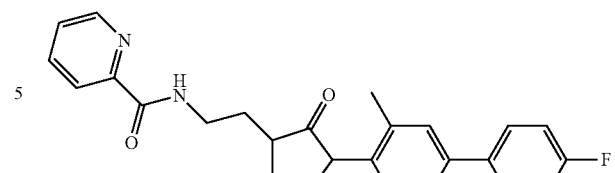
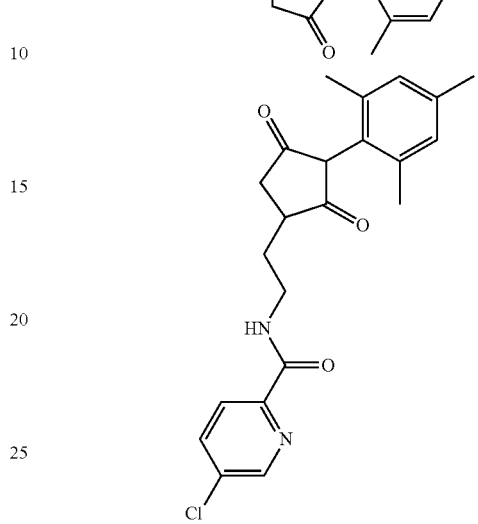
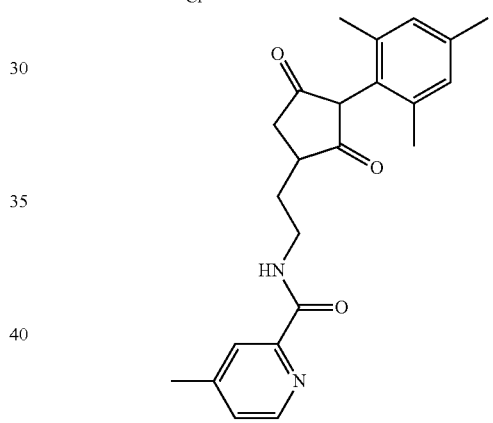
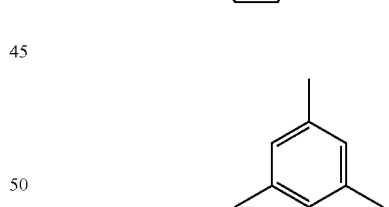
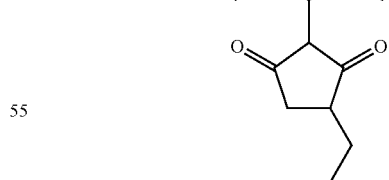
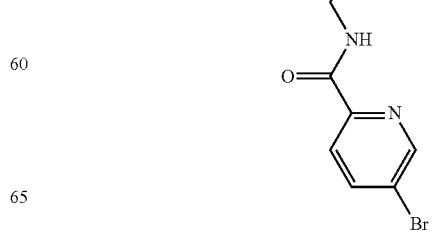

313
-continued
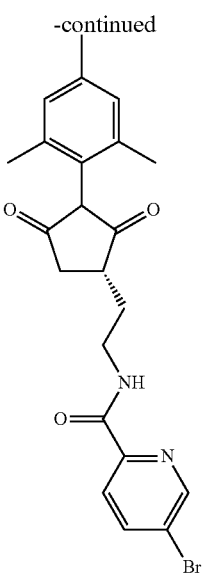
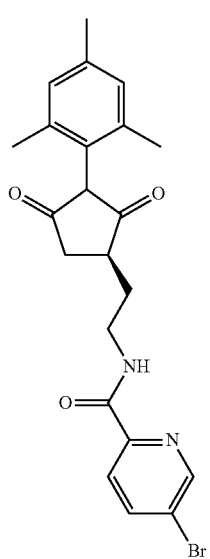
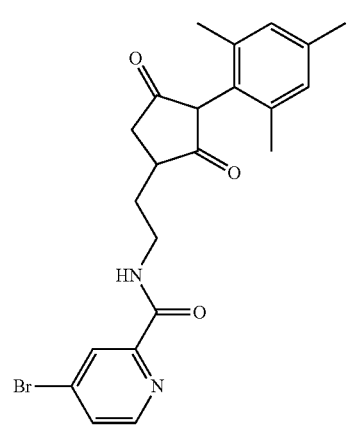
314
-continued
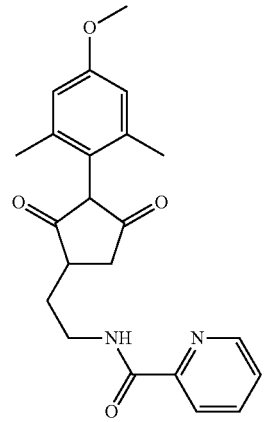
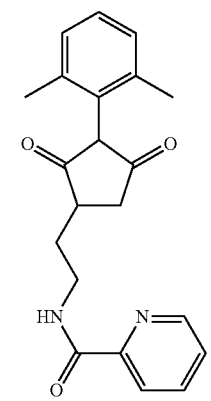
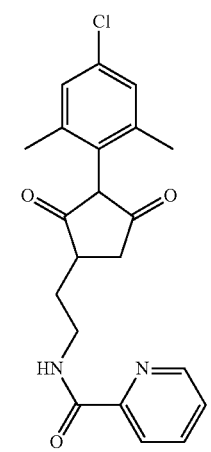
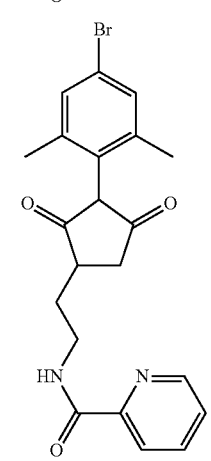

315
-continued
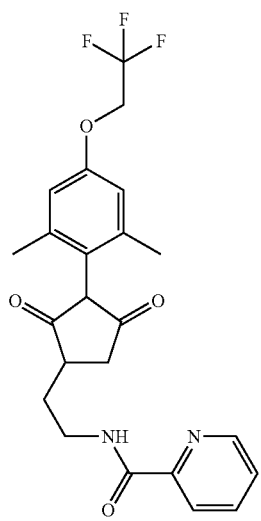
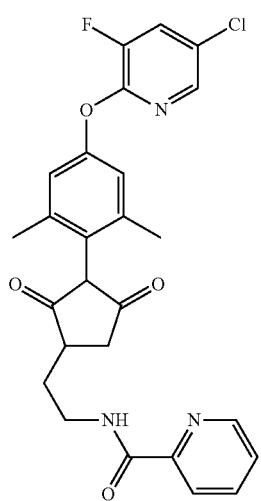
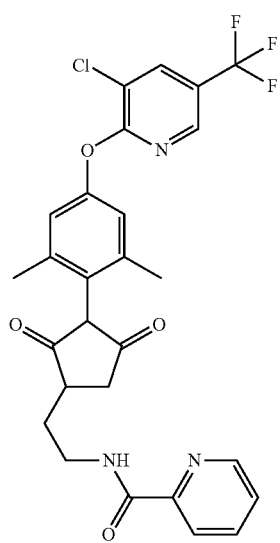
316
-continued
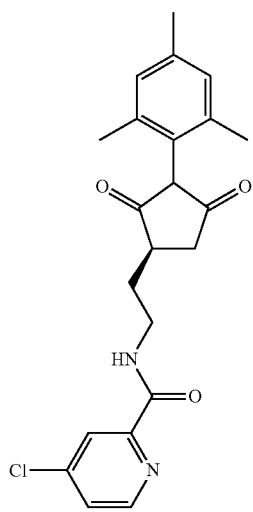
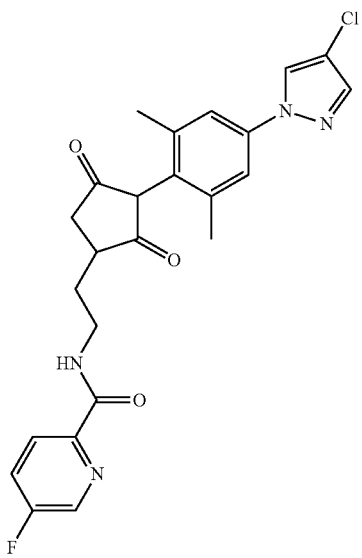

317
-continued
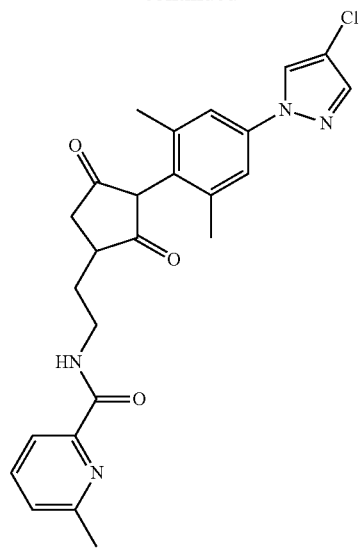
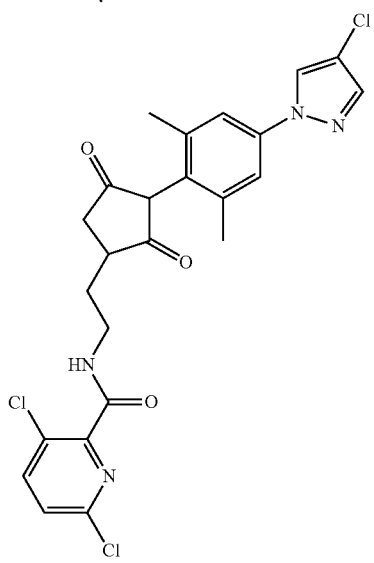
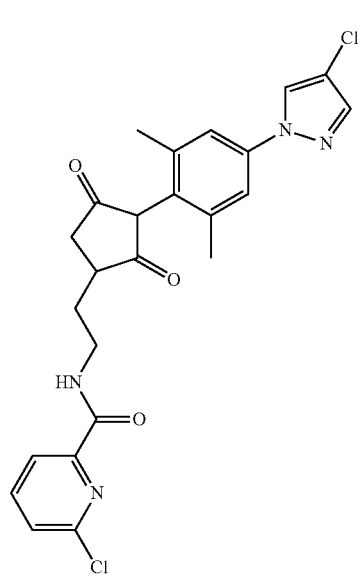
318
-continued
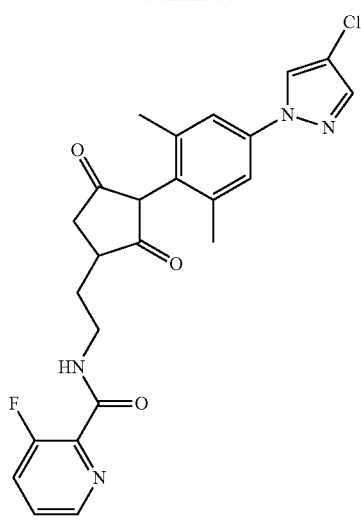
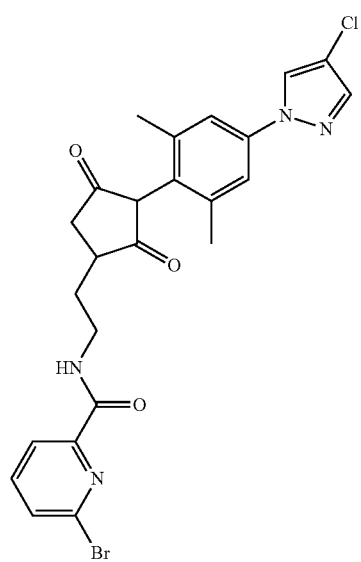
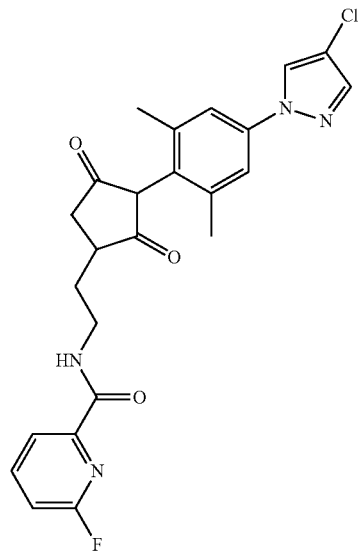

319
-continued
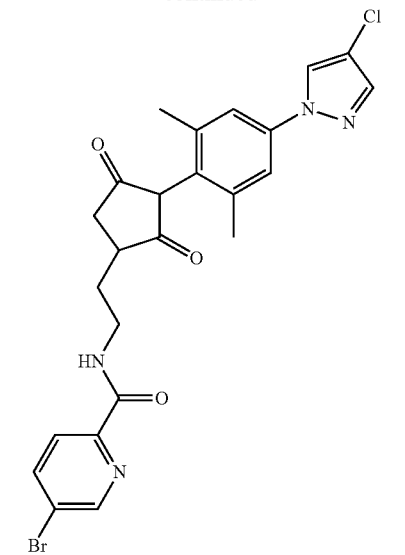
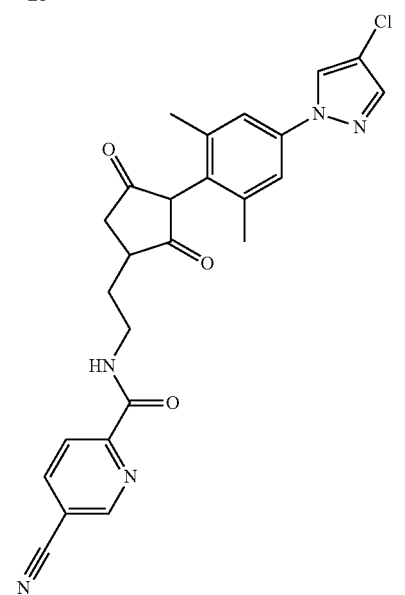
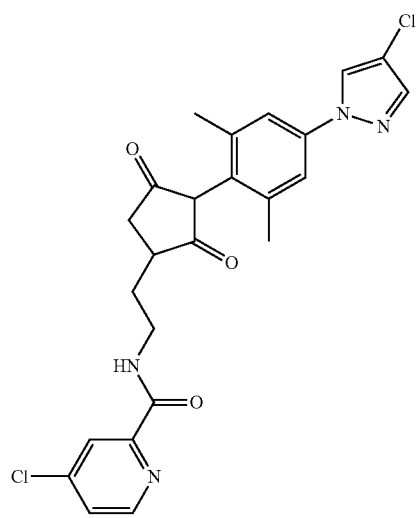
320
-continued
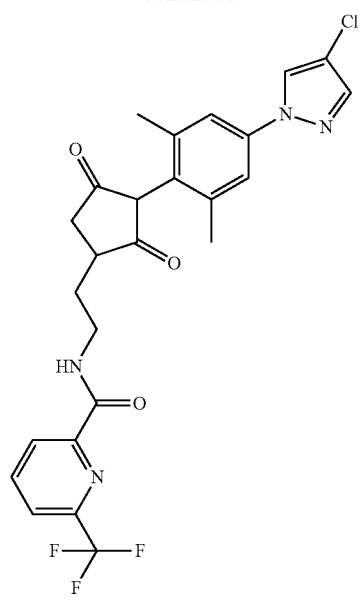
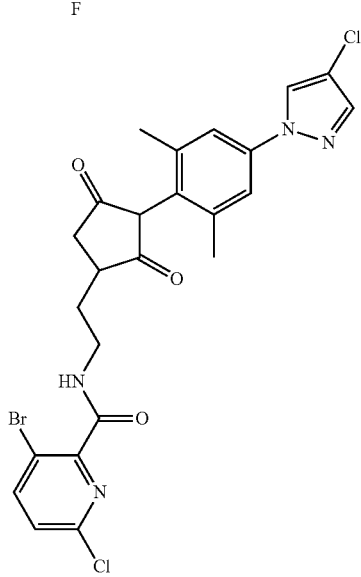
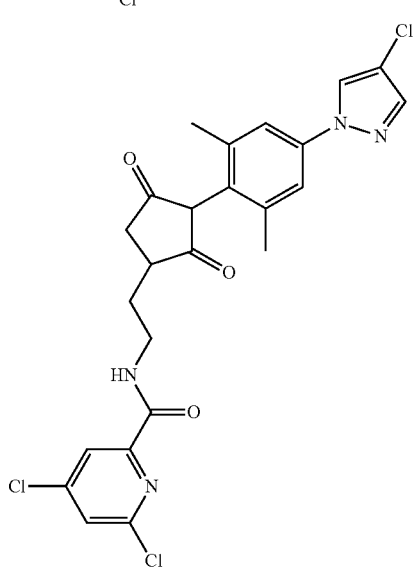

321
-continued
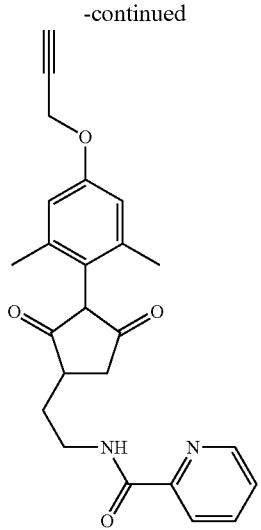
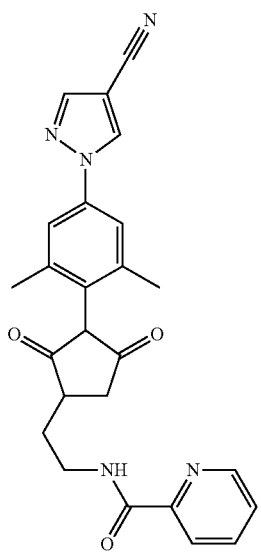
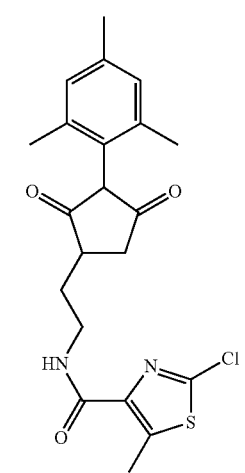
322
-continued
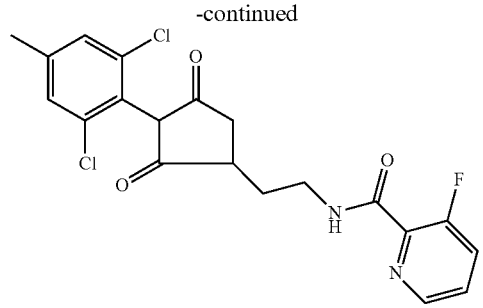
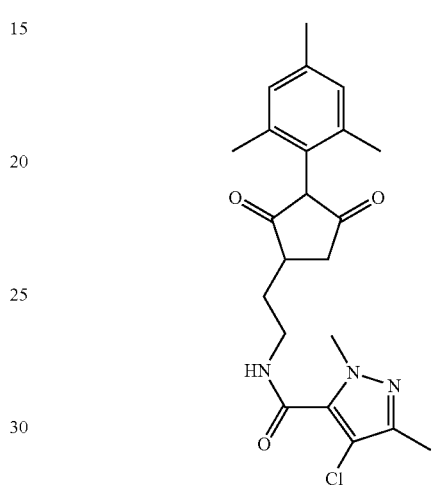
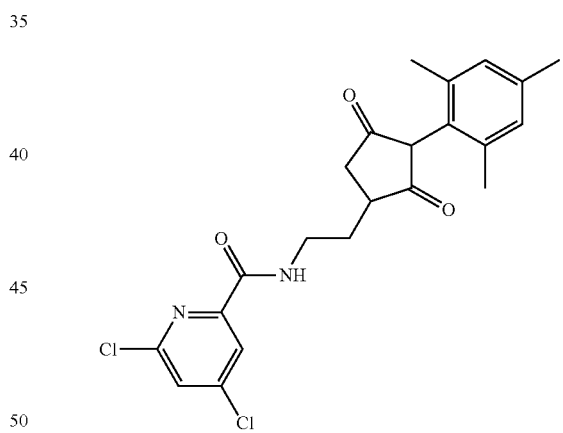
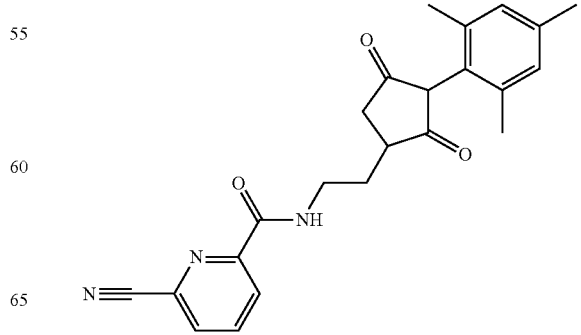

323
-continued
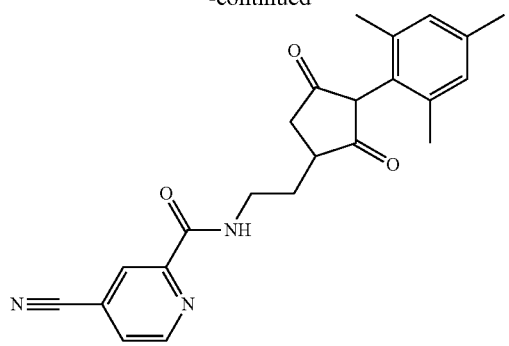
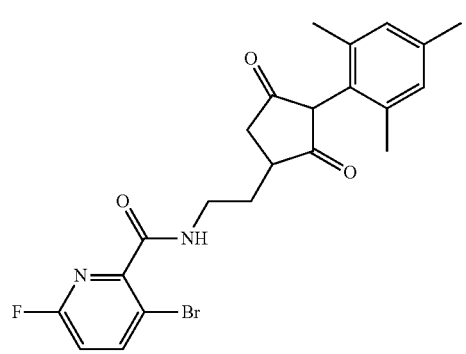
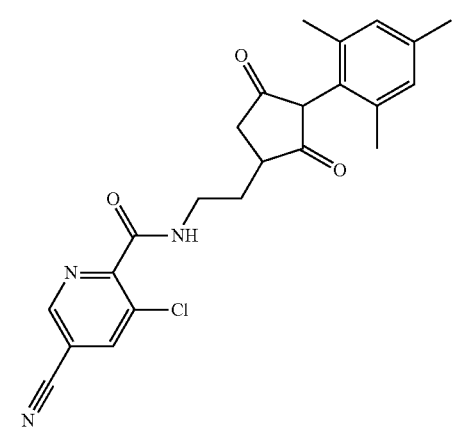
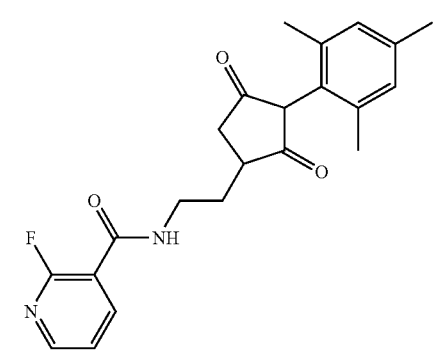
324
-continued
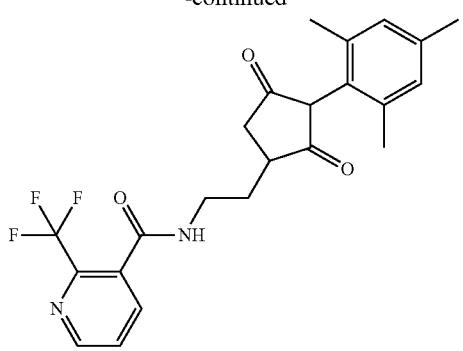
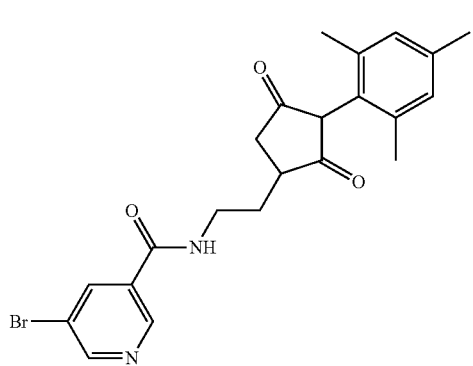
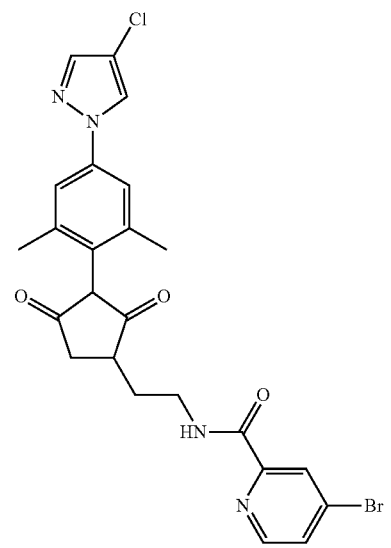

325
-continued
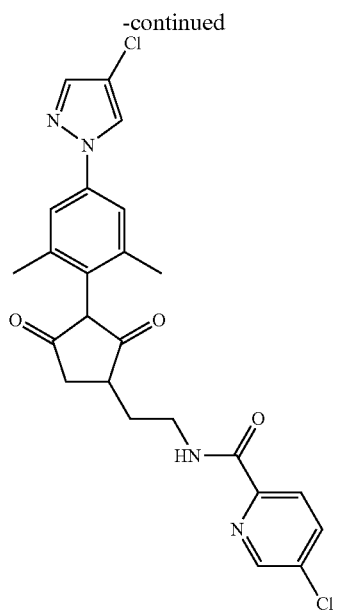
326
-continued
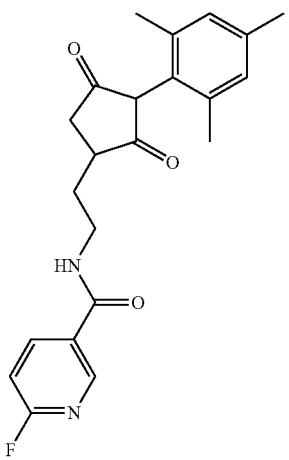
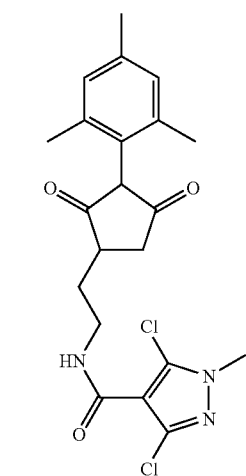
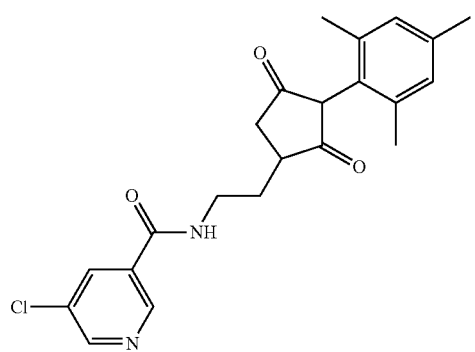
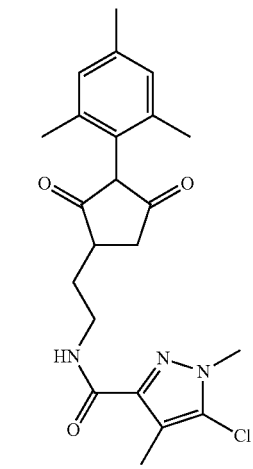

327
-continued
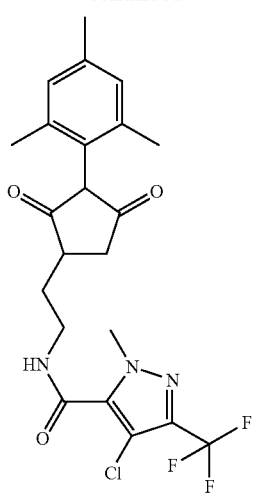
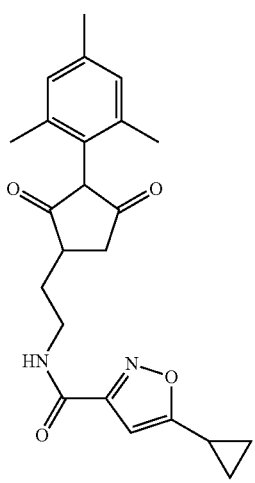
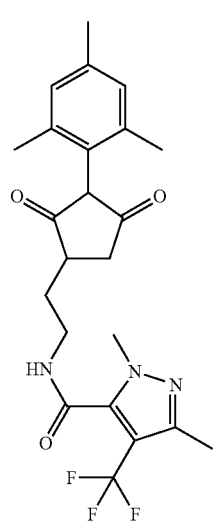
328
-continued
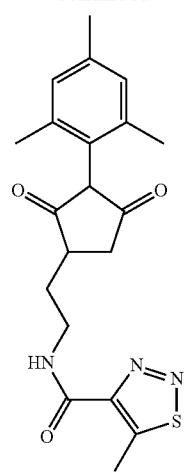
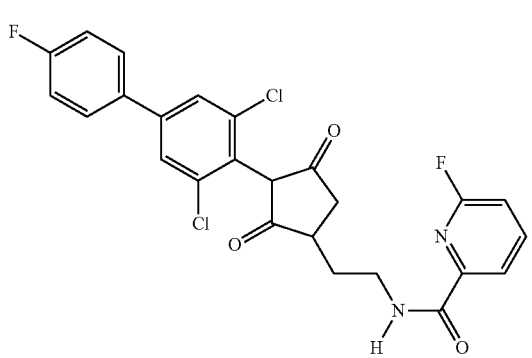
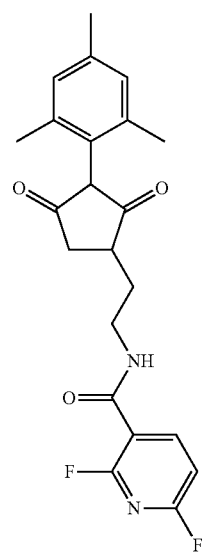

329
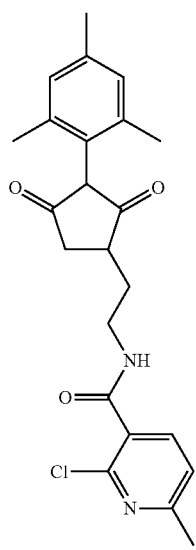
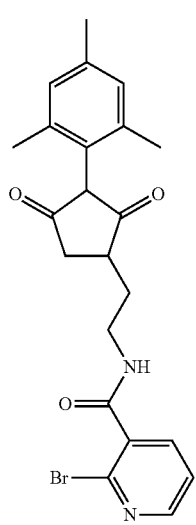
330
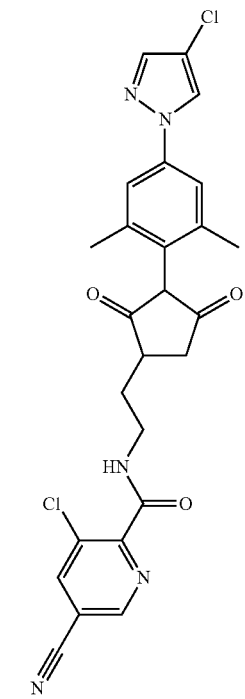
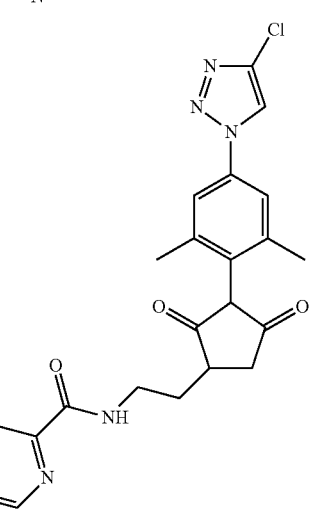
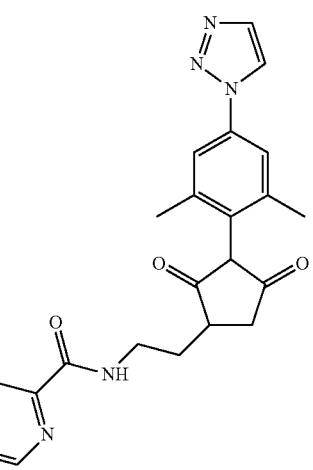

331
-continued
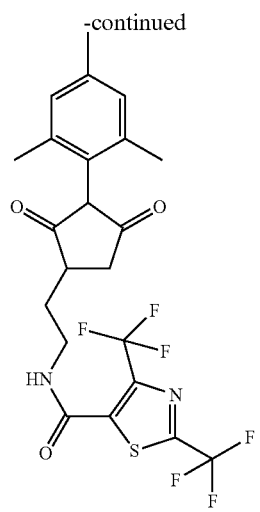
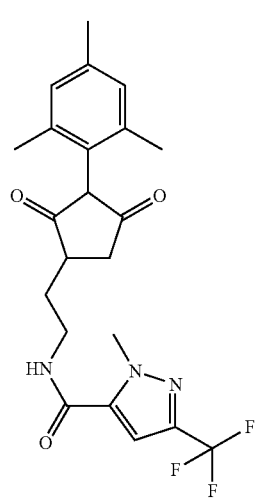
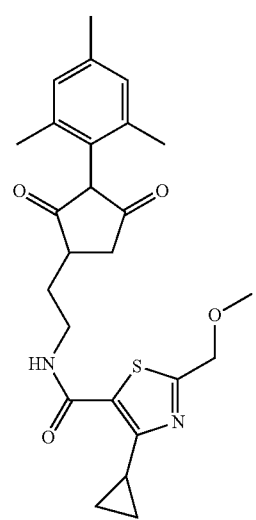
332
-continued
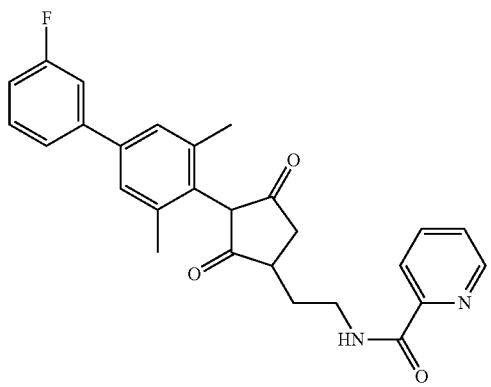
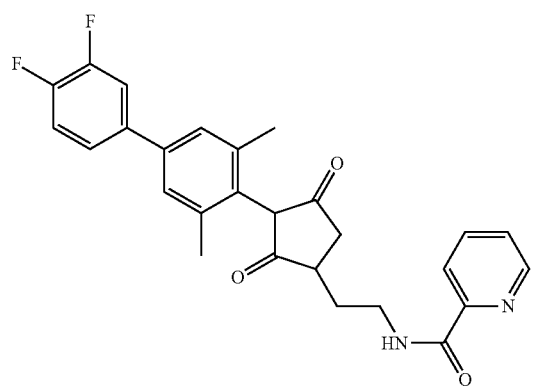
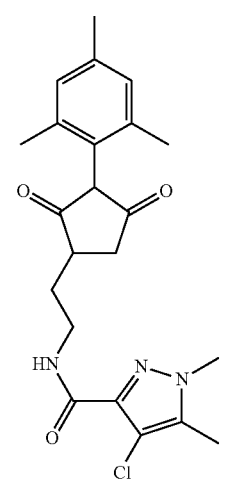

333
-continued
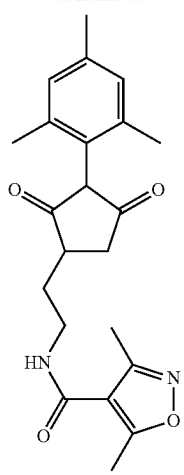
334
-continued
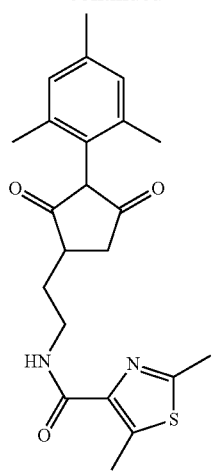
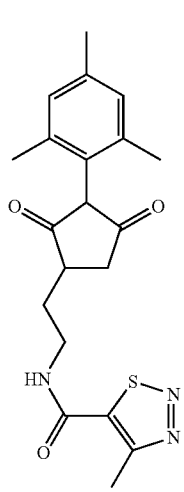
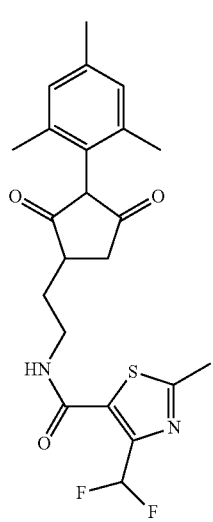
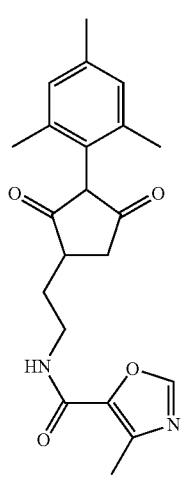
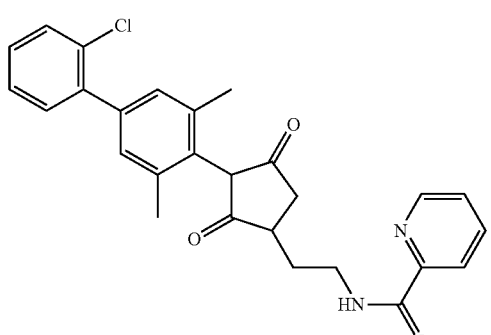

335
-continued
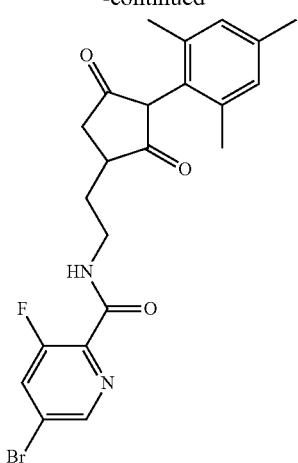
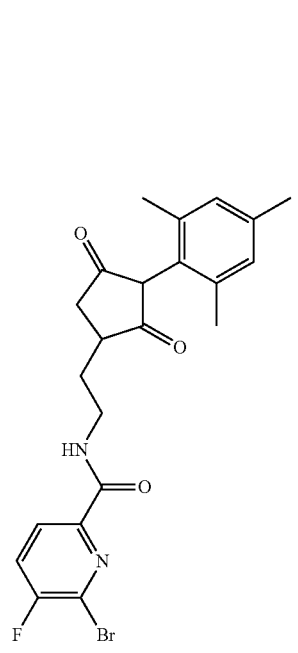
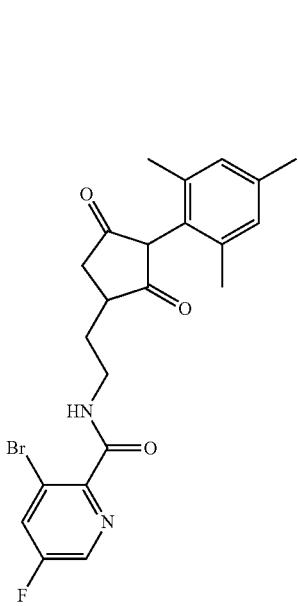
336
-continued
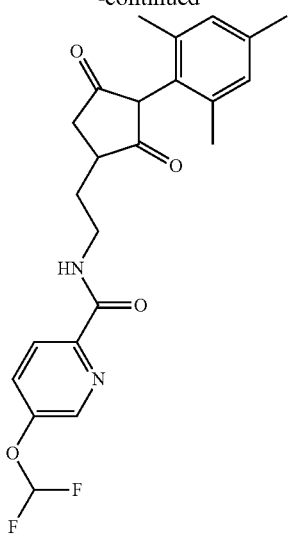
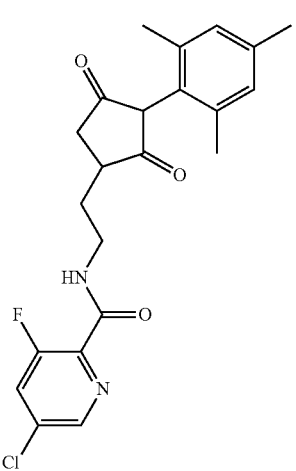
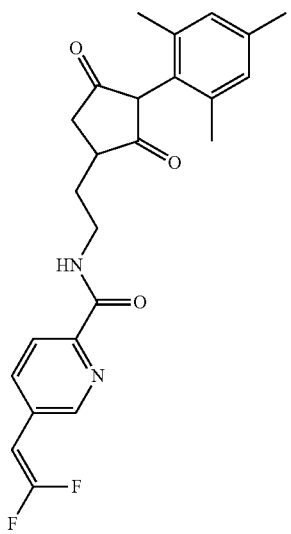

337
-continued
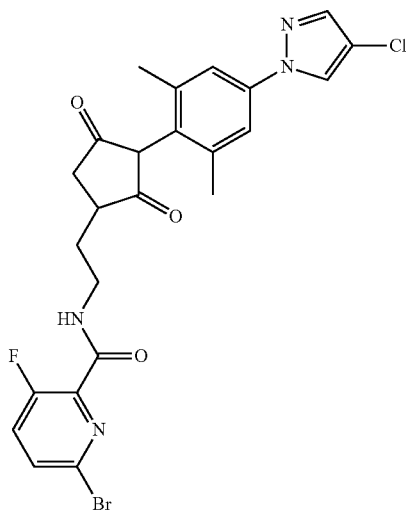
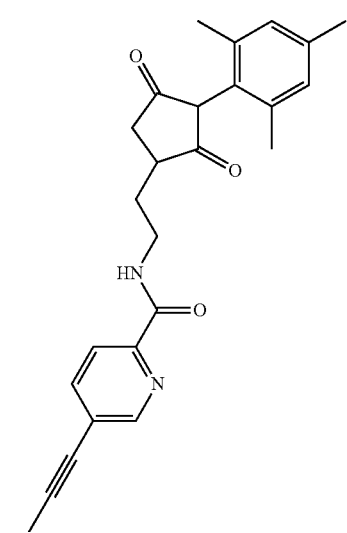
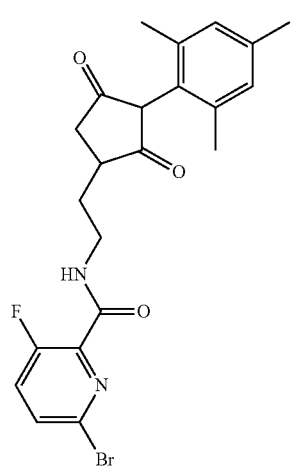
338
-continued
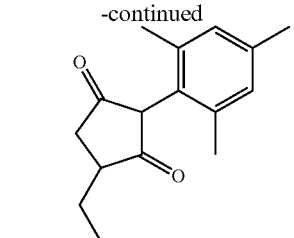
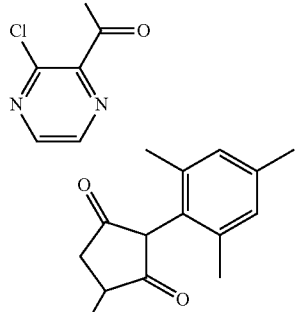
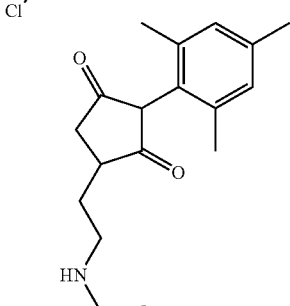
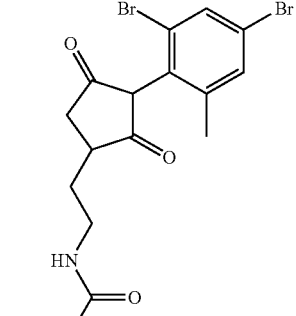
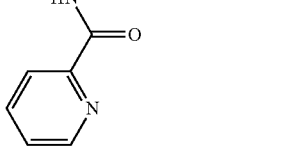

339
-continued
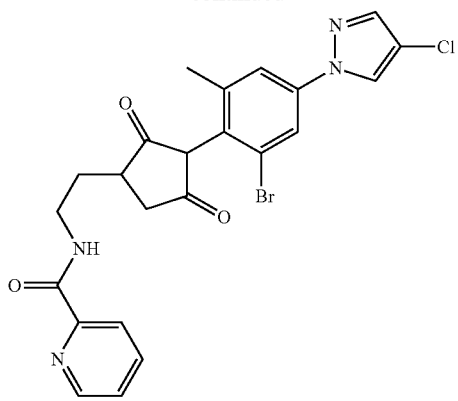
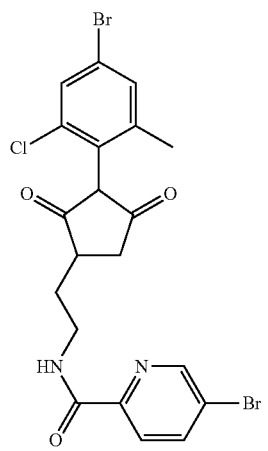
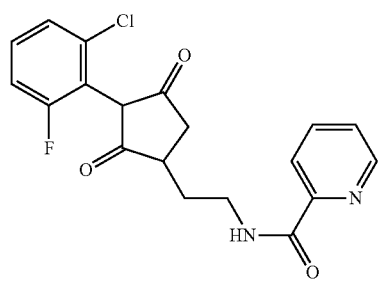
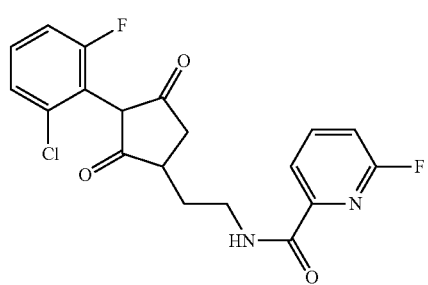
340
-continued
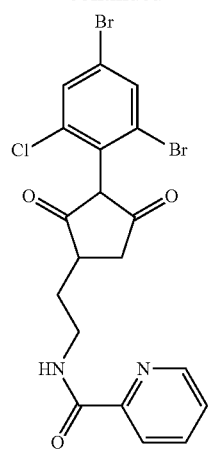
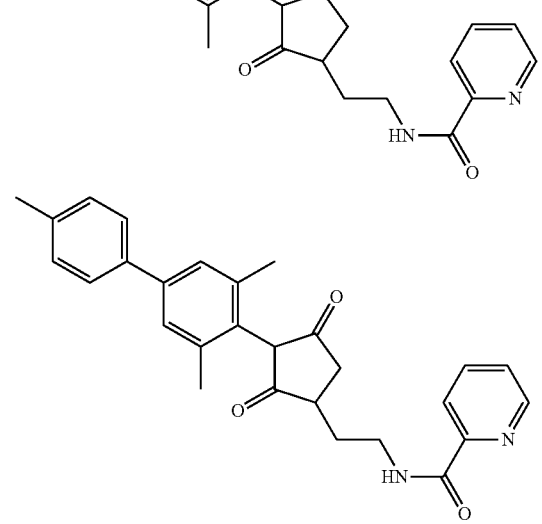
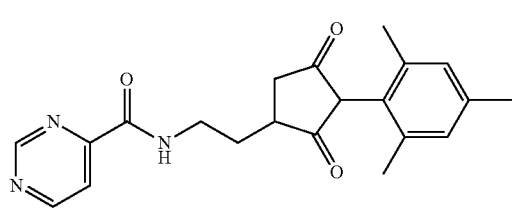
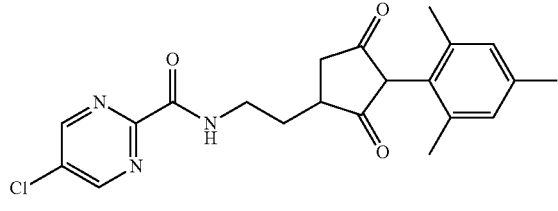

341
-continued
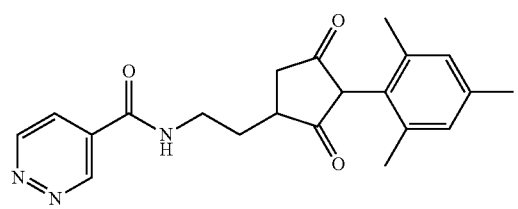
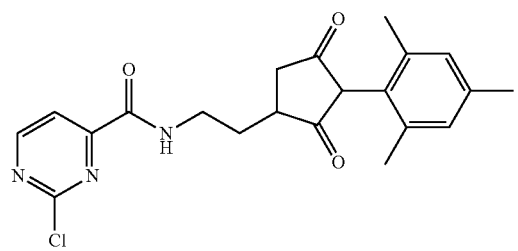
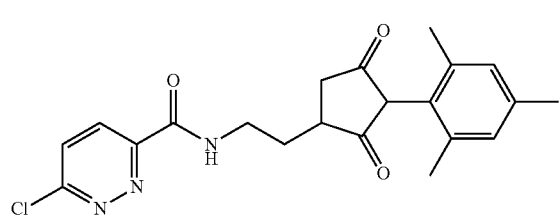
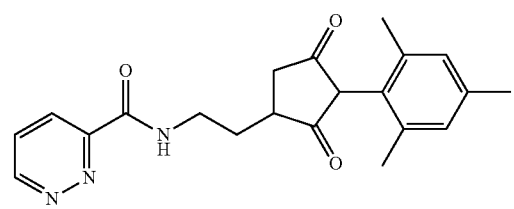
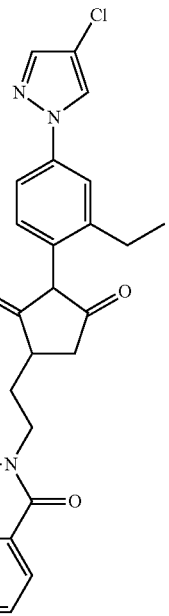
342
-continued
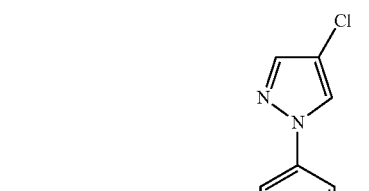
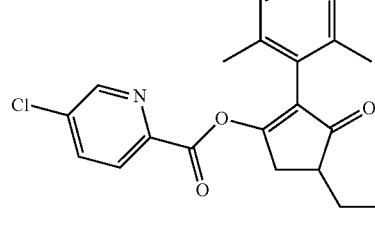
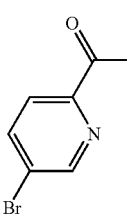

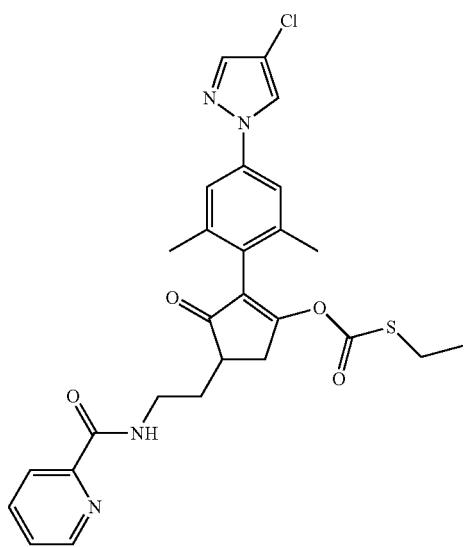
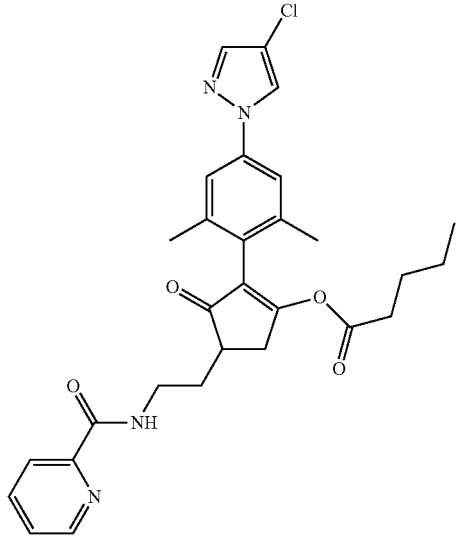
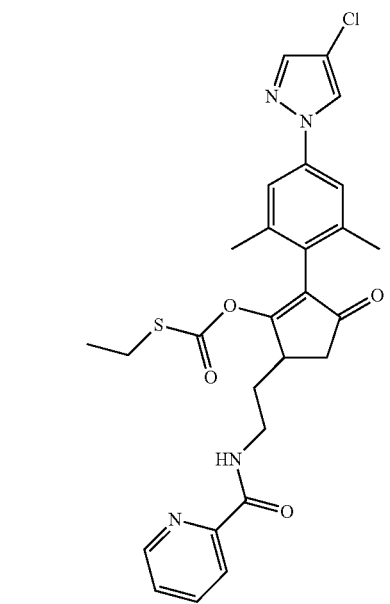
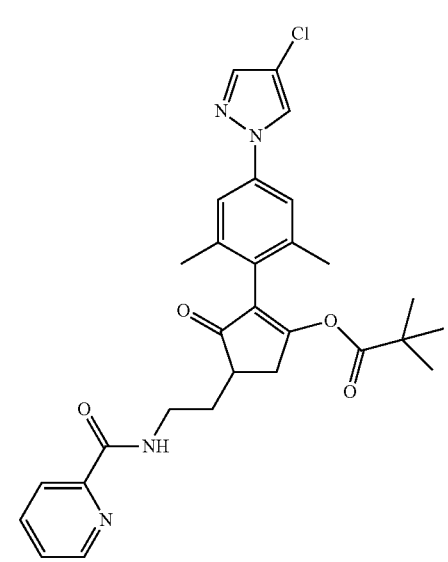
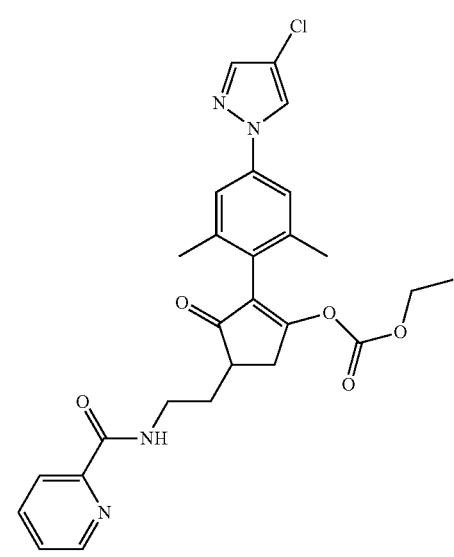
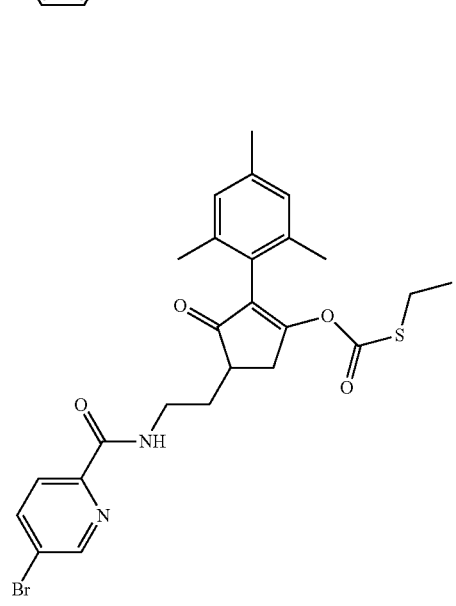

345
-continued
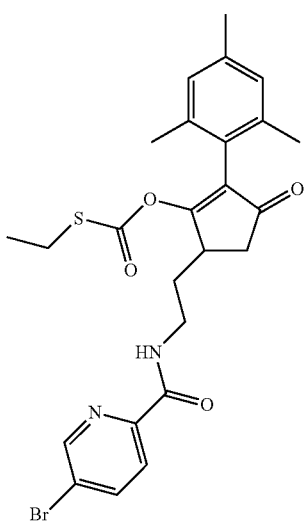
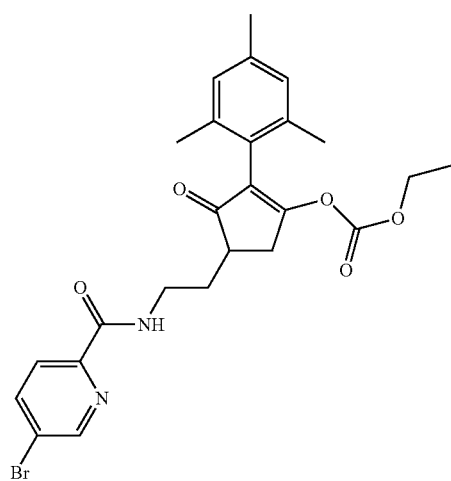
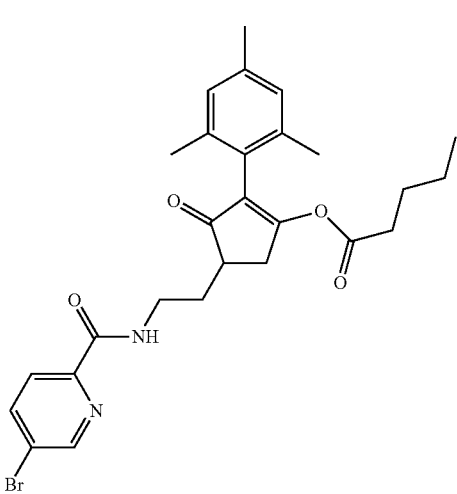
346
-continued
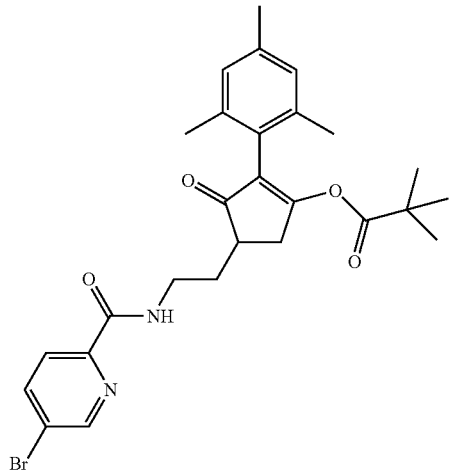
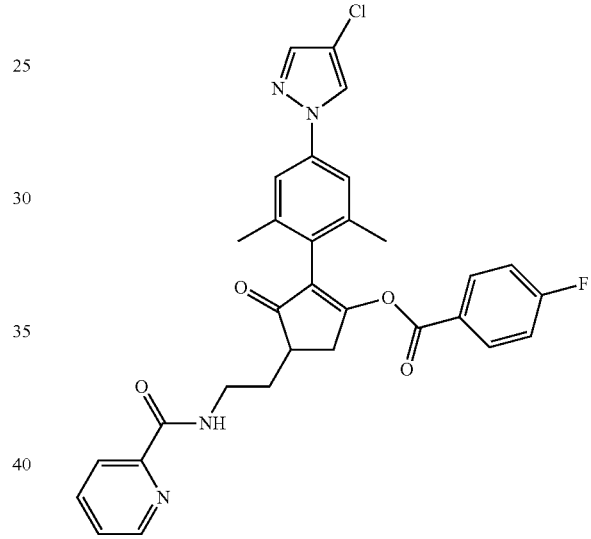
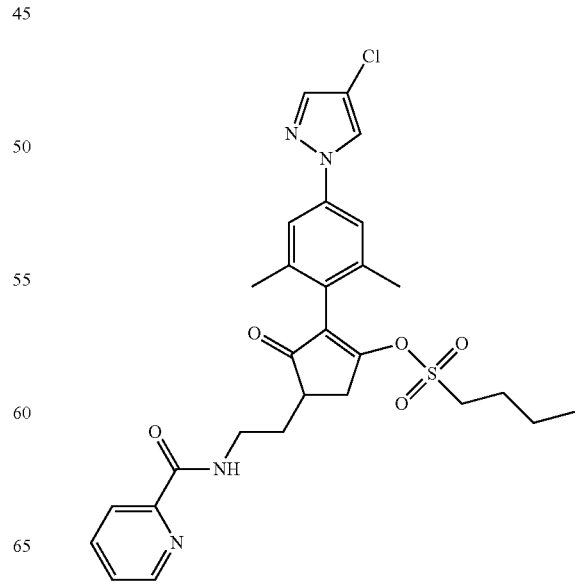

347
-continued
348
-continued
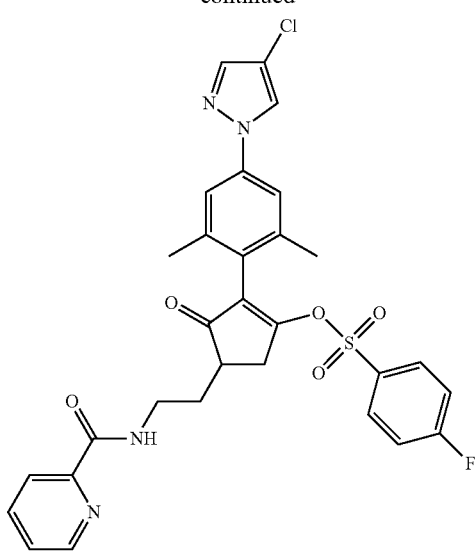
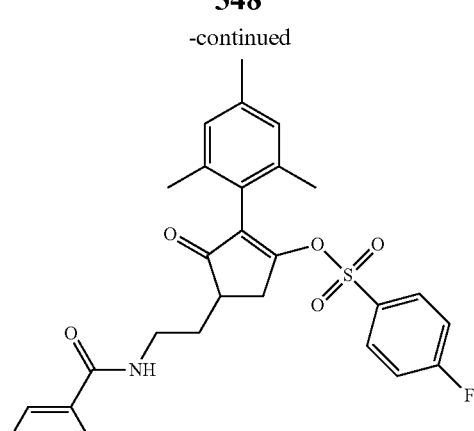
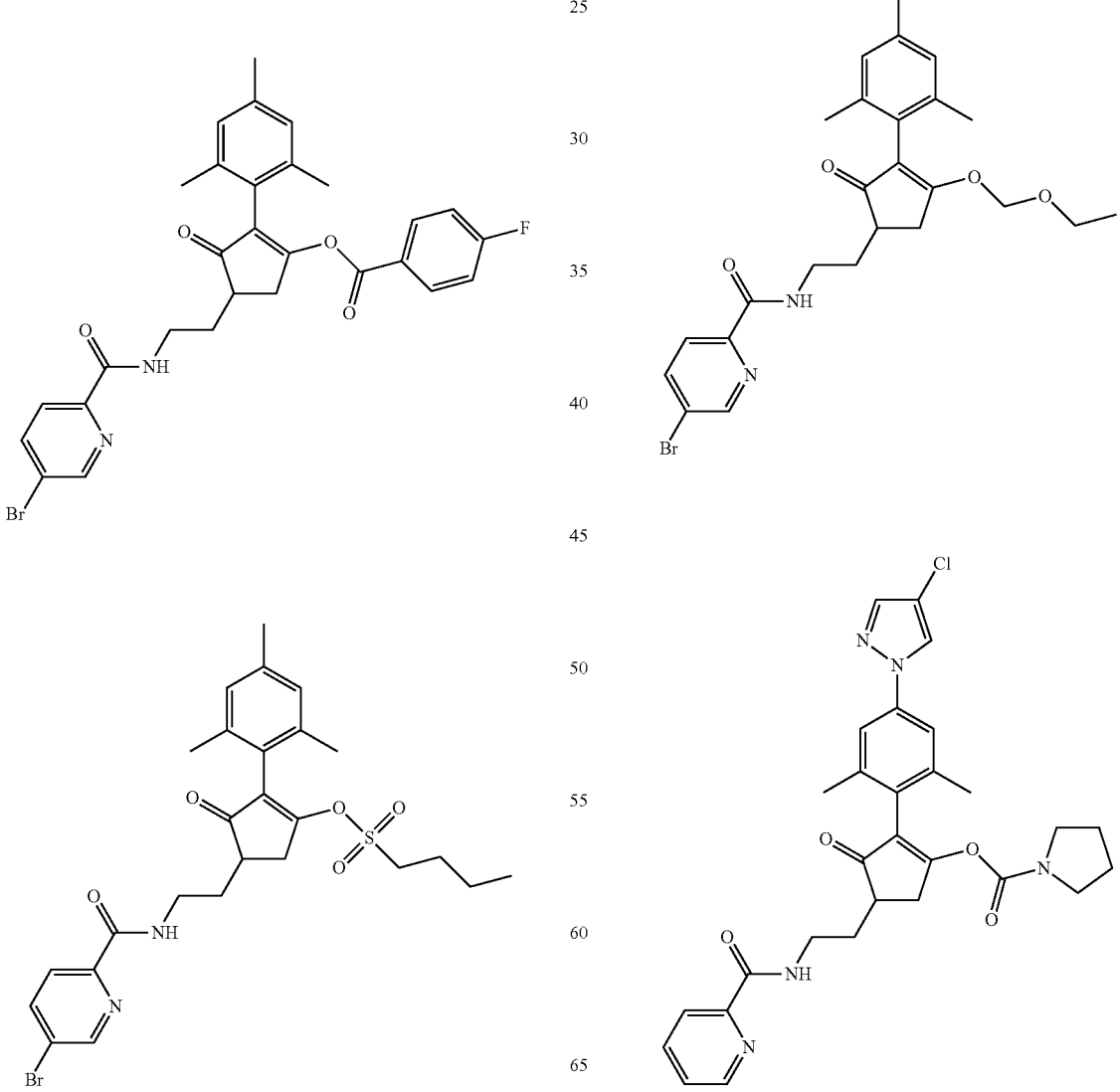
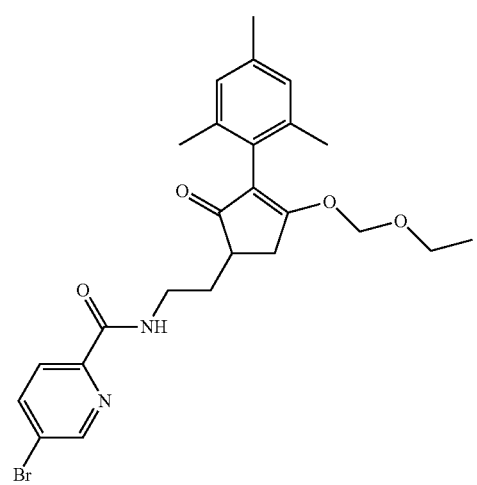
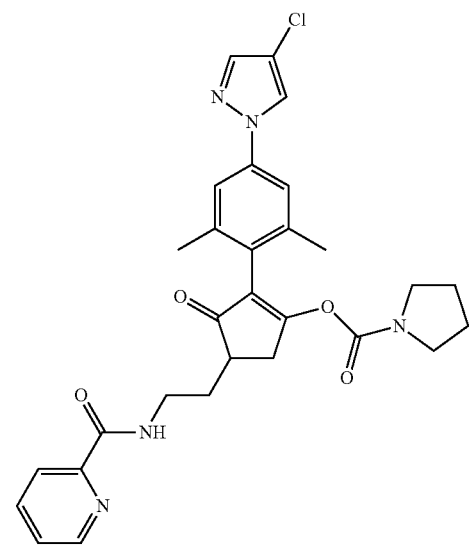

349
-continued
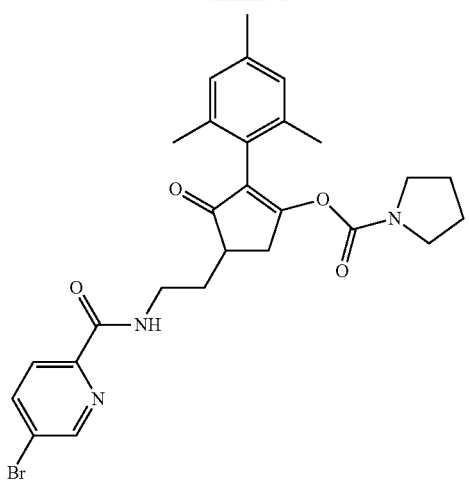
350
-continued
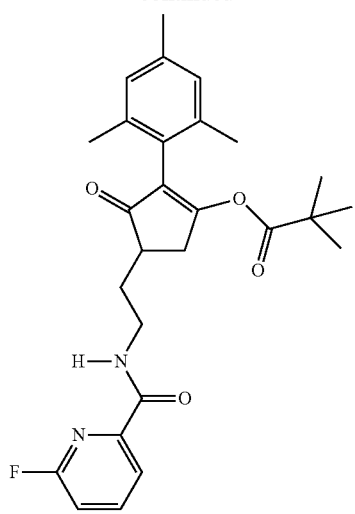
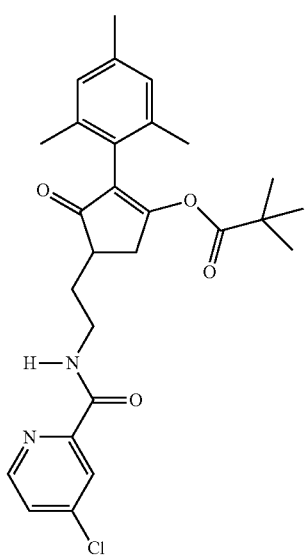
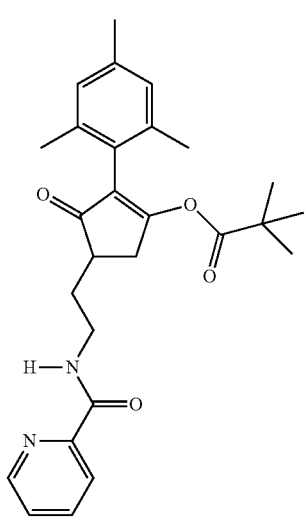
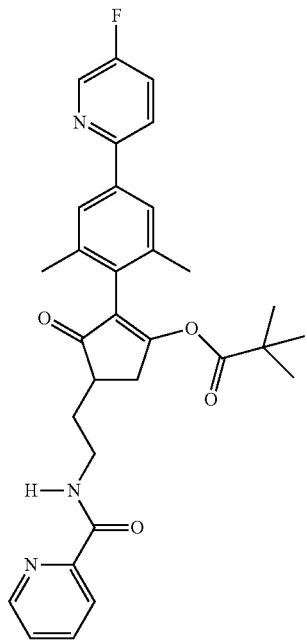

351
-continued

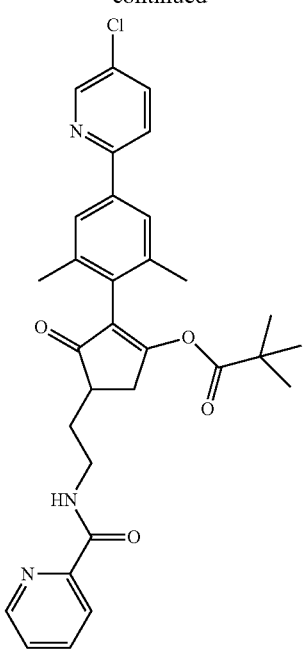

352
-continued

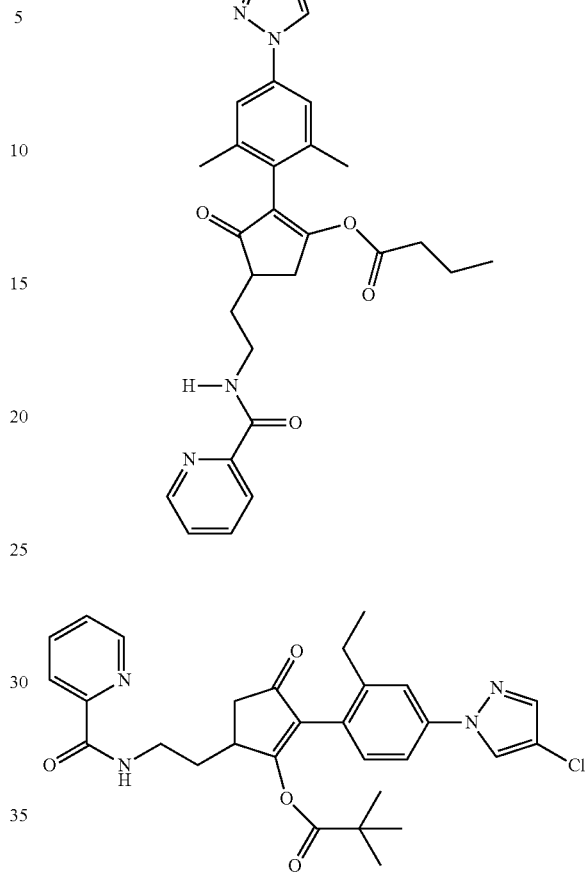

18. A compound of formula (Q):

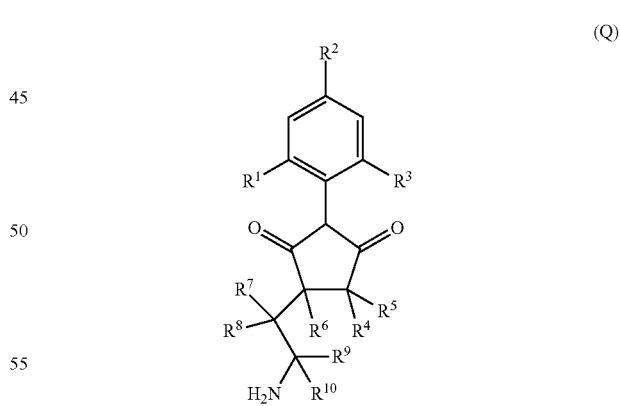

or a salt thereof, when $R^1$, $R^2$, $R^3$, $R^4$, $R^5$, $R^6$, $R^7$, $R^8$, $R^9$, $R^{10}$ are defined in claim 1.

19. A herbicidal composition which comprises a compound of formula (I), as defined in claim 1, and an agrochemically acceptable carrier, diluent and/or solvent.

20. The herbicidal composition according to claim 19, which comprises one or more further herbicides and/or a safener.

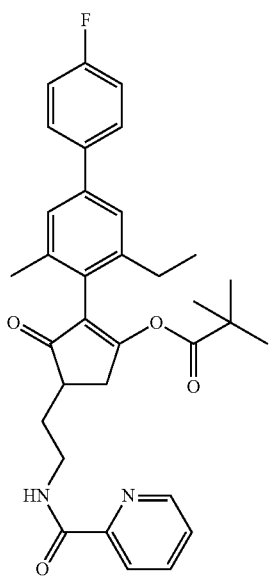

21. A method of controlling grassy monocotyledonous weeds in crops of useful plants, comprising applying a compound of formula (I), as defined in claim 1, or a herbicidal composition comprising such a compound, to the plants or to locus thereof.

* * * * *